US010905769B2

(12) United States Patent
Burke, Jr. et al.

(10) Patent No.: US 10,905,769 B2
(45) Date of Patent: Feb. 2, 2021

(54) PEPTIDE AND PEPTIDE MIMETIC BINDING ANTAGONISTS OF POLO-LIKE KINASE 1 POLO BOX DOMAIN AND METHODS OF USE

(71) Applicant: The United States of America, as represented by the Secretary, Department of Health & Human Services, Rockville, MD (US)

(72) Inventors: Terrence R. Burke, Jr., Bethesda, MD (US); David T. Hymel, Rockville, MD (US); Kohei Tsuji, Frederick, MD (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 0 days.

(21) Appl. No.: 15/977,768

(22) Filed: May 11, 2018

(65) Prior Publication Data

US 2018/0296686 A1     Oct. 18, 2018

Related U.S. Application Data

(63) Continuation-in-part of application No. PCT/US2015/060629, filed on Nov. 13, 2015.

(60) Provisional application No. 62/525,160, filed on Jun. 26, 2017, provisional application No. 62/520,907, filed on Jun. 16, 2017.

(51) Int. Cl.
| | | |
|---|---|---|
| *A61K 38/00* | (2006.01) | |
| *A61K 47/64* | (2017.01) | |
| *C07K 7/06* | (2006.01) | |
| *A61K 31/519* | (2006.01) | |
| *A61K 31/585* | (2006.01) | |
| *C07K 7/56* | (2006.01) | |
| *C07K 7/64* | (2006.01) | |

(52) U.S. Cl.
CPC ............ *A61K 47/64* (2017.08); *A61K 31/519* (2013.01); *A61K 31/585* (2013.01); *A61K 47/645* (2017.08); *C07K 7/06* (2013.01); *C07K 7/56* (2013.01); *C07K 7/64* (2013.01)

(58) Field of Classification Search
None
See application file for complete search history.

(56) References Cited

FOREIGN PATENT DOCUMENTS

WO    WO 2014/153101    9/2014

OTHER PUBLICATIONS

Barr, Nature Reviews: Molecular Cell Biology, vol. 5, Jun. 2004, 429-440 (Year: 2004).*

International Search Report and Written Opinion for PCT/US2015/060629, dated Jul. 11, 2016.
Diezel, Sonja et al: "Tandem Regioselective Rhodium-Catalyzed Hydroformylation-Enantioselective Aminocatalytic anti-Mannich Reaction"Synthesisvol. 46, No. 10, Mar. 26, 2014 (Mar. 26, 2014), pp. 1311-1320, XP55285279STUTTGART, DE. ISSN: 0039-7881, DOI: 10.1055/s-0033-1338602.
Galzerano, Patrizia et al: "Controlling Stereoselectivity in the Aminocatalytic Enantioselective Mannich Reaction of Aldehydes with In Situ Generated N-Carbamoyl Imines"Chemistry—A European Journal.vol. 16, No. 20, May 25, 2010 (May 25, 2010), pp. 6069-6076, XP055224039Weinheim, DE ISSN: 0947-6539, DOI: 10.1002/chem.200903217.
Galzerano, Patrizia et al: "Supporting Information Controlling Stereoselectivity in the Aminocatalytic Enantioselective Mannich Reaction of Aldehydes with In Situ Generated N-Carbamoyl Imines"Apr. 15, 2010 (Apr. 15, 2010), XP55285805Retrieved from the Internet: URL:http://onlinelibrary.wiley.com/store/10.1002/chem.200903217/asset/supinfo/chem_200903217_sm_miscellaneous_information.pdf? v=1 &s=aea80c4b69c3c5da4a25369ef8b697ec4a7dbe51.
Gao, Jiuzhi et al: "Highly efficient asymmetric anti-Mannich reactions of carbonyl compounds with N-carbamoyl imines catalyzed by amino-thiourea organocatalysts"Organic & Biomolecular Chemistryvol. 10, No. 18, Jan. 1, 2012 (Jan. 1, 2012), p. 3730, XP55285273GB ISSN: 1477-0520, DOI: 10.1039/c2ob00049k.
Gao, Jiuzhi et al: Supporting Information "Highly Efficient Asymmetric anti-Mannich Reactions of Carbonyl Compounds with N-Carbamoyl (mines Catalyzed by Amino-thiourea Organocatalysts", Mar. 2, 2012 (Mar. 2, 2012), XP55285350D01: 10.1039/b000000x/ Retrieved from the Internet: URL:http://www.rsc.org/suppdata/ob/c2/c2ob00049k/c2ob00049k.pdf.
Liu, Fa, et al: "Serendipitous alkylation of a Plk1 ligand uncovers a new binding channel"Nature Chemical Biologyvol. 7, No. 9, Jan. 1, 2011 (Jan. 1, 2011), pp. 595-601, XP0550326171SSN: 1552-4450, DOI: 10.1038/nchembio.614.

(Continued)

*Primary Examiner* — Satyanarayana R Gudibande
(74) *Attorney, Agent, or Firm* — Locke Lord LLP; Nicholas J. DiCeglie, Jr.

(57) ABSTRACT

The description provides novel compounds that may serve as anticancer therapeutics. The compounds of the description bind to polo-like kinases through the polo-box domain. The peptide derivatives of the description have achieved improved efficacy in biochemical assays against Plk1. Exemplary compounds of the description include macrocyclic peptidomimetics with high affinity and selectivity for polo-like kinases, which may provide the basis for a new genre of anticancer therapeutics. Other exemplary compounds of the description include bi-valent compounds with that bind to polo-like kinases through both kinase domain and polo-box domain simultaneously by incorporating additional moieties that target Plk1 kinase domain, which significantly enhances affinity relative and may provide the basis for a new genre of anticancer therapeutics. The description also provides methods of use, methods of preparation, compositions, and kits thereof. Further, the description provides a novel method of design and/or synthesis of phosphoryl-derived peptide derivatives useful as therapeutic agents.

6 Claims, 27 Drawing Sheets

(56) References Cited

OTHER PUBLICATIONS

Nagano, T et al: "A new and convenient method for the synthesis of dehydroamino acids starting from ethyl n-boc- and n-z-alpha-tosylglycinates and various nitro compounds" Bulletin of the Chemical Society of Japan, Chemical Society of Japan, Tokyo, JPvol. 73, No. 7, Jan. 1, 2000 (Jan. 1, 2000), pp. 1605-1613, XP009010575155N: 0009-2673, DOI: 10.1246/BCSJ.73.1605.

\* cited by examiner

1, Ac-PLH*SpT (*4j*) [X=O]
2, Ac-PLH*S(Pmab) (*4j**) [X=CH$_2$]

| Cpd | Sequence | Lot | IC$_{50}$ (nM; n=3) |
|---|---|---|---|
| 1 *(4j)* | PLH*SpT | DH_222A_82 | 110 ± 16 |
| 7a | cPLH*(n4)SpT | DH_222J_35 | 160 ± 35 |
| 7b | cPLH*(n5)SpT | DH_222J_34 | 44 ± 11 |
| 7c | cPLH*(n6)SpT | DH_222J_33 | 43 ± 5 |
| 7d | cH*(n5)SpT | DH_222J_82 | 319 ± 23 |
| 15a | cPLE*SpTO | DH_222J_57 | 103 ± 29 |
| 15b | cPLE*SpTo | DH_222J_58 | ~10,000 |
| 15c | cPLE*SpTK | DH_222J_45 | 136 ± 45 |
| 15d | cPLE*SpTk | DH_222J_59 | >10,000 |

TOC Graphic

Ac-PLHS(pT)-OH (1)

Ac-PLH*S(pT)-NH$_2$ (3)
H* = His-[$N(\pi)$-(CH$_2$)$_8$-Ph]

1: R = CH₃, X = O
1*: R = CH₃-(OCH₂CH₂)₈-, X = CH₂

BI2536* 6
(N to O mutant)

BI2536† 7
(N to O and isobutyl mutant)

4: BI2536, R = cyclopentyl, X = N
8: BI2536*, R = cyclopentyl, X = O
10: BI2536†, R = isobutyl, X = O

5: BI2536, R = cyclopentyl, X = N
9: BI2536*, R = cyclopentyl, X = O
11: BI2536†, R = isobutyl, X = O

PEPTIDE AND PEPTIDE MIMETIC BINDING ANTAGONISTS OF POLO-LIKE KINASE 1 POLO BOX DOMAIN AND METHODS OF USE

CROSS REFERENCE TO RELATED APPLICATIONS

The present disclosure is a continuation-in-part of International Patent Application No. PCT/US2015/060629, filed on 13 Nov. 2015 and published as WO 2017/082924, and the present disclosure claims priority to U.S. Provisional Application No. 62/520,907, filed 16 Jun. 2017, and U.S. Provisional Application No. 62/525,160, filed 26 Jun. 2017, all of which are incorporated herein by reference in their entirety for all purposes.

STATEMENT OF FEDERALLY SPONSORED RESEARCH

This work was supported by an intramural grant from the National Institutes of Health. The U.S. government has certain rights in the invention.

BACKGROUND

Phosphorylated amino acids are responsible for numerous binding interactions within cells that mediate protein-protein interactions and biochemical pathways. As such, synthetic phosphopeptides and peptide mimetics or peptidomimetics have received interest as competitive inhibitors of these interactions.

For example, polo-like kinases (collectively, Plks) are a conserved subfamily of Ser/Thr protein kinases that play critical roles in cell proliferation. The serine/threonine specific polo-like kinase 1 (Plk1) is an important cell cycle regulator that has been defined as a molecular target for anti-cancer therapy development. Plk1 is a critical protein involved in regulation of mitosis, and aberrant expression of this kinase is found in various types of cancer. Inhibition of Plk1 is currently being pursued in pre-clinical drug development for novel anti-cancer therapeutics. Aside from a canonical ATP-dependent kinase domain, Plk1 contains an allosteric domain, known as the polo-box domain (PBD), that is responsible for localizing the kinase domain to mitotic structures through protein-protein interactions (PPIs). Plk1 requires the coordinated actions of both an N-terminal kinase domain (KD), which executes its catalytic function and a C-terminal polo-box domain (PBD), which engages in protein-protein interactions (PPIs) with phospho-serine (pS) and phosphothreonine (pT)-containing sequences. Multiple forms of Plks, designated Plk1, Plk2/Snk, Plk3/Prk/Fnk, and Plk4/Sak, exist in mammals. Plk4 is the most distantly related member of the Plk subfamily and one of the two Plk4 variants, Sak-a, contains only the PB1 motif near the end of an unusually long C-terminal extension. Among the Plks, Plk1 has been studied most extensively because of its ability to override cellular checkpoints and induce genetic instability, leading to oncogenic transformation of human cells. Not surprisingly, Plk1 is overexpressed in a broad spectrum of human cancers and has been proposed as a new prognostic marker for many types of malignancies.

Furthermore, interference with Plk1 function induces apoptotic cell death in most tumor cells, but not in normal cells, and reduces tumor growth in mouse xenograft models. A Plk1 inhibitor known as BI 6727 (volasertib) is presently undergoing clinical trials for the treatment of various human cancers, including acute myeloid leukemia. In contrast to the role of Plk1 in cell proliferation and tumorigenesis, the two most closely related kinases, Plk2 and Plk3, appear to play a role in checkpoint-mediated cell cycle arrest to ensure genetic stability and prevent oncogenic transformation. Thus, specific inhibition of Plk1, but not Plk2 or Plk3, is critically important for anti-Plk1 cancer therapy.

The PBD of Plk1 plays a critical role in proper subcellular localization and mitotic functions of Plk1 by interacting with phosphorylated Ser/Thr peptides with the invariable Ser residue at the −1 position (S-p-S/T motif). Crystal structures of the Plk1 PBD in complex with artificial phosphopeptides optimized for PBD binding have revealed that the PB1 and PB2 motifs have identical folds described as $\beta 6\alpha$ (a six-stranded anti-parallel $\beta$-sheet and an $\alpha$-helix) and form a hetero-dimeric phosphopeptide-binding module.

The phosphopeptide binds to a cleft formed between PB1 and PB2 and interacts with key amino acid residues from both polo-boxes. His538 and Lys540 from PB2 are pivotal for electrostatic interactions with the negatively charged phosphate group of phospho-Ser/Thr (p-Ser/Thr) residue, whereas Trp414 from PB1 is critical for the selection of Ser at the −1 position by engaging in two hydrogen bonding interactions and van der Waals interactions with the Ser-1 residue. These residues are conserved in the PBDs of Plk1, Plk2, and Plk3 (in short, Plk1-3), attesting to their importance (Plk4 has a distinct binding module and forms a homodimer through a motif called cryptic polo-box).

Although Plk1 KD-directed agents are currently in the clinical trials for the treatment of cancers, issues related to cytotoxicity have arisen that may result from off-target effects. PBD-directed antagonists may potentially afford attractive alternatives to ATP-competitive KD inhibitors for down-regulating Plk1 activity. This is due in part to the fact that PBDs are limited to the five members of the Plk family of kinases and accordingly that this may impart a degree of selectivity. Accordingly, significant efforts have been devoted to develop PBD-binding antagonists. U.S. Pat. No. 9,175,038 issued Nov. 3, 2015) and two pending Applications (U.S. patent application Ser. No. 14/776,512, and PCT Application No. PCT/US2015/060629) related to current disclosure have been disclosed in its entirety herein.

Efforts to develop PBD-binding antagonists have utilized peptides based on a region of the polo-box domain interacting protein 1 (PBIP1) proximal to the phosphorylated pT78 residue PLHSpT (1). It has been found by tethering alkylphenyl groups from different positions on this sequence, that a hydrophobic "cryptic binding pocket" formed by Y417, Y421, Y481, F482, Y485 and L478, which is revealed by a more than 100° rotation of the Y481 side chain can be accessed. Occupying the cryptic binding pocket can provide up to three-orders-of-magnitude enhancement in PBD-binding affinity. Of particular note, the pocket was approached from the His residue using peptides of the form PLH*SpT (2), where H* indicates the presence of a $-(CH_2)_8$ Ph group on the His N3($\pi$) nitrogen [ie, the His-[N($\pi$)-$(CH_2)_8$Ph]. By tethering long-chain alkylphenyl groups from a variety of amino acids at the pT-2 position, it was confirmed that significant PBD affinity enhancement could be achieved relative to the parent PLHSpT (1), however peptide 2, with a $-(CH_2)_8$Ph group on the His N3($\pi$) nitrogen, has continued to be the highest affinity ligand. Peptide 2 is significant for developing minimally sized binding antagonists, since its cryptic pocket-accessing His-

[N(π)-(CH$_2$)$_8$Ph] residue is at the pT-2 position, which is immediately adjacent to the minimal PBD recognition motif of "SpT".

The current primary limitation of peptide-based PBD-binding inhibitors is poor potency in cell-based assays (as measured by mitotic block and induction of apoptosis). This potentially reflects low cell membrane penetration arising from peptide character and anionic charge arising from the phosphoamino acid phosphoryl moiety. Attempts to address the latter "phosphoryl problem" were made in a number of ways, including through the use of pT mimetics, prodrug protection, and "charge masking" (induced by converting the alkyl-His residue to a bis-alkylated imidazolium cation). However, to date, these efforts have not significantly enhanced cellular potencies. Likewise, reducing the peptide character of parent 2 by deleting N-terminal amino acids results in significant loss of PBD-binding affinities, although this can be partially regained by re-introducing N-terminal functionality of significant size and complexity. As an alternative to shortening 2, different approaches were investigated for increasing the PBD-binding affinity of the parent pentameric structure. A four-fold affinity enhancement relative to 2 has been received recently by optimizing interactions within the key hydrophobic cryptic binding pocket and by varying the structure of the phosphoamino acid component. Although the work outlined above provides important advances in the design of PBD-binding ligands, a more radical approach may be needed to overcome existing impediments to cellular potency.

With this as background, the acknowledged power of multi-valency in ligand design has been noted. Several recent report have exemplified the power of multi-valency in ligand design. For example, kinase domain-binding inhibitors have been joined together with agents that interact with substrate-recognition or allosteric regions outside the catalytic site. Such constructs can result in exceptionally selective and high affinity bivalent ligands.

Efforts have been focused on developing inhibitors of PPIs by generating high affinity peptidomimetic ligands targeting the PBD. These ligands are designed to selectively cause mitotic arrest in cancer cells with abnormal Plk1 expression by inhibiting proper localization of Plk1. In doing so, such ligands could avoid issues of off-target activity and dose-limiting toxicities that are characteristic of some ATP-competitive kinase inhibitors. The work presented in this report details the latest iterations of medicinal chemistry efforts to inhibit the PBD. Specifically, it has been discovered that generating macrocyclic analogs of currently availble peptidomimetic scaffolds can result in several-fold enhancements of inhibitory potency in biochemical assays. Importantly, these new macrocyclic ligands could display improved pharmacokinetic properties when utilized in cell-based systems and future ligand development.

By examining PBD-binding phosphopeptides, the phosphopeptide "PLHSpT" was identified that specifically interacts with the Plk1 PBD with a high affinity, but not with the two closely-related Plk2 and Plk3 PBDs. Based on this peptide sequence, peptides with high PBD-binding affinity may be designed and prepared; however, even with high PBD-binding affinity, it is difficult for the peptides to achieve activity in whole-cell systems, possibly due to poor bioavailability arising from poor solubility or limited membrane transport (or both). Therefore, there is a need in the art to design and prepare PBD-binding peptides with improved pharmaceutical properties, including increased bioavailability.

Furthermore, because of the importance of Plk1 as a target of therapeutic intervention, there exists a need for compounds capable of inhibiting Plk1 with potency and specificity. New bi-valent ligands must be capable of simultaneously binding to multiple Plk1 domains. While high affinity ligands for the individual domains of Plk1 are known, to date, there have been no structures (either crystal or solution) of full-length Plk1, which would indicate the relative orientation of the two domains. As such, the creation of new multi-valent ligands represents a new and potentially powerful approach to modulating Plk1 activity as well.

SUMMARY

The present disclosure relates to high affinity peptide mimetic ligands of the polo-like kinase 1 (Plk1) that contain a phospho-threonine (pThr) analog residue. This pThr residue is critical to maintain high affinity binding, but it is also a substrate of cellular phosphotases that hydrolyze the phosphate group and render the compound(s) inactive. Thus, the description provides novel compounds that inhibit polo-like kinases by binding to the polo-box domain. The use of the phosphonate analog, (2S,3R) 2-amino-3-methyl-4-phosphonobutanoic acid (Pmab), prevents inactivation by cellular phosphatases.

The present disclosure also relates to the surprising and unexpected discovery that multi-valent ligands for Plk1, e.g., bi-valent ligands that including moieties that bind the KD and PBD domains of Plk1, demonstrate desirable efficacy, potency, and/or specificity making them desirable for use as therapeutics. As such, the disclosure provides multi-valent ligands, including synthetic peptides and peptidomimetics that demonstrate high Plk1 binding affinity.

The present disclosure further related to cyclized iterations of high-affinity peptidomimetic ligands (i.e., cyclic PBD-binding ligands) that target the polo-box domain of Polo-like kinase 1 that demonstrate marked improvement in affinity and potency in biochemical assays. Thus, the present disclosure relates to the high affinity Plk1 binding macrocyclic ligands, synthetic peptides and peptidomimetics with desirable efficacy, specificity and pharmacokinetic properties making them desirable for use as therapeutics. Thus, the disclosure provides marocyclic PBD-binding ligands with high Plk1 binding affinity.

In certain aspects, the description provides peptido-mimetic compounds comprising an amino acid analog selected from the group consisting of a phospho-(p)Thr analog, pSer analog, Pmab or C-3 substituted Pmab derivative as described herein, and combinations thereof. In certain embodiments, the peptide-mimetic compound comprises at least one natural (i.e., alpha) amino acid and a Pmab-derivative amino acid analog as described herein. In certain embodiments, the description provides peptido-mimetic compounds comprising at least one C-3 substituted Pmab derivative, phosphatase stable C-3 substituted Pmab derivative phospho-amino acid analog or a combination thereof.

In additional embodiments, the description provides peptido-mimetic ligands of polo box domains (PBD) comprising an amino acid analog as described herein, e.g., a phosphatase stable phospho-amino acid analog. In certain embodiments, the peptide-mimetic ligand of PBD comprises a dipeptide having the structure: Ser-[Z], wherein Z is a phosphatase stable phospho-amino acid analog as described herein, e.g., a C-3 substituted Pmab derivative as described herein.

In certain embodiments, the peptide-mimetic ligand of PBD comprises, consists or consists essentially of the structure: $X_{0-6}$-Ser-[Z]-$X'_{0-8}$, wherein X is any amino acid, and Z is phosphatase stable phospho-amino acid analog as described herein, and wherein only one of X or X' can be zero.

In certain embodiments, the peptide-mimetic ligand of PBD comprises, consists or consists essentially of the structure: $X_{0-3}$-Ser-[Z]-$X'_{0-2}$, wherein X is any amino acid, and Z is phosphatase stable phospho-amino acid analog as described herein, and wherein only one of X or X' can be zero.

In certain additional embodiments, the description provides a peptido-mimetic ligand of PBD comprising, consisting or consisting essentially of the structure $X_{0-3}$-His-Ser-[Z]—$X'_{0-2}$, wherein X is any amino acid, and Z is phosphatase stable phospho-amino acid analog as described herein In certain embodiments, the PBD is that of polo-like kinase 1 (Plk1), which is a critical regulator of mitotic events and cellular proliferative potential, and includes methods synthesis and use of the same. In particular, the description provides novel compounds that inhibit polo-like kinases by binding to the polo-box domain.

In one aspect, the description provides novel PBD-binding peptides (also referred to as "peptide derivatives") that may serve as anti-cancer therapeutics. The description also provides methods of use and kits thereof. In a further aspect, the description provides a novel method of design or synthesis (or both) of phosphoryl-derived peptide derivatives useful as therapeutic agents.

In certain embodiments, the novel compounds are peptide derivatives that contain 4-5 residue peptides, comprising, such as, a pThr analog, pSer analog, Pmab (i.e., phosphonomethylamino butyric acid) or C-3 substituted Pmab residue as described herein.

The peptide derivatives in accordance with the description demonstrate good cellular uptake. Certain peptide derivatives of the description demonstrate good cellular efficacy. In certain embodiments, the peptide derivatives in accordance with the description demonstrate high PBD-binding affinity.

In one aspect, the description provides a compound of Formula II or IIa, or salt, solvate, or hydrate thereof:

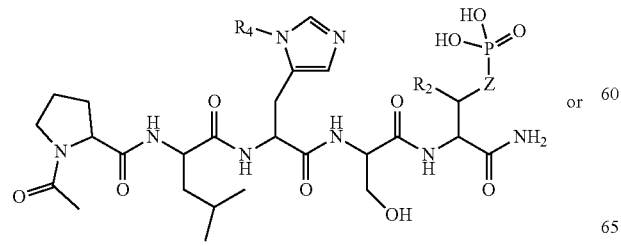

Formula II

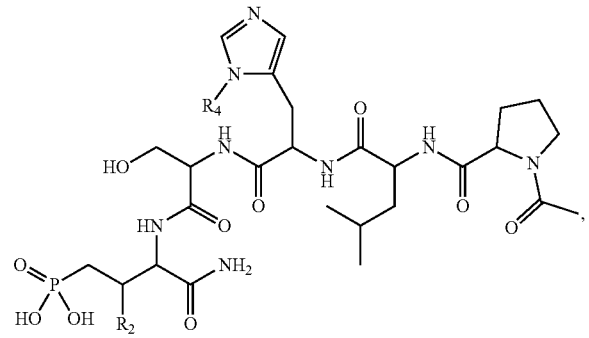

Formula IIa wherein:
$R_2$ is H, optionally substituted alkyl (e.g. optionally substituted $C_2$-$C_4$ alkyl), optionally substituted cycloalkyl, optionally substituted aralkyl, optionally substituted heteroarylalkyl, haloalkyl, optionally substituted morpholinomethyl,

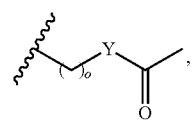

or optionally substituted indolylalkyl;
Y is $CH_2$, NH, or O;
Z is O or $CH_2$; and
$R_4$ is optionally substituted aralkyl.
In another aspect, $R_2$ is Et, Pr, i-Pr, Bu,

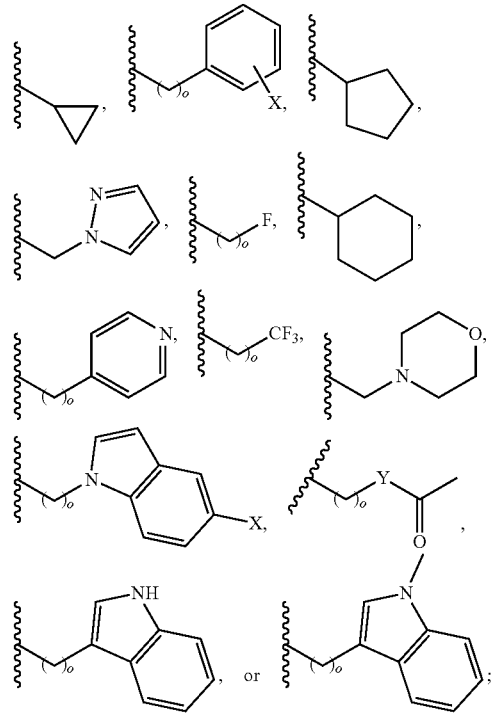

each o is independently 1-3; each X is independently H, Me, Et, CF₃, F, Cl, Br, OMe, or N(Me)₂; and Y is CH₂, NH, or O. In another aspect, $R_4$ is —(CH₂)₈-Ph. In another aspect, $R_2$ is Et, Pr, i-Pr, Bu,

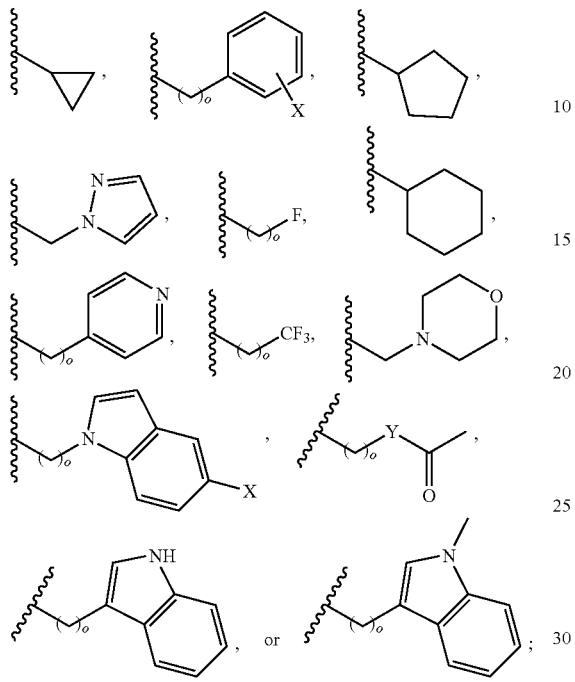

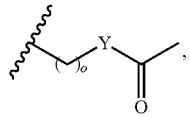

each o is independently 1-3; each X is independently H, Me, Et, CF₃, F, Cl, Br, OMe, or N(Me)₂; Y is CH₂, NH, or O; and $R_4$ is —(CH₂)₈-Ph.

In an aspect, the description provides a peptido-mimetic bivalent ligand comprising or according to the structure:

KD-IDL-PBD [I]

wherein:
KD is a kinase domain-binding ligand (i.e., a ligand that binds a kinase domain or a kinase domain-binding ligand);
IDL is a flexible interdomain linker comprising a bond or a chemical group; and
PBD is a polo-box domain-binding ligand (i.e., a ligand that binds a pol-box domain or a polo-box domain-binding ligand).

In some embodiment, the PBD is a PBD ligand of the present disclosure.

In certain embodiments, the description discloses the bivalent ligand, wherein PBD ligand has the structure:

Formula IIb

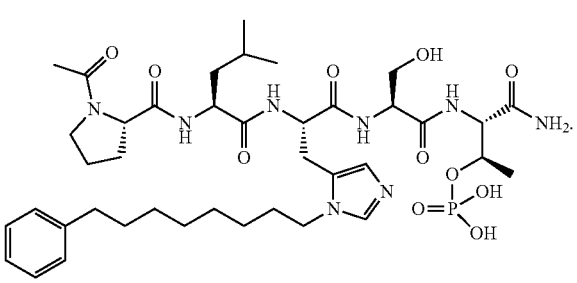

wherein:
n is an integer from 1-20;
Z is O or CH₂;
R1 is H, optionally substituted alkyl, optionally substituted cycloalkyl, optionally substituted aralkyl, optionally substituted heteroarylalkyl, haloalkyl, optionally substituted morpholinomethyl, or optionally substituted indolylalkyl;
Y is CH₂, NH, or O; and
Ar is an optionally substituted aryl, an optionally substituted heteroaryl, an optionally substituted aralkyl; an optionally substituted heteroarylalkyl;
$X_4$, for each occurrence independently, is H, alkyl, aryl-(C1-20) alkyl-, or alkenyl-(C1-20) alkyl;
or a pharmaceutically acceptable salt, solvate, hydrate, prodrug, or stereoisomer thereof.

In certain embodiments, the description provides a bivalent ligand, wherein PBD ligand has the structure:

4j

In certain additional embodiments, description provides a bivalent ligand wherein the KD ligand has a structure according to or comprising:

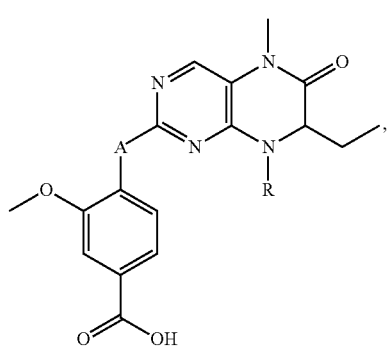

wherein:
A is O or NH; and
R is an alkyl, a cycloalkyl or an aromatic ring.

In a particular embodiment, the description provides a bivalent ligand, wherein R is isobutyl or cyclopentyl.

In certain embodiments, the description provides a bivalent ligand, wherein the KD ligand is:

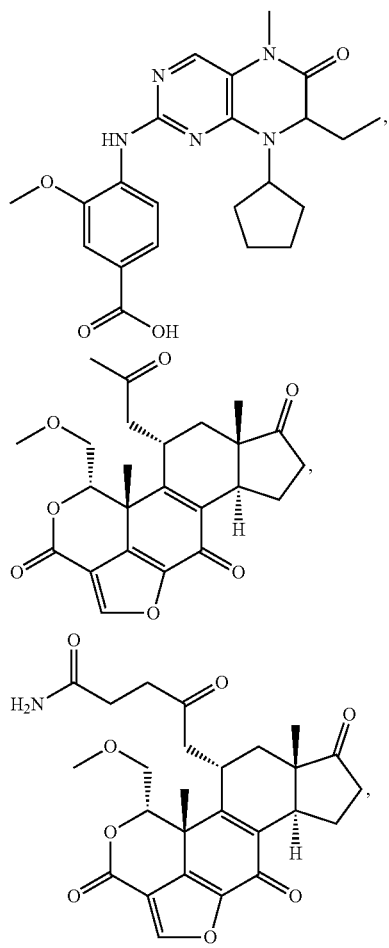

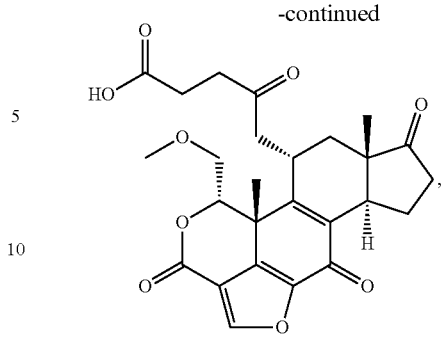

or a pharmaceutically acceptable salt, solvate, hydrate, or stereoisomer thereof.

In certain embodiments, "IDL" is a bond. In additional embodiments, the linker "IDL" is a connector with a linear non-hydrogen atom number in the range of 1 to 20. The connector "IDL" can contain, but not limited to the functional groups such as polyethylene glycol (PEG), ether, amide, alkane, alkene, alkyne, ketone, hydroxyl, carboxylic acid, thioether, sulfoxide, and sulfone. The linker can contain aromatic, heteroaromatic, cyclic, bycyclic and tricyclic moieties. Substitution with halogen, such as Cl, F, Br and I can be included in the linker. In the case of fluorine substitution, single or multiple fluorines can be included.

In certain embodiments, the description provides a bivalent ligand, wherein IDL is a polyethylene glycol of the structure: (PEG)n, wherein n=0-8. In an embodiment, n=0-4.

In certain embodiments, the description provides a bivalent ligand, wherein KD is attached to PBD through its C-terminal.

In certain embodiments, the description provides a bivalent ligand, wherein KD is attached to PBD through its N-terminal.

In a specific embodiment, the description provides a bivalent ligand comprising a structure:

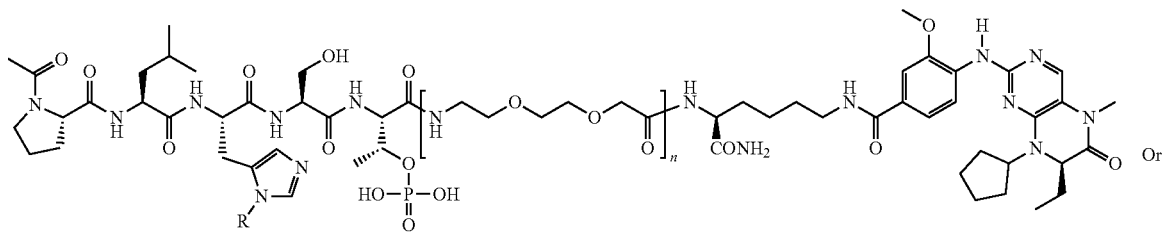

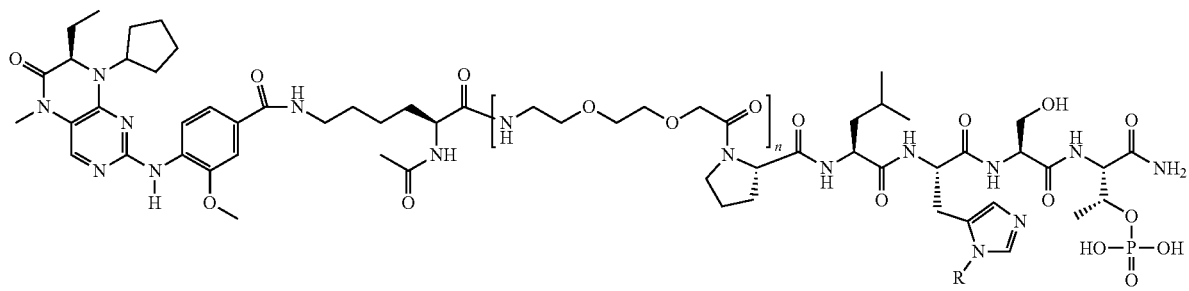

wherein, n = 0-4
R = (CH$_2$)$_8$Ph or H

-continued
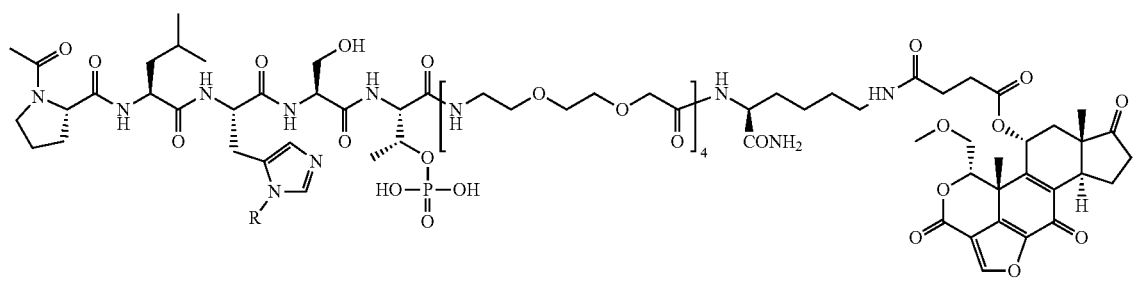
2: R = -(CH$_2$)$_8$Ph
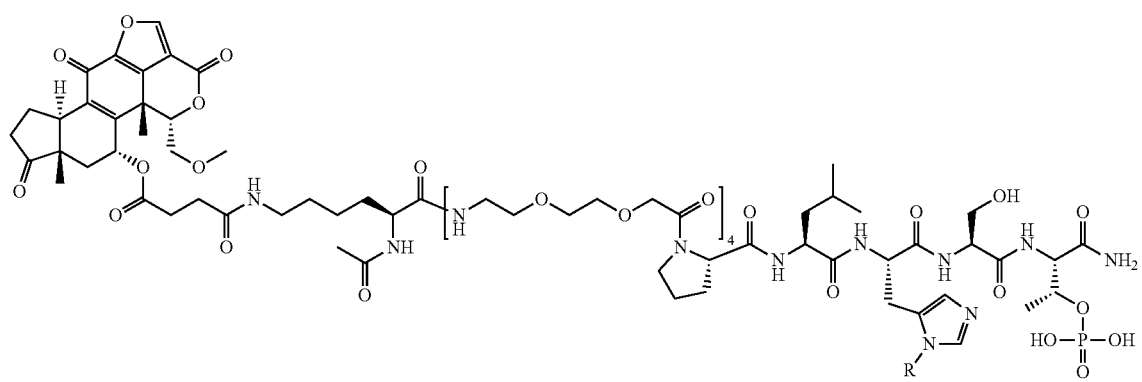
3: R = -(CH$_2$)$_8$Ph
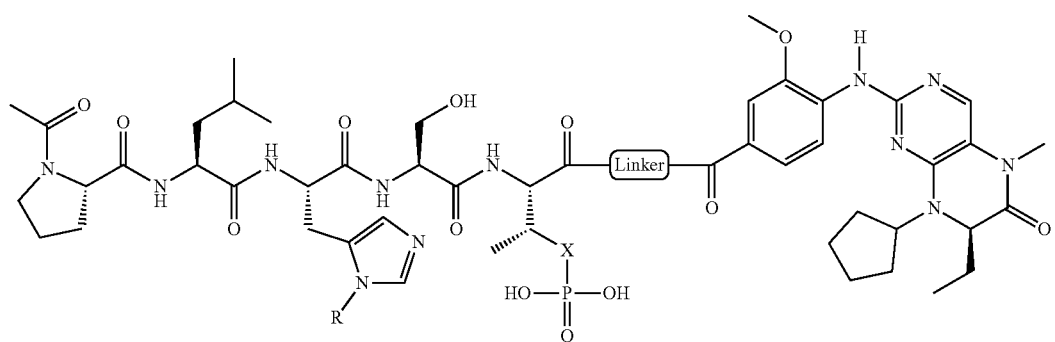
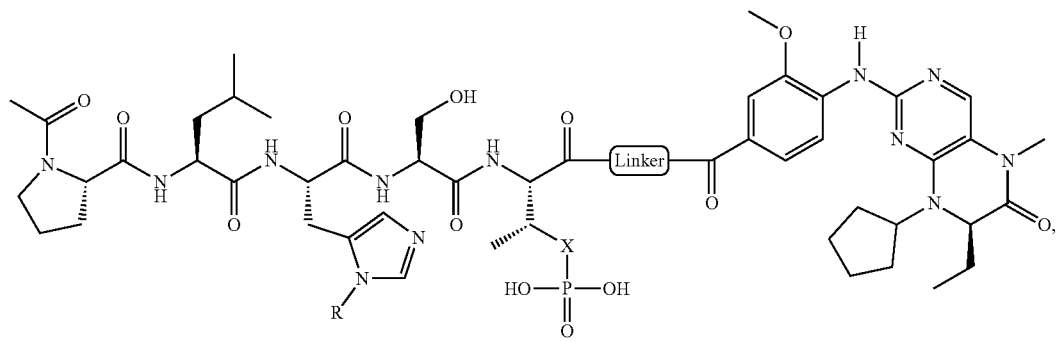

wherein:
R is —(CH2)8Ph;
X is O or CH2; and

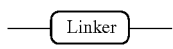

is selected from:

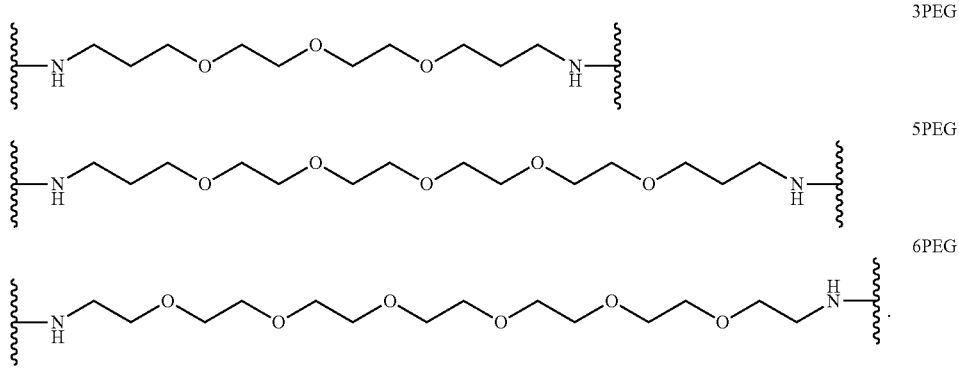

or a pharmaceutically acceptable salt, solvate, hydrate, or stereoisomer thereof.

In an aspect, the description provides a peptidomimetic macrocyclic ligand comprising general Formula 1:

Formula 1 wherein:
Z is O or CH$_2$;
R$_1$ is an optionally substituted alkyl, optionally substituted cycloalkyl, optionally substituted aralkyl, optionally substituted heteroarylalkyl, haloalkyl, optionally substituted morpholinomethyl, or optionally substituted indolylalkyl;
R$^2$ is an optionally substituted alkyl group or polyethylene glycol;
n or n' is 1-20;
Y is CH$_2$, NH, or O; o is 0-10 and
Ar is an optionally substituted aryl, an optionally substituted heteroaryl, an optionally substituted aralkyl; an optionally substituted heteroarylalkyl;

each X$_4$ is independently, is H, alkyl, aryl-(C1-20) alkyl-, or alkenyl-(C1-20) alkyl, or a pharmaceutically acceptable salt, solvate, hydrate, prodrug, or stereoisomer thereof.

In some specific embodiments, the description provides macrocyclic ligands, wherein n is 6-8, n' is 4-6, and R is methylene group.

In certain embodiments, the description provides a macrocyclic PBD ligand, wherein the PBD ligand has the structure according to:

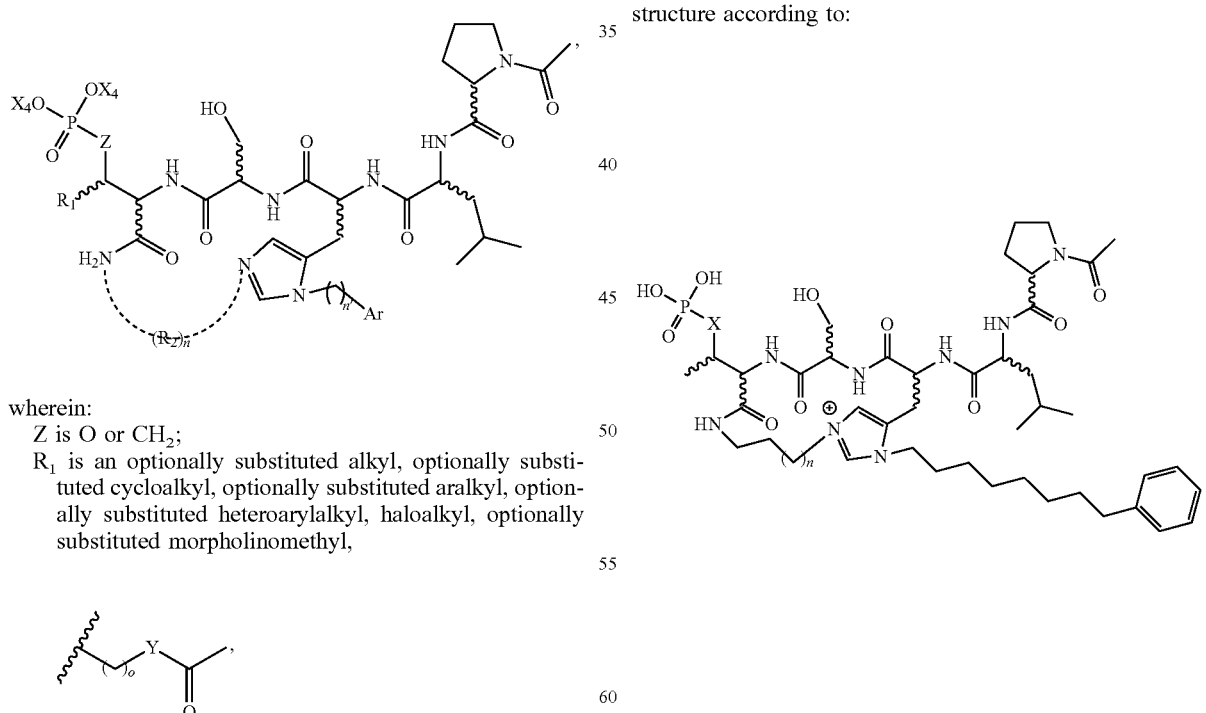

wherein X is CH2 or O; and
n is 2-4 or a pharmaceutically acceptable salt, solvate, hydrate, or stereoisomer thereof.

In an aspect, the description provides a peptidomimetic macrocyclic ligand comprising general Formula IIb:

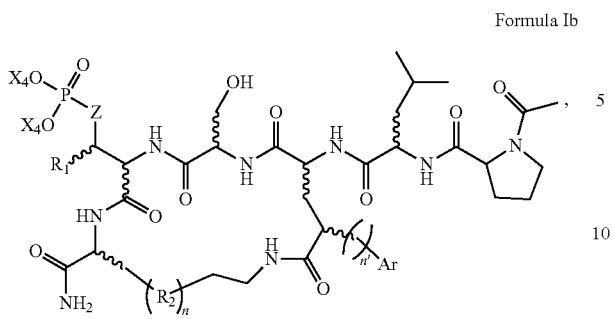

Formula Ib wherein:
Z is O or CH$_2$;
R$_1$ is an optionally substituted alkyl, optionally substituted cycloalkyl, optionally substituted aralkyl, optionally substituted heteroarylalkyl, haloalkyl, optionally substituted morpholinomethyl,

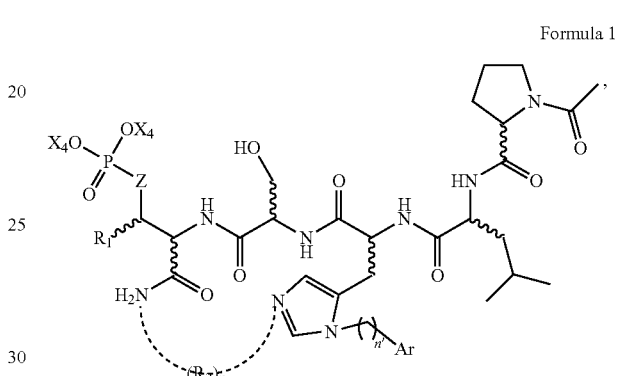

or optionally substituted indolylalkyl;
R$^2$ is an optionally substituted alkyl group or polyethylene glycol;
n or n' is 1-20;
Y is CH$_2$, NH, or O; o is 0-10 and
Ar is an optionally substituted aryl, an optionally substituted heteroaryl, an optionally substituted aralkyl; an optionally substituted heteroarylalkyl;
each X$_4$ is independently, is H, alkyl, aryl-(C1-20) alkyl-, or alkenyl-(C1-20) alkyl, or a pharmaceutically acceptable salt, solvate, hydrate, prodrug, or stereoisomer thereof.

In some specific embodiments, the description provides macrocyclic ligands, wherein n is 6-8, n' is 3-6, and R is a methylene group.

In some embodiments, the description provides macrocyclic ligands with the structure:

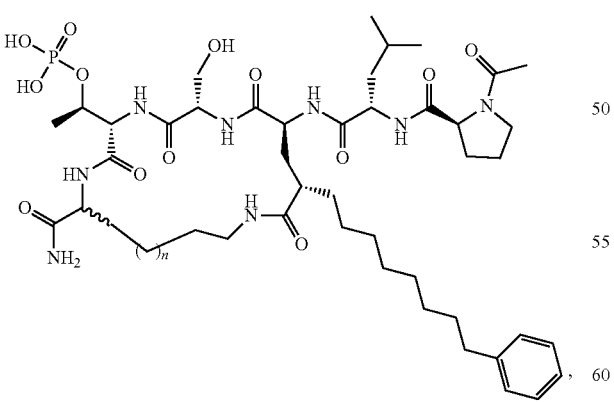

wherein n is 3-5 or salt, solvate, stereoisomer or hydrate thereof.

In some embodiments, the disclosure provides novel intermediates required for synthesis of macrocyclic ligands wherein the intermediate is:

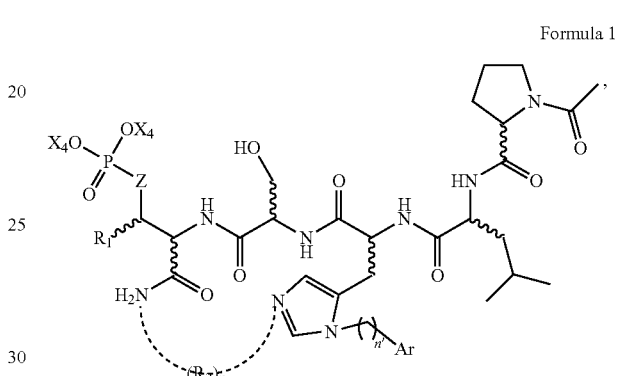

Structure III

In one aspect, the disclosure provides a process to prepare a compound of Formula Ib, or salt, solvate, stereoisomer or hydrate thereof:

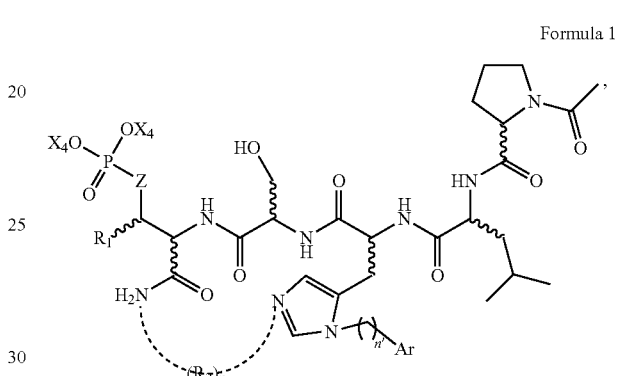

Formula 1 the process comprising:
performing solid state peptide synthesis (SSPS) on (4-hydroxymethyl-3-methoxyphenoxy) butanoic acid resin (HMPB resin) to get desired protected peptide backbone;
coupling an alkylene linker at N(τ) nitrogen using a microwave-assisted on-resin alkylation with alkyl iodides;
cleaving the peptide from resin and deprotection under mild acidic conditions; cyclizing using PyBOP and phosphate deprotection using Pd/C to yield ligands of formula 1.

In an additional aspect, the description provides a process to prepare a compound of Formula IIb, or salt, solvate, stereoisomer or hydrate thereof:

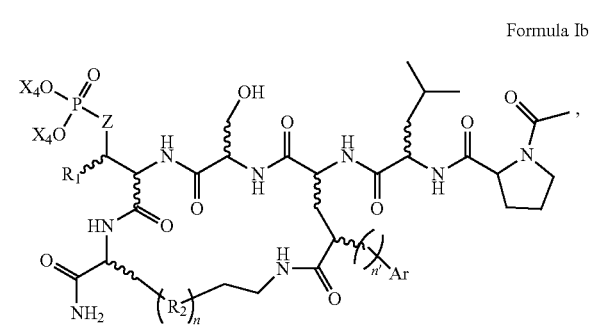

Formula Ib the process comprising:
performing solid state peptide synthesis (SSPS) on alloc protected amino acids using Rink amide resin to get desired protected peptide backbone;

deprotecting alloc group using Pd(PPh$_3$)$_4$;
inducing on-resin cyclization using PyBOP;
performing FMOC deprotection followed by continued SPPS; and
cleaving and deprotecting in trifluoroacetic acid to yield ligands of Formula 1.

In some embodiments, the description provides a process to prepare an intermediate required for preparation of macrocyclic ligands of Formula Ib,

Structure IIIb wherein:
R' is an alkyl-aryl group
the process comprises:
alloc protection of Boc protected Glutamic acid using allyl alochol;
stereospecific alkylation at C-4 position using lithium chelation-controlled enolate addition;
deprotection of Boc and t-butyl group;
protection with Fmoc group to yield Structure III.

An aspect of the present disclosure provides a cyclic polo-box domain ligand comprising the structure:

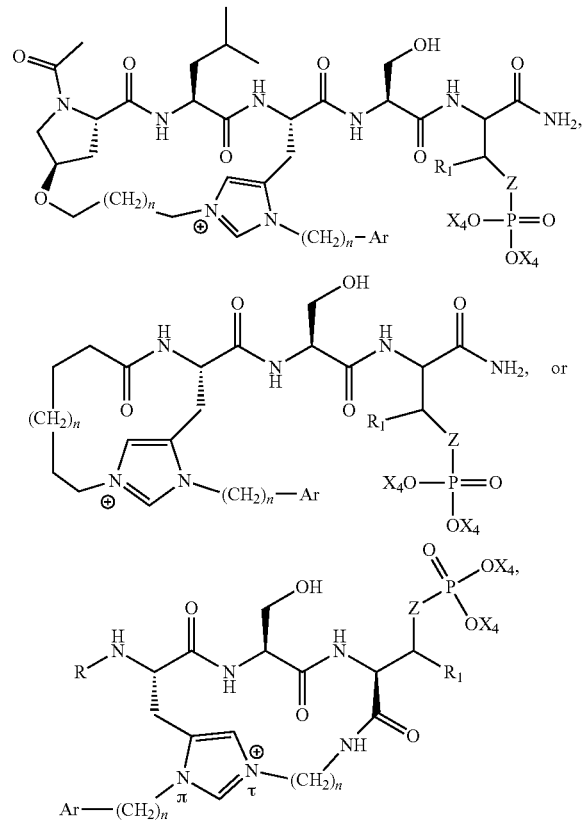

wherein:
n is 1-20;
Z is O or CH$_2$;

R$_1$ is an optionally substituted H, alkyl, optionally substituted cycloalkyl, optionally substituted aralkyl, optionally substituted heteroarylalkyl, haloalkyl, optionally substituted morpholinomethyl,

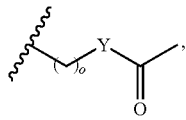

or optionally substituted indolylalkyl;
Y is CH$_2$, NH, or O;
Ar is an optionally substituted aryl, an optionally substituted heteroaryl, an optionally substituted aralkyl; an optionally substituted heteroarylalkyl;
X$_4$, for each occurrence independently, is H, alkyl, aryl-(C1-20) alkyl-, or alkenyl-(C1-20) alkyl;
or a pharmaceutically acceptable salt, solvate, hydrate, prodrug, or stereoisomer thereof.

An aspect of the present disclosure provides a bivalent compound comprising the compound or ligand of the present disclosure, a cyclic PBD ligand of the present disclosure, or the bivalent ligand of claim of the present disclosure covalently linked to a cell-surface ligand or binding moiety.

In certain embodiments, at least one of: the cell-surface ligand or binding moiety is a cell surface integrin binding moiety; the cell-surface ligand or binding moiety is LLP2A or a derivative or analog thereof; the cell-surface ligand or binding moiety binds a cell surface integrin; the cell-surface ligand or binding moiety binds α$_4$β$_1$ integrin; the compound or the bivalent ligand is covalently linked to the cell-surface ligand or binding moiety via a cleavable linker; or combinations thereof.

In other embodiments, the cleavable linker includes a disulfide bond or a valine-citruline dipeptide cathepsin substrate.

In a particular aspect, the description provides a pharmaceutical composition comprising an effective amount of a bivalent ligand in combination with a pharmaceutically acceptable carrier, additive or excipient.

The description also provides the compounds as pharmaceutically acceptable salts, solvates, hydrates, prodrugs, or stereoisomers thereof. In another aspect, the description provides the compounds in pharmaceutically acceptable carriers and the use of the compounds for the preparation of a medicament.

In any of the aspects or embodiments described herein, the peptido-mimetic compound as described herein is from 3 to 500 residues, or from 3 to 250 residues, or from 3 to 150 residues, or from 3 to 50 residues, including all values in between. In certain embodiments, the peptido-mimetic compound as described herein is 3, 4, 5, 6, 7, 8, 9, 10, 11, 12, 13, 14, 15, 16, 17, 18, 19, 20, 21, 22, 23, 24 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more residues.

The description further provides kits containing the compounds of the description, and kits for synthesizing the compounds of the description.

Exemplified compounds of the above formulae include, but are not limited to, the compounds provided infra.

The description provides compositions for the preparation of a medicament. The medicament can be, for example, a medicament for the prevention, amelioration, or treatment of a hyperproliferative disorder such as cancer.

The compounds of the description can be used in methods for the prevention, amelioration, or treatment of a subject for a hyperproliferative disorder. Such methods can further include identification of a subject suffering from or suspected of suffering from a hyperproliferative disorder and/or monitoring the subject for prevention, amelioration, or treatment of a hyperproliferative disorder.

In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, Thyroid Cancer.

The description provides kits containing at least one compound of the descriptions and instructions for use.

The description also provides a compound (including a peptide derivative) prepared according to any preparation method of the description.

The description also includes methods of designing, synthesizing, and/or using the compounds of the description. In certain embodiments, the description provides compounds made according to any synthetic method disclosed herein.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference. Other aspects of the description are discussed infra.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

The protein ribbon and semi-transparent electrostatic surface are associated with the 5b structure.

Figure 18A:
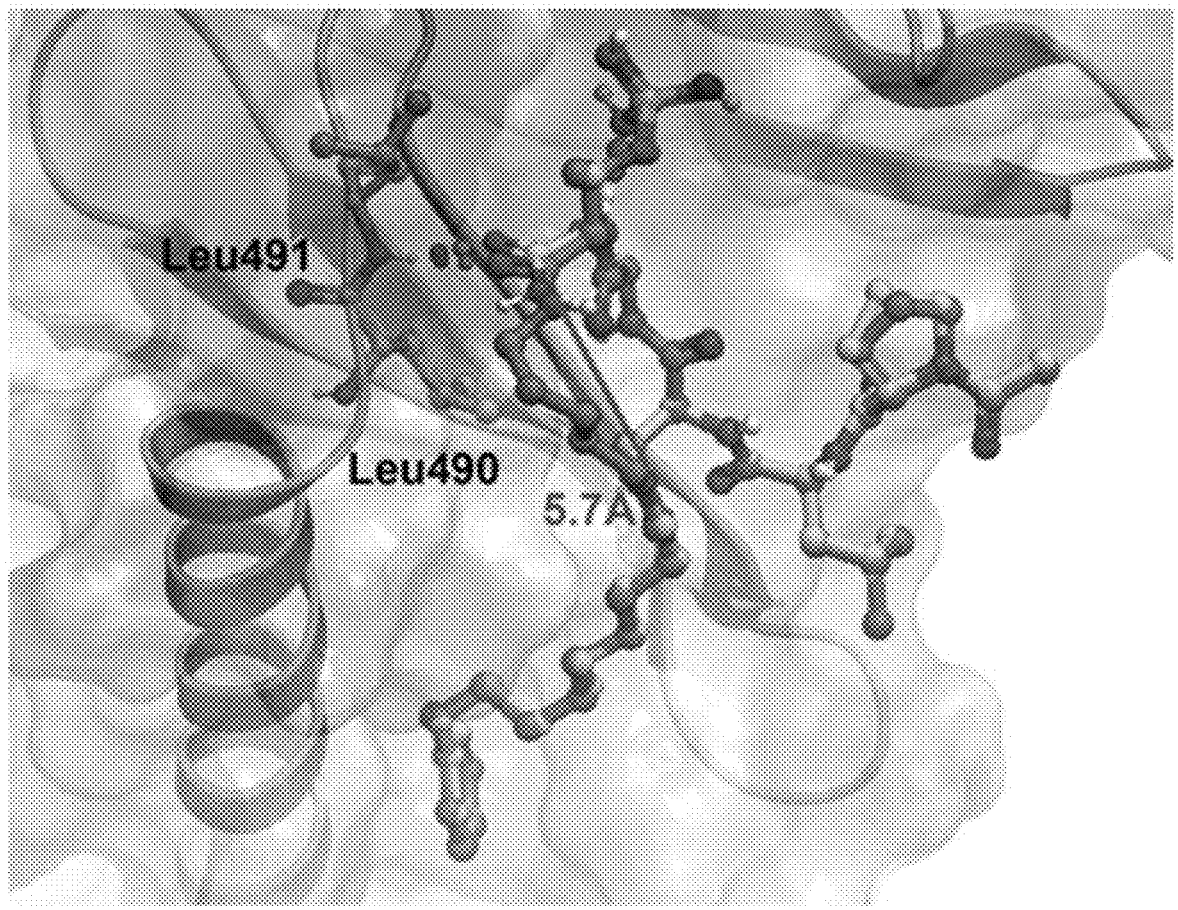
FIG. 18A. X-ray co-crystal structures of Plk1 PBD-bound macrocyclic ligand 5b (cyan) superimposed onto the structure of PBDbound linear peptide 2 (yellow, PDB: 3RQ7).
Figure 18B:
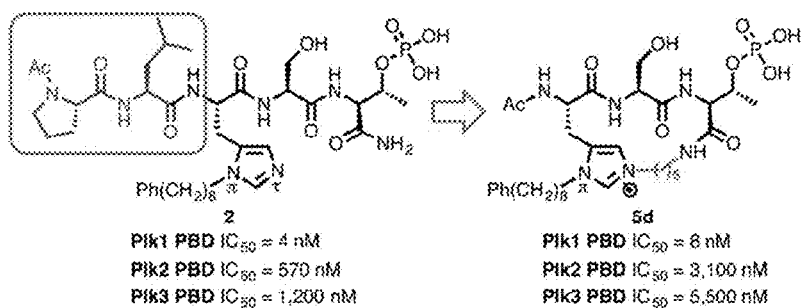

FIG. 18B. Illustrates that the histidine N(τ)-cyclized Macrocycles of the present disclosure have reduced size, while retaining Plk1-binding affinity and has enhanced Plk2, Plk3 selectivity.

Figure 19A:
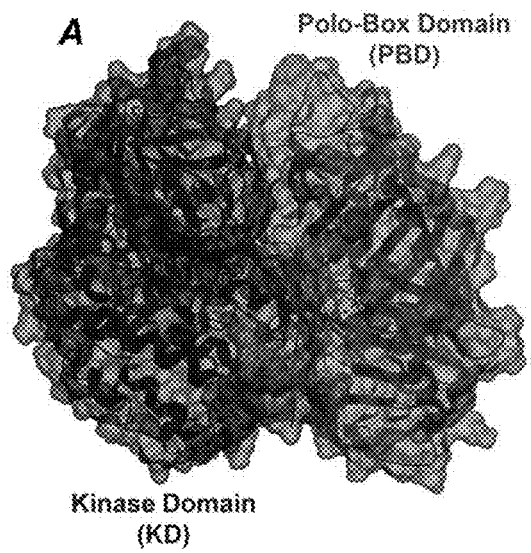
Figure 19B:
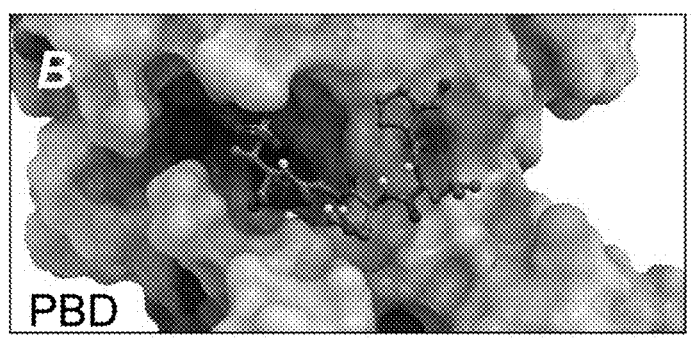
Figure 19B:
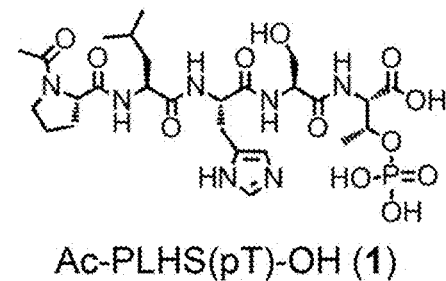
Figure 19C:
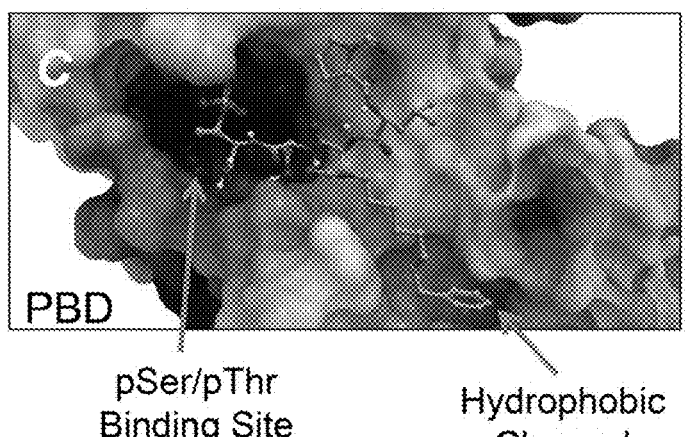
Figure 19C:
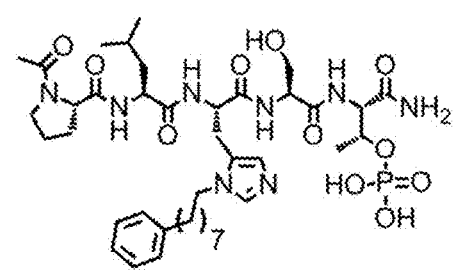

FIGS. 19A, 19B, and 19C. Crystal structures of Polo-like kinase 1 (19A, PDB: 4J7B) and the polo-box domain bound to peptides containing a "Ser-pThr" binding motif (19B, PDB: 3HIK and 19C, PDB: 3RQ7). The alkyl-His containing peptide 3 accesses a cryptic hydrophobic channel in the PBD.

Figure 20:
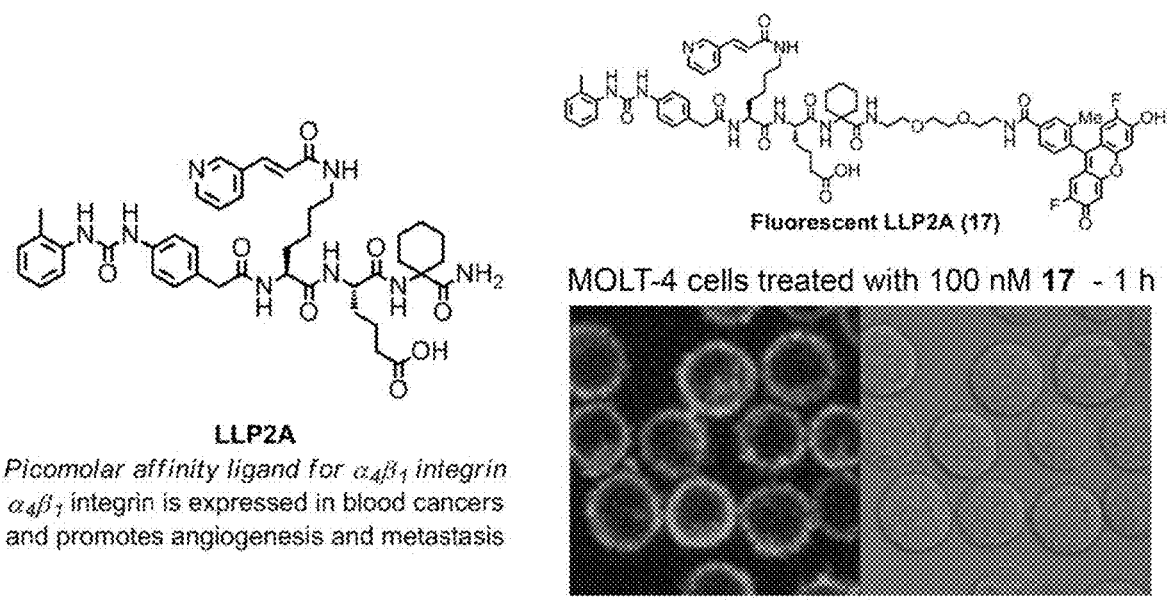
Figure 20:
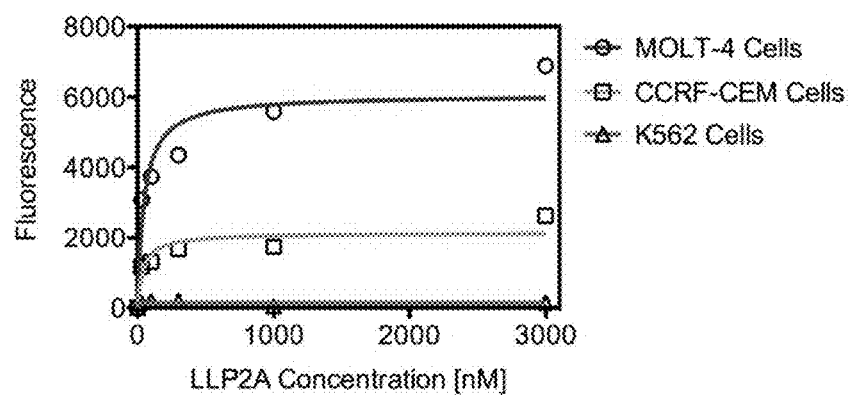

FIG. 20. LLP2A is a high-affinity ligand for α4β1 integrin expressed on the surface of various cancer types. A fluorescent LLP2A analog (17) was synthesized and used to stain MOLT-4 cells that express abundant α4β1 integrin. Distinct staining is observed at the cell surface following a 1-hour treatment with 100 nM 17 at 37° C. This same probe analyzed by flow cytometry to determine the relative levels of expression in various leukemia and lymphoma cell lines. K562 cells are known to express little to no α4β1 integrin and served as the negative control.

Figure 21:
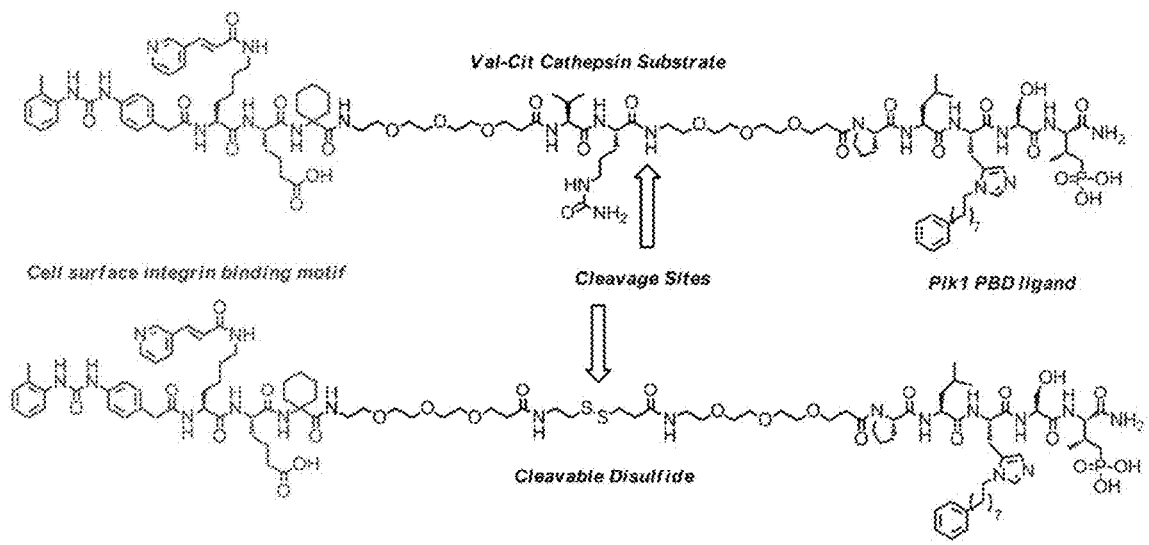

FIG. 21. The high-affinity PBD ligand PLH*S(Pmab) was conjugated to the integrin-binding LLP2A motif to induce cellular uptake through targeted delivery to the cell surface. Utilizing the valine-citruline dipeptide cathepsin substrate or a disulfide will allow for cleavage of the linker and release of the PBD ligand.

Figure 22:
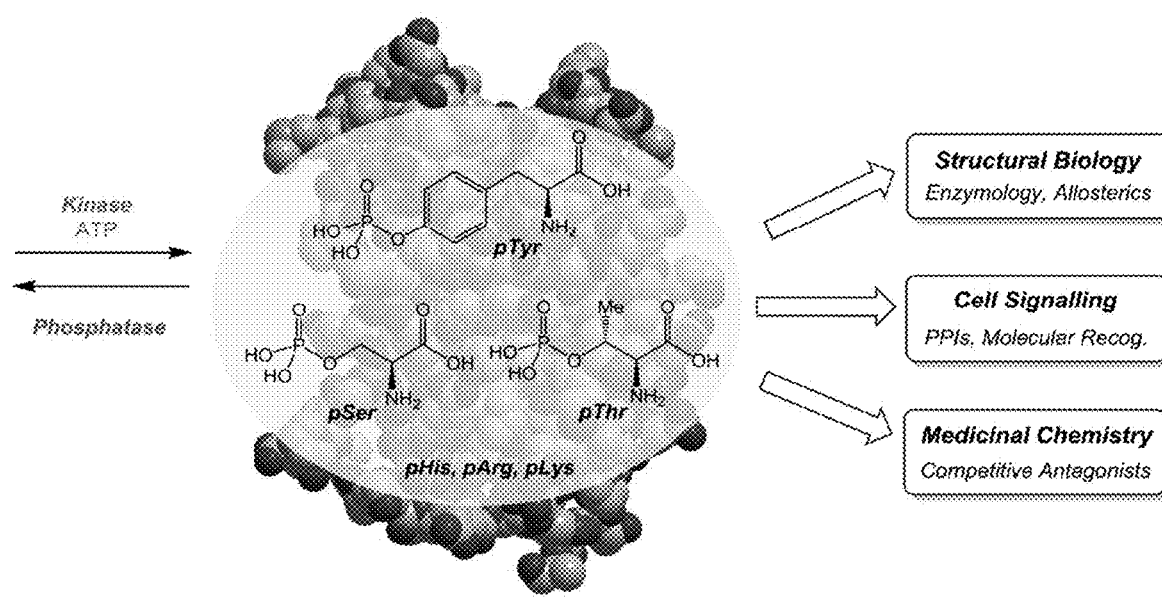

FIG. 22. Phosphorylation is critical to many aspects of protein biochemistry and cell biology. Numerous kinases and phosphatases regulate the phosphorylation of key amino acids involved in enzymatic processes and cell signalling pathways. Non-hydrolyzable analogs of these amino acids are important as biochemical probes and potentially therapeutic agents.

Figure 23A:
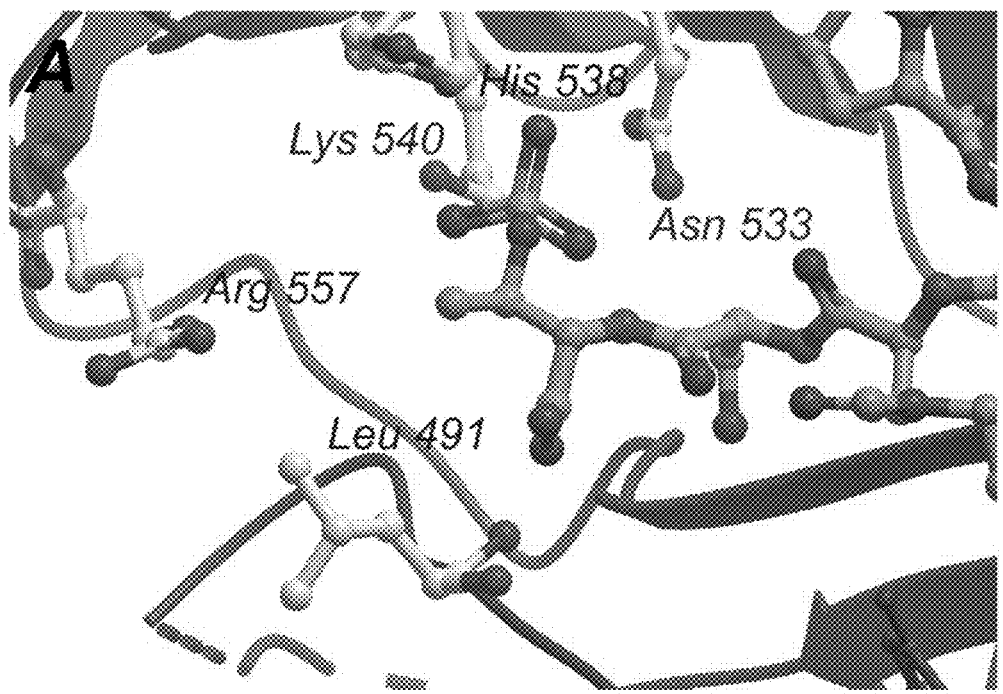
Figure 23B:
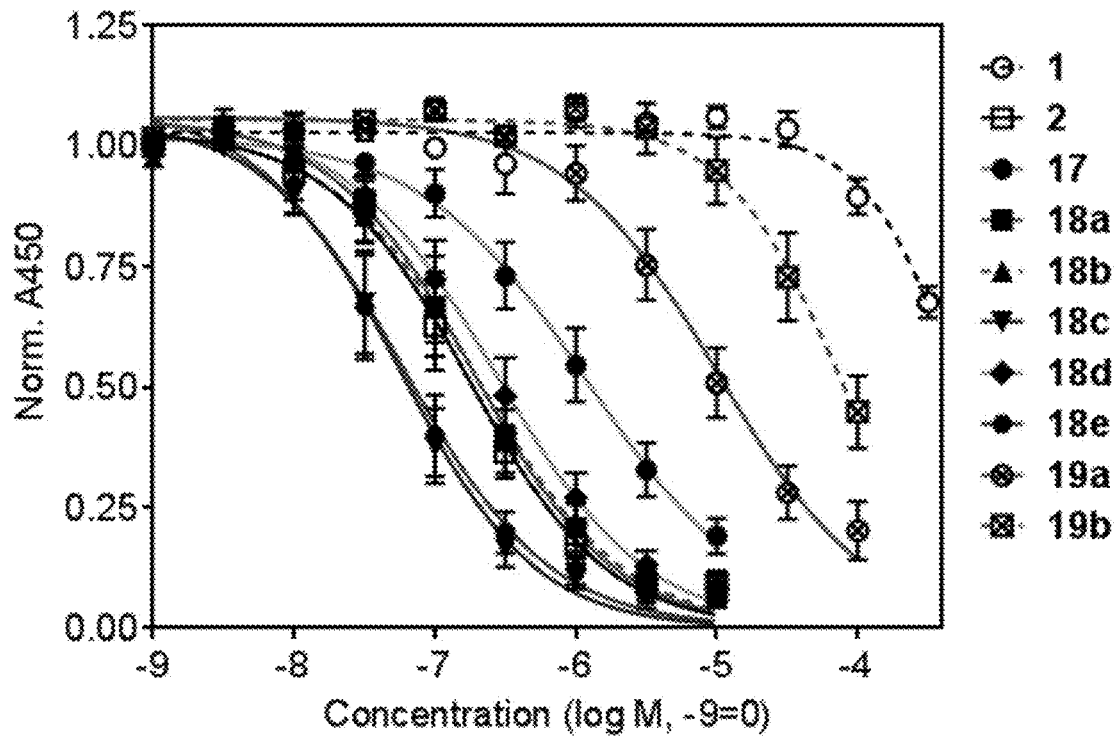

FIGS. 23A and 23B. (23A) X-ray co-crystal structure of the PBD bound to 2 illustrating the proximity of the C3-methyl group with Arg557 and Leu491. (23B) Competitive ELISA assays of PBD-binding ligands that utilize analogs of Pmab modified at the C3 position. Data points represent average±SEM from five independent experiments and fit using non-linear regression in GraphPad Prism 6.

Figure 24:
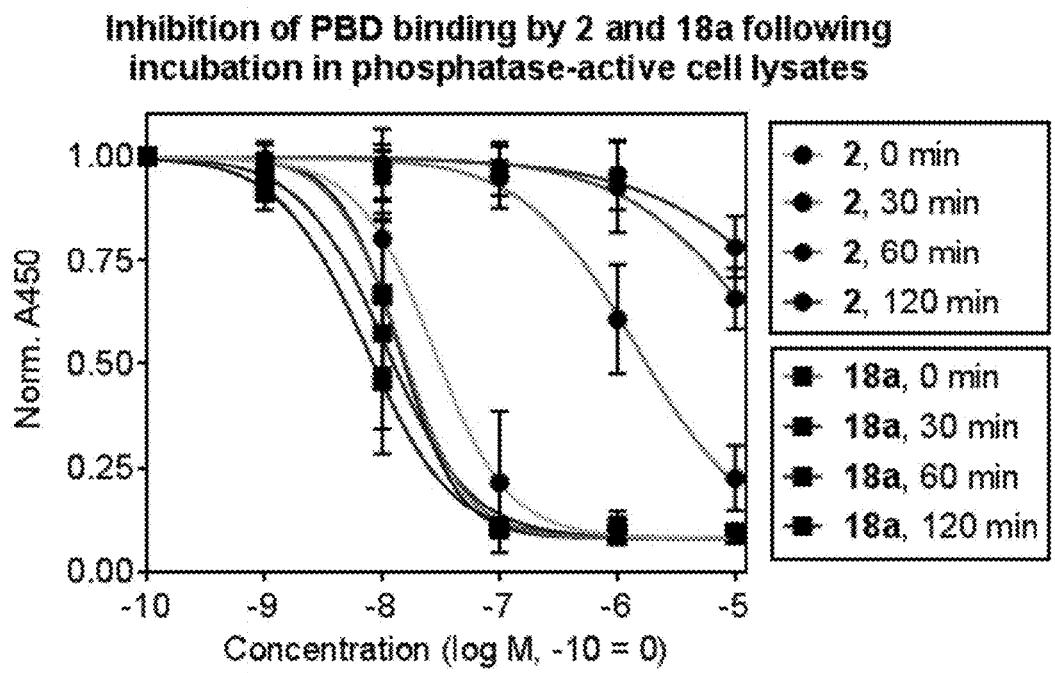

FIG. 24. Competitive ELISA assay of 2 and 18a following incubation in phosphatase-active crude cell lysates for the indicated times. Data points represent average±SEM from three independent experiments and fit using non-linear regression in GraphPad Prism 6.

Figure 25:
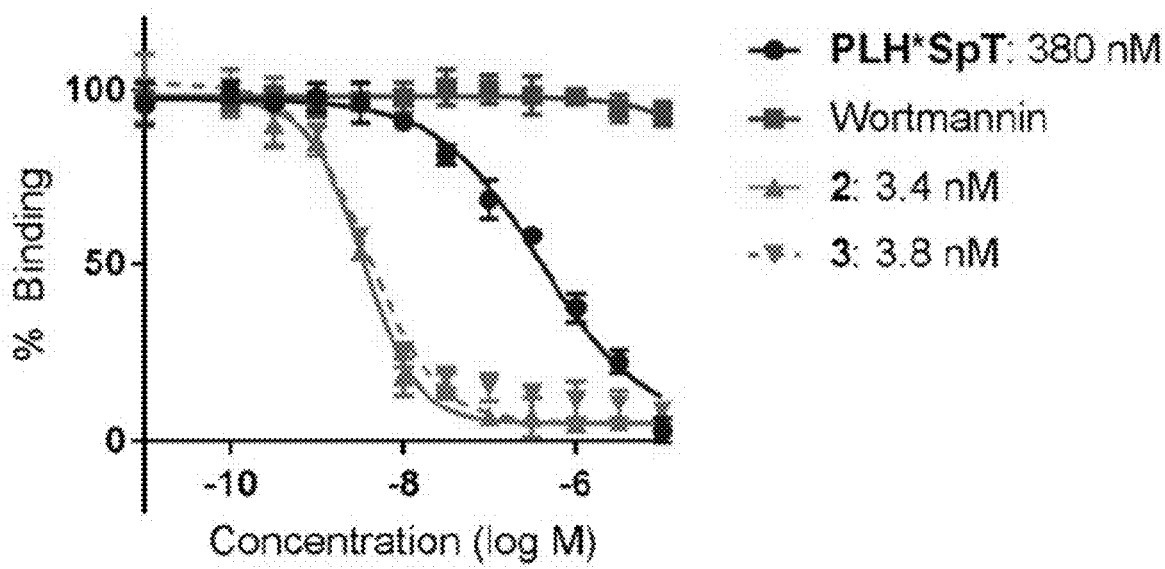

FIG. 25. Results from FP based Plk1 PBD-binding assays, which measured the ability of synthetic constructs to compete with FITC-labeled PLH*SpT for binding to full-length Plk1, for bi-valent compounds 2 and 3.

Figure 26:
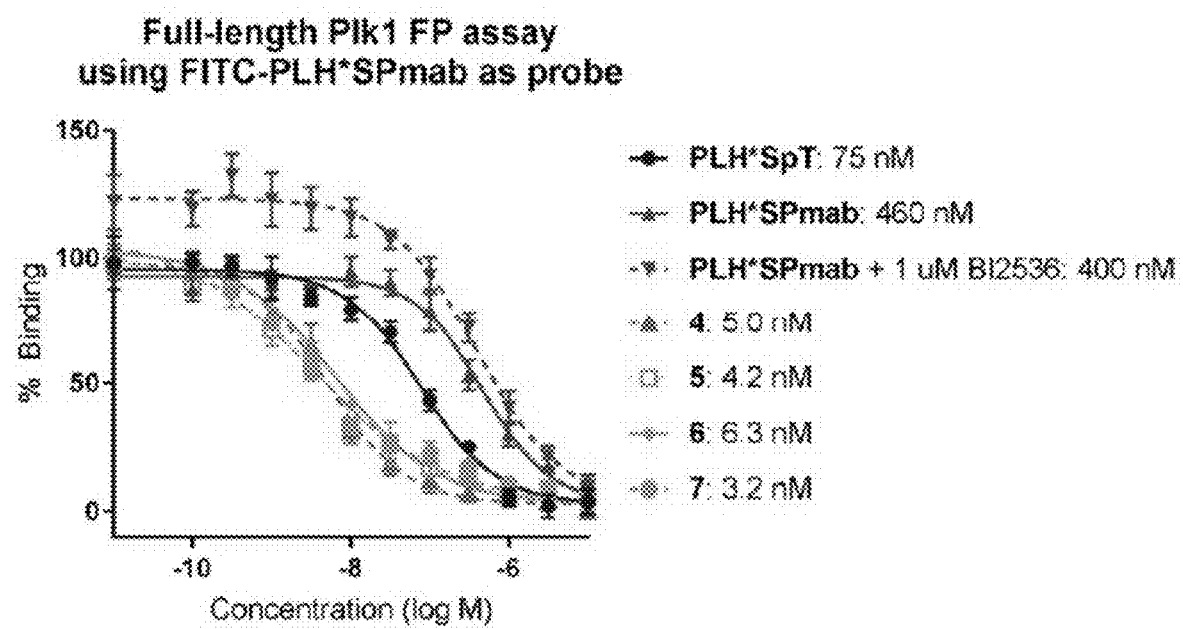

FIG. 26. Results from FP assays, which measured the ability of synthetic constructs to compete with FITC-labeled PLH*SPmab for binding to full-length Plk1, for exemplary compounds 4, 5, 6, and 7.

Figure 27A:
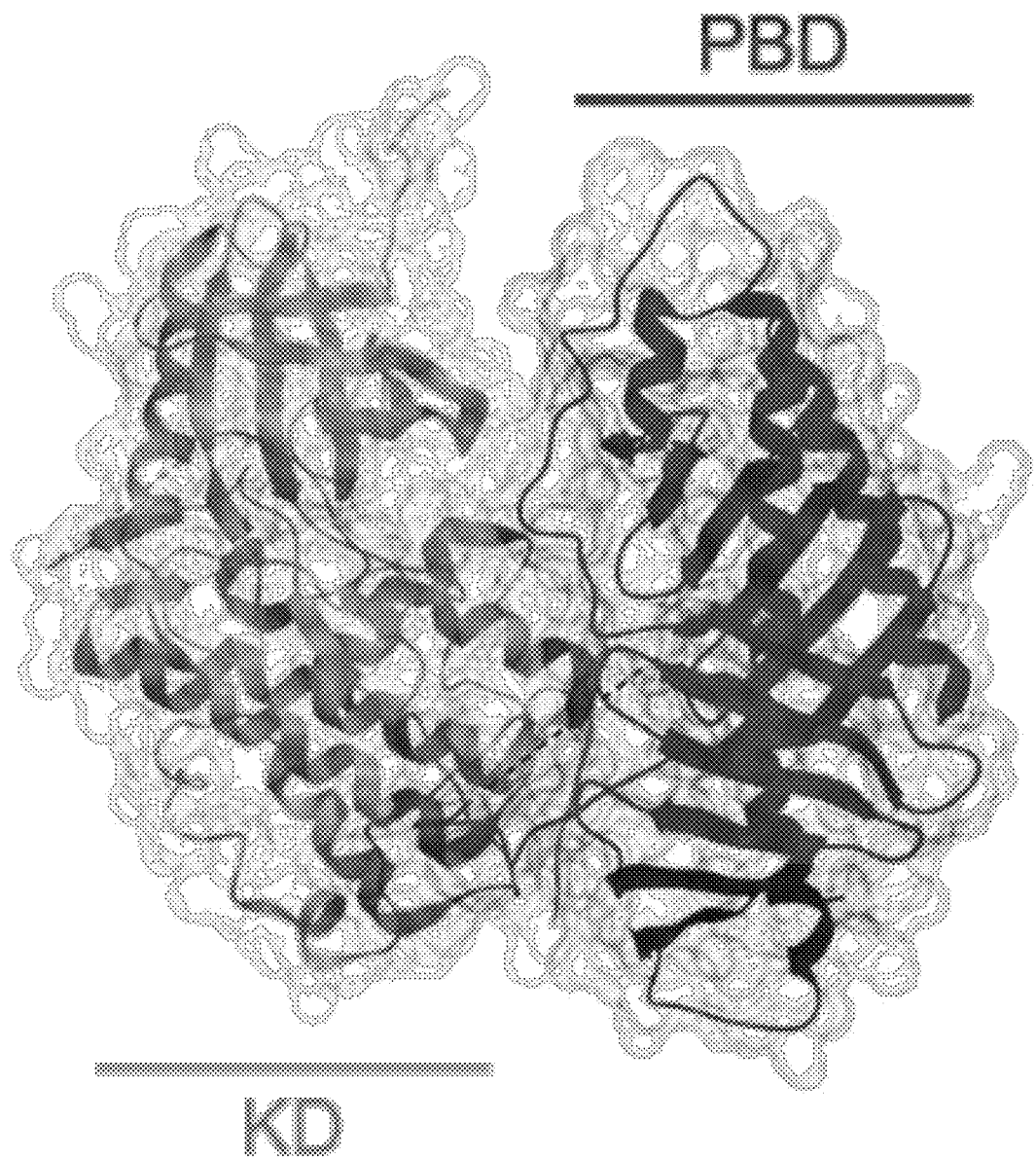
Figure 27B:
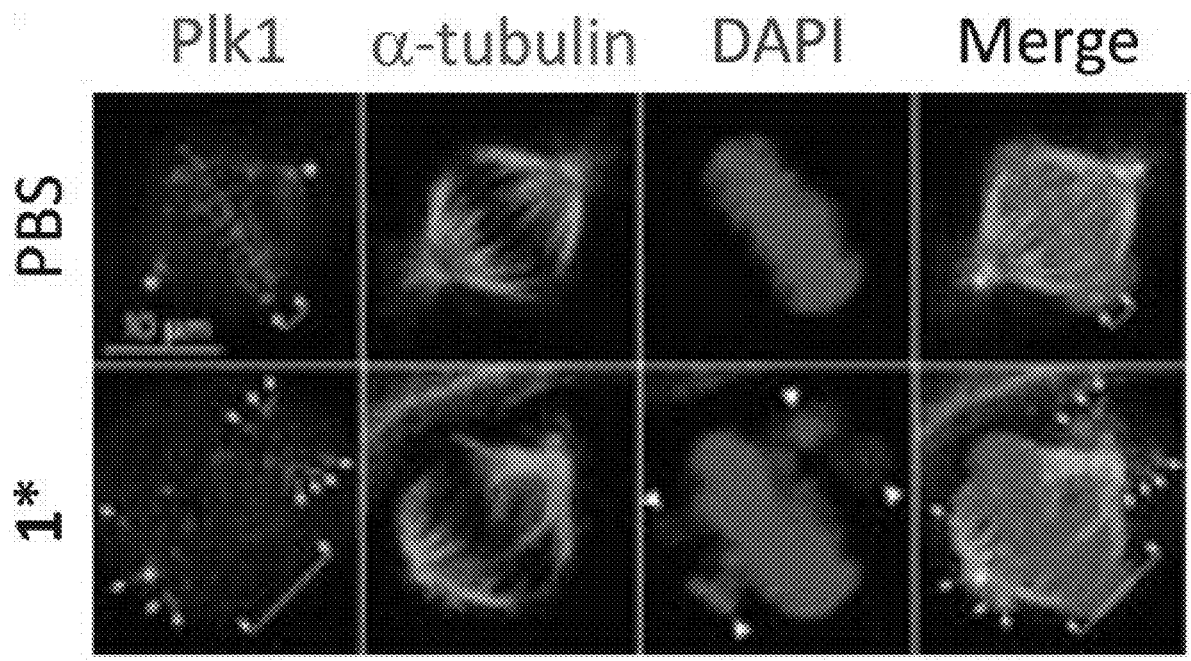
Figure 27C:
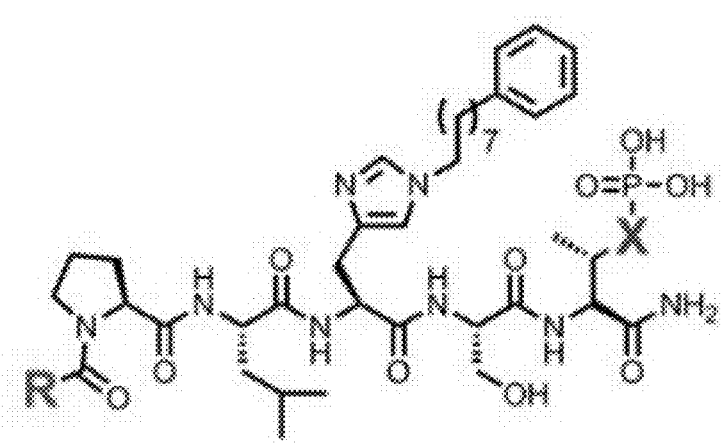
Figure 27D:
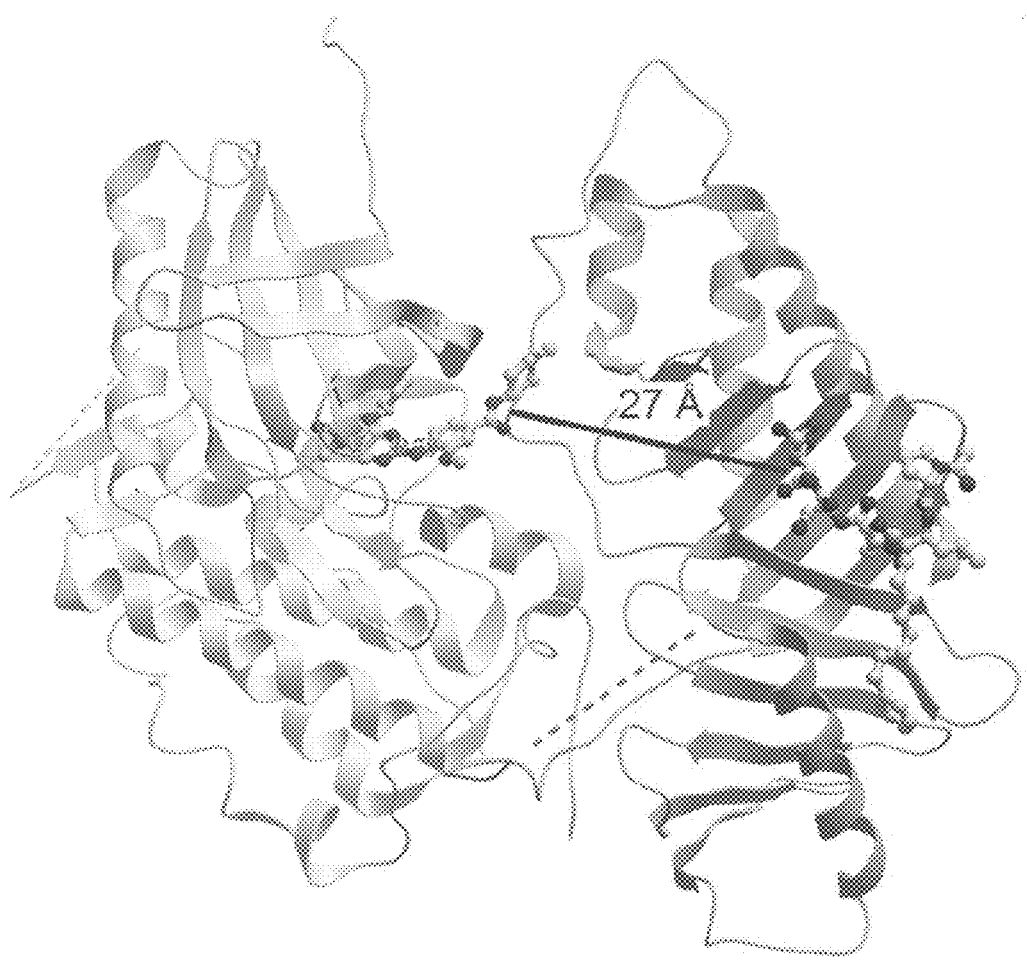
Figure 27E:
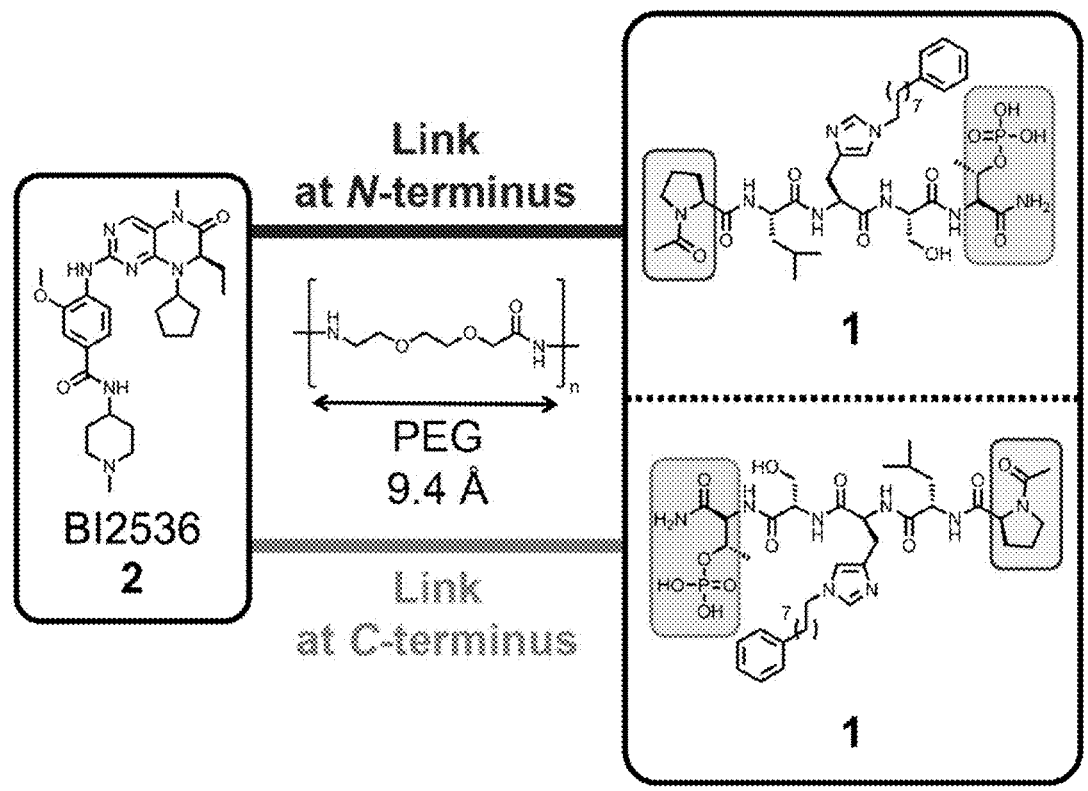
Figure 28A:
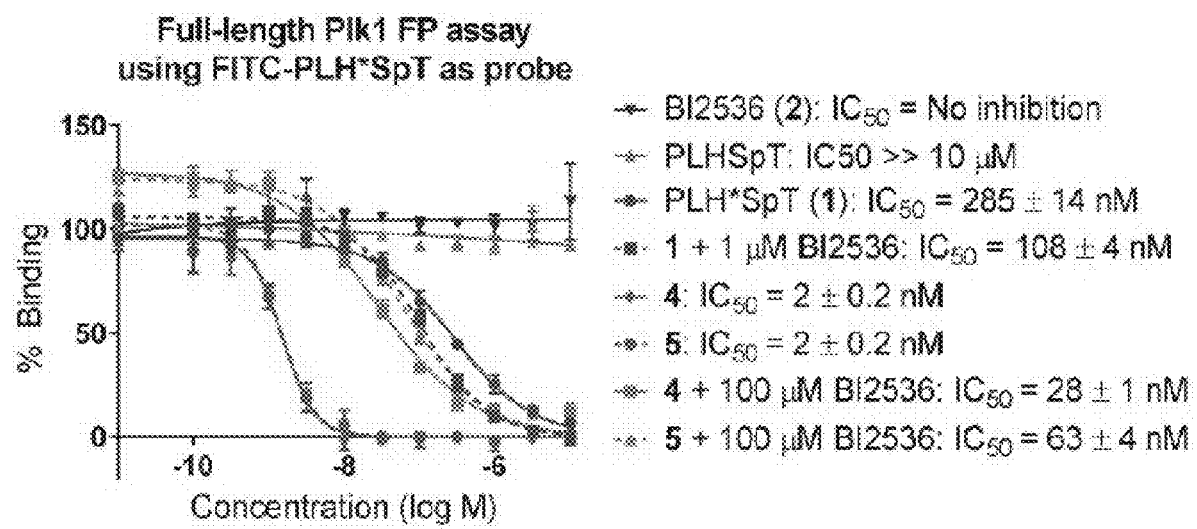
Figure 28B:
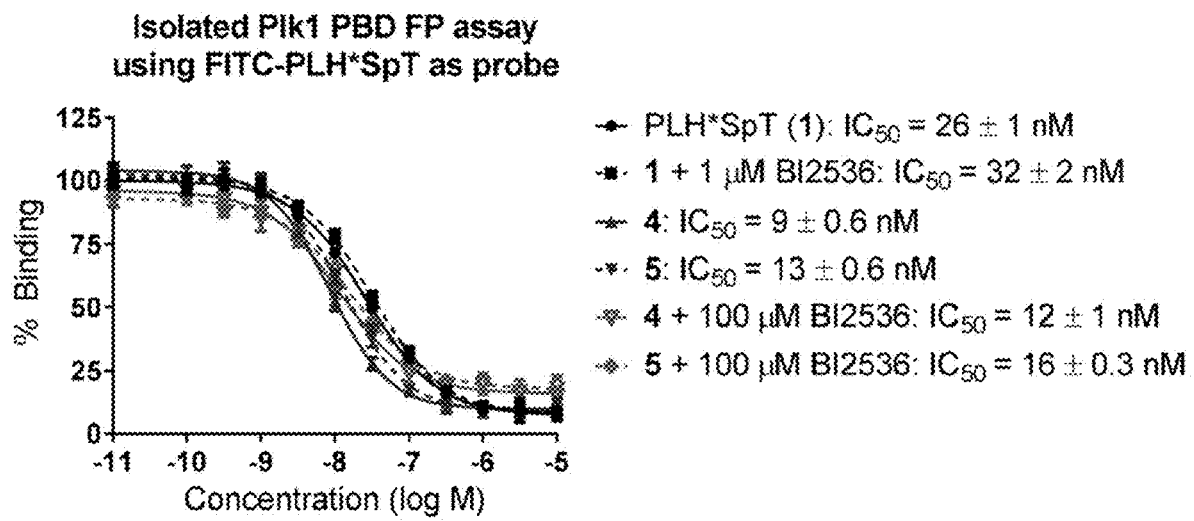

FIGS. 27A, 27B, 27C, 27D, 27E. FIG. 27A is a crystal structure of Zebrafish Plk1 KD and PBD domains (PBD code: 4J7B). FIG. 27B shows representative fluorescence microscopy images of immunostained cells treated with PBS (control) or compound 1*, wherein (1) the asterisks indicate centrosomally localized Plk1 signals, (2) the arrowed brackets indicate kinetochore-associated Plk1 signals, and (3) arrowheads indicate misaligned chromosomes. The structures of PBD-binding compounds 1 and 1* are shown in FIG. 27C. FIG. 27D shows the potential arrangement of human Plk1 KD complexed with Plk1 inhibitor BI2536 (2) and PBD complexted with 1 (PDB code: 3RQ7) obtained using a recent co-crystal structure of Zebrafish Plk1 domains (PDB: 4J7B). FIG. 27E illustrates bivalent ligands synthesized and evaluated wherein BI2536 (2) was tethered from the C-termini and N-termini of 1 using various length PEG chains FIGS. 28A and 28B. FIGS. 28A and 28B showFP assays for 4 and 5 against (28A) full-length Plk1 where over a 100-fold increase in binding affinity was observed relative to 1 and (28B) isolated Plk1 PBD, respectively.

Figure 29A:
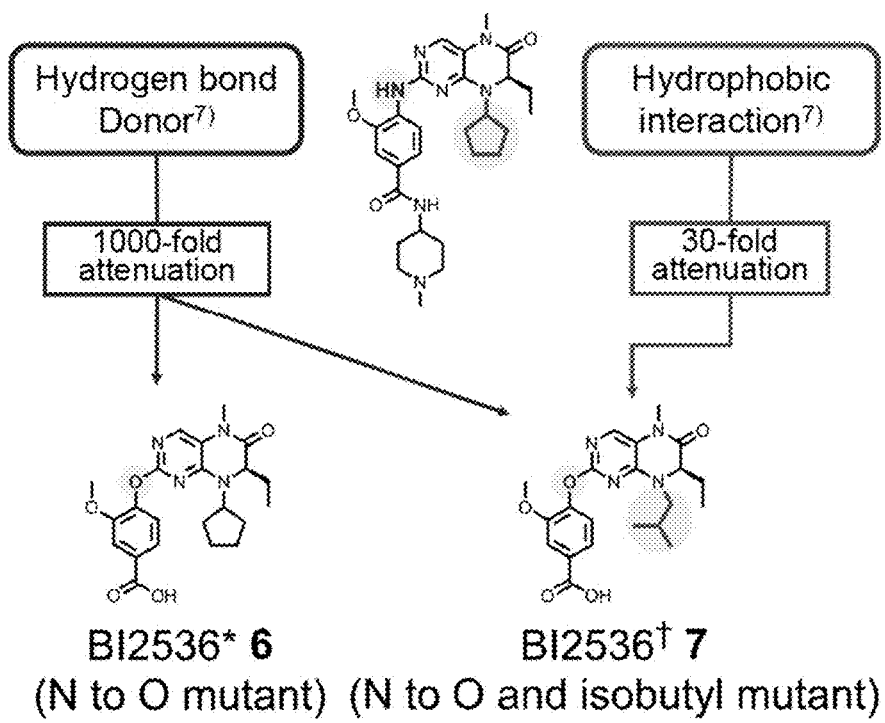
Figure 29B:
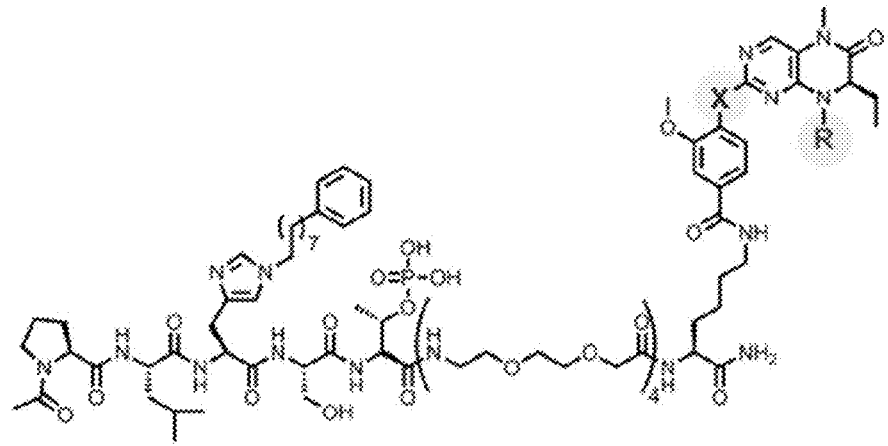
Figure 29B:
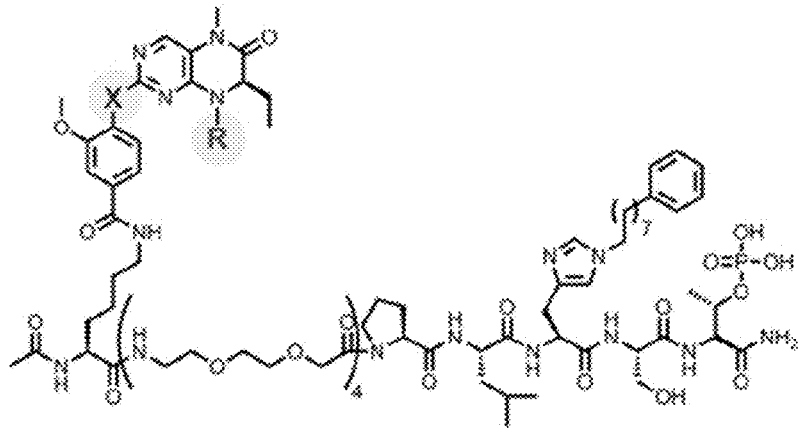

FIGS. 29A and 29B illustrates the design of attenuated KD-binding inhibitors and structures of bivalent inhibitors 8, 9, 10, and 11.

Figure 30A:
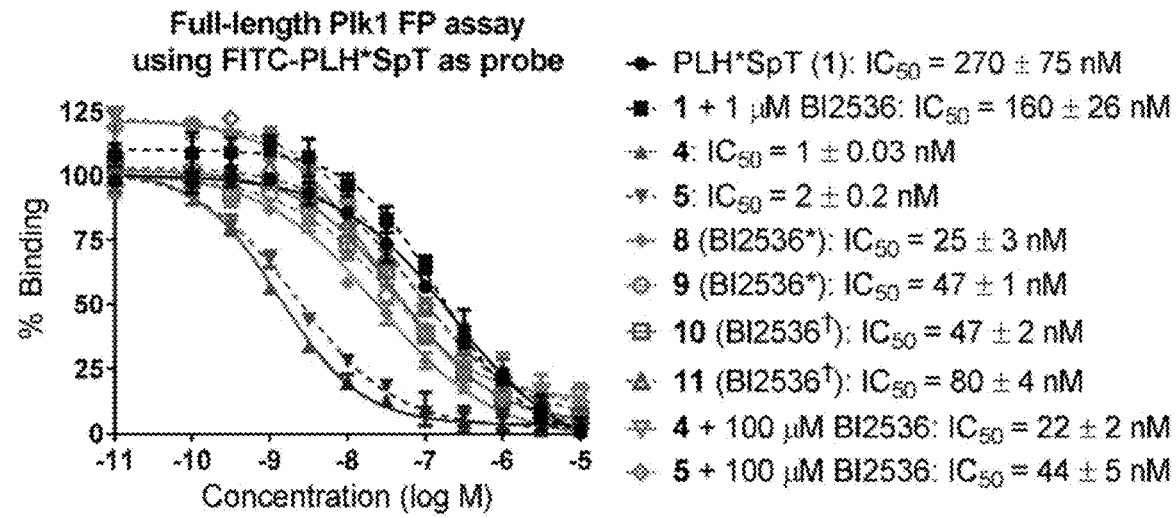
Figure 30B:
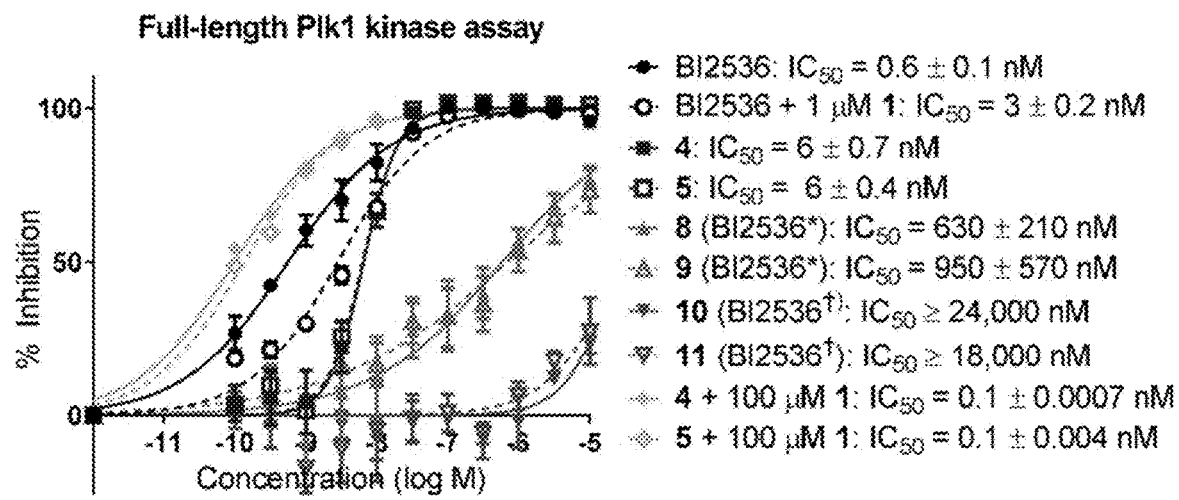

FIGS. 30A and 30B show the fffects of attenuated KD-binding components on biological activity of bivalent ligands. FIG. 30A shows FP assays of peptides possessing three different KD-binding components against full length Plk1. FIG. 30B shows kinase assay of peptides possessing three different KD-binding components against fulllength Plk1.

Figure 31:
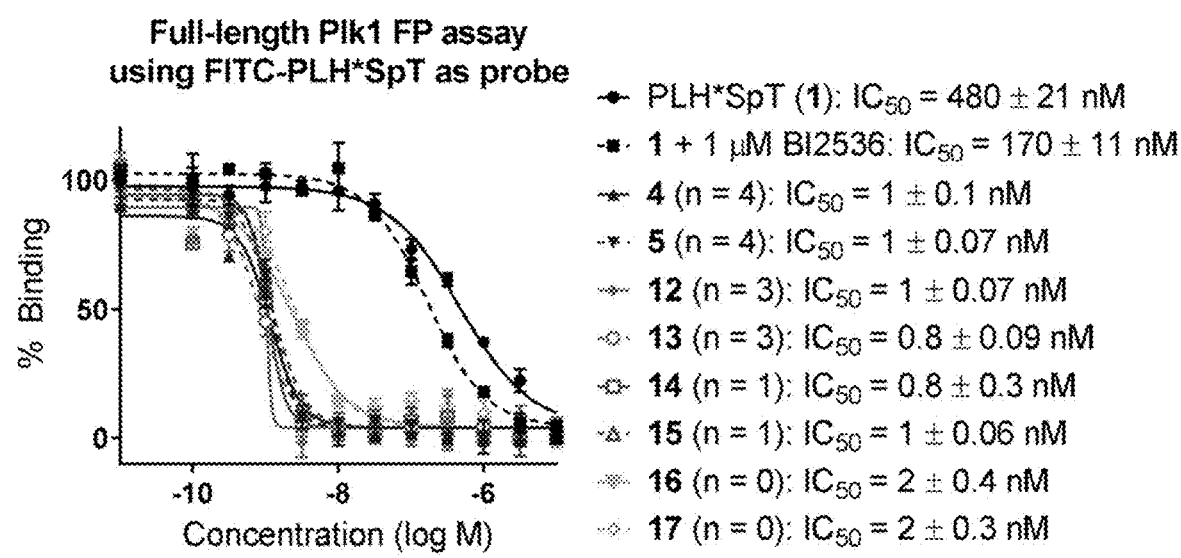

FIG. 31 shows FP assay results for compounds having varying linker length (4, 12, 14, 16, 5, 13, 15, and 17) against full length Plk1.

DETAILED DESCRIPTION

Presently described are high affinity peptide mimetic ligands of the polo-like kinase 1 (Plk1) that contain a phospho-threonine (pThr) analog residue. This pThr residue is critical to maintain high affinity binding, but it is also a substrate of cellular phosphotases that hydrolyze the phosphate group and render the compound(s) inactive. Thus, the description provides novel compounds that inhibit polo-like kinases by binding to the polo-box domain. The use of the phosphonate analog, (2S,3R) 2-amino-3-methyl-4-phosphonobutanoic acid (Pmab), prevents inactivation by cellular phosphatases.

In certain aspects, the orthogonally protected amino acid, (N-Fmoc, O,O-(bis-(tert-butyl))-Pmab, must be custom synthesized to allow for its use in solid-phase peptide synthesis (SPPS). The previous synthetic routes, developed in our lab, required either 15 or 20 steps with 12% and 14% overall yields, respectively. The work reported here provides a more efficient synthetic route to a key intermediate in the synthesis of Pmab. Using this method, along with a 7-step transformation previously reported by our group, this critical building block can now be produced on gram-scale in 9 steps and at least about 23% overall yield.

An important aspect of this new methodlology is that it allows for the efficient synthesis of Pmab analogs that differ at the C-3 position. Furthermore, these analogs can be synthesized with orthogonal protecting groups that render them suitable for facile incorporation into peptides or peptide mimetics using both solution-phase and solid-phase peptide synthesis. These analogs can be easily accessed by reacting diverse aldehydes using the anti-selective Mannich reaction followed by the 7-step transformation to the corresponding phosphonate. Very few of these C-3 analogs of phospho-threonine have been reported in the literature due to the previous requirement of a lengthy and impractical synthetic method. Therefore, the methodology allows for efficient preparation of orthogonally protected phosphonate-containing reagents that are compatible with the SPPS of new genres of phosphatase-stable pThr analogs, which may yield peptide mimetics having significantly improved biological properties.

The following is a detailed description provided to aid those skilled in the art in practicing the present invention.

Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

An "agent" is understood herein to include a therapeutically active compound or a potentially therapeutically active compound. An agent can be a previously known or unknown compound. As used herein, an agent is typically a non-cell-based compound, however, an agent can include a biological therapeutic agent, e.g., peptide or nucleic acid therapeutic, cytokine, antibody, etc.

An "agonist" is understood herein as a chemical substance capable of initiating the same reaction or activity typically produced by the binding of an endogenous substance or ligand to its target. An "antagonist" is understood herein as a chemical substance capable of inhibiting the reaction or activity typically produced by the binding of an endogenous substance (e.g., an endogenous agonist) to its target to prevent signaling through a receptor, to prevent downstream signaling, or to prevent cellular events (e.g., progression through cell cycle) that are the normal result of activation of the target. The antagonist can bind directly to the target or can act through other proteins or factors required for signaling. Agonists and antagonists can modulate some or all of the activities of the endogenous substance or ligand that binds to the target. Antagonists are typically characterized by determining the amount of the antagonist is required to inhibit the activity of the endogenous agonist. For example, an inhibitor at 0.01-, 0.1-, 1-, 5-, 10-, 50-, 100-, 200-, 500-, or 1000-fold molar concentration relative to the agonist can inhibit the activity of the agonist by at least 10%, 50%, 90%, or more.

As used herein, the term "macrocycle" refers to a molecule having a chemical structure including a ring or cycle formed by at least 9 covalently bonded atoms.

As used herein, the term "peptidomimetic macrocycle" or "marocyclic peptidomimetic" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycle include embodiments where the macrocycle-forming linker connects one amino acid residue (or analog) to the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle.

As used herein "amelioration" or "treatment" is understood as meaning to lessen or decrease at least one sign, symptom, indication, or effect of a specific disease or condition. For example, amelioration or treatment of cancer can be determined using the standard RECIST (Response Evaluation Criteria in Solid Tumors) criteria including the assessment of tumor burden, by survival time, reduced presence of tumor markers (e.g., prostate specific antigen), or any other clinically acceptable indicators of disease state or progression. Amelioration and treatment can require the administration of more than one dose of an agent or therapeutic. As used herein, "prevention" is understood as to limit, reduce the rate or degree of onset, or inhibit the development of at least one sign or symptom of a disease or condition. For example, a subject having a genetic predisposition to develop a disease may develop disease later in life, e.g., delay of BRCA1 or BRCA2 related breast cancer development from third or fourth decade of life to fifth or beyond. Prevention can require the administration of more than one dose of an agent or therapeutic.

Chemical classes and groups are provided herein and referred to by chemical names, common names, and/or chemical structures. In the absence of an explicit definition herein, definitions of chemical structures can be found in chemical dictionaries, science textbooks, such as organic chemistry textbooks, or in databases. Chemical classes and groups commonly referred to herein are provided as follows.

The term "alkoxy," as used herein, refers to an alkyl group which is linked to another moiety though an oxygen atom. Alkoxy groups can be optionally substituted with one or more substituents. As used herein, "$C_0$alkoxy" refers to a hydroxyl (—OH) group.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the description contemplates cyano and propargyl groups.

The term "alkyl" refers to the radical of saturated aliphatic groups, including straight-chain alkyl groups, branched-chain alkyl groups, and cycloalkyl substituted alkyl groups. In certain embodiments, the term "alkyl" refers to a group having two radical groups, such as "—$CH_2$—". The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), or 20 or fewer, even 10 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbons.

As used herein, an amide is understood as a derivative of an oxoacids in which an acidic hydroxyl group has been replaced by an amino or substituted amino group. Compounds having one, two or three acyl groups on a given nitrogen are generically included and may be designated as primary, secondary and tertiary amides, respectively, e.g. PhC(=O)NH$_2$ benzamide, CH$_3$S(=O)$_2$NMe$_2$ N,N-dimethylmethanesulfonamide, [RC(=O)]$_2$NH secondary amides (see imides), [RC(=O)]$_3$N tertiary amides, PhP(=O)(OH) NH$_2$ phenylphosphonamidic acid. An amide group as used herein is understood as a group with —NH$_2$, NHR and NR$_2$ Amide groups should not be distinguished by means of the terms primary, secondary and tertiary.

As used herein, an "allyl" group is understood as a structure containing a carbon-carbon double bond. For example, it includes a structural formula H$_2$C=CH—CH$_2$R, where R is the connection to the rest of the molecule.

As used herein, "amine" or "amino" is understood as Compounds formally derived from ammonia by replacing one, two or three hydrogen atoms by hydrocarbon groups, and having the general structures RNH$_2$ (primary amines), R$_2$NH (secondary amines), R$_3$N (tertiary amines). An amino group is understood as having the structure —NH$_2$, —NHR, or —NR$_2$.

As used herein, "aryl group" is understood as refers to any functional group or substituent derived from a simple aromatic ring, may it be phenyl, thiophene, indolyl, etc (see IUPAC nomenclature, goldbook.iupac.org/A00464.html). Aryl groups derived from arenes by removal of a hydrogen atom from a ring carbon atom. Groups similarly derived from heteroarenes are sometimes subsumed in this definition. "Aryl" is used for the sake of abbreviation or generalization. For example, a simple aryl group is phenyl, C$_6$H$_5$; it is derived from benzene. The tolyl group, CH$_3$C$_6$H$_4$, is derived from toluene (methylbenzene). The xylyl group, (CH$_3$)$_2$C$_6$H$_3$, is derived from xylene (dimethylbenzene). The class of heterocyclyl groups derived from heteroarenes by removal of a hydrogen atom from any ring atom is referred to as heteroaryl.

As used herein, "carboxylic acid" is understood as a group having the structure RC(=O)OH. A carboxylic acid group is understood to denote the —C(=O)OH group including its carbon atom.

As used herein, "carbonyl group" is understood as a group containing the carbonyl group, C=O. The term is commonly used in the restricted sense of aldehydes and ketones, however as used herein it includes carboxylic acids and derivatives.

As used herein, "carboxyl" or "carboxy" group is understood as a structure containing —COOH or —COOR. The term includes carboxylic acids and derivatives.

The term "enantiomers" refers to two stereoisomers of a compound which are non-superimposable mirror images of one another. An equimolar mixture of two enantiomers is called a "racemic mixture" or a "racemate."

As used herein, a "halogen" or "halo" is understood as an element located in Group VIIA of the periodic table. Halogens are reactive nonmetals having seven valence electrons. Halogen groups include —F, —Cl, —Br, and —I.

As used herein, modification of a class of chemical group with the term "hetero" is understood as the class of functional groups derived from the particular class of the functional group by removal of a hydrogen atom from any carbon atom.

"Heterocyclyl" groups as used herein are univalent groups formed by removing a hydrogen atom from any ring atom of a heterocyclic compound.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moieties include, are not limited to, pyridine, pyrimidine, pyrrolidine, furan, tetrahydrofuran, tetrahydrothiophene, and dioxane.

As used herein, "olefin group" is understood as an acyclic and or cyclic hydrocarbon having one or more carbon-carbon double bonds, apart from the formal ones in aromatic compounds. The class olefins subsumes alkenes and cycloalkenes and the corresponding polyenes.

In compounds, amino acid positions are determined relative to the phosphothreonine which is arbitrarily defined as position zero (0). Amino acids to the C-terminus of the peptide (to the right) are indicated as positions +1 (adjacent to the phosphothreonine), +2 (adjacent to the +1 position, but not the phosphothrenine), etc. Similarly, amino acids towards the N-terminus are defined as positions -1 (adjacent to the phosphothreonine), -2 (adjacent to the -1 position, but not the phosphothrenine), etc.

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., PSA) or a substance produced by a reporter construct (e.g, β-galactosidase or luciferase). Depending on the method used for detection the amount and measurement of the change can vary. For example, a change in the amount of cleavage of analyte present will depend on the exact reaction conditions and the amount of time after exposure to the agent the sample is collected. Changed as compared to a control reference sample can also include decreased binding of a ligand to a receptor in the presence of an antagonist or other inhibitor. Determination of statistical significance is within the ability of those skilled in the art.

As used herein, "detecting", "detection" and the like are understood that an assay performed for identification of a specific analyte in a sample or a product from a reporter construct in a sample. Detection can also include identification of activation of a kinase or other enzyme. Detection can include the identification of a mutation in a gene sequence, such as a point mutation, a deletion of all or part of the coding sequence or transcriptional/translational regulatory sequences of the gene, a truncation of the gene sequence, or any other alteration that can alter the expression level or the sequence of the protein expressed by the gene, particularly when the alteration of the sequence results in a phenotypic change in the subject. Detection can include the determination of the size of a tumor, the presence or absence of metastases, the presence or absence of angiogenesis, etc. The amount of analyte detected in the sample can be none or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the description includes the observation of the subject for other signs or symptoms of the disease, disorder, or condition by physical examination, imaging, further laboratory tests, etc.

As used herein, a "diagnostic marker" is understood as one or more signs or symptoms of a disease or condition that can be assessed, preferably quantitatively to monitor the progress or efficacy of a disease treatment or prophylactic treatment or method. A diagnostic marker can be a substance that is released by a tumor (e.g., antigens such as PSA or enzymes). A diagnostic marker can be tumor size and/or grade of tumor and/or growth rate of tumor. A diagnostic marker can be the presence or absence of angiogenesis. A diagnostic marker can be a change in blood counts or cellular function measured in an in vitro assay, or the presence and characteristics of metastases (number and size).

The term "effective" can mean an amount of a compound, composition or component which, upon single or multiple dose administration to the cell or subject, when used within the context of its intended use, effects an intended result. The term effective subsumes all other effective amount or effective concentration terms, which are otherwise described or used in the present application. The terms "effective" and "effectiveness" can include both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

"Therapeutically effective amount," as used herein refers to an amount of an agent which is effective, upon single or multiple dose administration to the cell or subject, in ameliorating or treating or preventing a symptom of a disease or disorder, including prolonging the survivability of a patient with such a disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments such as radiation.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "Fmoc" is understood as 9-fluorenylmethyloxycarbonyl having the molecular formula $C_{15}H_{11}ClO_2$. The structure of this protective group is well known.

As used herein, "Boc" is understood as tert-butyloxycarbonyl having the molecular formula $C_5H_9O_2$. The structure of this protective group is well known.

As used herein, "Trt" is understood as triphenylmethyl or trityl having the molecular formula $C_{19}H_{15}$. The structure of this protective group is well known.

As used herein, "heterologous" as in "heterologous protein" is understood as a protein not natively expressed in the cell in which it is expressed. The heterologous protein may be, but need not be, from a different species.

The term "hyperproliferative disorder" or "neoplasia" includes malignancies characterized by excess cell proliferation or growth, or reduced cell death. In specific embodiments, the term "cancer" includes but is not limited to carcinomas, sarcomas, leukemias, and lymphomas. The term "cancer" also includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor. Tumors include solid tumors (i.e., non-blood tumors) and blood tumors. Cancers include, but are not limited to, Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

The term "stereoisomers" as used herein refers to isomeric molecules that have the same molecular formula and sequence of bonded atoms (constitution), but that differ only in the three-dimensional orientations of their atoms in space. The structural isomers share the same molecular formula, but the bond connections and/or their order between different atoms/groups differs. In certain embodiments of the description, stereoisomers refer to the compounds having the same order and bond connections of the constituent atoms, but different orientation in space (such as, enantiomers, and diastereomers).

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "label" or "detectable label" as used herein refers to any atom or molecule which can be used to provide a detectable (preferably quantifiable) signal, and which can be attached to a chemical compound, a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP), Yellow Fluorescent Protein (YFP).

"Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

"Obtaining" is understood herein as manufacturing, purchasing, or otherwise coming into possession of.

A "peptide" or "peptide derivative" as used herein is understood as two or more independently selected natural or non-natural amino acids joined by a peptide bond. A peptide can include 2, 3, 4, 5, 6, 7, 8, 9, 10, 11, 12 or more natural or non-natural amino acids joined by peptide bonds.

As used herein, pharmaceutically acceptable salts include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of peptide mimetic is suitable for use in the methods of the present description, e.g., a pharmaceutically acceptable salt of a peptide mimetic, a free base of a peptide mimetic, or a mixture thereof.

As used herein, "plurality" is understood to mean more than one. For example, a plurality refers to at least two, three, four, five, or more.

A "polo-like kinase" or "Plk" as used herein collectively refers to the proteins called Plk-1, (human sequence available as under Accession No. P53350.1 GI:1709658; mouse sequence available under Accession No. Q07832.2 GI:1709659; rat sequence available under Accession No. Q62673.1 GI:12230396; Pan troglodytes sequence available under Accession No. XP_001163585.1 GI:114661620); Plk-2 (human sequence available under Accession No. Q9NYY3.3 GI:22096374); Plk-3 (human sequence available under Accession No. Q9H4B4.2 GI:51338822); and Plk-4 (human sequence available under Accession No. 000444.3 GI:160113150), from any organism, preferably a mammalian organism, preferably from a human organism. Such proteins can be encoded by any nucleic acid that provides the appropriate translation product; however, in certain embodiments, the polo-like kinases are encoded by the native genes which can easily be identified using GenBank or any of a number of publicly available databases. All GenBank Nos. incorporated herein by reference as of the filing date of the instant application.

A "sample" as used herein refers to a biological material that is isolated from its environment (e.g., blood or tissue from an animal, cells, or conditioned media from tissue culture) and is suspected of containing, or known to contain an analyte, such as a tumor cell or a product from a reporter construct. A sample can also be a partially purified fraction of a tissue or bodily fluid. A reference sample can be a "normal" sample, from a donor not having the disease or condition, or from a normal tissue in a subject having the disease or condition (e.g., normal tissue vs. tumor tissue). A reference sample can also be from an untreated donor or cell culture not treated with an active agent (e.g., no treatment or administration of vehicle only) and/or stimulus. A reference sample can also be taken at a "zero time point" prior to contacting the cell or subject with the agent or cell to be tested.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to non-specific compounds, or a pool of non-specific compounds. "Specifically binds" can be used in relation to binding one of two or more related compounds that have physically related structures, e.g., two kinases, particularly 2 polo-like kinases. For example, an agent, antibody, polypeptide, nucleic acid, or other compound can "specifically bind" one polo-like kinase (e.g., Plk1) with at least a 10-fold, 50-fold, 100-fold, 500-fold, 1000-fold, 5000-fold, 10,000-fold or more preference over another polo-like kinase, e.g., Plk2, Plk3, or Plk4. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as cancer is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The term "disubstituted histidine" refers to a histidine residue substituted on the imidazole ring with at least two moieties such as aryl-$(C_{1-20})$alkyl (including aryl-$(C_{1-6})$alkyl-), heteroaryl-$(C_{1-20})$alkyl (including heteroaryl-$(C_{1-6})$alkyl), $(C_{1-20})$alkyl (including $(C_{1-6})$alkyl), allyl-$(C_{1-20})$alkyl (including allyl-$(C_{1-6})$alkyl), $(C_{0-20})$alkoxy-C(O)—$(C_{1-20})$alkyl, or amino$(C_{1-20})$ alkyl; wherein each of the said alkyl, aryl, and heteroaryl moieties is further optionally substituted by one or more same or different subtituents selected from the group of $(C_{1-6})$alkyl, carboxyl, halo, hydroxyl, amine, and $(C_{1-6})$alkoxy groups. In certain embodiments, at least two moieties on the imidazole ring are $(C_{1-10})$alkyl, aryl-$(C_{1-10})$alkyl (including aryl-$(C_{1-6})$alkyl-), or heteroaryl-$(C_{1-10})$alkyl, allyl-$(C_{1-6})$alkyl, or $(C_{1-6})$alkyl optionally substituted by one or more carboxyl, $(C_{1-8})$alkoxyl, or hydroxyl groups. In certain embodiments, the two moieties are attached to the two nitrogen atoms of the imidazole ring.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

All oligonucleotide sequences are written from the 5'-end to the 3'-end unless otherwise specifically noted.

The polo-like kinase 1 (Plk1) represents a new target for anticancer therapeutic development. Plk1 contains a C-terminal polo-box domain (PBD) that recognizes phospho-Ser (pSer)/phospho-Thr (pThr)-containing motifs, which provides sub-cellular localization that is critical for proper Plk1 function. Spatial disruption of Plk1 distribution by blocking PBD-dependent protein-protein interactions may afford an attractive alternative to kinase-directed inhibitors for the down-regulation of Plk1 function and Plk1 PBD-binding antagonists and may serve as a new class of anticancer agents.

One aspect of the description provides a novel class of compounds (or peptide derivatives) that are useful as anticancer therapeutics. An additional aspect of the description provides small high affinity ligands targeting PBD binding domain and auxiliary region proximal to the cryptic pocket (or peptide derivatives) that are useful as anticancer therapeutics. A further aspect of the present disclosure provides high affinity and selective peptidomimetic macrocycles that are useful as anticancer therapeutics. In another aspect, the description provides novel compounds used as intermediates in the synthetic preparation of the anticancer compounds of the present description. In another aspect, the description provides methods for the preparation of the anticancer compounds of the present description. In another aspect, the description provides methods for the preparation of intermediates used in the preparation of the anticancer compounds of the present description.

The compounds, compositions and methods provided herein represent new design and synthesis of peptides or peptide derivatives, as well as high affinity binding Plk1 macrocyclic peptidomimetics or peptide derivative ligands and high affinity Plk1 bi-valent ligands. The description can lead to the development of clinically useful Plk agents.

The description can also lead to peptide derivatives that are useful in unrelated therapeutic areas.

Compounds

The description provides high affinity compounds bearing non-natural amino acid. The compounds of the description contain a phosphoryl amino acid residue. In certain embodiments, the compound of the description is a peptide/peptide derivative comprising a pThr analog, pSer analog, Pmab, C-3 substituted Pmab residue.

In certain embodiments, the PBD is that of polo-like kinase 1 (Plk1), which is a critical regulator of mitotic events and cellular proliferative potential and includes methods synthesis and use of the same. In particular, the description provides novel compounds that inhibit polo-like kinases by binding to the polo-box domain.

In certain embodiments, the compounds of the description have achieved good inhibition of Plk1 in biochemical assays.

In one aspect, the description provides a compound of Formula II or IIa, or salt, solvate, or hydrate thereof:

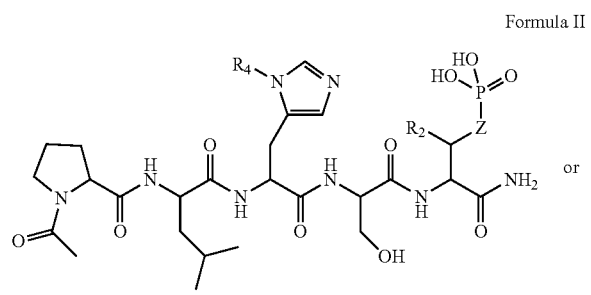

Formula II

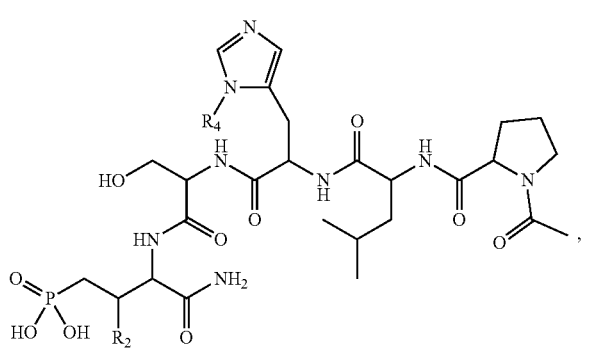

Formula IIa wherein:

R₂ is H, optionally substituted alkyl (e.g., optionally substituted $C_2$-$C_4$ alkyl), optionally substituted cycloalkyl, optionally substituted aralkyl, optionally substituted heteroarylalkyl, haloalkyl, optionally substituted morpholinomethyl,

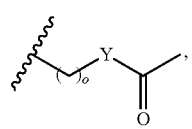

or optionally substituted indolylalkyl;
Y is $CH_2$, NH, or O;
Z is O or $CH_2$; and
R₄ is optionally substituted aralkyl. In another aspect, R₂ is Et, Pr, i-Pr, Bu,

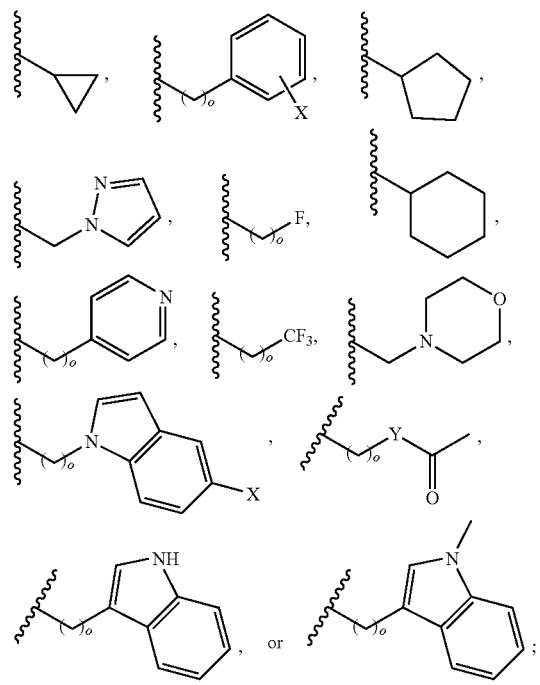

each o is independently 1-3; each X is independently H, Me, Et, $CF_3$, F, Cl, Br, OMe, or $N(Me)_2$;
Y is $CH_2$, NH, or O. In another aspect, R₄ is —$(CH_2)_8$-Ph. In another aspect, R₂ is Et, Pr, i-Pr, Bu,

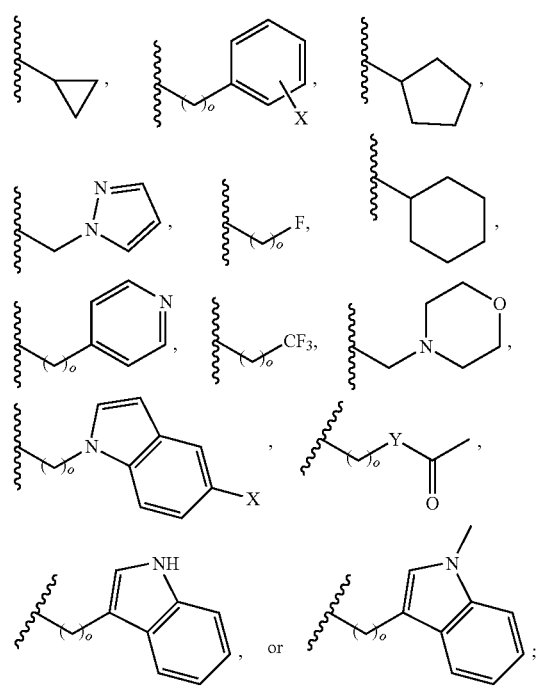

each o is independently 1-3; each X is independently H, Me, Et, $CF_3$, F, Cl, Br, OMe, or $N(Me)_2$;
Y is $CH_2$, NH, or O; and R₄ is —$(CH_2)_8$-Ph.

In another aspect, the description provides a compound of Formula 2, or salt, solvate, or hydrate thereof:

Formula 2

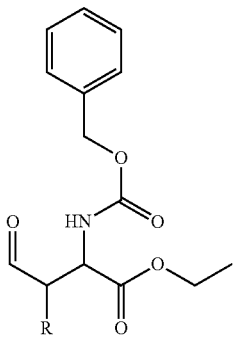

wherein, R is optionally substituted cycloalkyl, optionally substituted phenylethyl, optionally substituted phenylpropyl, optionally substituted heteroarylalkyl, haloalkyl, optionally substituted morpholinomethyl,

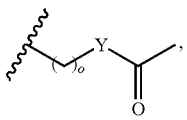

or optionally substituted indolylalkyl; and Y is $CH_2$, NH, or O. In another aspect, R is

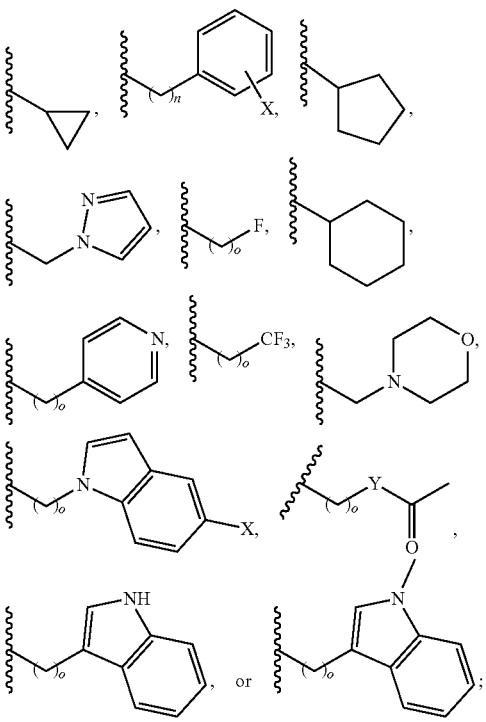

n is 1-3; each o is independently 1-3; each X is independently H, Me, Et, $CF_3$, F, Cl, Br, OMe, or $N(Me)_2$; and Y is $CH_2$, NH, or O.

In certain aspects, the description provides peptide-mimetic compounds comprising a peptide derivative selected from the group consisting of pThr analong, pSer analog, Pmab, C-3 substituted Pmab and combinations thereof. In certain embodiments, the peptide-mimetic compound comprises a peptide analog of Formula 2. In certain additional embodiments, the peptide-mimetic compounds comprise at least one natural (i.e., alpha) amino acid and a peptide analog of Formula 2. In certain embodiments, the peptide analog is a C-3 substituted Pmab derived phosphatase-stable analog of phospho-threonine or phosphor-serine.

In certain embodiments, the peptide-mimetic ligand of PBD comprises a dipeptide having the structure: Ser-[Y], wherein Y is a phosphatase stable phospho-amino acid analog of Formula 2.

In certain embodiments, the peptide-mimetic ligand of PBD comprises, consists or consists essentially of the structure: $X_{0-6}$-Ser-[Z]-$X'_{0-8}$, wherein X is any amino acid, and Z is phosphatase stable phospho-amino acid analog of Formula 2, and wherein only one of X or X' can be zero.

In certain additional embodiments, the peptide-mimetic ligand of PBD comprises, consists or consists essentially of the structure: $X_{0-3}$-Ser-[Z]-$X'_{0-2}$, wherein X is any amino acid, and Z is phosphatase stable phospho-amino acid analog of Formula 2, and wherein only one of X or X' can be zero.

In certain additional embodiments, the description provides a peptido-mimetic ligand of PBD comprising, consisting or consisting essentially of the structure $X_{0-3}$-His-Ser-[Z]-$X'_{0-2}$, wherein X is any amino acid, and Z is phosphatase stable phospho-amino acid analog of Formula 2.

In any of the aspects or embodiments described herein, Z can be a C-3 substituted Pmab derived phosphatase-stable analog of phospho-threonine or phosphor-serine.

In additional embodiments, the description provides peptide-mimetic ligands of polo box domains (PBD) comprising an amino acid analog of Formula 2 as described herein. In certain embodiments, the peptide-mimetic ligand of PBD comprises the structure: X-X-X-Ser-[Z]-X-X, wherein X is any amino acid (or no amino acid), and Z refers to an amino acid analog of Formula 2 as described herein, e.g., a C-3 substituted Pmab derived phosphatase stable analog of phospho-threonine or phosphor-serine. In certain additional embodiments, X is a naturally occurring amino acid.

In certain embodiments, the ligand of the PBD comprises or consists essentially of a structure selected from the group consisting of:
FSQHKTS(Z)I,
HS(Z),
N-terminal modified HS(Z) peptidomimetic,
GVLS(Z)LI,
VLS(Z)L,
N-terminal modified PLHS(Z)M and LHS(Z)M peptidomimetic,
Cyclic GLH(oct-Ph)S(Y)C thioether peptidomimetic,
FDPPLHS(Z)A,
XDPPLHS(Z)A peptidomimetic (X=natural or non-natural amino acid),
PLHS(Z)A,
MQS(Z)PL,
FMPPPMS(Z)M,
LLCS(Z)PNGL,
MQS(Z)PL,
PMQS(Z)PLN, and
MAGPMQS(Z)PLNGAYKK,
   wherein Z is an amino acid analog of Formula 2 as described herein. In certain embodiments, Z is a C-3 substituted Pmab derived phosphatase stable analog of phospho-threonine or phosphor-serine.

In another aspect, the description provides a compound of Formula 1, or salt, solvate, or hydrate thereof:

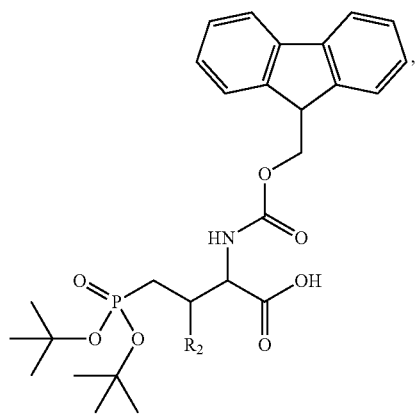

Formula 1 wherein R₂ is optionally substituted $C_2$-$C_4$ alkyl, optionally substituted cycloalkyl, optionally substituted aralkyl, optionally substituted heteroarylalkyl, haloalkyl, optionally substituted morpholinomethyl,

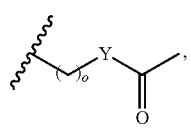

or optionally substituted indolylalkyl; and Y is $CH_2$, NH, or O. In another aspect, R₂ is Et, Pr, i-Pr, Bu,

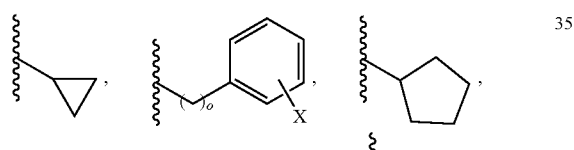

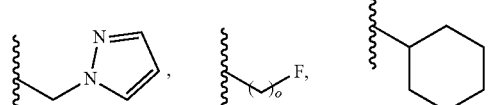

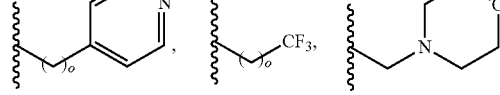

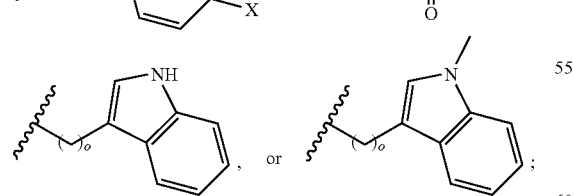

each o is independently 1-3; each X is independently H, Me, Et, $CF_3$, F, Cl, Br, OMe, or $N(Me)_2$; and Y is $CH_2$, NH, or O.

Certain exemplified compounds of the description include, but are not limited to, the compounds of Table 1 as follows:

TABLE 1

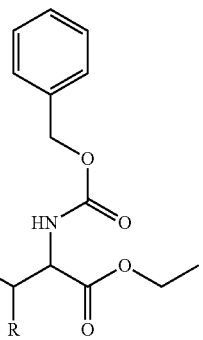

Formula 2

| Comp. No. | R |
|---|---|
| 2-1 | 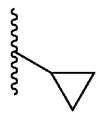 |
| 2-2 | 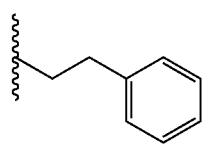 |
| 2-3 | 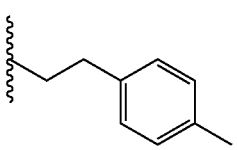 [SMILES: *CCc1ccc(C)cc1] |
| 2-4 | 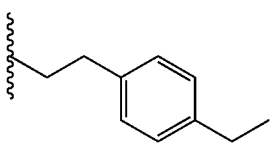 [SMILES: *CCc1ccc(CC)cc1] |
| 2-5 | 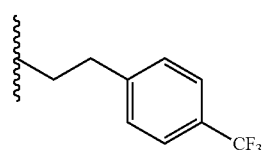 |
| 2-6 | 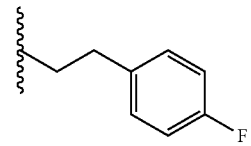 [SMILES: *CCc1ccc(F)cc1] |
| 2-7 | 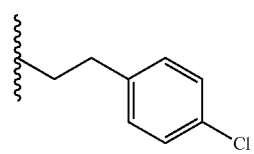 [SMILES: *CCc1ccc(Cl)cc1] |
| 2-8 | 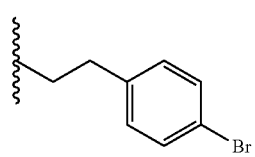 [SMILES: *CCc1ccc(Br)cc1] |

TABLE 1-continued
Formula 2
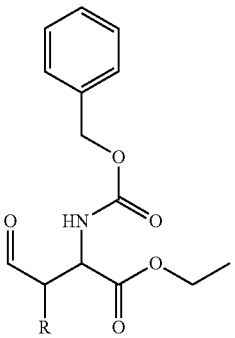
| Comp. No. | R |
|---|---|
| 2-9 | 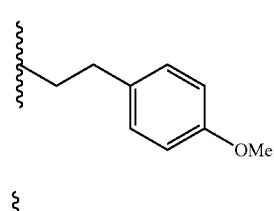 |
| 2-10 | 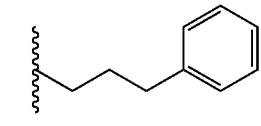 [SMILES: *CCCc1ccccc1] |
| 2-11 | 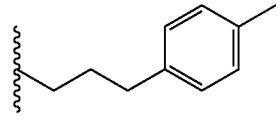 [SMILES: *CCCc1ccc(C)cc1] |
| 2-12 | 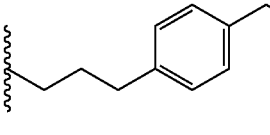 |
| 2-13 | 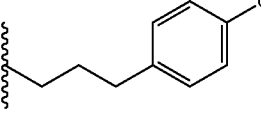 |
| 2-14 | 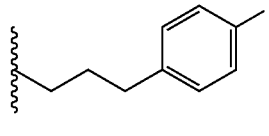 |
| 2-15 | 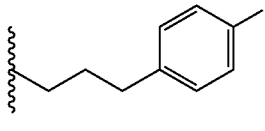 |
| 2-16 | 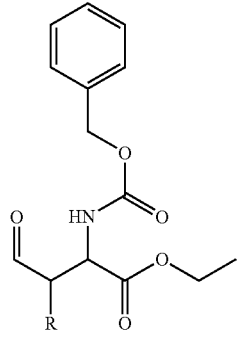 |
TABLE 1-continued
Formula 2
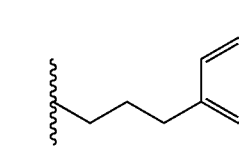
| Comp. No. | R |
|---|---|
| 2-17 | 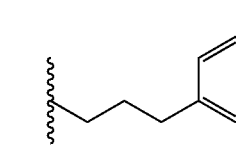 |
| 2-18 | 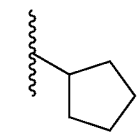 [SMILES: *C1CCCC1] |
| 2-19 | 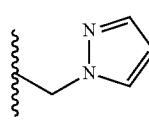 |
| 2-20 | 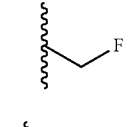 |
| 2-21 | 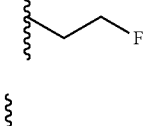 |
| 2-22 | 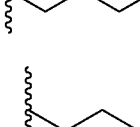 |
| 2-23 | 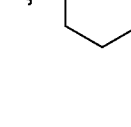 |
| 2-24 | |
| 2-25 | |

TABLE 1-continued
Formula 2
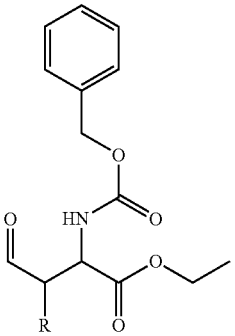
| Comp. No. | R |
|---|---|
| 2-26 | 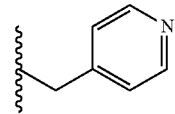 |
| 2-27 | 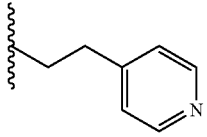 [SMILES: *CCc1ccncc1] |
| 2-28 | 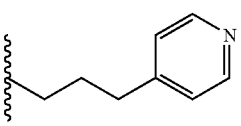 [SMILES: *CCCc1ccncc1] |
| 2-29 | 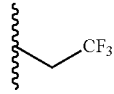 |
| 2-30 | 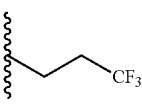 |
| 2-31 | 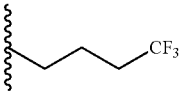 [SMILES: *CCCC(F)(F)F] |
| 2-32 | 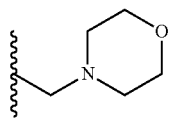 |
| 2-33 | 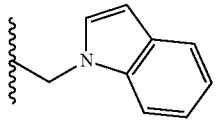 [SMILES: *Cn1ccc2ccccc21] |
| 2-34 | 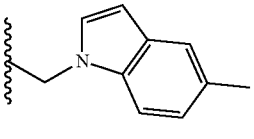 [SMILES: *Cn1ccc2cc(C)ccc21] |
TABLE 1-continued
Formula 2
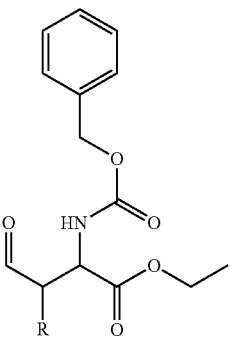
| Comp. No. | R |
|---|---|
| 2-35 | 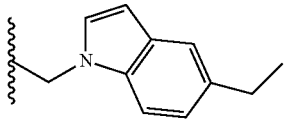 [SMILES: *Cn1ccc2cc(CC)ccc21] |
| 2-36 | 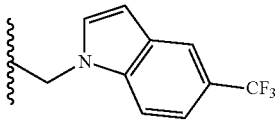 [SMILES: *Cn1ccc2cc(C(F)(F)F)ccc21] |
| 2-37 | 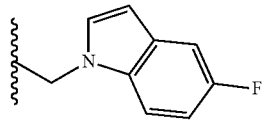 [SMILES: *Cn1ccc2cc(F)ccc21] |
| 2-38 | 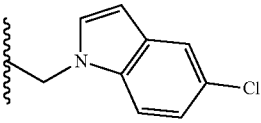 [SMILES: *Cn1ccc2cc(Cl)ccc21] |
| 2-39 | 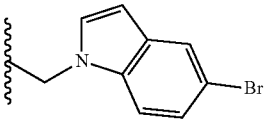 [SMILES: *Cn1ccc2cc(Br)ccc21] |
| 2-40 | 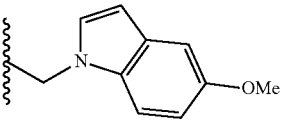 [SMILES: *Cn1ccc2cc(OC)ccc21] |
| 2-41 | 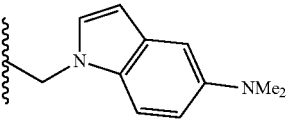 [SMILES: *Cn1ccc2cc(N(C)C)ccc21] |
| 2-42 | 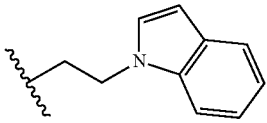 [SMILES: *CCn1ccc2ccccc21] |

TABLE 1-continued

Formula 2

| Comp. No. | R |
|---|---|
| 2-43 | propyl-(5-methyl-indol-1-yl) |
| 2-44 | propyl-(5-ethyl-indol-1-yl) |
| 2-45 | propyl-(5-CF3-indol-1-yl) |
| 2-46 | propyl-(5-F-indol-1-yl) |
| 2-47 | propyl-(5-Cl-indol-1-yl) |
| 2-48 | propyl-(5-Br-indol-1-yl) |
| 2-49 | propyl-(5-OMe-indol-1-yl) |
| 2-50 | propyl-(5-NMe2-indol-1-yl) |
| 2-51 | butyl-(indol-1-yl) |
| 2-52 | butyl-(5-methyl-indol-1-yl) |
| 2-53 | butyl-(5-ethyl-indol-1-yl) |
| 2-54 | butyl-(5-CF3-indol-1-yl) |
| 2-55 | butyl-(5-F-indol-1-yl) |
| 2-56 | butyl-(5-Cl-indol-1-yl) |
| 2-57 | butyl-(5-Br-indol-1-yl) |
| 2-58 | butyl-(5-OMe-indol-1-yl) |

TABLE 1-continued

Formula 2

| Comp. No. | R |
|---|---|
| 2-59 | (4-(5-(dimethylamino)-1H-indol-1-yl)butyl) |
| 2-60 | (3-oxobutyl) |
| 2-61 | (acetamidomethyl) |
| 2-62 | (2-acetoxyethyl) |
| 2-63 | (4-oxopentyl) |
| 2-64 | (3-acetamidopropyl) |
| 2-65 | (3-acetoxypropyl) |
| 2-66 | (5-oxohexyl) |
| 2-67 | (4-acetamidobutyl) |
| 2-68 | (4-acetoxybutyl) |
| 2-69 | ((1H-indol-3-yl)methyl) |
| 2-70 | (2-(1H-indol-3-yl)ethyl) |
| 2-71 | (3-(1H-indol-3-yl)propyl) |
| 2-72 | ((1-methyl-1H-indol-3-yl)methyl) |
| 2-73 | (2-(1-methyl-1H-indol-3-yl)ethyl) |
| 2-74 | (3-(1-methyl-1H-indol-3-yl)propyl) |

Certain exemplified compounds of the description include, but are not limited to, the compounds of Table 2 as follows:

TABLE 2

Formula 1

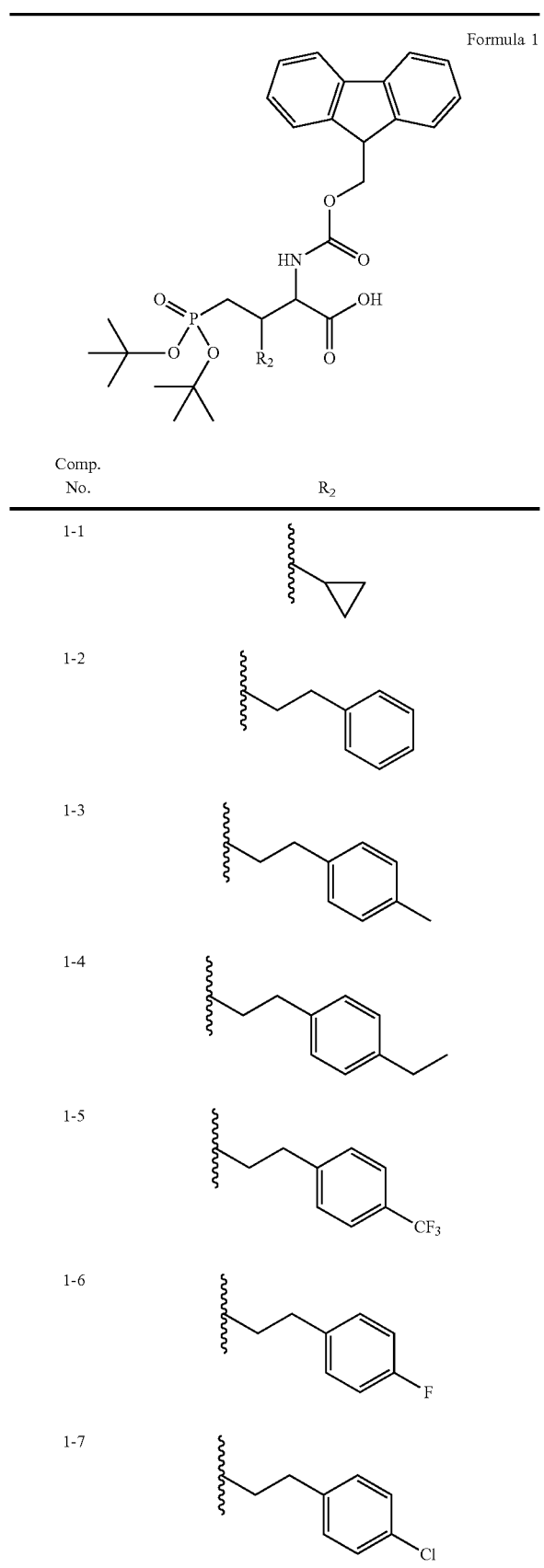

| Comp. No. | R₂ |
|---|---|
| 1-1 | cyclopropyl |
| 1-2 | -CH₂CH₂-phenyl |
| 1-3 | -CH₂CH₂-(4-methylphenyl) |
| 1-4 | -CH₂CH₂-(4-ethylphenyl) |
| 1-5 | -CH₂CH₂-(4-CF₃-phenyl) |
| 1-6 | -CH₂CH₂-(4-fluorophenyl) |
| 1-7 | -CH₂CH₂-(4-chlorophenyl) |

TABLE 2-continued

Formula 1

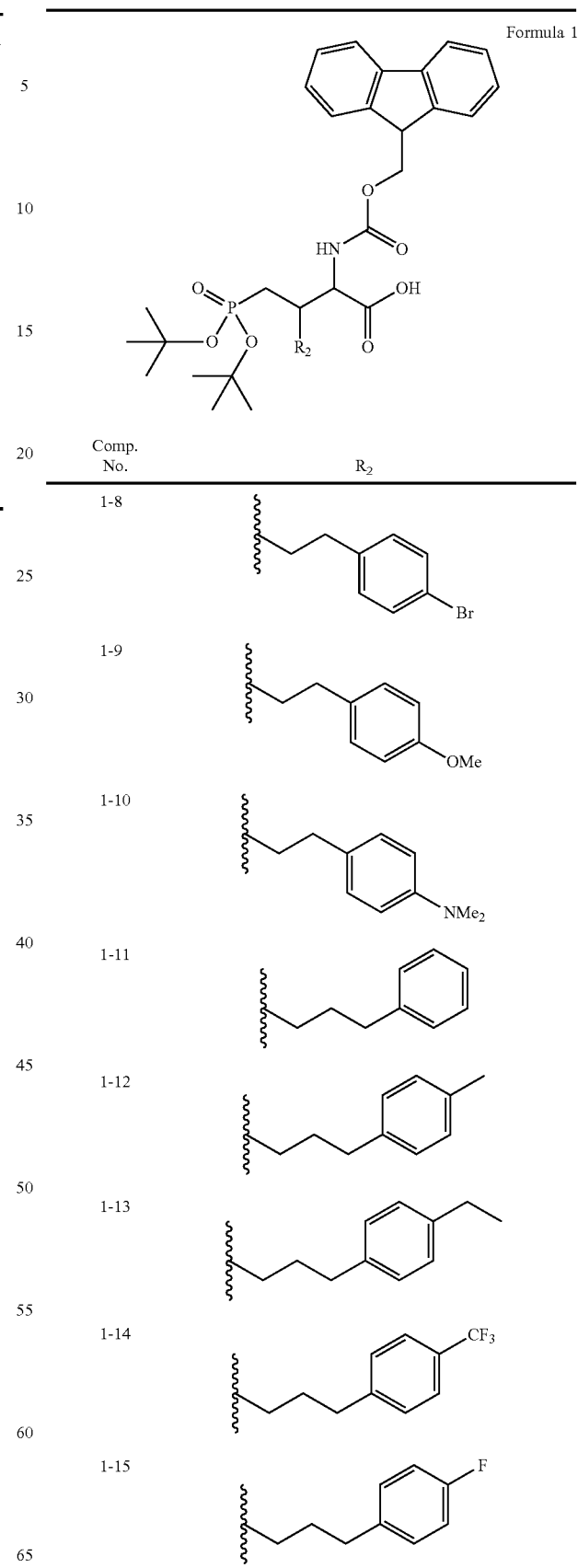

| Comp. No. | R₂ |
|---|---|
| 1-8 | -CH₂CH₂-(4-bromophenyl) |
| 1-9 | -CH₂CH₂-(4-methoxyphenyl) |
| 1-10 | -CH₂CH₂-(4-NMe₂-phenyl) |
| 1-11 | -CH₂CH₂CH₂-phenyl |
| 1-12 | -CH₂CH₂CH₂-(4-methylphenyl) |
| 1-13 | -CH₂CH₂CH₂-(4-ethylphenyl) |
| 1-14 | -CH₂CH₂CH₂-(4-CF₃-phenyl) |
| 1-15 | -CH₂CH₂CH₂-(4-fluorophenyl) |

TABLE 2-continued

Formula 1

| Comp. No. | R₂ |
|---|---|
| 1-16 | 4-chlorophenyl-butyl |
| 1-17 | 4-bromophenyl-butyl |
| 1-18 | 4-methoxyphenyl-butyl |
| 1-19 | 4-(dimethylamino)phenyl-butyl |
| 1-20 | cyclopentylmethyl |
| 1-21 | (1H-pyrazol-1-yl)methyl |
| 1-22 | fluoromethyl |
| 1-23 | 2-fluoroethyl |
| 1-24 | 3-fluoropropyl |
| 1-25 | cyclohexyl |
| 1-26 | (pyridin-4-yl)methyl |
| 1-27 | 2-(pyridin-4-yl)ethyl |
| 1-28 | 3-(pyridin-4-yl)propyl |
| 1-29 | 2,2,2-trifluoroethyl |
| 1-30 | 3,3,3-trifluoropropyl |
| 1-31 | 4,4,4-trifluorobutyl |
| 1-32 | (morpholin-4-yl)methyl |

TABLE 2-continued

Formula 1

| Comp. No. | R₂ |
|---|---|
| 1-33 | indol-1-ylmethyl |
| 1-34 | (5-methylindol-1-yl)methyl |
| 1-35 | (5-ethylindol-1-yl)methyl |
| 1-36 | (5-trifluoromethylindol-1-yl)methyl |
| 1-37 | (5-fluoroindol-1-yl)methyl |
| 1-38 | (5-chloroindol-1-yl)methyl |
| 1-39 | (5-bromoindol-1-yl)methyl |
| 1-40 | (5-methoxyindol-1-yl)methyl |
| 1-41 | (5-dimethylaminoindol-1-yl)methyl |
| 1-42 | 2-(indol-1-yl)ethyl |
| 1-43 | 2-(5-methylindol-1-yl)ethyl |
| 1-44 | 2-(5-ethylindol-1-yl)ethyl |
| 1-45 | 2-(5-trifluoromethylindol-1-yl)ethyl |
| 1-46 | 2-(5-fluoroindol-1-yl)ethyl |
| 1-47 | 2-(5-chloroindol-1-yl)ethyl |
| 1-48 | 2-(5-bromoindol-1-yl)ethyl |

TABLE 2-continued

Formula 1

| Comp. No. | R₂ |
|---|---|
| 1-49 | 3-(5-methoxyindol-1-yl)propyl |
| 1-50 | 3-(5-dimethylaminoindol-1-yl)propyl |
| 1-51 | 4-(indol-1-yl)butyl |
| 1-52 | 4-(5-methylindol-1-yl)butyl |
| 1-53 | 4-(5-ethylindol-1-yl)butyl |
| 1-54 | 4-(5-trifluoromethylindol-1-yl)butyl |
| 1-55 | 4-(5-fluoroindol-1-yl)butyl |
| 1-56 | 4-(5-chloroindol-1-yl)butyl |
| 1-57 | 4-(5-bromoindol-1-yl)butyl |
| 1-58 | 4-(5-methoxyindol-1-yl)butyl |
| 1-59 | 4-(5-dimethylaminoindol-1-yl)butyl |
| 1-60 | ethyl |
| 1-61 | n-propyl |
| 1-62 | isopropyl |
| 1-63 | n-butyl |
| 1-64 | benzyl |
| 1-65 | 4-methylbenzyl |

TABLE 2-continued
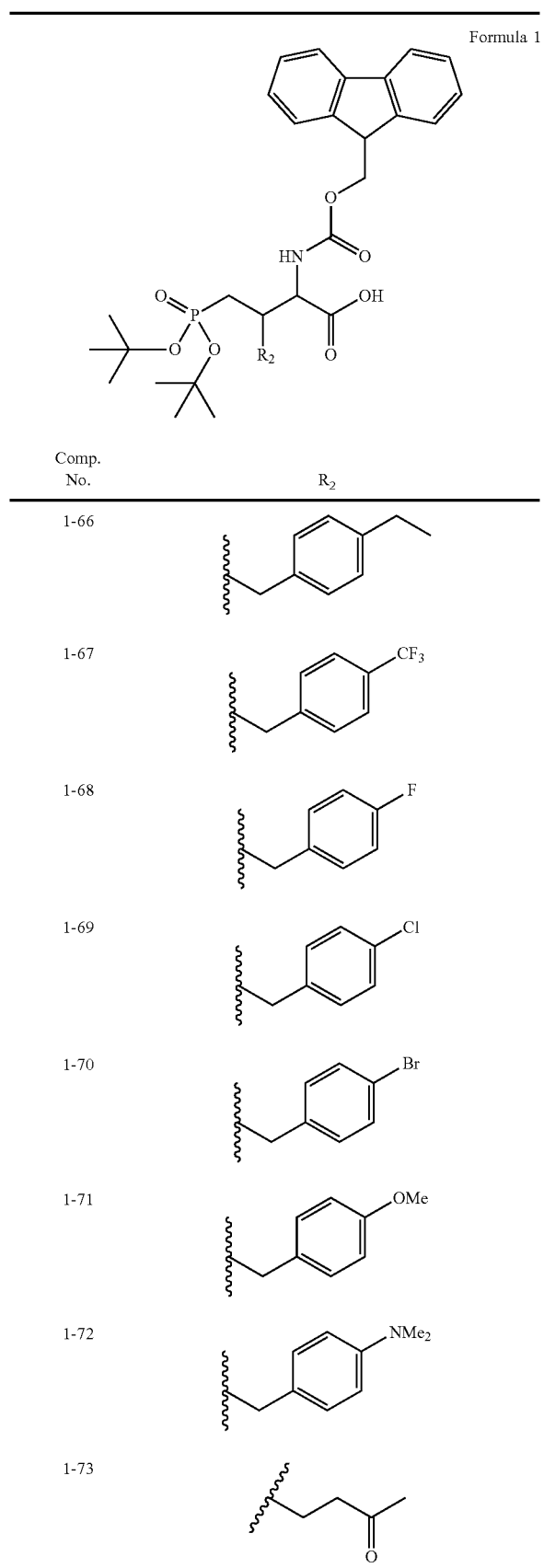
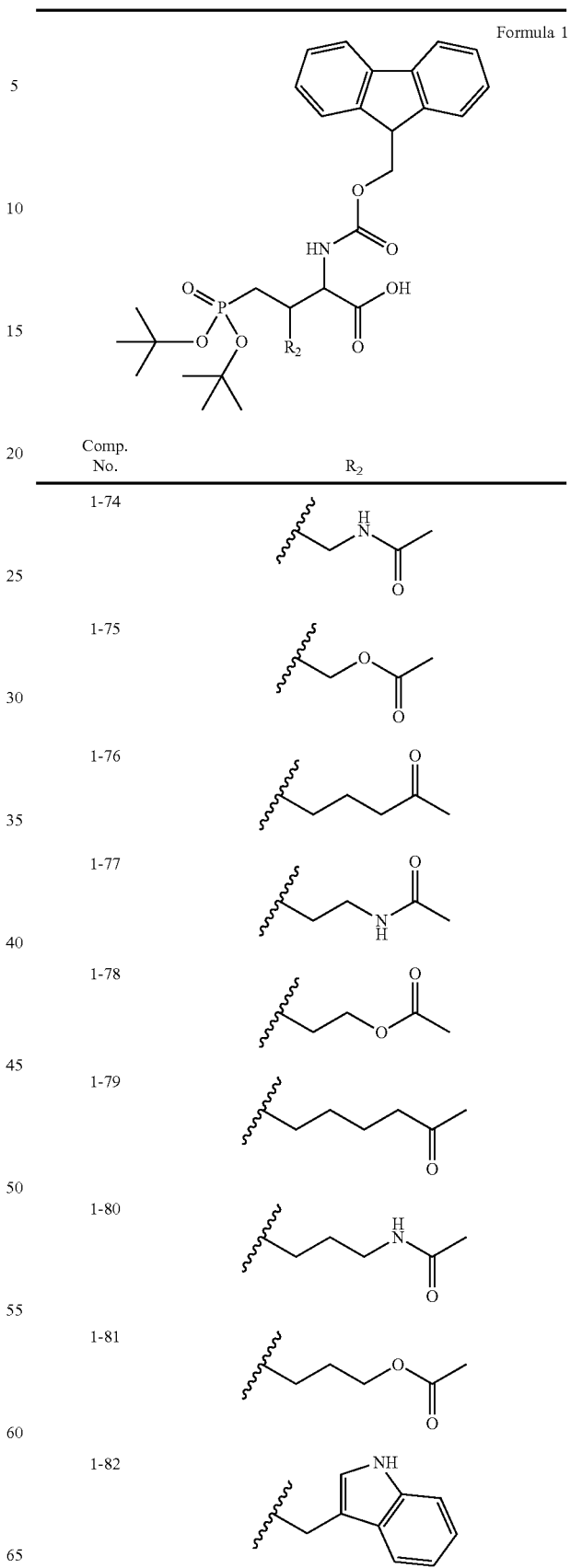

TABLE 2-continued
Formula 1
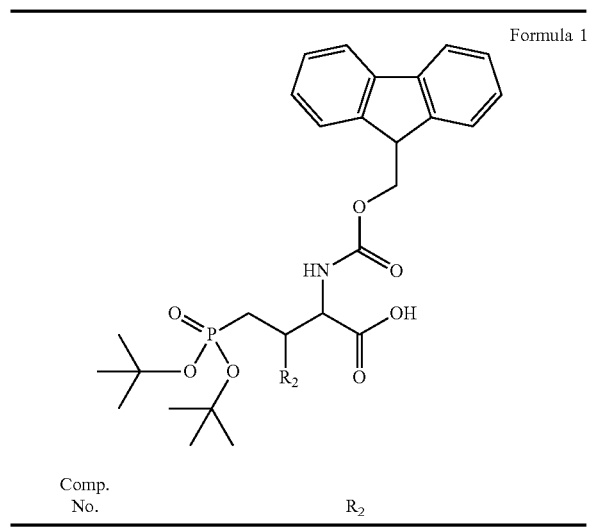
| Comp. No. | $R_2$ |
|---|---|
| 1-83 | (3-indolyl)propyl |
| 1-84 | (3-indolyl)butyl |
| 1-85 | (1-methyl-3-indolyl)propyl |
TABLE 2-continued
Formula 1
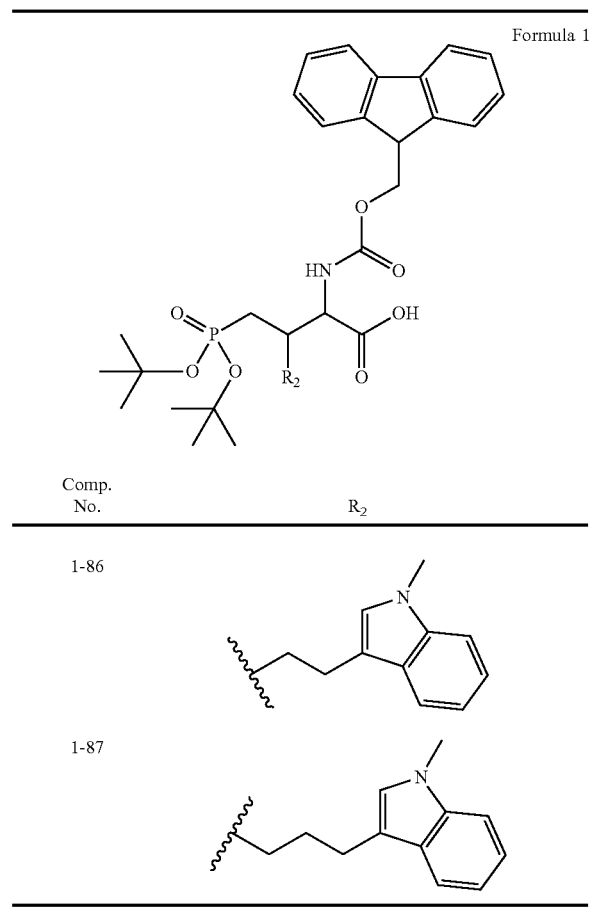
| Comp. No. | $R_2$ |
|---|---|
| 1-86 | (1-methyl-3-indolyl)propyl |
| 1-87 | (1-methyl-3-indolyl)butyl |
Certain exemplified compounds of the description include, but are not limited to, the compounds of Table 3 as follows:
TABLE 3
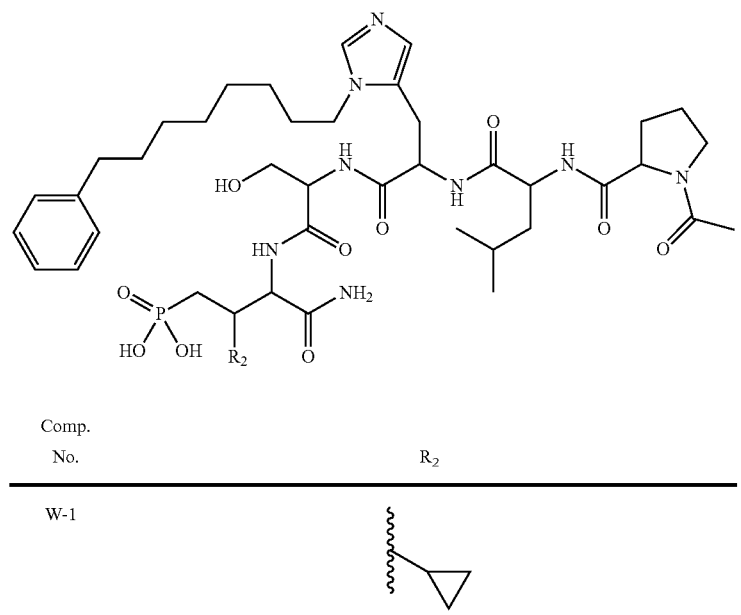
| Comp. No. | $R_2$ |
|---|---|
| W-1 | cyclopropyl |

TABLE 3-continued
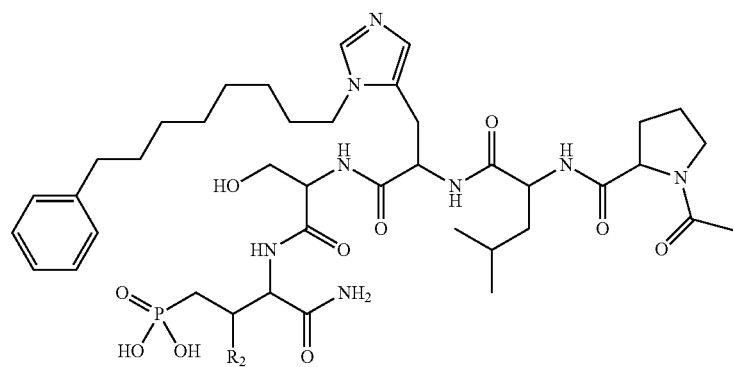
| Comp. No. | R₂ |
|---|---|
| W-2 | 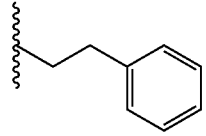 [SMILES: *CCc1ccccc1] |
| W-3 | 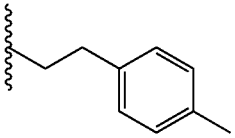 [SMILES: *CCc1ccc(C)cc1] |
| W-4 | 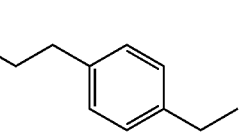 |
| W-5 | 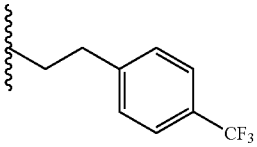 [SMILES: *CCc1ccc(C(F)(F)F)cc1] |
| W-6 | 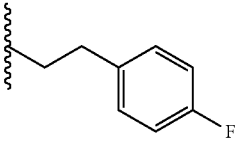 [SMILES: *CCc1ccc(F)cc1] |
| W-7 | 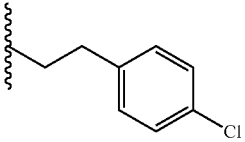 [SMILES: *CCc1ccc(Cl)cc1] |
| W-8 | 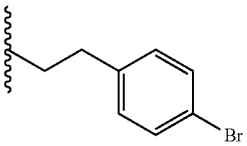 [SMILES: *CCc1ccc(Br)cc1] |

TABLE 3-continued
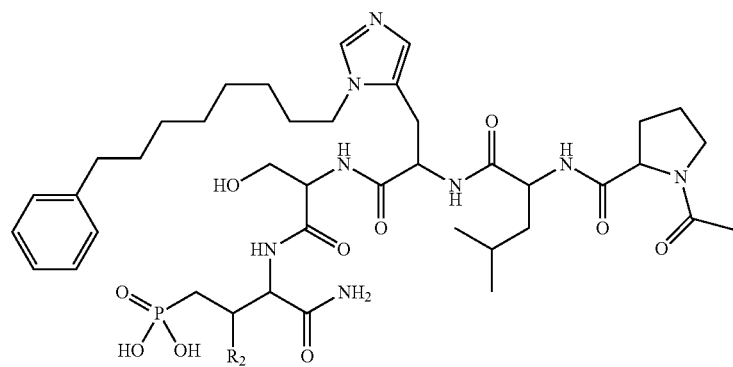
| Comp. No. | R$_2$ |
|---|---|
| W-9 | 4-methoxyphenethyl (–CH$_2$CH$_2$–C$_6$H$_4$–OMe) |
| W-10 | 4-(dimethylamino)phenethyl (–CH$_2$CH$_2$–C$_6$H$_4$–NMe$_2$) |
| W-11 | 3-phenylpropyl |
| W-12 | 3-(4-methylphenyl)propyl |
| W-13 | 3-(4-ethylphenyl)propyl |
| W-14 | 3-(4-trifluoromethylphenyl)propyl |
| W-15 | 3-(4-fluorophenyl)propyl |
| W-16 | 3-(4-chlorophenyl)propyl |

TABLE 3-continued
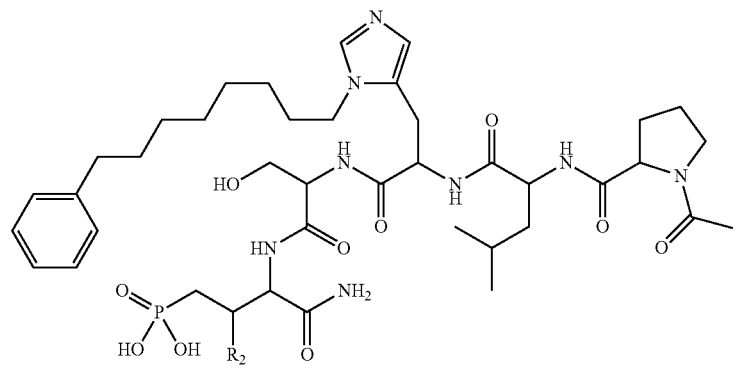
| Comp. No. | R₂ |
|---|---|
| W-17 | 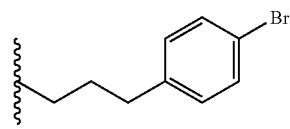 [SMILES: *CCCc1ccc(Br)cc1] |
| W-18 | 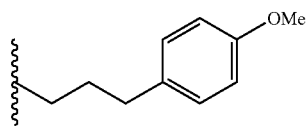 [SMILES: *CCCc1ccc(OC)cc1] |
| W-19 | 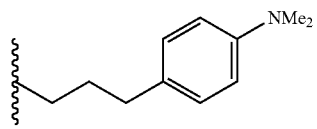 [SMILES: *CCCc1ccc(N(C)C)cc1] |
| W-20 | 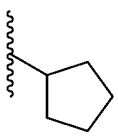 [SMILES: *C1CCCC1] |
| W-21 | 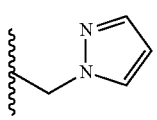 [SMILES: *Cn1cccn1] |
| W-22 | 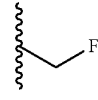 |
| W-23 | 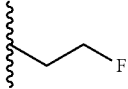 [SMILES: *CCF] |
| W-24 | 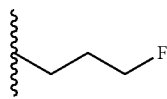 [SMILES: *CCCF] |
| W-25 | 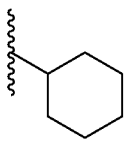 [SMILES: *C1CCCCC1] |

TABLE 3-continued
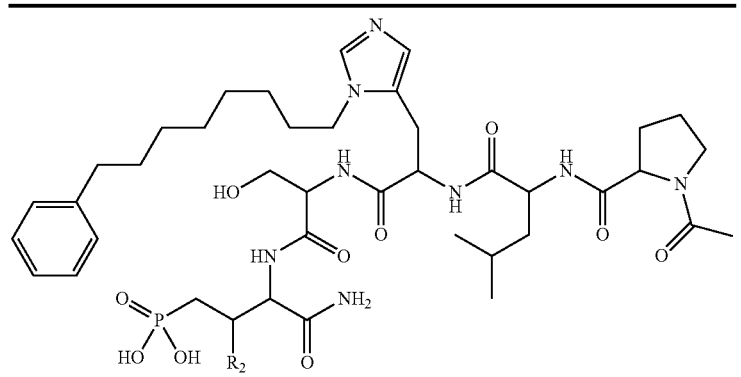
| Comp. No. | R₂ |
|---|---|
| W-26 | 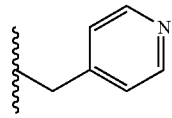 [SMILES: *Cc1ccncc1] |
| W-27 | 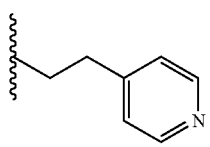 [SMILES: *CCc1ccncc1] |
| W-28 | 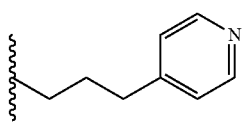 [SMILES: *CCCc1ccncc1] |
| W-29 | 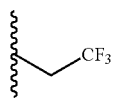 |
| W-30 | 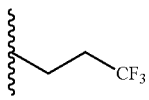 [SMILES: *CCC(F)(F)F] |
| W-31 | 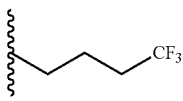 |
| W-32 | 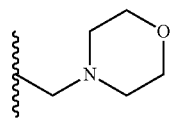 |
| W-33 | 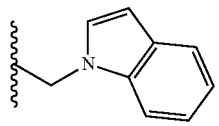 [SMILES: *Cn1ccc2ccccc21] |
| W-34 | 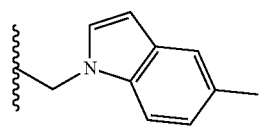 [SMILES: *Cn1ccc2cc(C)ccc21] |

TABLE 3-continued
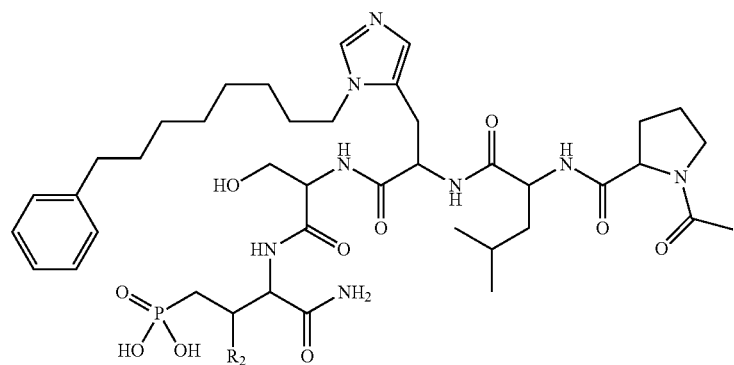
| Comp. No. | R$_2$ |
|---|---|
| W-35 | 5-ethyl-indol-1-ylmethyl |
| W-36 | 5-CF$_3$-indol-1-ylmethyl |
| W-37 | 5-F-indol-1-ylmethyl |
| W-38 | 5-Cl-indol-1-ylmethyl |
| W-39 | 5-Br-indol-1-ylmethyl |
| W-40 | 5-OMe-indol-1-ylmethyl |
| W-41 | 5-NMe$_2$-indol-1-ylmethyl |
| W-42 | 2-(indol-1-yl)ethyl |

TABLE 3-continued
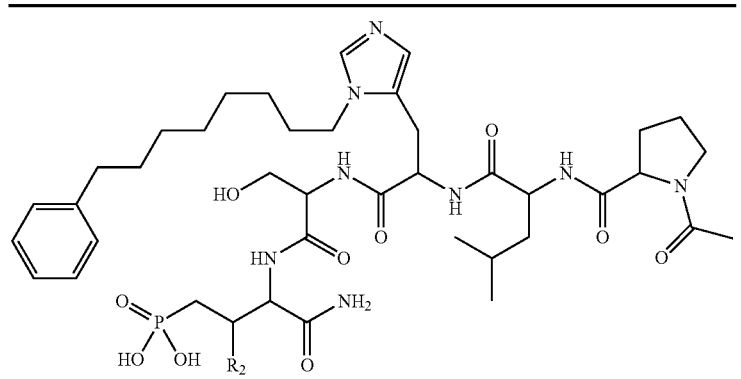
| Comp. No. | R$_2$ |
|---|---|
| W-43 | [indole with 5-methyl, N-propyl linker] |
| W-44 | [indole with 5-ethyl, N-propyl linker] |
| W-45 | [indole with 5-CF$_3$, N-propyl linker] |
| W-46 | [indole with 5-F, N-propyl linker] |
| W-47 | [indole with 5-Cl, N-propyl linker] |
| W-48 | [indole with 5-Br, N-propyl linker] |
| W-49 | [indole with 5-OMe, N-propyl linker] |
| W-50 | [indole with 5-NMe$_2$, N-propyl linker] |

TABLE 3-continued
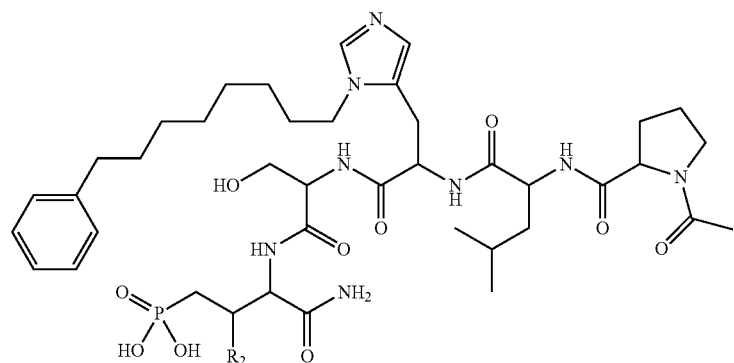
| Comp. No. | R₂ |
|---|---|
| W-51 | indole linked via N with butyl chain |
| W-52 | 5-methyl indole linked via N with butyl chain |
| W-53 | 5-ethyl indole linked via N with butyl chain |
| W-54 | 5-CF₃ indole linked via N with butyl chain |
| W-55 | 5-F indole linked via N with butyl chain |
| W-56 | 5-Cl indole linked via N with butyl chain |
| W-57 | 5-Br indole linked via N with butyl chain |
| W-58 | 5-OMe indole linked via N with butyl chain |

TABLE 3-continued
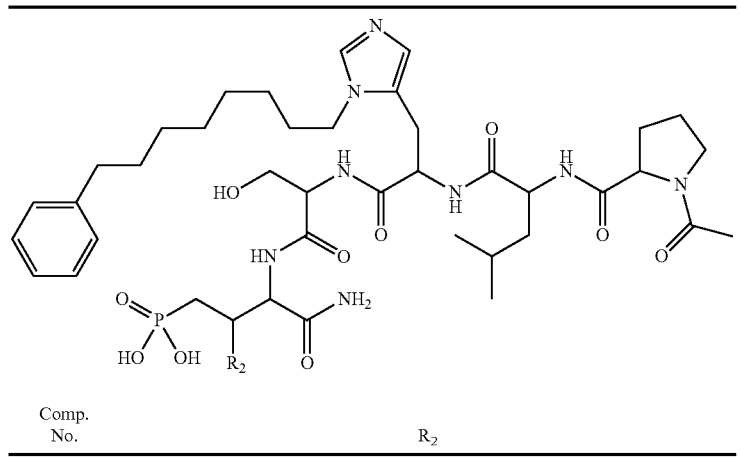
| Comp. No. | R$_2$ |
|---|---|
| W-59 | *-(CH$_2$)$_4$-N(indole-5-NMe$_2$) |
| W-60 | ethyl |
| W-61 | n-propyl (sec attachment) |
| W-62 | isopropyl |
| W-63 | n-butyl (sec attachment) |
| W-64 | methyl |
| W-65 | H |
| W-66 | benzyl |
| W-67 | 4-methylbenzyl |
| W-68 | 4-ethylbenzyl |

TABLE 3-continued
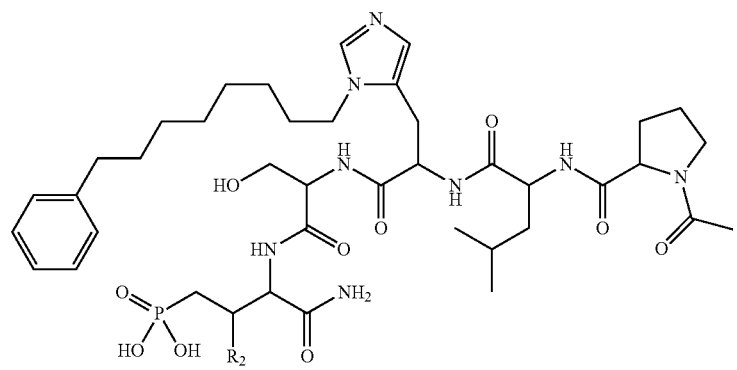
| Comp. No. | R$_2$ |
|---|---|
| W-69 | 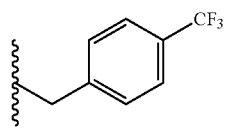 [SMILES: *Cc1ccc(C(F)(F)F)cc1] |
| W-70 | 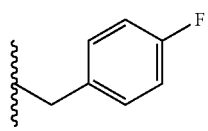 [SMILES: *Cc1ccc(F)cc1] |
| W-71 | 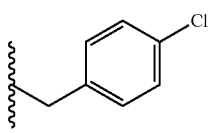 [SMILES: *Cc1ccc(Cl)cc1] |
| W-72 | 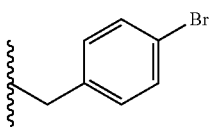 [SMILES: *Cc1ccc(Br)cc1] |
| W-73 | 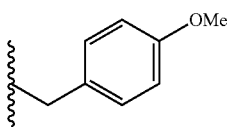 [SMILES: *Cc1ccc(OC)cc1] |
| W-74 | 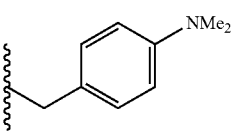 [SMILES: *Cc1ccc(N(C)C)cc1] |
| W-75 | 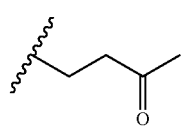 [SMILES: *CCC(C)=O] |
| W-76 | 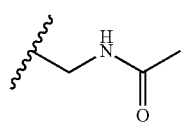 |

TABLE 3-continued
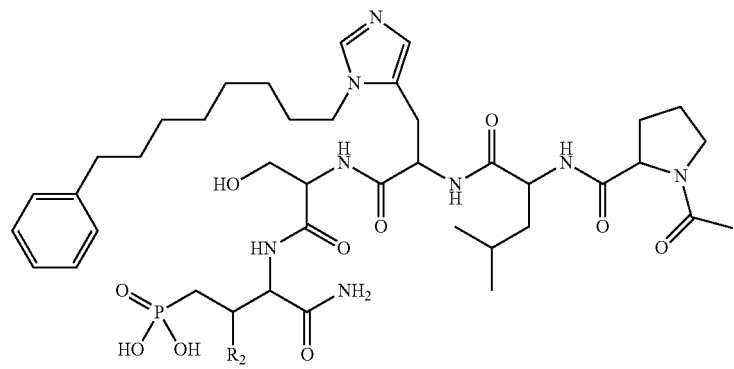
| Comp. No. | R$_2$ |
|---|---|
| W-77 | ⸺CH$_2$OC(O)CH$_3$ |
| W-78 | ⸺(CH$_2$)$_3$C(O)CH$_3$ |
| W-79 | ⸺(CH$_2$)$_2$NHC(O)CH$_3$ |
| W-80 | ⸺(CH$_2$)$_2$OC(O)CH$_3$ |
| W-81 | ⸺(CH$_2$)$_4$C(O)CH$_3$ |
| W-82 | ⸺(CH$_2$)$_3$NHC(O)CH$_3$ |
| W-83 | ⸺(CH$_2$)$_3$OC(O)CH$_3$ |
| W-84 | ⸺CH$_2$-(indol-3-yl) |
| W-85 | ⸺(CH$_2$)$_2$-(indol-3-yl) |

TABLE 3-continued

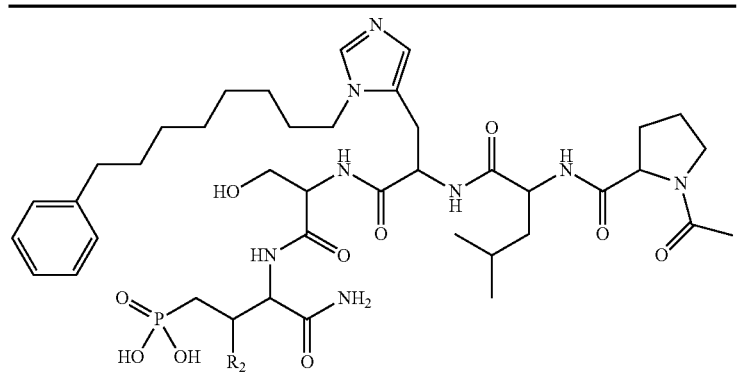

| Comp. No. | R₂ |
|---|---|
| W-86 | 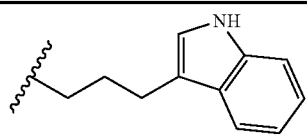 |
| W-87 | 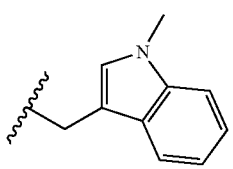 [SMILES: *Cc1cn(C)c2ccccc12] |
| W-88 | 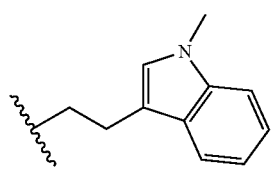 [SMILES: *CCc1cn(C)c2ccccc12] |
| W-89 | 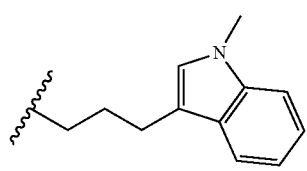 [SMILES: *CCCc1cn(C)c2ccccc12] |

In another aspect, the description relates to a pharmaceutical composition comprising any compound of the description in a pharmaceutically acceptable carrier.

In another aspect, the description provides a method for the prevention, amelioration, or treatment of a subject for a hyperproliferative disorder comprising administration of a composition comprising any of the compounds according to the description.

In certain embodiments, the method further includes identification of a subject suffering from or suspected of suffering from a hyperproliferative disorder.

In certain embodiments, the method further comprises monitoring the subject for prevention, amelioration, or treatment of a hyperproliferative disorder. In certain embodiments, the hyperproliferative disorder comprises cancer. In certain embodiments, the cancer is selected from the group consisting of Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-Small Cell Lung Cancer, Small Cell Lung Cancer, Lymphoma, Medulloblastoma, Melanoma, Pancreatic Cancer, Prostate Cancer, Renal Cancer, Rectal Cancer, and Thyroid Cancer.

In another aspect, the description provides a kit comprising at least one compound of the description (e.g., at least one PBD ligand or compound, at least one cyclic PBD ligand, at least one bivalent ligand, at least one bivalent compound, or a combination thereof), and instructions for use.

In certain aspect, the description provides a chemical library including two or more compounds of the description.

In another embodiment, the description provides a process to prepare of a compound of Formula 2, or salt, solvate, or hydrate thereof:

Formula 2

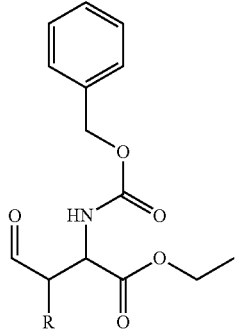

the process comprising:
reacting

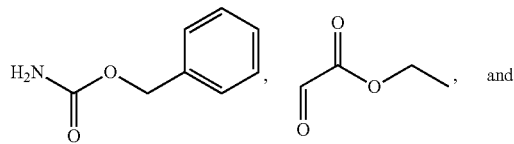 and

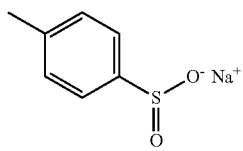

to afford compound 3,

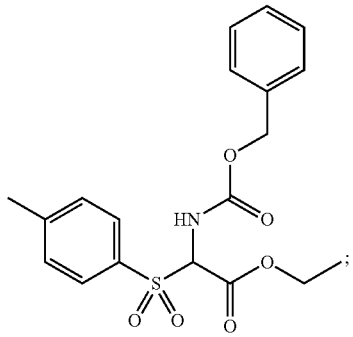 [SMILES: CCOC(=O)C(NC(=O)OCc1ccccc1)S(=O)(=O)c1ccc(C)cc1]

and
reacting compound 3,

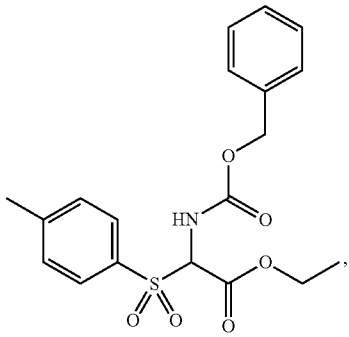 [SMILES: CCOC(=O)C(NC(=O)OCc1ccccc1)S(=O)(=O)c1ccc(C)cc1]

with a compound of Formula, to

afford a compound of Formula 2,

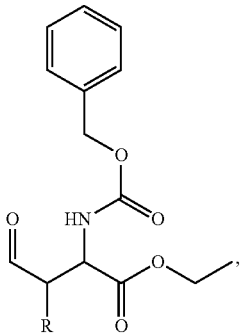

wherein R is optionally substituted cycloalkyl, optionally substituted phenylethyl, optionally substituted phenylpropyl, optionally substituted heteroarylalkyl, haloalkyl, optionally substituted morpholinomethyl,

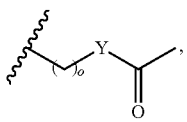

or optionally substituted indolylalkyl; Y is $CH_2$, NH, or O; and o is 1-3. In another aspect, R is

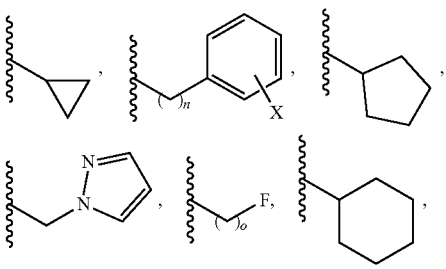

-continued

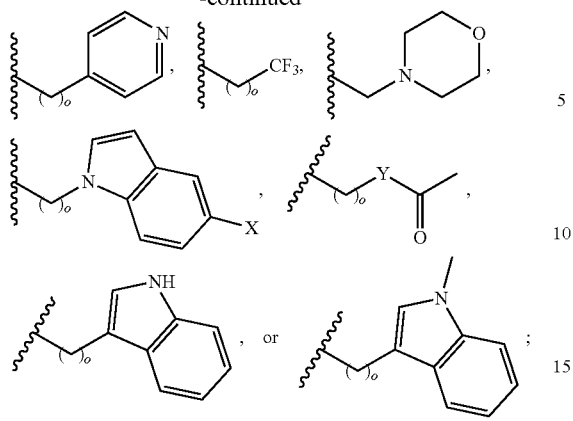

n is 1-3; each o is independently 1-3; each X is independently H, Me, Et, $CF_3$, F, Cl, Br, OMe, or $N(Me)_2$; and Y is $CH_2$, NH, or O. In another aspect, the compound of Formula 2 is any of compounds 2-1 to 2-74.

In another embodiment, the description provides a process to prepare of a compound of Formula 1, or salt, solvate, or hydrate thereof:

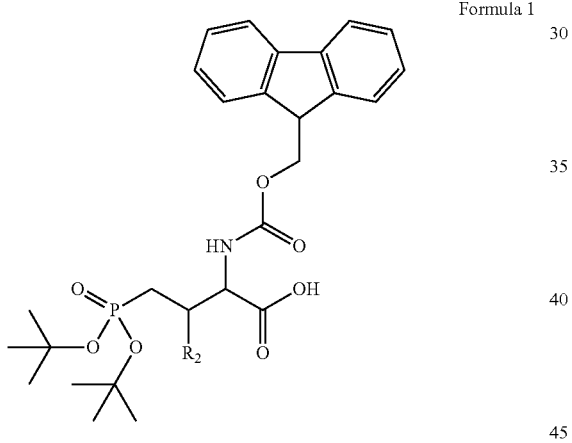

Formula 1 the process comprising:
  phosphorylating a compound of Formula 3,

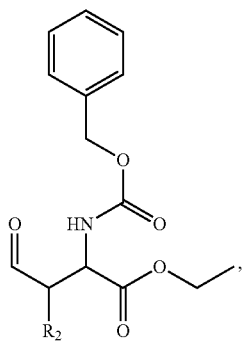

with di-tert-butylphosphite to afford a compound of Formula 4,

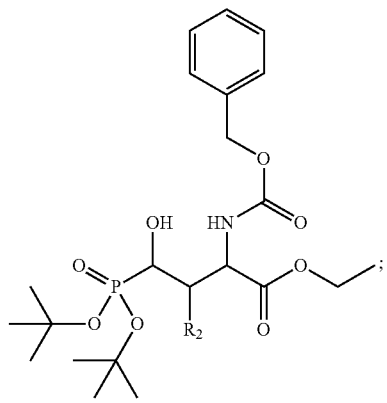

activating the alcohol within the compound of Formula 4,

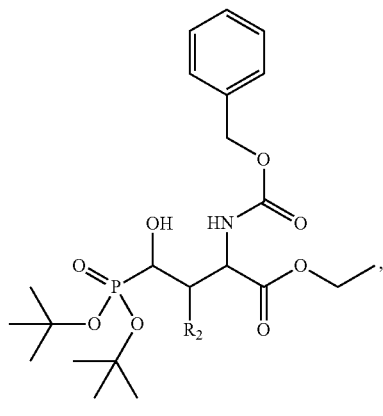

with O-phenyl thiochloroformate to afford a compound of Formula 5,

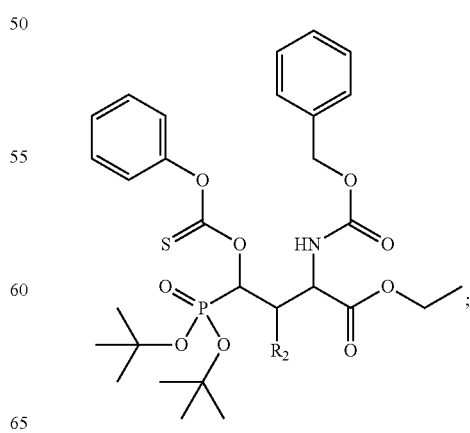

reducing a compound of Formula 5,
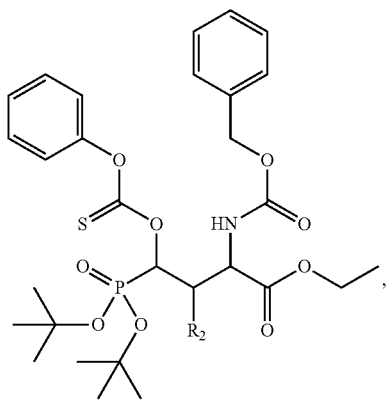
to afford a compound of Formula
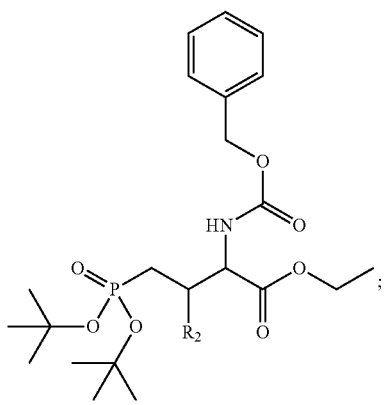
hydrolyzing the ethyl ester of a compound of Formula 6,
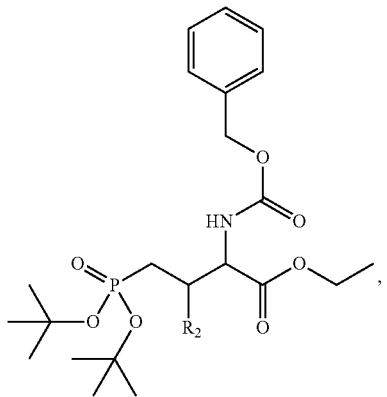
to afford a compound of Formula 7,
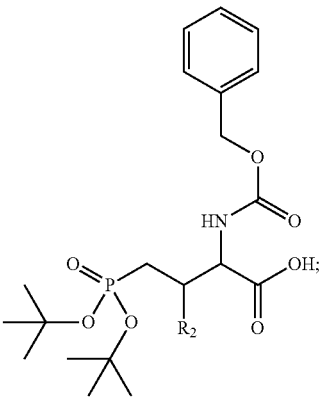
deprotecting the benzyl carbamate of a compound of Formula 7,
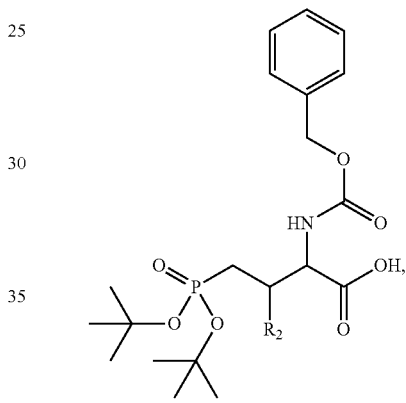
to afford a compound of Formula 8,
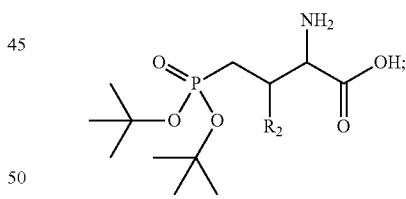
and
protecting the amino functionality of a compound of Formula 8,
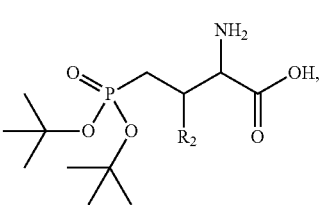

to afford a compound of Formula 1,

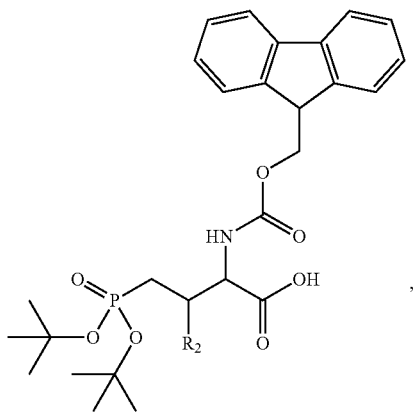

wherein $R_2$ is optionally substituted $C_2$-$C_4$ alkyl, optionally substituted cycloalkyl, optionally substituted aralkyl, optionally substituted heteroarylalkyl, haloalkyl, optionally substituted morpholinomethyl,

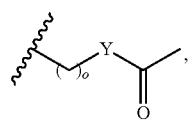

or optionally substituted indolylalkyl; Y is $CH_2$, NH, or O; and o is 1-3. In another aspect, $R_2$ is Me, Et, Pr, i-Pr, Bu,

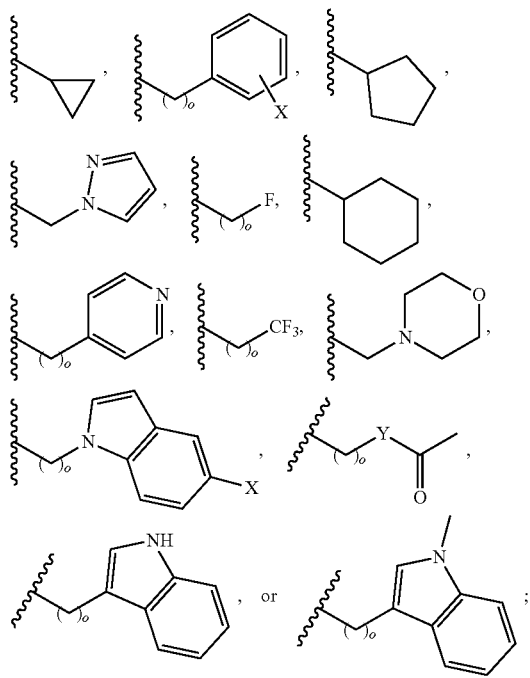

each o is independently 1-3; each X is independently H, Me, Et, $CF_3$, F, Cl, Br, OMe, or $N(Me)_2$; and Y is $CH_2$, NH, or O. In another aspect, the compound of Formula 1 is any of compounds 1-1 to 1-87.

In another embodiment, the description provides a process to prepare a compound of Formula 4, or salt, solvate, or hydrate thereof:

(Formula 4)

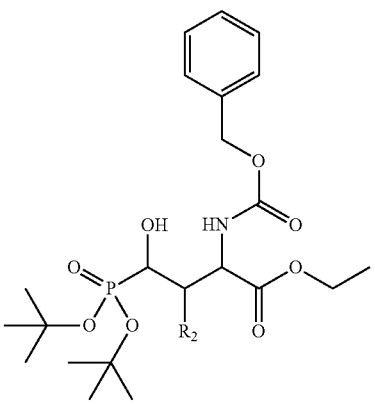

the process comprising:
phosphorylating a compound of Formula 3,

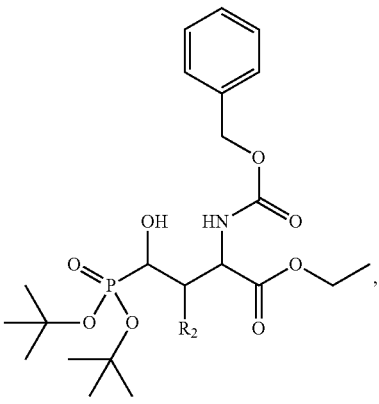

with di-tert-butylphosphite to afford a compound of Formula 4,

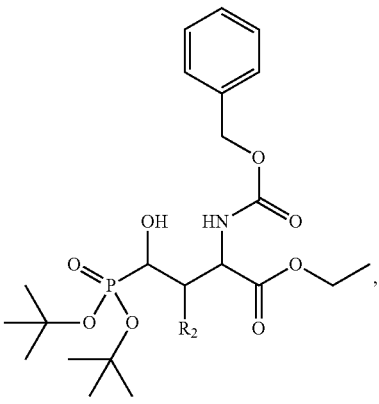

wherein $R_2$ is optionally substituted $C_2$-$C_4$ alkyl, optionally substituted cycloalkyl, optionally substituted aralkyl, optionally substituted heteroarylalkyl, haloalkyl, optionally substituted morpholinomethyl,

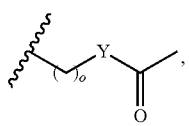

or optionally substituted indolylalkyl; Y is CH$_2$, NH, or O; and o is 1-3.

In certain embodiments, the method further comprises the step of activating the alcohol within the compound of Formula 4,

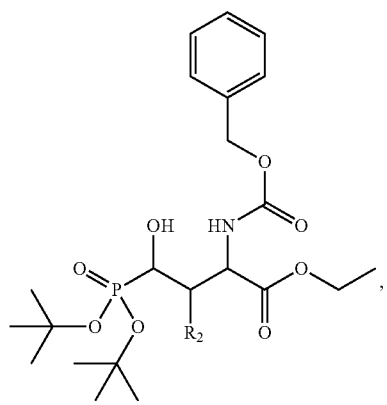

with O-phenyl thiochloroformate to afford a compound of Formula 5,

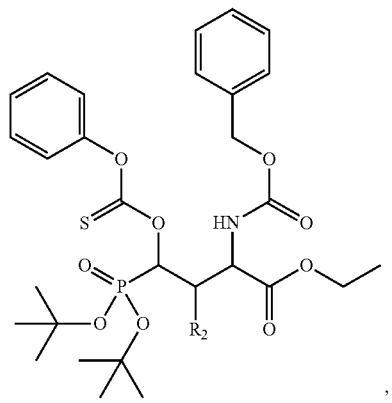

wherein R$_2$ is as above.

In certain additional embodiments, the method further comprises the step of reducing a compound of Formula 5,

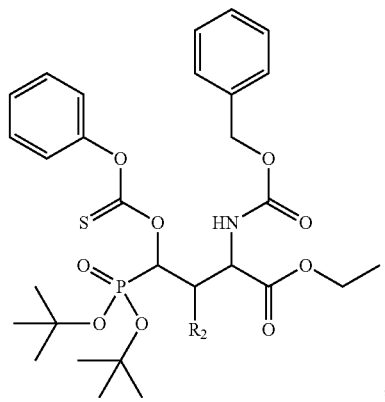

to afford a compound of Formula 6,

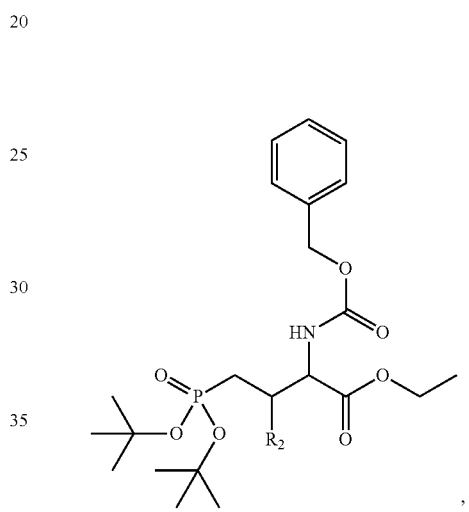

wherein R$_2$ is as above.

In an additional embodiment, the method further comprises the step of hydrolyzing the ethyl ester of a compound of Formula 6,

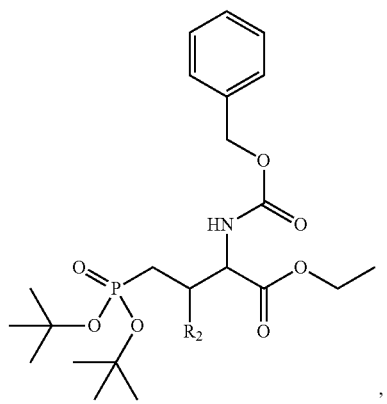

to afford a compound of Formula 7,

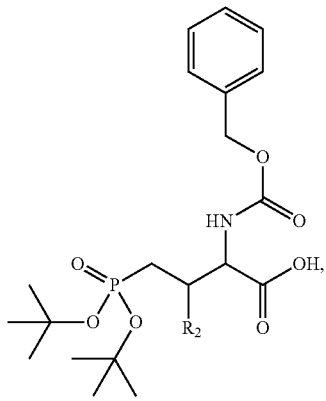

wherein R$_2$ is as above.

In another embodiment, the method further comprises the step of deprotecting the benzyl carbamate of a compound of Formula 7,

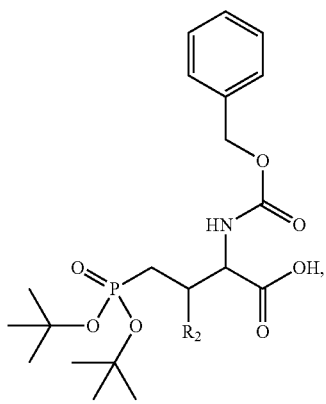

to afford a compound of Formula 8,

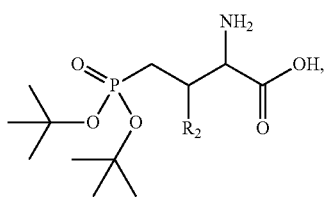

wherein R$_2$ is as above.

In certain embodiments, the method further comprises the step of protecting the amino functionality of a compound of Formula 8,

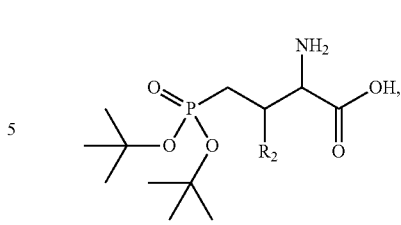

to afford a compound of Formula 1,

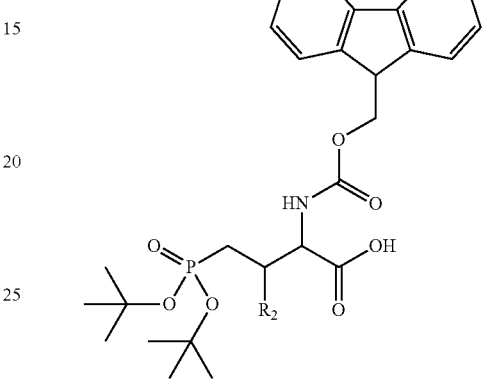

wherein R$_2$ is as above.

In another embodiment, the description provides a process to prepare of a compound of Formula IIa, or salt, solvate, or hydrate thereof:

Formula IIa

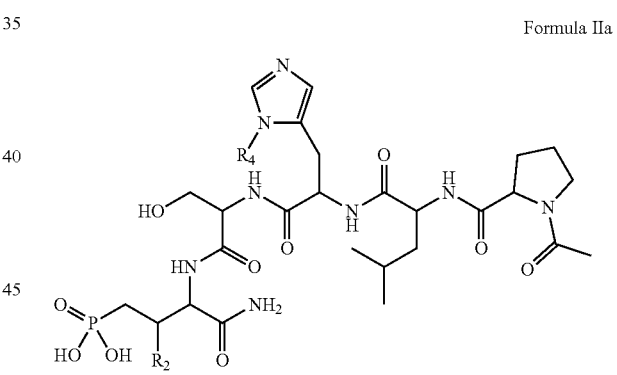

the process comprising:
phosphorylating a compound of Formula 9,

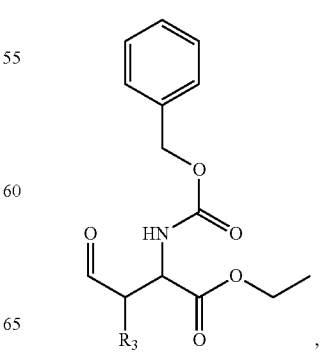

with di-tert-butylphosphite to afford a compound of Formula 10,
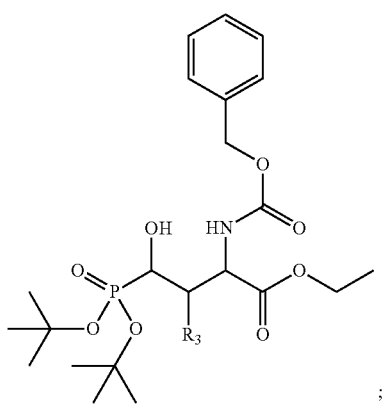
activating the alcohol within the compound of Formula 10,
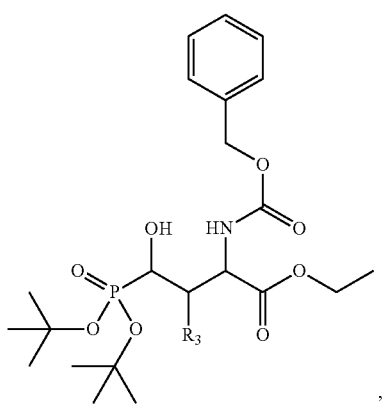
with O-phenyl thiochloroformate to afford a compound of Formula 11,
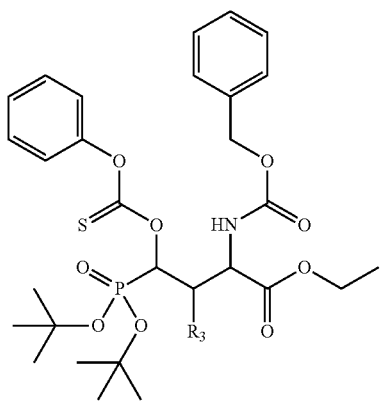
reducing a compound of Formula 11,
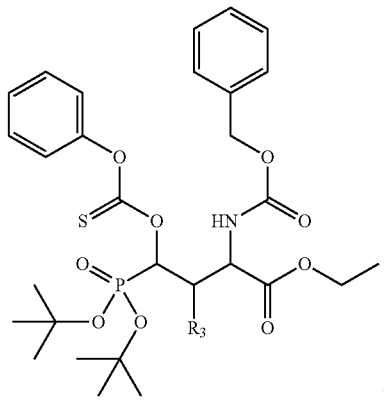
to afford a compound of Formula 12,
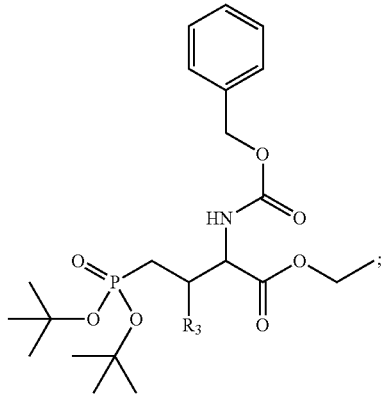
hydrolyzing the ethyl ester of a compound of Formula 12,
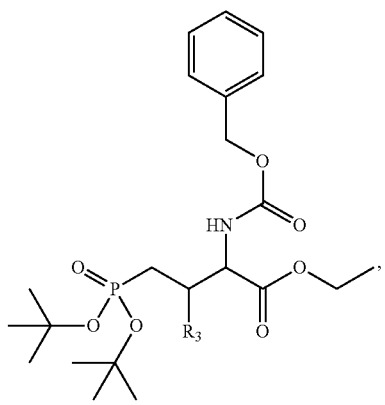

to afford a compound of Formula 13,

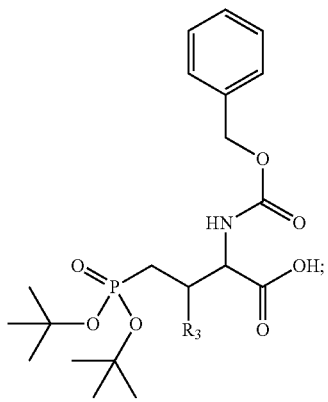

deprotecting the benzyl carbamate of a compound of Formula 13,

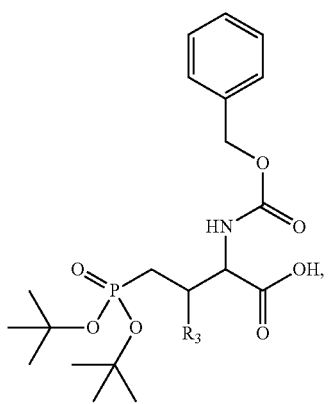

to afford a compound of Formula 14,

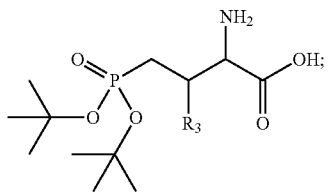

and protecting the amino functionality of a compound of Formula 14,

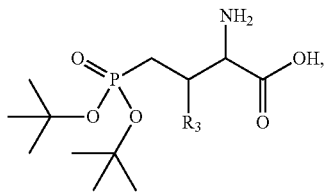

to afford a compound of Formula 15,

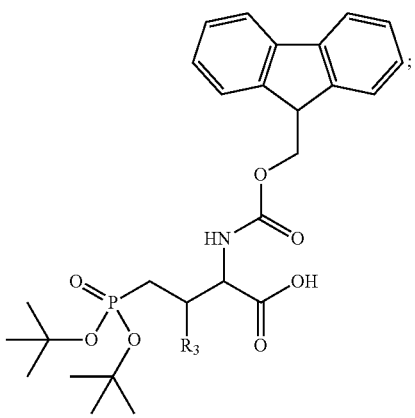

coupling an amino acid, analog or derivative thereof to the compound of Formula 15;

wherein $R_3$ is optionally substituted $C_1$-$C_4$ alkyl, optionally substituted cycloalkyl, optionally substituted aralkyl, optionally substituted heteroarylalkyl, haloalkyl, optionally substituted morpholinomethyl,

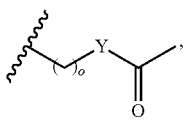

or optionally substituted indolylalkyl; $R_4$ is optionally substituted aralkyl; Y is $CH_2$, NH, or O; and o is 1-3. In another aspect, $R_2$ is Me, Et, Pr, i-Pr, Bu,

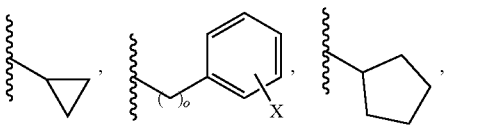

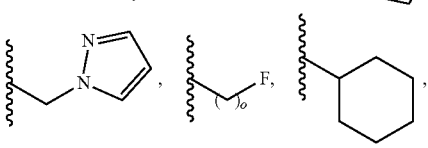

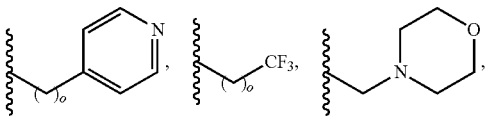

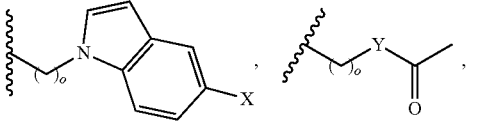

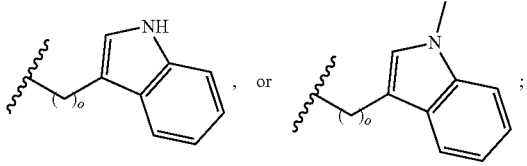

each o is independently 1-3; each X is independently H, Me, Et, $CF_3$, F, Cl, Br, OMe, or $N(Me)_2$; and Y is $CH_2$, NH, or O. In another aspect, R$_4$ is —(CH$_2$)$_8$-Ph. In another aspect, R$_2$ is Me, Et, Pr, i-Pr, Bu,

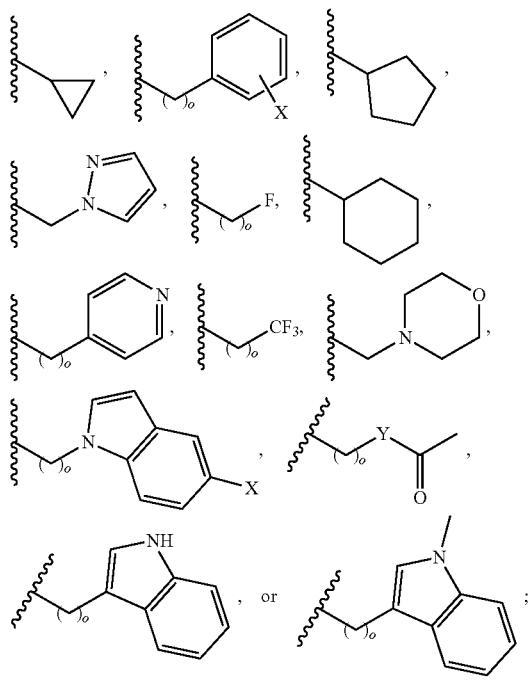

each o is independently 1-3; each X is independently H, Me, Et, CF$_3$, F, Cl, Br, OMe, or N(Me)$_2$; Y is CH$_2$, NH, or O; and R$_4$ is —(CH$_2$)$_8$-Ph. In another aspect the compound of Formula IIa is one of W-1 to W-89.

In certain aspects, the description relates to a peptide derivative prepared from any method described herein, including the methods described herein.

The description also provides an isotopically labeled compound of any of the formulae delineated herein. Such compounds have one or more isotope atoms which may or may not be radioactive (e.g., $^3$H, $^2$H, $^{14}$C, $^{13}$C, $^{35}$S, $^{32}$P, $^{125}$I, and $^{131}$I) introduced into the compound. Such compounds are useful for drug metabolism studies and diagnostics, as well as therapeutic applications.

The structures of the compounds of the description may include asymmetric carbon atoms. Accordingly, the isomers arising from such asymmetry (e.g., racemates, racemic mixtures, single enantiomers, individual diastereomers, diastereomeric mixtures) are included within the scope of this description, unless indicated otherwise. Other stereoisomeric forms may be defined, in terms of absolute stereochemistry, as (R)- or (S)-, or as (D)- or (L)- for amino acids.

Such isomers can be obtained in substantially pure form by classical separation techniques and/or by stereochemically controlled synthesis. For example, optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this description may also be represented in multiple tautomeric forms, in such instances, the description expressly includes all tautomeric forms of the compounds described herein (e.g., alkylation of a ring system may result in alkylation at multiple sites, the description expressly includes all such reaction products).

In addition, some of the compounds of this description may have one or more double or triple bonds. Such compounds can occur as cis- or trans- or E- or Z- double isomeric forms, which are included within the scope of this description. Further, the configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

All crystal forms of the compounds described herein are also expressly included in the present description.

A compound of the description can be prepared as a pharmaceutically acceptable acid addition salt by reacting the free base form of the compound with a pharmaceutically acceptable inorganic or organic acid. Alternatively, a pharmaceutically acceptable base addition salt of a compound of the description can be prepared by reacting the free acid form of the compound with a pharmaceutically acceptable inorganic or organic base.

Alternatively, the salt forms of the compounds of the description can be prepared using salts of the starting materials or intermediates.

The free acid or free base forms of the compounds of the description can be prepared from the corresponding base addition salt or acid addition salt from, respectively. For example, a compound of the description in an acid addition salt form can be converted to the corresponding free base by treating with a suitable base (e.g., ammonium hydroxide solution, sodium hydroxide, and the like). A compound of the description in a base addition salt form can be converted to the corresponding free acid by treating with a suitable acid (e.g., hydrochloric acid, etc.).

Prodrug derivatives of the compounds of the description can be prepared by methods known to those of ordinary skill in the art (e.g., for further details see Saulnier et al., (1994), *Bioorganic and Medicinal Chemistry Letters*, Vol. 4, p. 1985). For example, appropriate prodrugs can be prepared by reacting a non-derivatized compound of the description with a suitable carbamylating agent (e.g., 1,1-acyloxyalkyl-carbanochloridate, para-nitrophenyl carbonate, or the like).

Protected derivatives of the compounds of the description can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present description can be conveniently prepared, or formed during the process of the description, as solvates (e.g., hydrates). Hydrates of compounds of the present description can be conveniently prepared by recrystallization from an aqueous/organic solvent mixture, using organic solvents such as dioxane, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present description. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this description may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the description are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.The recitation of an embodiment for a variable herein includes that embodiment as any single embodiment or in combination with any other embodiments or portions thereof.

Bivalent ligands as described herein must be capable of simultaneously binding to both KD and PBD domains. While high affinity ligands for the individual domains are known, to date there have been no structures (either crystal or solution) of full-length Plk1, which would indicate the relative orientation of the two domains.

Design of the Compounds of the Description

The description provides design and/or synthesis of a novel class of compounds that act as kinase directed inhibitors, such as high affinity macrocyclic Plk1 inhibitors and high affinity bivalent compound Plk1 inhibitors. It is contemplated that the novel class of compounds down-regulate Plk1 function and Plk1 PBD-binding antagonists, the high affinity bivalent compounds of the present disclosure down-regulate Plk1 function with high potency, and the high affinity macrocyclic Plk1 inhibitors down-regulate Plk1 function with high potency and desirable pharmacokinetic properties, each of which may serve as anticancer agents. The description also provides methods of use of the compounds of the present disclosure. In certain embodiments, the compounds of the present disclosure achieve enhanced efficacy in biochemical and/or cellular studies.

The polo-like kinase 1 (Plk1) represents a new target for anticancer therapeutic development. Plk1 contains a C-terminal polo-box domain (PBD) that recognizes phospho-Ser (pS)/phospho-Thr (pT)-containing motifs, which recruits Plk1 to specific sub-cellular sites. This event is critical for proper Plk1 function. Another domain is N-terminal Kinase Domain (KD). Certain compounds of the present disclosure, such as the bi-valent compounds, will simultaneously bind to both the KD and PBD regions of the protein and thereby provide target selectivity greater than agents interacting with a single domain.

Over-expression of Plk1 induces neoplastic transformation of human cells, whereas interference with Plk1 function induces apoptosis in tumor cells but not in normal cells. Moreover, Plk1 over-expression is associated with aggressive disease stage and poor patient survival in various types of cancers (Elia et al., *Modular Protein Domains*, 2005, 163-179). Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1 (Strebhardt, K. et al., Nat. Rev. Cancer 6, 321-330. (2006)).

Over-expression of Plk1 induces neoplastic transformation of human cells, whereas interference with Plk1 function induces apoptosis in tumor cells but not in normal cells. Moreover, Plk1 over-expression is associated with aggressive disease stage and poor patient survival in various types of cancers (Elia et al., *Modular Protein Domains*, 2005, 163-179). Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1 (Strebhardt, K. et al., Nat. Rev. Cancer 6, 321-330. (2006)). However, largely because of the structural similarities among the catalytic domains of all Plks and other related kinases, it has been difficult to generate Plk1-specific inhibitors. Thus, since the non-catalytic PBD is found only in the members of the Plk subfamily, development of novel inhibitors that target the PBD of Plk1 may prove to be an alternative strategy for selectively targeting Plk1.

While conducting studies on the interaction between Plk1 and its physiological binding target PBIP1, a minimal phosphopeptide derived from the Thr78 region of PBIP1 was identified that exhibits a high level of affinity and specificity for the Plk1 PBD. Testing of a non-hydrolyzable p-T78 mimetic peptide demonstrated that inhibition of the Plk1 PBD function results in a chromosome congression defect that leads to mitotic arrest and apoptotic cell death, as observed previously in cells expressing a dominant-negative PBD (Seong, Y. S. et al. J. Biol. Chem. 277, 32282-32293 (2002); & Hanisch, A. et al., Mol. Biol. Cell 17, 448-459 (2006)). Since interference with Plk1 function induces apoptosis in most tumor cells but not in normal cells, these findings demonstrate that inhibition of the PBD function is sufficient to interfere with cell proliferation activity of tumor cells.

It has been demonstrated that SpT-dependent electrostatic interactions with His538 and Lys540 residues are critical for the interaction between optimal peptides (PMQSpTPL and MQSpTPL) and the Plk1 PBD12,13. Comparative in vitro binding studies and analyses of the phosphopeptide-binding pockets of PBDS+G and PBDS with PBDPL, PBDPP, and PBDLH revealed that, in addition to the SpT motif of the phosphopeptide that acts as a high affinity anchor, the N-terminal residues provide additional binding affinity and specificity to the Plk1 PBD through three distinct interactions. First, the polar contact between the carbonyl oxygen N-terminal to the Leu-3 of PLHSpT or LHSpTA and the guanidinium moiety of Arg516 of Plk1 PBD provides a molecular basis for a high affinity and specificity interaction. Second, docking of the N-terminal Pro-4 side chain into the pocket generated by the surrounding Trp414 and Phe535 offers additional affinity and likely another level of specificity to the interaction. Notably, the PBDs from both Plk2 and Plk3 possess Lys and Tyr residues at positions analogous to the Plk1 Arg516 and Phe535 residues, respectively, in Plk1, and, as a consequence, may fail to generate as favorable an environment to accommodate the N-terminal Pro residue. Third, peptide pull-down assays demonstrate that the His-2 residue adds another layer of Plk1 PBD specificity.

Besides each amino acid residue of the p-T78 peptide involved in defining the Plk1 binding affinity and specificity, the positions of the phosphopeptide and glycerol in the pocket, along with the network of water molecules that mediate contacts between the phosphopeptide and the PBD, suggest that both the glycerol and the network of water molecules surrounding the phosphopeptide could be important elements of the PBD recognition by phosphopeptides. Furthermore, the structures of the $PBD^{S+G}$, $PBD^{S}$, and $PBD^{PL}$ were remarkably similar, hinting that the other glycerol molecule and the sulfate anion occupying the phosphopeptide-binding cleft may substitute the role of the SpT dipeptide.

The collected data demonstrate that the Plk1 PBD-binding pocket accommodates (i) the core SpT motif, (ii) the N-terminal hydrophobic residue, (iii) glycerol, and (iv) a network of contacting water molecules. A combination of some or all of these four elements could be potentially used for targeted drug design. Better understanding of the PBD interaction as well as further isolation and development of PBD-binding agents would greatly facilitate the discovery of a new class of Plk1-specific anti-cancer therapeutic agents.

In an aspect, the description provides a peptido-mimetic bivalent ligand comprising or according to the structure:

KD-IDL-PBD        [I]

wherein:
KD is a kinase domain ligand;
IDL is a flexible interdomain linker comprising a bond or a chemical group; and
PBD is a polo-box domain ligand.

In certain embodiments, the description discloses the bivalent ligand, wherein PBD ligand has the structure:

Formula IIb

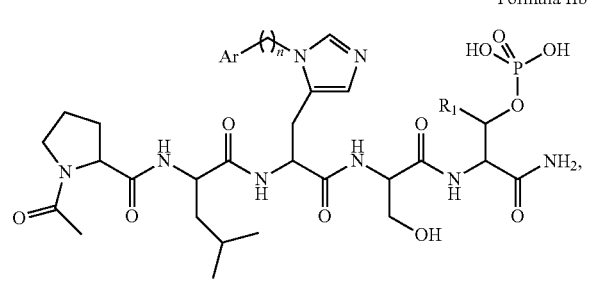

wherein:
n is an integer from 1-20;
$R_1$ is H, optionally substituted alkyl, optionally substituted cycloalkyl, optionally substituted aralkyl, optionally substituted heteroarylalkyl, haloalkyl, optionally substituted morpholinomethyl,

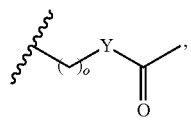

or optionally substituted indolylalkyl;
Y is $CH_2$, NH, or O; and
Ar is an optionally substituted aryl, an optionally substituted heteroaryl, an optionally substituted aralkyl; an optionally substituted heteroarylalkyl,
or a pharmaceutically acceptable salt, solvate, hydrate, or stereoisomer thereof.

In certain embodiments, the description provides a bivalent ligand, wherein PBD ligand has the structure:

4j

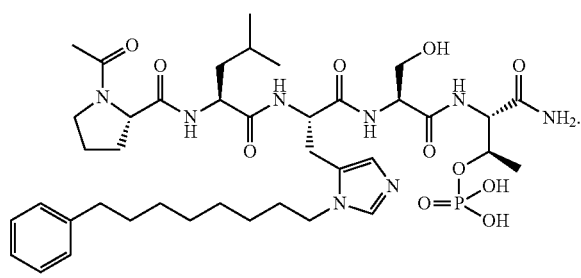

In certain additional embodiments, description provides a bivalent ligand wherein the KD ligand has a structure according to or comprising:

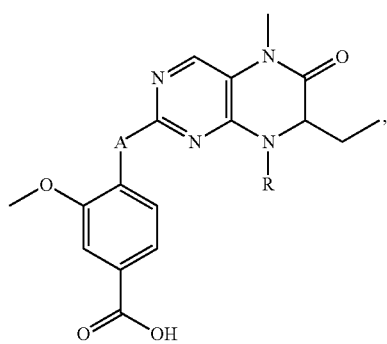

wherein:
A is O or NH; and
R is an alkyl, a cycloalkyl or an aromatic ring.

In a particular embodiment, the description provides a bivalent ligand, wherein R is isobutyl or cyclopentyl.

In certain embodiments, the description provides a bivalent ligand, wherein the KD ligand is:

105

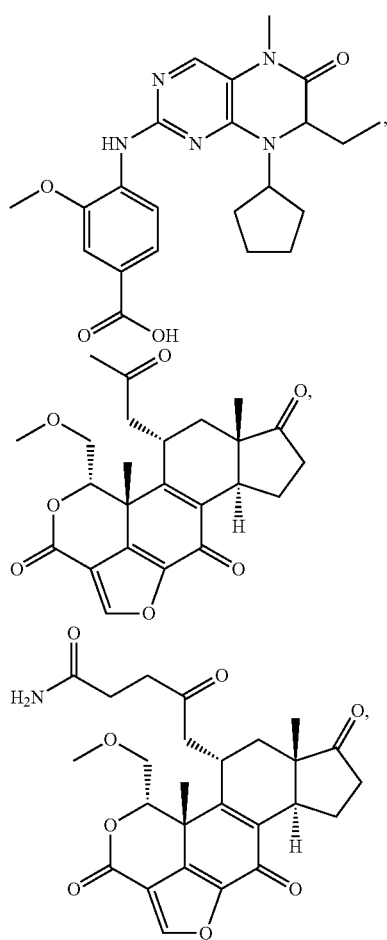

106

-continued

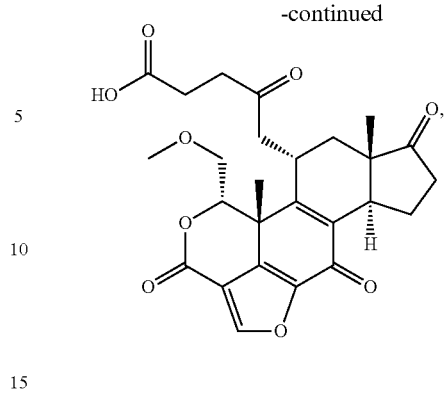

or a pharmaceutically acceptable salt, solvate, hydrate, or stereoisomer thereof.

In certain embodiments, the description provides a bivalent ligand, wherein IDL is a polyethylene glycol of the structure: (PEG)n, wherein n=0-8. In an embodiment, n=0-4.

In certain embodiments, the description provides a bivalent ligand, wherein KD is attached to PBD through its C-terminal.

In certain embodiments, the description provides a bivalent ligand, wherein KD is attached to PBD through its N-terminal.

In a specific embodiment, the description provides a bivalent ligand comprising a structure:

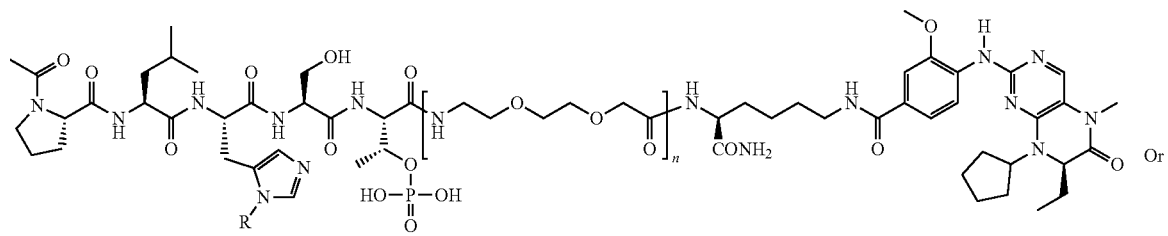

Or

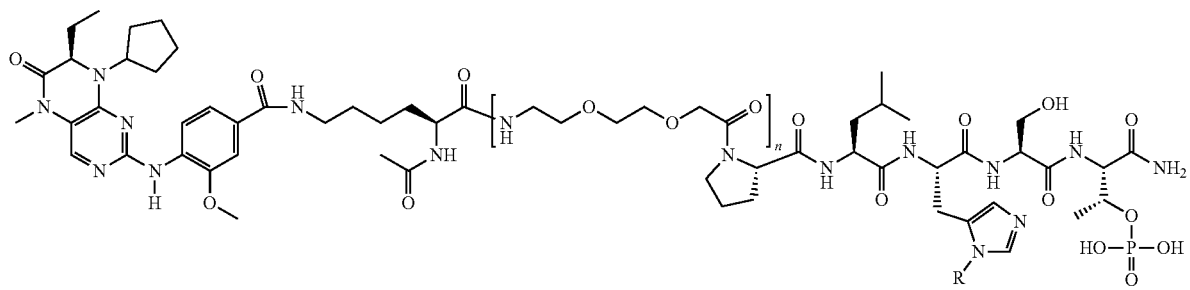

wherein, n = 0-4
R = (CH$_2$)$_8$Ph or H

-continued
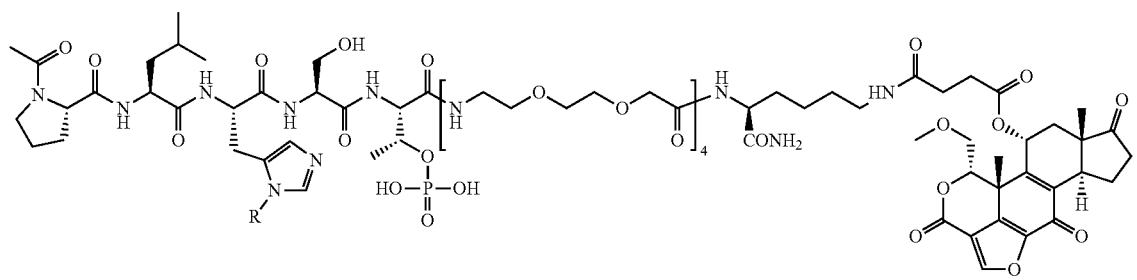
2: R = -(CH$_2$)$_8$Ph
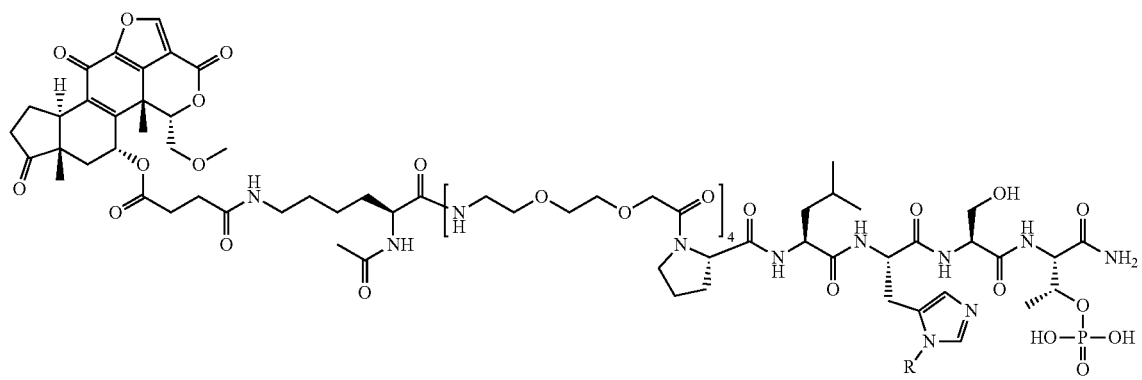
3: R = -(CH$_2$)$_8$Ph
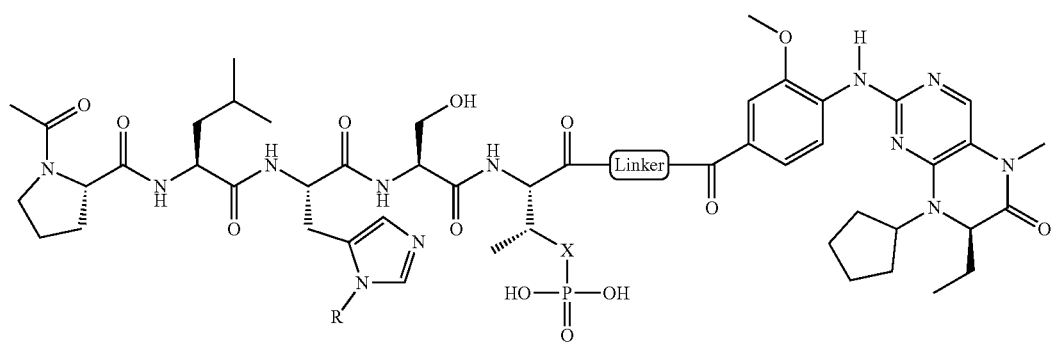
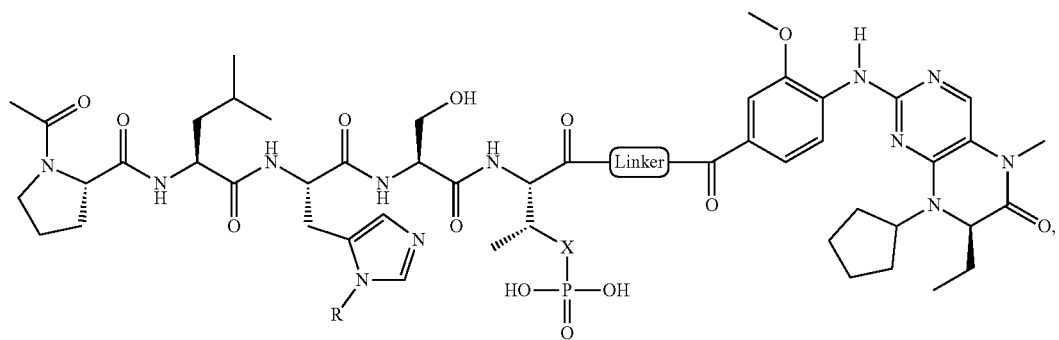

wherein:
R is —(CH2)8Ph;
X is O or CH2; and

is selected from:

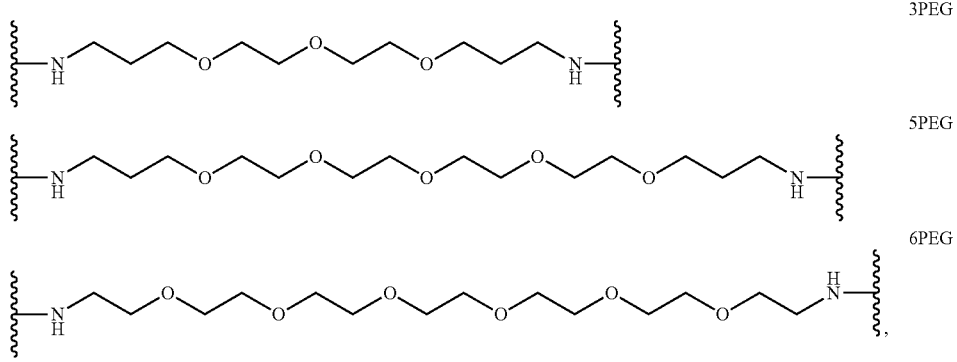

or a pharmaceutically acceptable salt, solvate, hydrate, or stereoisomer thereof.

In any of the aspects or embodiments described herein, the peptido-mimetic compound as described herein is from 3 to 500 residues, or from 3 to 250 residues, or from 3 to 150 residues, or from 3 to 50 residues, including all values in between. In certain embodiments, the peptido-mimetic compound as described herein is 3, 4, 5, 6, 7, 8, 9, 10, 11, 12, 13, 14, 15, 16, 17, 18, 19, 20, 21, 22, 23, 24 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more residues.

The description provides the design, synthesis and biological evaluation of anticancer therapeutics, which act through down-regulation of oncogenic Plk1 through spatial dis-regulation achieved by blocking the function of its PBD or KD and PBD simultaneously, which provides higher affinity and selectivity. The macrocyclic peptidomimetic Plk1 ligands act through the down-regulation of oncogenic Plk1 through their higher affinity, pharmacokinetic properties and selectivity. The macrocyclic peptidomimetic Plk1 ligands of the rpesent disclosure are cyclized iterations of other synthesized high-affinity peptidomimetic ligands that target polo-box domain of Polo-like kinase 1. These macrocyclic PBD-binding ligands demonstrate improved affinity and potency in biochemical assays. These macrocyclic peptidomimetics are supposed to have desirable pharmacokinetic properties.

It has been observed that the compounds of the description achieve enhanced efficacy in cellular studies.

Compositions, Methods, and Kits

The description provides compositions including any of the compounds of the description in a pharmaceutically acceptable carrier, for use, for example, for the preparation of a medicament. The medicament can be, for example, a medicament for the prevention, amelioration, or treatment of a hyperproliferative disorder such as cancer.

In a particular aspect, the description provides a pharmaceutical composition comprising an effective amount of a bivalent ligand as described herein in combination with a pharmaceutically acceptable carrier, additive or excipient.

In any of the aspects or embodiments described herein, the described compounds may be pharmaceutically acceptable salts, solvates, hydrates, prodrugs or stereoisomers thereof. In another aspect, the description provides the compounds as described herein in pharmaceutically acceptable carriers, and the use of the compounds for the preparation of a medicament.

The description further provides kits containing the compounds of the description, and kits for synthesizing the compounds of the description.

The description provides compositions for the preparation of a medicament. The medicament can be, for example, a medicament for the prevention, amelioration, or treatment of a hyperproliferative disorder such as cancer.

The compounds of the description can be used in methods for the prevention, amelioration, or treatment of a subject for a hyperproliferative disorder. Such methods can further include identification of a subject suffering from or suspected of suffering from a hyperproliferative disorder and/or monitoring the subject for prevention, amelioration, or treatment of a hyperproliferative disorder.

In still other embodiments, such compositions are labeled for the treatment of a hyperproliferative disorder such as cancer. In a further embodiment, the effective amount is effective to treat or prevent a hyperproliferative disorder such as cancer in a subject, as described herein.

In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, Thyroid Cancer.

In an additional aspect, the description provides a method of treating cancer in a patient, wherein the method comprising administering to a patient in need thereof, an effective amount of a bivalent pharmaceutical composition as described herein, wherein the composition inhibits, prevents or treats cancer in the patient.

The description also includes methods of designing, synthesizing, and/or using the compounds of the description. In certain embodiments, the description provides compounds made according to any synthetic method disclosed herein.

In an embodiment, the compound is administered to the subject using a pharmaceutically-acceptable formulation. In certain embodiments, these pharmaceutical compositions are suitable for oral or parenteral administration to a subject. In still other embodiments, as described in detail below, the pharmaceutical compositions of the present description may be specially formulated for administration in solid or liquid form, including those adapted for the following: (1) oral administration, for example, drenches (aqueous or nonaqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. In certain embodiments, the subject is a mammal, e.g., a primate, e.g., a human.

The methods of the description further include administering to a subject a therapeutically effective amount of a compound in combination with a pharmaceutically acceptable excipient. The phrase "pharmaceutically acceptable" refers to those compounds of the description, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association a compound(s) with the carrier and, optionally, one or more accessory ingredients. In general, the formulations are prepared by uniformly and intimately bringing into association a compound with liquid carriers, or finely divided solid carriers, or both, and then, if necessary, shaping the product.

Compositions of the description suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) as an active ingredient. A compound may also be administered as a bolus, electuary or paste.

In solid dosage forms of the description for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present description, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants, such as wetting agents, emulsifying and suspending agents, sweetening, flavoring, coloring, perfuming and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the description for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present description which are suitable for vaginal administration also include pessaries, tampons, creams, gels, pastes, foams or spray formulations containing such carriers as are known in the art to be appropriate.

Dosage forms for the topical or transdermal administration of a compound(s) include powders, sprays, ointments, pastes, creams, lotions, gels, solutions, patches and inhalants. The active compound(s) may be mixed under sterile conditions with a pharmaceutically-acceptable carrier, and with any preservatives, buffers, or propellants which may be required.

The ointments, pastes, creams and gels may contain, in addition to compound(s) of the present description, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Transdermal patches have the added advantage of providing controlled delivery of a compound(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of this description.

Pharmaceutical compositions of this description suitable for parenteral administration comprise one or more compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the description include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound(s), which may be used in a suitable hydrated form, and/or the pharmaceutical compositions of the present description, are formulated into pharmaceutically-acceptable dosage forms by conventional methods known to those of skill in the art.

Actual dosage levels and time course of administration of the active ingredients in the pharmaceutical compositions of this description may be varied so as to obtain an amount of the active ingredient which is effective to achieve the desired therapeutic response for a particular patient, composition, and mode of administration, without being toxic to the patient. An exemplary dose range is from about 0.1 µg to 20 milligram per kilogram of body weight per day (mg/kg/day) (e.g., 0.1 µg/kg to 2 mg/kg, 0.3-3 µg/kg, 0.18-0.54 mg/kg). In other embodiments, the amount varies from about 0.1 mg/kg/day to about 100 mg/kg/day. In still other embodiments, the amount varies from about 0.001 µg to about 100 µg/kg (e.g., of body weight). Ranges intermediate to the above-recited values are also intended to be part of the description.

The description also provides methods including identification of a subject suffering from or suspected of suffering from a hyperproliferative disorder and/or monitoring the subject for prevention, amelioration, or treatment of a hyperproliferative disorder.

The description provides kits for the treatment or prevention of a hyperproliferative disorder such as cancer. The kits contain at least one compound of the descriptions and instructions for use. In one embodiment, the kit includes a therapeutic or prophylactic composition containing an effective amount of a compound of the description in unit dosage form. The description also provides kits having 2, 3, 4, 5, 6, 7, 8, 9, or 10 compounds of the description.

As used herein, "kits" are generally understood to contain at least the non-standard laboratory reagents for use in the methods of the description. For example, a kit can include at least one of, preferably at least two of at least one peptide for modification, one or more aldehyde molecules for modification of peptides, and instructions for use, all in appropriate packaging. The kit can further include any other components required to practice the method of the description, as dry powders, concentrated solutions, or ready to use solutions. In some embodiments, the kit comprises one or more containers that contain reagents for use in the methods of the description; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

In some embodiments, a compound of the description is provided in combination with a conventional therapeutic agent. In other embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a compound of the description is provided together with instructions for administering the compound to a subject having or at risk of developing neoplasia. The instructions will generally include information about the use of the composition for the treatment or prevention of neoplasia. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The description further provides libraries including at least two compounds of the description."Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

Any compositions or methods provided herein can be combined with one or more of any of the other compositions and methods provided herein.

The practice of the present description employs, unless otherwise indicated, conventional techniques that are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). Particularly useful techniques for particular embodiments will be discussed in the sections that follow.

The following non-limiting examples are illustrative of the description.

I. SYNTHESIS AND CHEMICAL ANALYSIS OF THE COMPOUNDS OF THE DESCRIPTION

A. Synthesis and Preparation

Compounds of the description can be synthesized and/or prepared by methods described in this section, the examples, and the chemical literature. For example, Scheme 1 illustrates the synthesis of the compounds of the description, beginning with reacting compounds of Formula 2 with di-tert-butyl phosphonate to afford compounds of Formula 16. Deoxygenation of compounds of Formula 16 affords compounds of Formula 18, which after ester hydrolysis, Fmoc-protection, and benzyloxycarbonyl (Cbz) removal affords compounds of Formula 1. Compounds of Formula 1 are then converted to the Final Compounds via primary amide formation, and peptide synthesis.

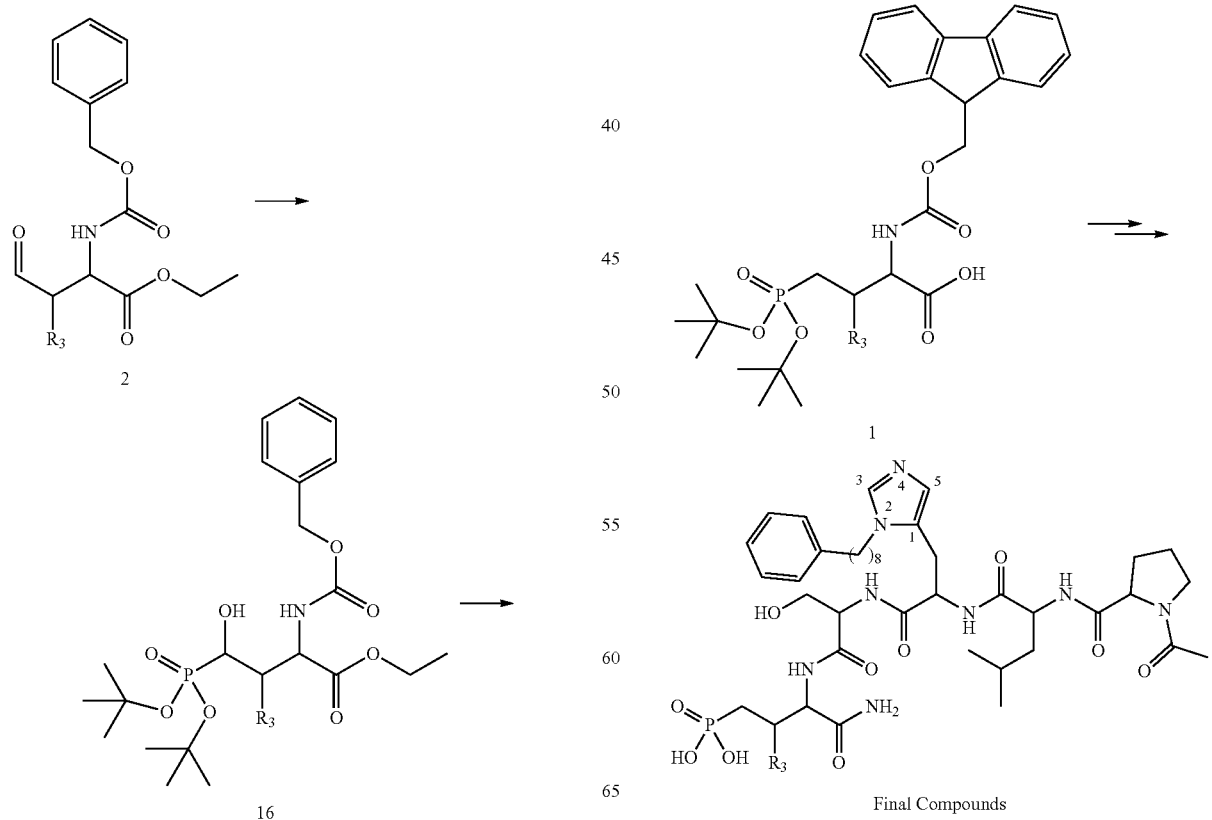

Scheme 1

Final Compounds

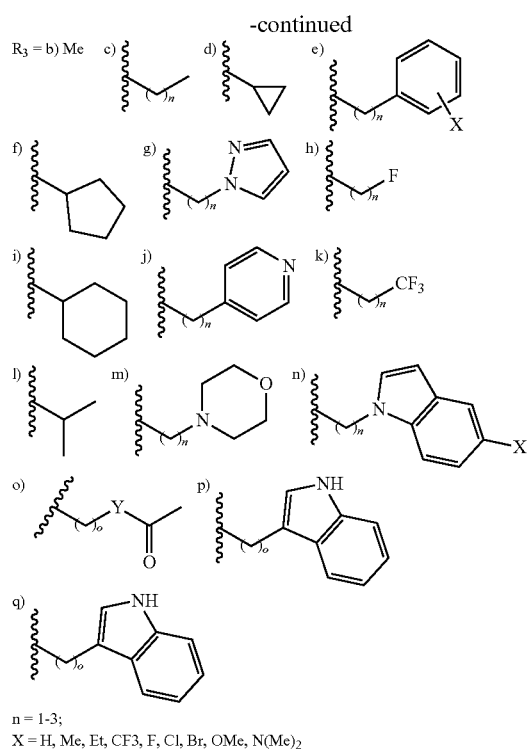

n = 1-3;
X = H, Me, Et, CF3, F, Cl, Br, OMe, N(Me)₂

In an exemplary scheme, Compound 2 is treated with (a) di-tert-butyl phosphite (1.5 equiv.), chlorotrimethylsilane (TMS-Cl, 1.5 equiv.), triethylamine (TEA, 2.0 equiv.), dichloromethane (DCM), 6 h, rt; and (b) 20% aq. citric acid (w/v), MeOH, 16 h at RT to afford in compound 16. Compound 16 is then treated with O-phenyl thiochloroformate (1.5 equiv.), N, N-dimethylaminopyridine (DMAP, 3.0 equiv.), acetonitrile (MeCN) at RT to result in Compound 17. Compound 17 is treated with tributyltin hydride (3.0 equiv.), azoisobutylnitrile (AIBN, 1.0 equiv.), toluene, reflux, 20 min., to result in Compound 18. Compound 18 is treated with (a) LiOH (2.0 equiv.), tetrahydrofuran (THF)/H2O (3:1), 16 h, rt; (b) 1 atm $H_2$, Pd/C (10% w/w, 0.1 equiv.), MeOH, 3 h, RT; (c) Fmoc-OSu (1.5 equiv.), $NaHCO_3$ (2.0 equiv.), THF/H2O (1:1), 16 h, rt, to yield Compound 1. As indicated above, the description provides a synthetic scheme capable of producing Compound 1 from Compound 2 in seven steps.

Figure 1:
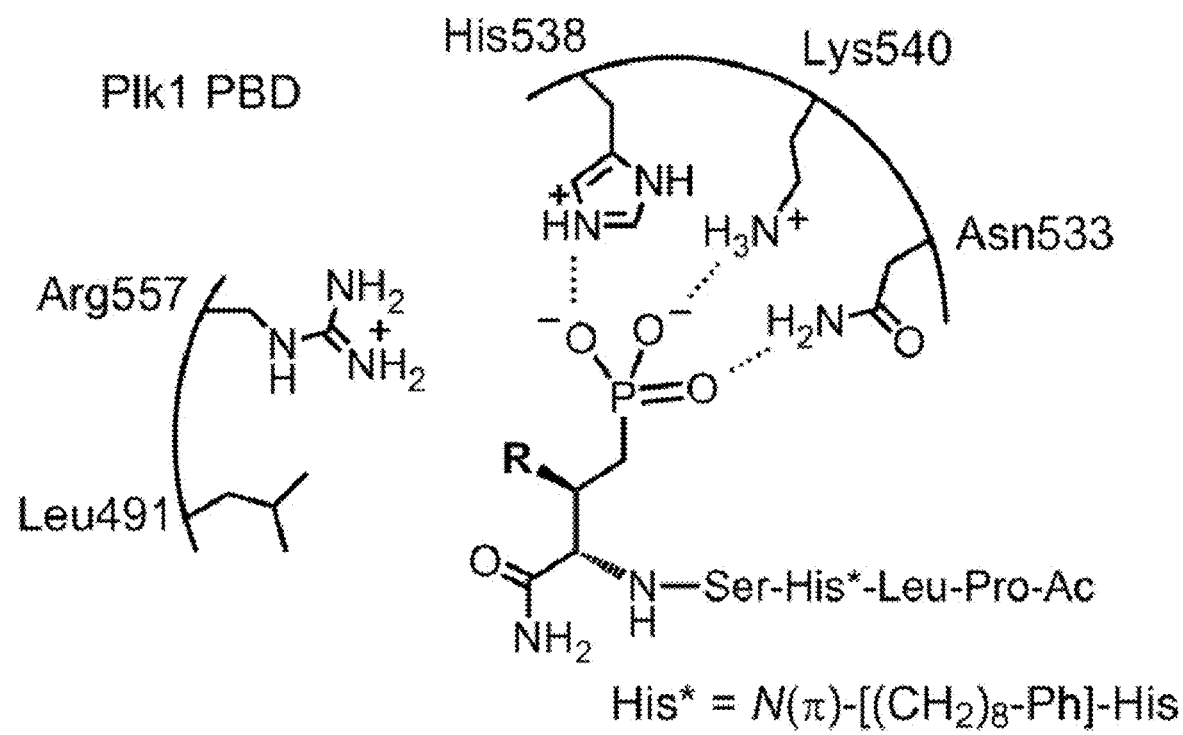
FIG. 1. Peptide mimetics as described herein afford enhanced interactions with Arg557 and Leu491 of Plk1-PBD, which are located proximal to the 3-position of Pmab in the pThr-binding pocket.
Figure 2:
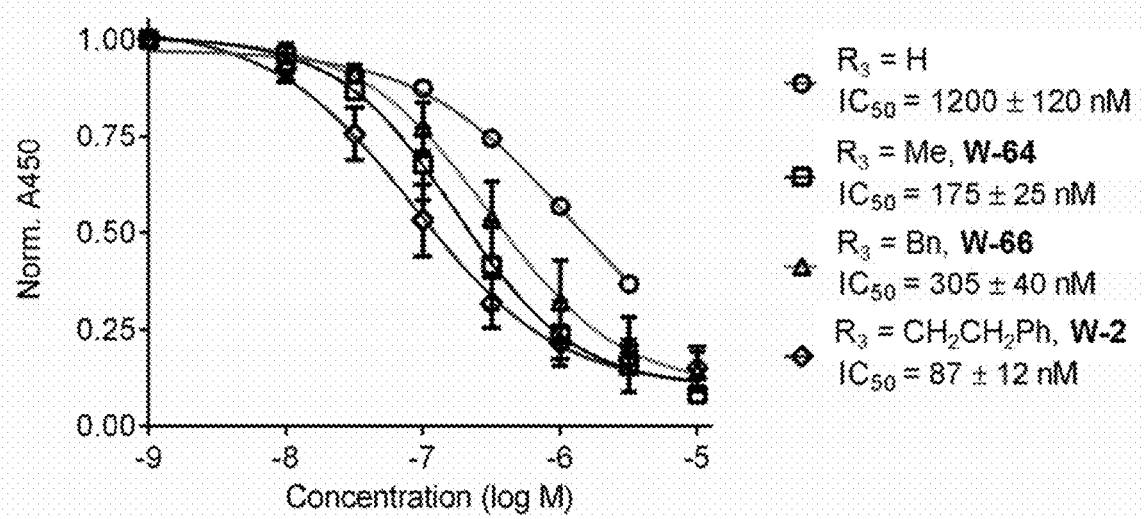
FIG. 2. ELISA-based inhibition of full-length Polo-like kinase 1 by Compounds W-64, W-66, and W-2.

Phosphatase-stable analogs of phospho-threonine containing a variety of orthogonal protecting groups, which can be efficiently accessed via the key (2S)-,(3R)-alkyl intermediate and the synthetic route described herein. The new analogs are intended to afford enhanced interactions with Arg557 and Leu491 (See FIG. 1), which are located proximal to the 3-position of Pmab in the pThr-binding pocket.

2. General Procedures:
General Methods.

All experiments involving moisture-sensitive compounds were conducted under anhydrous conditions (positive argon pressure) using standard syringe, cannula, and septa apparatus. Commercial reagents were purchased from Sigma, TCI America, Acros, or Chem-Impex. Fmoc-Ser(Trt)-OH, Fmoc-His(Mtt)-OH, Fmoc-Leu-OH, Fmoc-Pro-OH and Fmoc-Thr[PO(OH)((OBn)]-OH were purchased from Chem-Impex. Fmoc-His[N(π)-(CH₂)₈-Ph]-OH (His*) was synthesized as previously described (39). All solvents were purchased in anhydrous form (Aldrich) and used directly.

High-performance liquid chromatography (HPLC)-grade hexanes, ethyl acetate (EtOAc), dichloromethane (DCM), and methanol (MeOH) were used in chromatography purifications. Analytical thin-layer chromatography (TLC) was performed using Analtech precoated plates (Uniplate, silica gel GHLF, 250 nm) containing a fluorescence indicator. Silica column chromatography employed a Telodyne CombiFlash Rf 200i instrument with either hexane/EtOAc or DCM/MeOH gradients. Nuclear magnetic resonance (NMR) spectra were recorded using a Varian Inova 400 MHz spectrometer. Coupling constants are reported in Hertz, and peak shifts are reported in δ (ppm) relative to $CDCl_3$. Infrared (IR) spectra were measured on a Jasco FT/IR-4100 spectrometer. Optical rotation was measured on a Jasco P-1010 polarimeter. Low-resolution mass spectra (LRMS) were measured with either an Agilent 260 1200 LC/MSD-SL system or a Shimadzu 2020 LC/MS system. High resolution mass spectra (HRMS) were obtained by positive ion, ESI analysis on a Thermo Scientific LTQ-XL Orbitrap mass spectrometer with HPLC sample introduction using a short narrow-bore C1s reversed-phase column with $CH_3CN$—$H_2O$ gradients. Preparative HPLC purification of final peptides was performed using a Waters 2545 binary pump (MeCN/water gradient) with a Phenomenex Gemini-C18 (5 μm, 250×21 mm) preparative column and ultraviolet (UV) detection. Analytical HPLC of final peptides was performed using an Agilent 1200 series quaternary pump (MeCN/water gradient) with a Phenomenex Kinetix-C18 (5 μm, 250×4 mm) analytical column and UV detection.

Synthetic Procedures

General Procedure A. Compounds 2 were prepared using a similar procedure as was previously disclosed. (40, 41) The aldehyde ($R_3CH_2$—CHO, 1.2-2 equiv.) was dissolved in chloroform (0.2 M) and stirred at room temperature (RT). (S)-2-(bis(3,5-bis(trifluoromethyl)phenyl)((trimethylsilyl)oxy)methyl) pyrrolidine (0.1 equiv., Sigma) was added and the reaction was allowed to stir for 5 minutes. Ethyl ((benzyloxy) carbonyl)-tosylglycinate (1 equiv.; synthesized by a literature procedure (42)) and potassium fluoride (5 equiv.) were then added and the reaction was allowed to stir at RT for 24-96 hours (h). Following completion, the reaction mixture was filtered through Celite and the eluent was concentrated. Purification by silica column chromatography (hexane/EtOAc gradient) afforded the corresponding product. ¹H NMR was used to determine anti/syn diastereomeric ratio.

General Procedure B. Di-tert-butyl phosphite (1.5 equiv.) and triethylamine (2 equiv.) were added to DCM (0.2 M) in a round bottom flask at 0° C. Chlorotrimethylsilane (1.5 equiv.) was then added and was allowed to stir at 0° C. for an additional 5 minutes to generate a white precipitate. The corresponding aldehyde 2 (1 equiv.) from General Procedure A was added and the reaction was further stirred for 3-6 h at RT. Following completion, the reaction was diluted with DCM, washed with brine, and the aqueous layer extracted with additional DCM. The combined organic layers were dried over $Na_2SO_4$ and concentrated. The resulting residue was re-dissolved in MeOH (0.05 M), followed by the addition of 20% aqueous citric acid (30% v/v) and the reaction was stirred at RT overnight. Following removal of the TMS-group by TLC, the reaction was diluted with EtOAc and washed with saturated (sat.) aqueous (aq.) $NaHCO_3$. The aqueous layer was extracted with EtOAc and the combined organic layers were dried over $Na_2SO_4$ and concentrated. Purification by silica column chromatography (hexane/EtOAc gradient) afforded the corresponding product as a mixture of diastereomers.

General Procedure C. Secondary alcohol 16 from General Procedure B was dissolved in DCM (0.1-0.2 M) and placed in a round-bottom flask with stirring at RT. Diisopropylethylamine (DIEA, 4 equiv.) and N, N-dimethylaminopyridine (DMAP, 0.2 equiv.) were added, followed by O-phenyl chlorothionoformate (3 equiv.). The reaction was allowed to stir for 3-16 h and the reaction progress was followed by TLC. Following completion, water was added and the reaction was allowed to quench for 30 minutes with stirring at RT. The mixture was then diluted with DCM and water and the aqueous layer was extracted with DCM. The combined organic layers were dried over $Na_2SO_4$, filtered, and concentrated. Purification by silica column chromatography (hexane/EtOAc gradient) afforded the corresponding phenylthiocarbonate as a mixture of diastereomers. The phenylthiocarbonate was dissolved in toluene (0.1 M) and placed in a round-bottom flask with stirring. Azobisisobutylnitrile (AIBN, 1 equiv.) and tributyltin hydride (3 equiv.) were added and the reaction was heated to 110° C. for 20 minutes. Upon reaction completion, the reaction was cooled to RT and the toluene was removed under vacuum. The resulting residue was directly purified by silica column chromatography (hexane/EtOAc gradient) to afford the corresponding product.

General Procedure D. Benzyloxycarbonyl (Cbz)-protected ethyl ester 18 from General Procedure D was dissolved in tetrahydrofuran (THF, 0.1 M) and added to a round-bottom flask at RT. Lithium hydroxide (3 equiv.) was dissolved in water (25% v/v) and added to the THF solution. The reaction was allowed to stir overnight at RT. Following saponification, the THF was removed under vacuum and the aqueous solution was diluted with 0.5 M HCl and extracted with EtOAc twice. The combined organic layers were dried over $Na_2SO_4$ and concentrated. The resulting residue was dissolved in MeOH (0.05 M) and degassed with argon for several minutes. Palladium on carbon (0.2 equiv., 10% w/w) was added with stirring. The reaction was placed under a blanket of hydrogen gas and stirred at RT for 3 h to remove the Cbz group. Once completed, the reaction mixture was filtered through Celite and concentrated. The resulting residue was dissolved in 1:1 THF/water (0.05 M). Sodium bicarbonate (5 equiv.) was added, followed by 9-Fluorenylmethyl-N-succinimidyl carbonate (Fmoc-Osu, 1.5 equiv.) and the reaction was allowed to stir overnight. Once completed, the THF was removed under vacuum and the aqueous mixture was diluted with 0.5 M HCl. The aqueous solution was extracted twice with EtOAc and the combined organic layers were dried over $Na_2SO_4$ and concentrated. Purification by silica column chromatography (DCM/MeOH gradient) afforded compound 1.

General Solid-Phase Peptide Synthesis (SPPS) procedure. NovaSyn TG Sieber resin was pre-swollen in DMF (4 mL) for 1 h with shaking. The resin was Fmoc-deprotected using 20% piperidine in DMF (4 mL) twice for 10 minutes each. Fmoc-protected amino acids (2-4 equivalents based on resin) were dissolved in DMF (3-4 mL) containing 4% DIEA and pre-activated by the addition of (1-[bis(dimethylamino)methylene]-1H-1,2,3-triazolo[4,5-b]pyridinium 3-oxid hexafluorophosphate) (HATU, 0.95 mol equivatents relative to the amino acid) for 5 minutes with gentle agitation. The resin was washed 4 times with DMF (6-8 mL), and the HATU-activated amino acid solution was added to the washed resin. Coupling reactions were shaken at room temperature and allowed to proceed from 3-16 hours depending on the equivalents used and steric bulk of each amino acid. Coupling reactions were routinely checked for completion using the Kaiser test. Once completed, the resin was filtered and washed 4 times with DMF (6-8 mL), followed by Fmoc-deprotection using 20% piperidine in DMF (4 mL, 2×10 minutes each). Cleavage from Sieber resin and global deprotection was performed using 33% TFA with 2% triisopropylsilane (TIPS) in DCM. Crude peptides were purified using preparative reverse-phase HPLC with gradient elution (89.9/10/0.1 water/acetonitrile/trifluoroacetic acid (TFA) to 99.9/0.1 acetonitrile/TFA over 30 minutes).

Example 1

Preparation of (3S,6S,9S,12R,13S)-1-((S)-1-acetylpyrrolidin-2-yl)-12-carbamoyl-9-(hydroxymethyl)-3-isobutyl-13-methyl-1,4,7,10-tetraoxo-6-((1-(8-phenyloctyl)-1H-imidazol-5-yl)methyl)-2,5,8,11-tetraazatetradecan-14-ylphosphonic acid (W-64)

Preparation of Ethyl (2S,3R)-2-(((benzyloxy)carbonyl)amino)-3-methyl-4-oxobutanoate (2b)

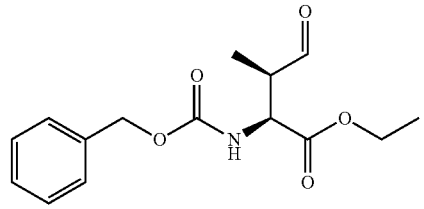 [SMILES: CCOC(=O)[C@@H](NC(=O)OCc1ccccc1)[C@@H](C)C=O]

Propionaldehyde (1.3 mL, 17.9 mmol, 2 equiv.) was reacted with ethyl ((benzyloxy)carbonyl)-tosylglycinate (3.4 g, 8.94 mmol) using a similar procedure as outlined in General Procedure A to provide ethyl (2S,3R)-2-(((benzyloxy)carbonyl)amino)-3-methyl-4-oxobutanoate (2b, 2.26 g, 86%, 12:1 anti/syn) as a white foam. $[\alpha]_D^{20}=+27.6$ (c 1.00, $CHCl_3$); $^1H$ NMR (400 MHz, Chloroform-d) δ 9.64 (s, 1H), 7.45-7.28 (m, 5H), 5.58 (d, J=8.3 Hz, 1H), 5.13 (s, 2H), 4.70 (dd, J=8.4, 3.8 Hz, 1H), 4.19 (q, J=7.1 Hz, 2H), 3.18 (dd, J=7.3, 3.8 Hz, 1H), 1.24 (t, J=7.1 Hz, 3H), 1.18 (d, J=7.4 Hz, 3H); $^{13}C$ NMR (101 MHz, $CDCl_3$) δ 201.58, 170.34, 156.39, 136.21, 128.68, 128.37, 128.18, 67.33, 62.15, 54.20, 48.84, 14.16, 9.61; IR (film) 2980, 1724, 1513, 1338, 1061, 1027, 920, 859 $cm^{-1}$; LR-MS ($ESI^+$) calculated for $C_{15}H_{19}NO_5$: 294.1 $[M+H^+]$; found: 294.3.

Preparation of Ethyl (2S,3R)-2-(((benzyloxy)carbonyl)amino)-4-(di-tert-butoxyphosphoryl)-4-hydroxy-3-methylbutanoate (16b)

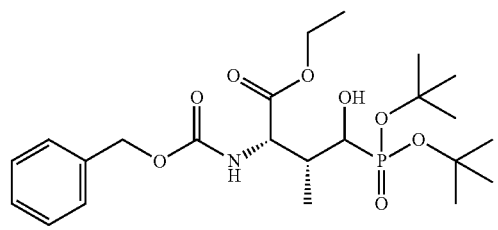 [SMILES: CCOC(=O)[C@@H](NC(=O)OCc1ccccc1)[C@@H](C)C(O)P(=O)(OC(C)(C)C)OC(C)(C)C]

Ethyl (2S,3R)-2-(((benzyloxy)carbonyl)amino)-3-methyl-4-oxobutanoate (2b, 2.1 g, 7.16 mmol) was reacted with di-tert-butyl phosphite using a similar procedure as outlined in General Procedure B to provide ethyl (2S,3R)-2-(((benzyloxy)carbonyl)amino)-4-(di-tert-butoxyphosphoryl)-4-hydroxy-3-methylbutanoate (16b, 2.88 g, 83%) as a mixture of diastereomers. $[\alpha]_D^{20}=-1.6$ (c 1.00, $CHCl_3$); $^1H$ NMR (400 MHz, Chloroform-d) δ 7.41-7.28 (m, 5H), 6.73 (d, J=7.5 Hz, 0.5H), 6.35 (d, J=9.8 Hz, 0.5H), 5.89 (d, J=8.2 Hz, 0.5H), 5.11 (s, 2H), 4.34-4.10 (m, 3H), 3.88 (d, J=8.1 Hz, 0.5H), 2.85-2.77 (m, 0.5H), 2.53-2.42 (m, 0.5H), 1.59-1.37 (m, 18H), 1.26 (t, J=6.9 Hz, 3H), 1.13 (d, J=7.0 Hz, 3H); $^{13}C$ NMR (101 MHz, $CDCl_3$) δ 172.05, 156.92, 136.56, 128.63, 128.59, 128.19, 83.71, 70.67, 69.02, 67.04, 61.51, 59.70, 59.53, 30.62, 30.47, 14.32, 11.55; IR (film) 2980, 1725, 1507, 1394, 1370, 1321, 1255, 1164, 1096, 1065, 1038, 980, 919, 697 $cm^{-1}$; LR-MS (ESI$^+$) calculated for $C_{23}H_{38}NO_8P$: 488.2 [M+H$^+$]; found: 488.4.

Preparation of Ethyl (2S,3R)-2-(((benzyloxy)carbonyl)amino)-4-(di-tert-butoxyphosphoryl)-3-methylbutanoate (18b)

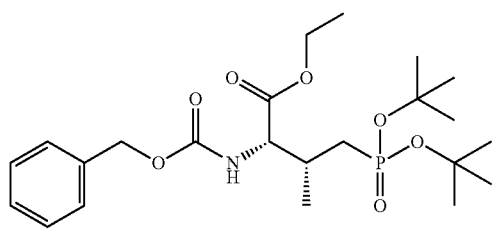 [SMILES: CCOC(=O)[C@@H](NC(=O)OCc1ccccc1)[C@@H](C)CP(=O)(OC(C)(C)C)OC(C)(C)C]

Ethyl (2S,3R)-2-(((benzyloxy)carbonyl)amino)-4-(di-tert-butoxyphosphoryl)-4-hydroxy-3-methylbutanoate (16b, 2.18 g, 5.13 mmol) was prepared using a similar procedure as outlined in General Procedure C to provide ethyl (2S,3R)-2-(((benzyloxy)carbonyl)amino)-4-(di-tert-butoxyphosphoryl)-3-methylbutanoate (18b, 1.3 g, 61% over 2 steps) as a white foam. $[\alpha]_D^{20}=+6.6$ (c 1.00, $CHCl_3$); $^1H$ NMR (400 MHz, Chloroform-d) δ 7.39-7.27 (m, 5H), 5.78 (d, J=8.5 Hz, 1H), 5.10 (s, 2H), 4.27 (dd, J=8.1, 5.3 Hz, 1H), 4.19 (q, J=7.1 Hz, 2H), 2.47-2.31 (m, 1H), 1.82-1.69 (m, 1H), 1.56-1.52 (m, 1H), 1.52-1.43 (m, 18H), 1.27 (t, J=7.9 Hz, 3H), 1.12 (d, J=6.8 Hz, 3H); $^{13}C$ NMR (101 MHz, $CDCl_3$) δ 171.72, 156.35, 136.48, 128.61, 128.24, 128.21, 82.12, 67.08, 61.55, 59.70, 59.56, 33.89, 32.44, 30.56, 30.54, 30.52, 30.50, 30.46, 17.62, 17.58, 14.34; IR (film) 2979, 1721, 1538, 1370, 1259, 1038, 1007, 980, 919, 698 $cm^{-1}$; LR-MS (ESI$^+$) calculated for $C_{23}H_{38}NO_7P$: 472.2 [M+H$^+$]; found: 472.4.

Preparation of (2S,3R)-2-((((9H-fluoren-9-yl)methoxy)carbonyl)amino)-4-(di-tert-butoxyphosphoryl)-3-methylbutanoic acid (1b)

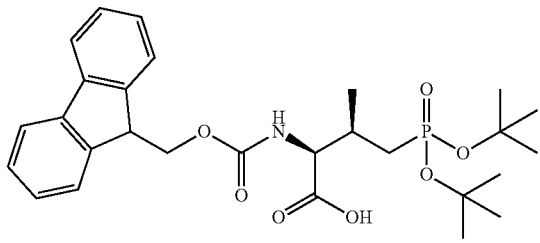 [SMILES: C[C@@H](CP(=O)(OC(C)(C)C)OC(C)(C)C)[C@H](NC(=O)OCC1c2ccccc2-c2ccccc21)C(=O)O]

Ethyl (2S,3R)-2-(((benzyloxy)carbonyl)amino)-4-(di-tert-butoxyphosphoryl)-4-hydroxy-3-methylbutanoate (18b, 1.28 g, 2.71 mmol) was prepared using a similar procedure as outlined in General Procedure D to provide (2S,3R)-2-((((9H-fluoren-9-yl)methoxy)carbonyl)amino)-4-(di-tert-butoxyphosphoryl)-3-methylbutanoic acid (1b, 1.25 g, 87%) as a white foam. $[\alpha]_D^{20}=+30.3$ (c 1.00, $CHCl_3$); $^1H$ NMR (400 MHz, Chloroform-d) δ 7.76 (d, J=7.5 Hz, 2H), 7.60 (dd, J=7.1, 4.3 Hz, 2H), 7.39 (t, J=7.5 Hz, 2H), 7.31 (t, J=7.1 Hz, 2H), 5.85 (d, J=7.3 Hz, 1H), 4.76 (dd, J=7.0, 4.7 Hz, 1H), 4.37 (d, J=7.1 Hz, 2H), 4.22 (t, J=7.1 Hz, 1H), 2.61-2.48 (m, 1H), 1.93-1.83 (m, 1H), 1.74-1.64 (m, 1H), 1.54 (d, J=22.8 Hz, 18H), 1.04 (d, J=6.9 Hz, 3H). $^{13}C$ NMR (101 MHz, $CDCl_3$) δ 171.83, 155.51, 143.91, 141.43, 127.82, 127.17, 125.32, 120.10, 83.96, 67.11, 56.97, 47.28, 30.55, 25.52, 16.98; IR (film) 2981, 1714, 1510, 1450, 1395, 1371, 1263, 1247, 1153, 1077, 1038, 989, 754, 703, 667, 621 $cm^{-1}$; LR-MS (ESI$^+$) calculated for $C_{28}H_{38}NO_7P$: 532.2 [M+H$^+$]; found: 532.5.

Preparation of (3S,6S,9S,12R,13S)-1-((S)-1-acetylpyrrolidin-2-yl)-12-carbamoyl-9-(hydroxymethyl)-3-isobutyl-13-methyl-1,4,7,10-tetraoxo-6-((1-(8-phenyloctyl)-1H-imidazol-5-yl)methyl)-2,5,8,11-tetraazatetradecan-14-ylphosphonic acid (W-64)

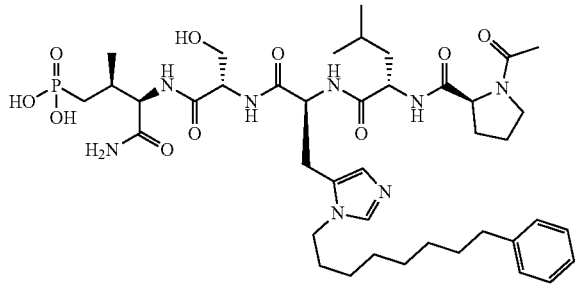 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@@H](C(N)=O)[C@H](C)CP(=O)(O)O]

The peptide 3S,6S,9S,12R,13S)-1-((S)-1-acetylpyrrolidin-2-yl)-12-carbamoyl-9-(hydroxymethyl)-3-isobutyl-13-methyl-1,4,7,10-tetraoxo-6-((1-(8-phenyloctyl)-1H-imidazol-5-yl)methyl)-2,5,8,11-tetraazatetradecan-14-ylphosphonic acid (W-64) was synthesized on a 0.1 mmol scale using the general SPPS procedure. Purification by preparative Reverse Phase (RP)-HPLC afforded the final peptide (W-64, 49 mg, 57% overall) with ≥95% purity by analytical HPLC. Low Resolution (LR)-MS (ESI$^+$) calculated for $C_{41}H_{65}N_8O_{10}P$: 861.5 [M+H$^+$]; found: 861.7.

Example 2: Preparation of (3S,6S,9S,12R,13S)-1-((S)-1-acetylpyrrolidin-2-yl)-13-benzyl-12-carbamoyl-9-(hydroxymethyl)-3-isobutyl-1,4,7,10-tetraoxo-6-((1-(8-phenyloctyl)-1H-imidazol-5-yl)methyl)-2,5,8,11-tetraazatetradecan-14-ylphosphonic acid (W-66)

Preparation of Ethyl (2S,3R)-3-benzyl-2-(((benzyloxy)carbonyl)amino)-4-oxobutanoate (2e, n=1, X=H

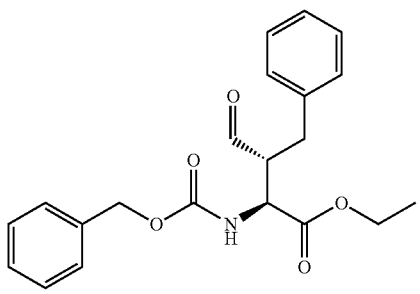 [SMILES: CCOC(=O)[C@@H](NC(=O)OCc1ccccc1)[C@H](C=O)Cc1ccccc1]

Hydrocinnamaldehyde (539 mg, 4.02 mmol, 2 equiv.) was reacted with ethyl ((benzyloxy)-carbonyl)-tosylglycinate (786 mg, 2.01 mmol) using a similar procedure as outlined in General Procedure A to provide ethyl (2S,3R)-3-benzyl-2-(((benzyloxy)carbonyl)amino)-4-oxobutanoate (2e, n=1, X=H; 425 mg, 57%; 12:1 anti/syn) as a white foam. $[\alpha]_D^{20}$=+32.2 (c 1.00, CHCl$_3$); $^1$H NMR (400 MHz, Chloroform-d) δ 9.65 (s, 1H), 7.44-7.12 (m, 10H), 5.55 (d, J=9.4 Hz, 1H), 5.15 (s, 2H), 4.60 (dd, J=9.5, 3.1 Hz, 1H), 4.17 (q, J=7.1 Hz, 2H), 3.49 (td, J=8.1, 3.5 Hz, 1H), 3.10 (dd, J=14.1, 6.8 Hz, 1H), 2.80 (dd, J=14.1, 8.4 Hz, 1H), 1.23 (t, J=7.1 Hz, 3H); $^{13}$C NMR (101 MHz, CDCl$_3$) δ 201.97, 170.73, 156.62, 137.77, 136.34, 129.17, 129.00, 128.69, 128.38, 128.19, 127.08, 67.35, 62.17, 55.59, 52.98, 31.79, 14.17; IR (film) 2935, 1721, 1498, 1455, 1370, 1331, 1255, 1050, 1028, 966, 699 cm$^{-1}$; LR-MS (ESI$^+$) calculated for C$_{21}$H$_{23}$NO$_5$: 370.2 [M+H$^+$]; found: 370.3.

Preparation of Ethyl (2S,3R)-3-benzyl-2-(((benzyloxy)carbonyl)amino)-4-(di-tert-butoxyphosphoryl)-4-hydroxybutanoate (16e, n=1, X=H)

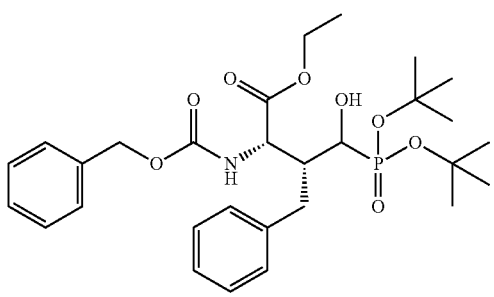 [SMILES: CCOC(=O)[C@@H](NC(=O)OCc1ccccc1)[C@@H](Cc1ccccc1)C(O)P(=O)(OC(C)(C)C)OC(C)(C)C]

Ethyl (2S,3R)-3-benzyl-2-(((benzyloxy)carbonyl)amino)-4-oxobutanoate (2e, n=1, X=H; 400 mg; 1.083 mmol) was reacted with di-tert-butyl phosphite using a similar procedure as outlined in General Procedure B to provide ethyl (2S,3R)-3-benzyl-2-(((benzyloxy)carbonyl)amino)-4-(di-tert-butoxyphosphoryl)-4-hydroxybutanoate (16e, n=1, X=H; 400 mg; 66%) as a mixture of diastereomers. $[\alpha]_D^{20}$=−14.8 (c 1.00, CHCl$_3$); $^1$H NMR (400 MHz, Chloroform-d) δ 7.44-7.27 (m, 5H), 7.25-7.11 (m, 5H), 6.20 (d, J=8.3 Hz, 0.7H), 5.97 (d, J=8.1 Hz, 0.3H), 5.17-5.10 (m, 2H), 4.21-4.08 (m, 2H), 3.99 (d, J=8.9 Hz, 1H), 3.37-3.30 (m, 1H), 2.91-2.44 (m, 3H), 1.53 (d, J=4.4 Hz, 18H), 1.19 (t, J=7.1 Hz, 3H); $^{13}$C NMR (101 MHz, CDCl$_3$) δ 172.39, 156.66, 139.52, 136.87, 129.28, 128.75, 128.54, 128.24, 128.12, 126.51, 84.02, 71.32, 66.85, 61.42, 56.19, 42.43, 31.17, 30.72, 14.28; IR (film) 2980, 1506, 1498, 1395, 1370, 1256, 1189, 1162, 1095, 1082, 1039, 982, 919, 699 cm$^{-1}$; LR-MS (ESI$^+$) calculated for C$_{29}$H$_{42}$NO$_8$P: 564.3 [M+H$^+$]; found: 564.5.

Preparation of Ethyl (2S,3R)-3-benzyl-2-(((benzyloxy)carbonyl)amino)-4-(di-tert-butoxyphosphoryl)butanoate (18e, n=1, X=H)

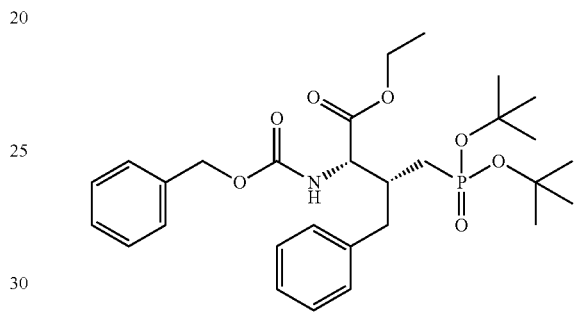

Ethyl (2S,3R)-3-benzyl-2-(((benzyloxy)carbonyl)amino)-4-(di-tert-butoxyphosphoryl)-4-hydroxybutanoate (16e, n=1, X=H; 380 mg; 0.674 mmol) was reacted using a similar procedure as outlined in General Procedure C to provide ethyl (2S,3R)-3-benzyl-2-(((benzyloxy)carbonyl)amino)-4-(di-tert-butoxyphosphoryl)butanoate (18e, n=1, X=H; 216 mg; 58% over 2 steps) as a white foam. $[\alpha]_D^{20}$=−2.3 (c 1.00, CHCl$_3$); $^1$H NMR (400 MHz, Chloroform-d) δ 7.45-7.11 (m, 10H), 6.21 (d, J=9.0 Hz, 1H), 5.28-4.99 (m, 2H), 4.40 (dd, J=9.0, 3.9 Hz, 1H), 4.15 (q, J=7.2 Hz, 2H), 3.01-2.84 (m, 1H), 2.78-2.54 (m, 2H), 1.75-1.57 (m, 2H), 1.46 (s, 18H), 1.24 (t, J=7.1 Hz, 3H); $^{13}$C NMR (101 MHz, CDCl$_3$) δ 172.07, 156.53, 139.44, 136.66, 129.53, 128.60, 128.56, 128.17, 128.16, 126.51, 82.57, 66.97, 61.56, 56.51, 38.97, 37.77, 30.50, 29.85, 14.31; IR (film) 2979, 1723, 1541, 1370, 1259, 1038, 1006, 979, 918, 699 cm$^{-1}$; LR-MS (ESI$^+$) calculated for C$_{29}$H$_{42}$NO$_7$P: 548.3 [M+H$^+$]; found: 548.5.

Preparation of (2S,3R)-2-((((9H-fluoren-9-yl)methoxy)carbonyl)amino)-3-benzyl-4-(di-tert-butoxyphosphoryl)butanoic acid (1-64)

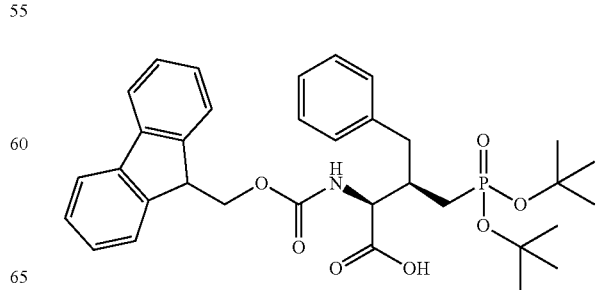

Ethyl (2S,3R)-3-benzyl-2-(((benzyloxy)carbonyl)amino)-4-(di-tert-butoxyphosphoryl)butanoate (18e, n=1, X=H; 200 mg; 0.365 mmol) was reacted using a similar procedure as outlined in General Procedure D to provide (2S,3R)-2-((((9H-fluoren-9-yl)methoxy)carbonyl)amino)-3-benzyl-4-(di-tert-butoxyphosphoryl)butanoic acid (1-64, 180 mg, 81%) as a white foam. $[\alpha]_D^{20}$=+40.3 (c 1.00, CHCl$_3$); $^1$H NMR (400 MHz, Chloroform-d) δ 7.76 (d, J=7.5 Hz, 2H), 7.62 (t, J=6.5 Hz, 2H), 7.39 (t, J=7.5 Hz, 2H), 7.34-7.07 (m, 7H), 5.98 (d, J=7.0 Hz, 1H), 4.97-4.92 (m, 1H), 4.39 (d, J=7.3 Hz, 2H), 4.23 (t, J=7.3 Hz, 1H), 3.10-3.04 (m, 1H), 2.82-2.69 (m, 1H), 2.31 (dd, J=13.8, 10.1 Hz, 1H), 1.88-1.75 (m, 1H), 1.62-1.40 (m, 19H). $^{13}$C NMR (101 MHz, CDCl$_3$) δ 171.82, 155.23, 143.76, 141.30, 139.05, 129.10, 128.65, 127.70, 127.08, 126.46, 125.18, 119.96, 83.91, 67.04, 55.76, 47.12, 38.28, 37.03, 30.39, 25.38; IR (film) 2980, 1714, 1509, 1450, 1395, 1371, 1247, 1153, 1077, 1039, 984, 918, 754, 700, 666, 621 cm$^{-1}$; LR-MS (ESI$^+$) calculated for C$_{34}$H$_{42}$NO$_7$P: 608.3 [M+H$^+$]; found: 608.5.

Preparation of (3S,6S,9S,12R,13S)-1-((S)-1-acetylpyrrolidin-2-yl)-13-benzyl-12-carbamoyl-9-(hydroxymethyl)-3-isobutyl-1,4,7,10-tetraoxo-6-((1-(8-phenyloctyl)-1H-imidazol-5-yl)methyl)-2,5,8,11-tetraazatetradecan-14-ylphosphonic acid (W-66)

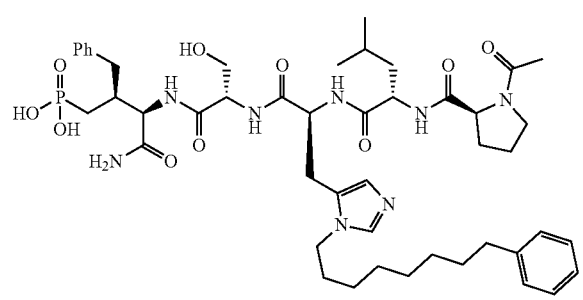 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@@H](C(N)=O)[C@H](Cc1ccccc1)CP(=O)(O)O]

The peptide 3S,6S,9S,12R,13S)-1-((S)-1-acetylpyrrolidin-2-yl)-13-benzyl-12-carbamoyl-9-(hydroxymethyl)-3-isobutyl-1,4,7,10-tetraoxo-6-((1-(8-phenyloctyl)-1H-imidazol-5-yl)methyl)-2,5,8,11-tetraazatetradecan-14-ylphosphonic acid (W-66) was synthesized on a 0.05 mmol scale using the general SPPS procedure. Purification by preparative RP-HPLC afforded the final peptide (W-66, 14 mg, 30% overall) with ≥95% purity by analytical HPLC. LR-MS (ESI$^+$) calculated for C$_{47}$H$_{69}$N$_8$O$_{10}$P: 937.5 [M+H$^+$]; found: 937.8.

Example 3

Preparation of (3S,6S,9S,12R,13S)-1-((S)-1-acetylpyrrolidin-2-yl)-12-carbamoyl-9-(hydroxymethyl)-3-isobutyl-1,4,7,10-tetraoxo-13-phenethyl-6-((1-(8-phenyloctyl)-1H-imidazol-5-yl)methyl)-2,5,8,11-tetraazatetradecan-14-ylphosphonic acid (W-2)

Preparation of Ethyl (2S,3R)-2-(((benzyloxy)carbonyl)amino)-3-formyl-5-phenylpentanoate (2-2)

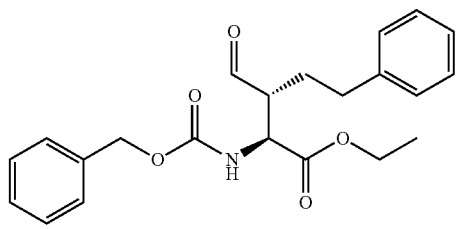 [SMILES: CCOC(=O)[C@@H](NC(=O)OCc1ccccc1)[C@H](C=O)CCc1ccccc1]

4-Phenyl butanal (320 mg, 2.159 mmol, 2 equiv.) was reacted with ethyl ((benzyloxy)carbonyl)-tosylglycinate (786 mg, 2.01 mmol) using a similar procedure as outlined in General Procedure A to provide ethyl (2S,3R)-2-(((benzyloxy)carbonyl)amino)-3-formyl-5-phenylpentanoate (2-2, 365 mg, 88%, 11:1 anti/syn) as a white foam. $[\alpha]_D^{20}$=+45.3 (c 1.00, CHCl$_3$); $^1$H NMR (400 MHz, Chloroform-d) δ 9.57 (s, 1H), 7.47-7.08 (m, 10H), 5.55 (d, J=9.4 Hz, 1H), 5.15 (s, 2H), 4.74 (dd, J=9.5, 3.7 Hz, 1H), 4.18 (q, J=6.4, 5.7 Hz, 2H), 3.19-3.12 (m, 1H), 2.94-2.85 (m, 1H), 2.80-2.70 (m, 1H), 2.14-1.97 (m, 1H), 1.83-1.71 (m, 1H), 1.24 (t, J=7.1 Hz, 3H); $^{13}$C NMR (101 MHz, CDCl$_3$) δ 202.09, 170.82, 159.54, 140.75, 136.31, 128.77, 128.72, 128.64, 128.38, 128.17, 126.50, 77.36, 77.36, 67.38, 62.15, 53.30, 52.44, 33.50, 26.99, 14.19; IR (film) 2933, 1720, 1498, 1455, 1370, 1083, 1061, 1028, 698 cm$^{-1}$; LR-MS (ESI$^+$) calculated for C$_{22}$H$_{25}$NO$_5$: 384.2 [M+H$^+$]; found: 384.3.

Preparation of Ethyl (2S,3R)-2-(((benzyloxy)carbonyl)amino)-3-((di-tert-butoxyphosphoryl)(hydroxy)methyl)-5-phenylpentanoate (16e, n=2, X=H)

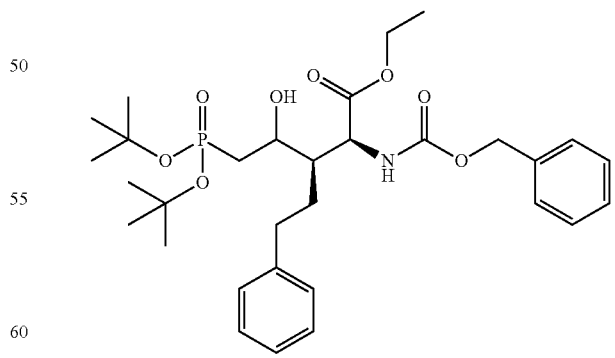

Ethyl (2S,3R)-2-(((benzyloxy)carbonyl)amino)-3-formyl-5-phenylpentanoate (2-2, 260 mg, 0.678 mmol) was reacted with di-tert-butyl phosphite using a similar procedure as outlined in General Procedure B to provide ethyl (2S,3R)-2-(((benzyloxy)carbonyl)amino)-3-((di-tert-butoxyphosphoryl)(hydroxy) methyl)-5-phenylpentanoate (16e, n=2, X=H; 302 mg; 77%) as a mixture of diastereomers. [α]$_D^{20}$=−7.7 (c 1.00, CHCl$_3$); $^1$H NMR (400 MHz, Chloroform-d) δ 7.41-7.27 (m, 5H), 7.26-7.09 (m, 5H), 6.44 (d, J=8.6 Hz, 0.7H), 5.71 (d, J=9.9 Hz, 0.3H), 5.17-5.05 (m, 2H), 4.70-4.61 (m, 0.7H), 4.26-4.21 (m, 0.3H), 4.21-4.05 (m, 2H), 3.88-3.77 (m, 0.7H), 3.77-3.67 (m, 0.7H), 3.51-3.40 (m, 0.3H), 3.27-3.19 (m, 0.3H), 2.86-2.51 (m, 2H), 2.26-2.13 (m, 0.6H), 2.02-1.80 (m, 1.4H), 1.56-1.38 (m, 18H), 1.26 (t, J=7.2, 3H); $^{13}$C NMR (101 MHz, CDCl$_3$) δ 172.42, 156.95, 140.94, 136.68, 128.65, 128.57, 128.40, 128.30, 128.13, 126.28, 83.93, 66.96, 61.51, 58.55, 50.48, 39.75, 33.30, 30.51, 26.39, 14.30; IR (film) 2979, 1746, 1723, 1507, 1498, 1395, 1370, 1257, 1166, 1038, 982, 919, 698, 686 cm$^{-1}$; LR-MS (ESI$^+$) calculated for C$_{30}$H$_{44}$NO$_8$P: 578.3 [M+H$^+$]; found: 578.5.

Preparation of Ethyl (2S,3R)-2-(((benzyloxy)carbonyl)amino)-3-((di-tert-butoxyphosphoryl)methyl)-5-phenylpentanoate (16e, n=2, X=H)

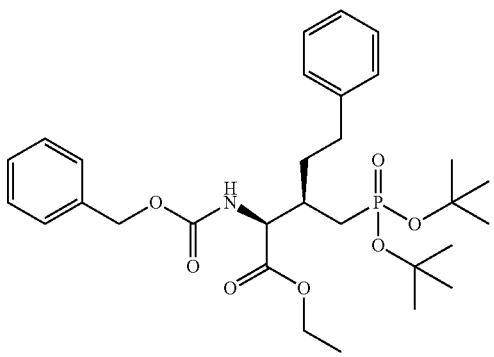 [SMILES: CCOC(=O)[C@@H](NC(=O)OCc1ccccc1)[C@@H](CCc1ccccc1)CP(=O)(OC(C)(C)C)OC(C)(C)C]

Ethyl (2S,3R)-2-(((benzyloxy)carbonyl)amino)-3-((di-tert-butoxyphosphoryl)(hydroxy) methyl)-5-phenylpentanoate (16e, n=2, X=H; 240 mg; 0.415 mmol) was reacted via General Procedure C to provide ethyl (2S,3R)-2-(((benzyloxy)carbonyl)amino)-3-((di-tert-butoxyphosphoryl) methyl)-5-phenylpentanoate (18e, n=2, X=H; 105 mg; 45% over 2 steps) as a white foam. [α]$_D^{20}$=−4.8 (c 1.00, CHCl$_3$); $^1$H NMR (400 MHz, Chloroform-d) δ 7.44-7.04 (m, 10H), 6.23 (d, J=8.9 Hz, 1H), 5.23-5.02 (m, 2H), 4.60 (dd, J=8.7, 4.5 Hz, 1H), 4.28-4.07 (m, 2H), 2.87-2.57 (m, 2H), 2.49-2.27 (m, 1H), 2.05-1.92 (m, 1H), 1.85-1.52 (m, 4H), 1.44 (d, J=9.0 Hz, 18H), 1.27 (t, J=7.1 Hz, 3H); $^{13}$C NMR (101 MHz, CDCl$_3$) δ 172.22, 156.73, 141.84, 136.63, 128.64, 128.58, 128.54, 128.45, 128.17, 125.92, 82.58, 67.01, 61.62, 56.52, 36.50, 33.41, 33.12, 31.59, 30.49, 14.30; IR (film) 2981, 1718, 1541, 1370, 1259, 1038, 1008, 982, 673 cm$^{-1}$; LR-MS (ESI$^+$) calculated for C$_{30}$H$_{44}$NO$_7$P: 562.3 [M+H$^+$]; found: 562.5.

Preparation of (2S,3R)-2-((((9H-fluoren-9-yl)methoxy)carbonyl)amino)-3-((di-tert-butoxyphosphoryl) methyl)-5-phenylpentanoic acid (1-2)

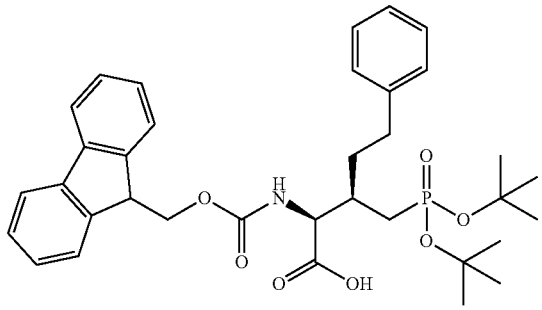 [SMILES: CC(C)(C)OP(=O)(C[C@H](CCc1ccccc1)[C@H](NC(=O)OCC1c2ccccc2-c2ccccc21)C(=O)O)OC(C)(C)C]

Ethyl (2S,3R)-2-(((benzyloxy)carbonyl)amino)-3-((di-tert-butoxyphosphoryl)methyl)-5-phenylpentanoate (18e, n=2, X=H; 100 mg; 0.178 mmol) was reacted using a similar procedure as outlined in General Procedure D to provide (2S,3R)-2-((((9H-fluoren-9-yl)methoxy)carbonyl) amino)-3-((di-tert-butoxyphosphoryl) methyl)-5-phenylpentanoic acid (1-2, 82 mg, 74%) as a white foam. [α]$_D^{20}$=+30.4 (c 1.00, CHCl$_3$); $^1$H NMR (400 MHz, Chloroform-d) δ 7.75 (d, J=7.2 Hz, 2H), 7.61 (t, J=7.7 Hz, 2H), 7.38 (t, J=7.3 Hz, 2H), 7.32-7.12 (m, 7H), 5.95 (d, J=7.3 Hz, 1H), 4.87 (dd, J=7.1, 4.2 Hz, 1H), 4.35 (d, J=7.2 Hz, 2H), 4.21 (t, J=7.1 Hz, 1H), 2.76-2.56 (m, 3H), 2.50-2.36 (m, 1H), 2.06-1.86 (m, 2H), 1.72-1.58 (m, 1H), 1.57-1.47 (m, 18H). $^{13}$C NMR (101 MHz, CDCl$_3$) δ 172.31, 155.60, 144.11, 143.92, 141.42, 128.55, 128.51, 127.82, 127.18, 126.12, 125.33, 120.10, 84.02, 67.17, 55.75, 47.26, 36.42, 33.51, 32.50, 30.53, 25.52; IR (film) 2979, 1716, 1509, 1450, 1395, 1371, 1319, 1255, 1248, 1219, 1156, 1078, 1040, 988, 758, 700, 667 cm$^{-1}$; LR-MS (ESI$^+$) calculated for C$_{35}$H$_{44}$NO$_7$P: 622.3 [M+H$^+$]; found: 622.6.

Preparation of 3S,6S,9S,12R,13S)-1-((S)-1-acetylpyrrolidin-2-yl)-12-carbamoyl-9-(hydroxymethyl)-3-isobutyl-1,4,7,10-tetraoxo-13-phenethyl-6-((1-(8-phenyloctyl)-1H-imidazol-5-yl)methyl)-2,5,8,11-tetraazatetradecan-14-ylphosphonic acid (W-2)

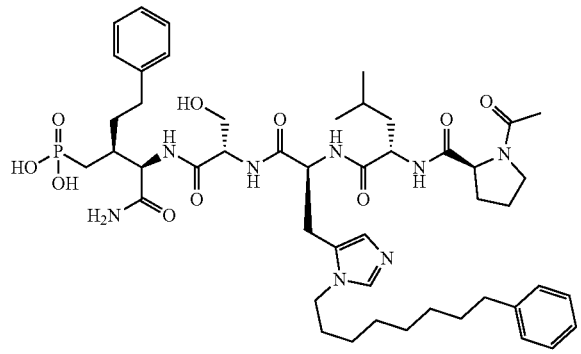 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@@H](C(N)=O)[C@H](CCc1ccccc1)CP(=O)(O)O]

The peptide 3S,6S,9S,12R,13S)-1-((S)-1-acetylpyrrolidin-2-yl)-12-carbamoyl-9-(hydroxymethyl)-3-isobutyl-1,4,7,10-tetraoxo-13-phenethyl-6-((1-(8-phenyloctyl)-1H-imidazol-5-yl)methyl)-2,5,8,11-tetraazatetradecan-14- ylphosphonic acid (W-2) was synthesized on a 0.05 mmol scale using the general SPPS procedure. Purification by preparative RP-HPLC afforded the final peptide (W-2, 22 mg, 46% overall) with ≥95% purity by analytical HPLC. LR-MS (ESI$^+$) calculated for $C_{48}H_{71}N_8O_{10}P$: 951.5 [M+H$^+$]; found: 951.8.

Example 4

Development of Macrocyclic PBD-Binding Peptidomimetic Ligands

Figure 3:
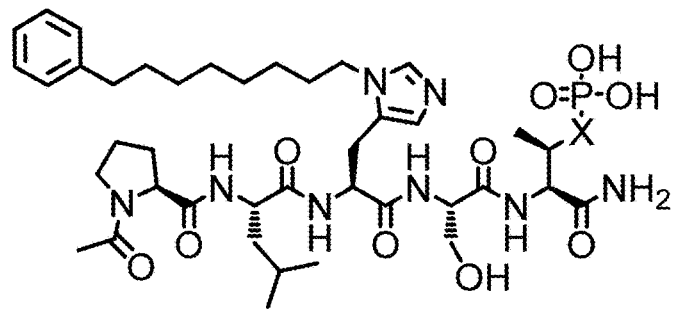
FIG. 3 Discloses structures of the high-affinity PBD-binding compounds claimed in previous applications.

In previously filed U.S. Provisional Applications, high-affinity peptidomimetic ligands targeting the polo-box domain (PBD) of polo-like kinase 1 (Plk1) with preferred embodiments of compounds 1 and 2 (FIG. 3) have been claimed. Compound 1 (4j)[3,4] was developed from the minimal penta-peptide "PLHSpT" and bears an alkylphenyl chain on the N(π) nitrogen of the histidine residue (referred to as His* or H*). This functionality provides access to a cryptic binding pocket in the PBD, resulting in greater than 1,000-fold improvements in PBD binding affinity. Further development resulted in compound 2 (4j*)[3,4], which substitutes the phosphothreonine residue for the phosphonate analog Pmab [(2S)-amino-(3R)-methyl-4-phosphonobutanoic acid]. The resulting compound 2 maintains PBD-binding affinity and prevents inactivation of the peptidomimetic through phosphate hydrolysis by cellular phosphatases. While these compounds represent the highest affinity ligands targeting the Plk1 PBD in the literature, they suffer from certain drawbacks that limit their therapeutic development, namely poor membrane penetration and stability to cellular proteases. In the current disclosure, the development of macrocyclic peptidomimetic ligands based on the high-affinity compounds has been reported. These ligands provide several-fold enhancements in binding affinity, and should also provide significantly improved stability to proteases when utilized in cellular contexts.

Figure 4:
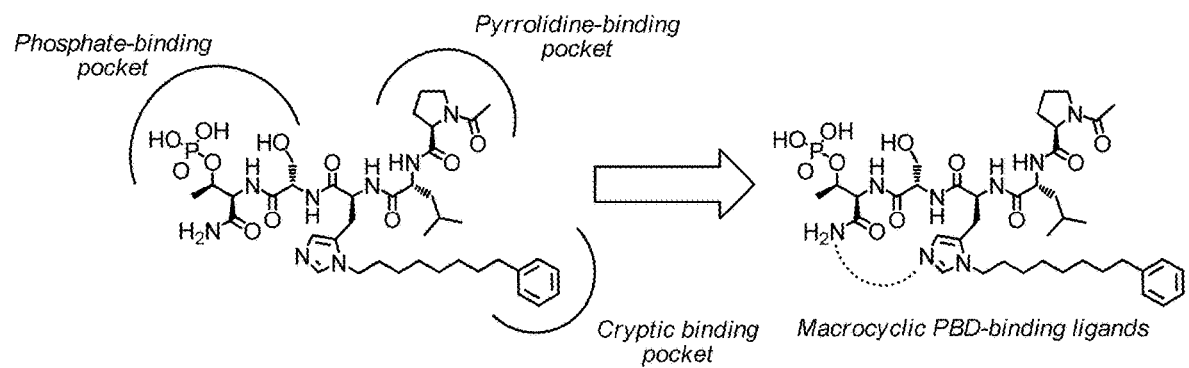
FIG. 4 Discloses schematic representation of the PBD binding site for compound 1 and design of macrocyclic ligands based on this scaffold.

Based upon the literature understanding and precedence, it is hypothesized that macrocyclization of high-affinity scaffold could potentially improve the stability of peptidomimetic ligands to cellular proteases and potentially improve the cell permeability. Peptide cyclization has been used extensively in medicinal chemistry as a means to improve the pharmacokinetic properties of peptide-based therapeutics. Evaluation of several X-ray co-crystal structures of peptide and peptidomimetic ligands bound to the PBD demonstrated that effective macrocyclization could be achieved through linkage of the N(τ) nitrogen of the histidine with the C-terminus of the peptide backbone (FIG. 4). Using this information, we designed cyclic analogs using the most straightforward approach of connecting these atoms through methylene-containing linkers of various lengths.

A synthetic route to synthesize these cyclic analogs that utilizes an on-resin, microwave-assisted S$_N$2 alkylation to install the key bis-alkyl histidine functionality (Scheme 1) has been designed. (4-hydroxymethyl-3-methoxyphenoxy) butanoic acid resin (HMPB resin) was specifically selected for this synthesis since it can be cleaved using mild acid conditions to retain orthogonal protection for cyclization, and also because it can better withstand microwave heating conditions better than trityl-based resins. General solid-phase peptide synthesis (SPPS) protocols were used to install the protected amino acids providing resins 3a (sequence Ac-PLH*SpT) and resin 3b (sequence Ac-H*SpT). Following completion of the peptide backbone, the methylene linker was installed on the N(τ) nitrogen using a microwave-assisted on-resin alkylation with alkyl iodides[15-17] of increasing lengths (4a-c [4, 5, and 6 methylenes] for Ac-PLH*SpT/4d [5 methylenes] for Ac-H*SpT) to provide resins 5a-d. Cleavage and partial deprotection of the peptide in mild acid provided the compounds 6a-d and PyBOP cyclization and phosphate deprotection with Pd/C provided the final cyclized compounds 7a-c (Ac-PLH*SpT containing 4, 5, and 6 methylene linkers) and 7d (Ac-H*SpT containing 5 methylene linker).

Scheme 1.

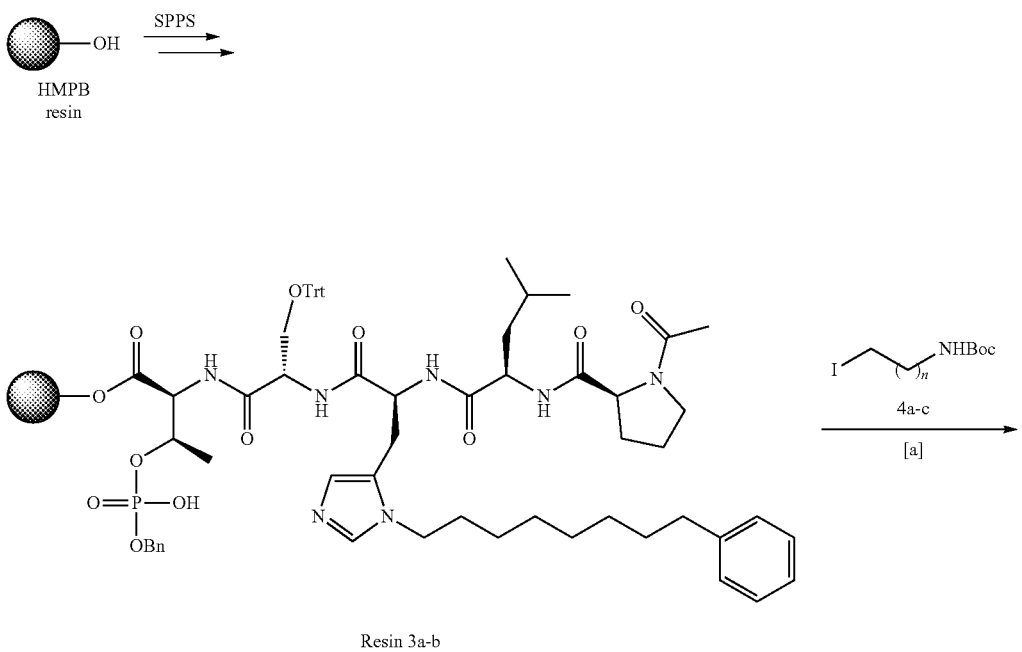

Resin 3a-b

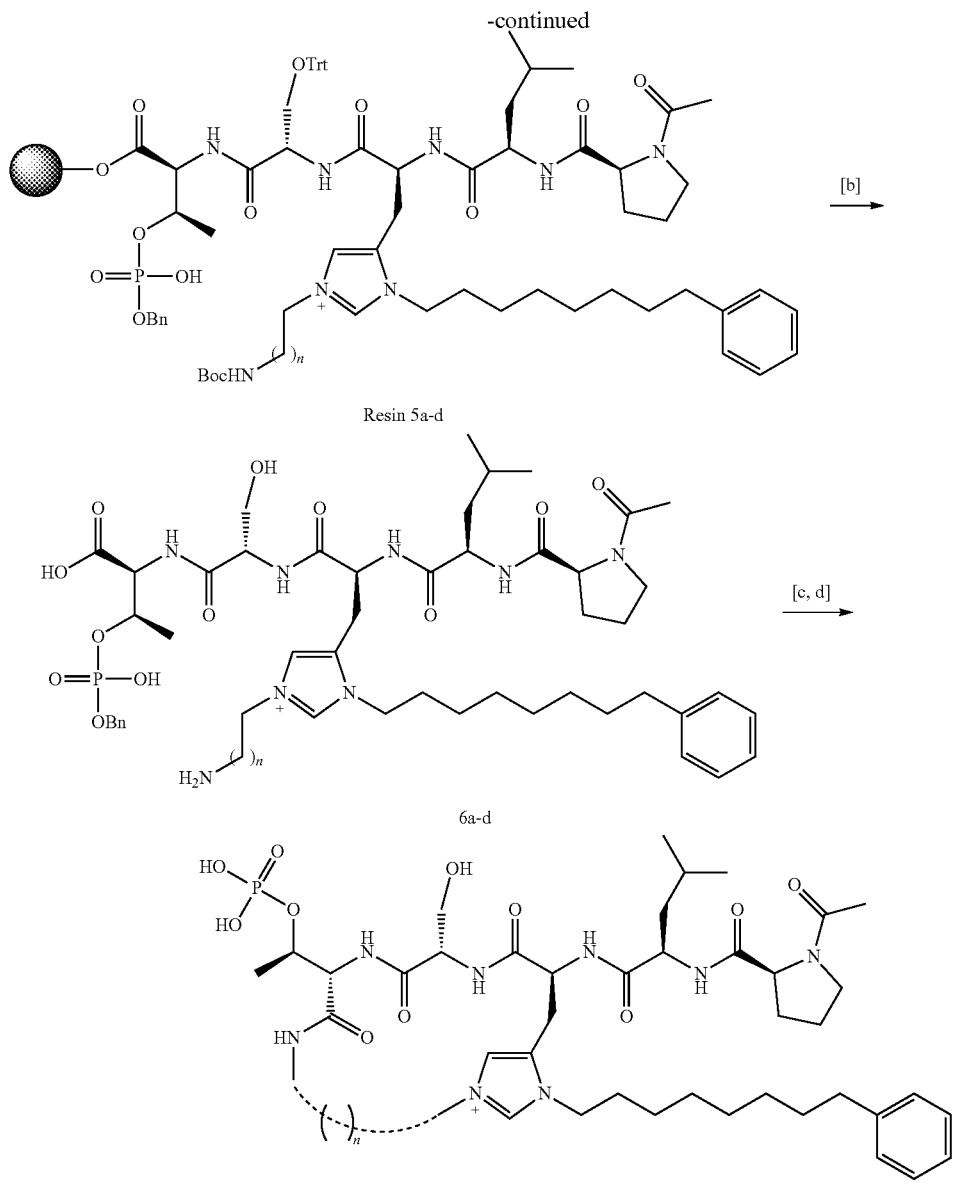

7a-d

Reagents and conditions. [a] 4a-c (5 equiv.), DIEA (6 equiv.), DMF, 18 h, 50° C. under microwave irradiation; [b] 20% trifluoroacetic acid (v/v), 2% triisopropylsilane (v.v), DCM, 2 × 30 minutes each, RT; [c] PyBOP (1.1 equiv.), DIEA (5 equiv.), DMF (1 mM concentration), 18 h, RT; [d] Pd/C (50 mol %), $H_2$ (1 atm), MeOH, 1 h, RT.

Figures 5A, 5B:
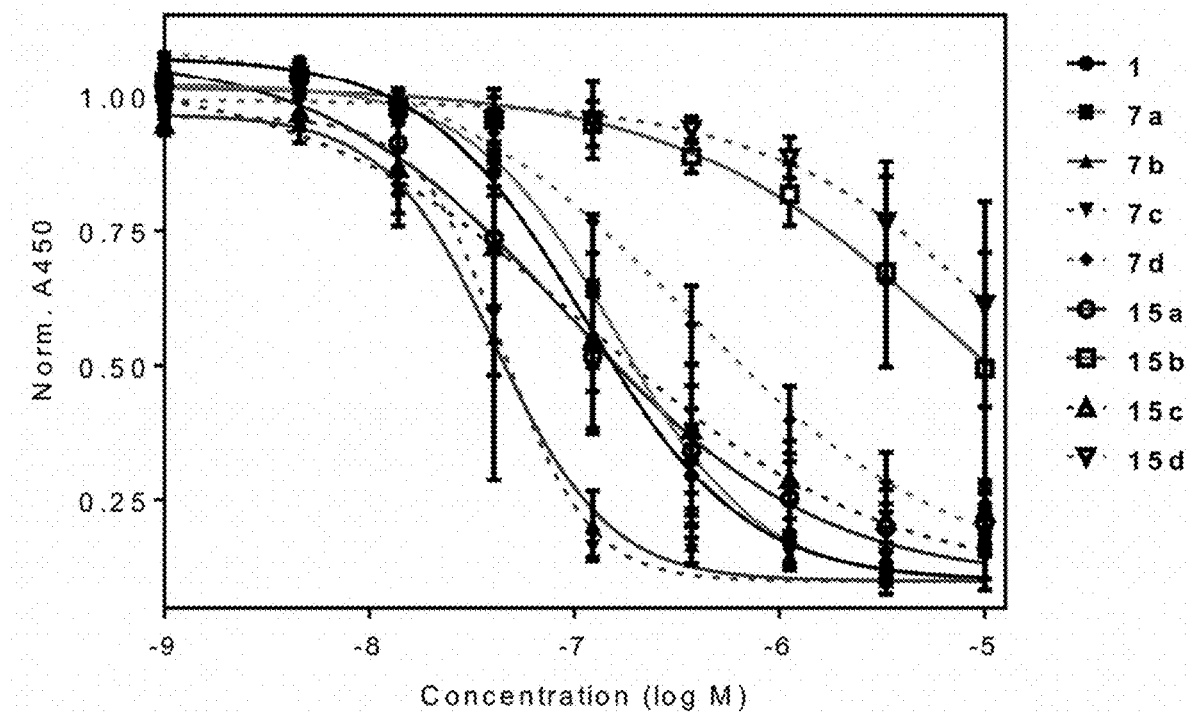
FIG. 5A Represents normalized ELISA data curves for cyclic PBD-binding ligands.
FIG. 5B Represents table dislosing IC50 values of cyclic PBD-binding ligands.
Figure 6:
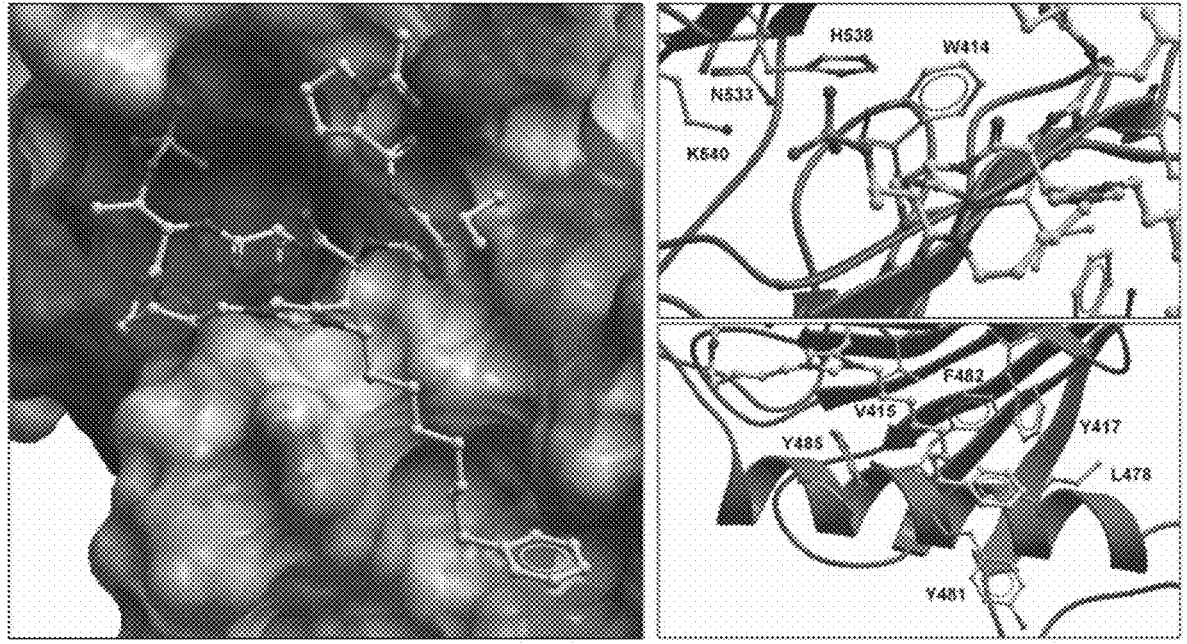
FIG. 6 Discloses X-ray structure of the Plk1 PBD co-crystallized with cPLH*$^{(n5)}$SpT (7b). Key residues within the phosphate and cryptic binding pockets are labeled (right panels).
Figure 7:
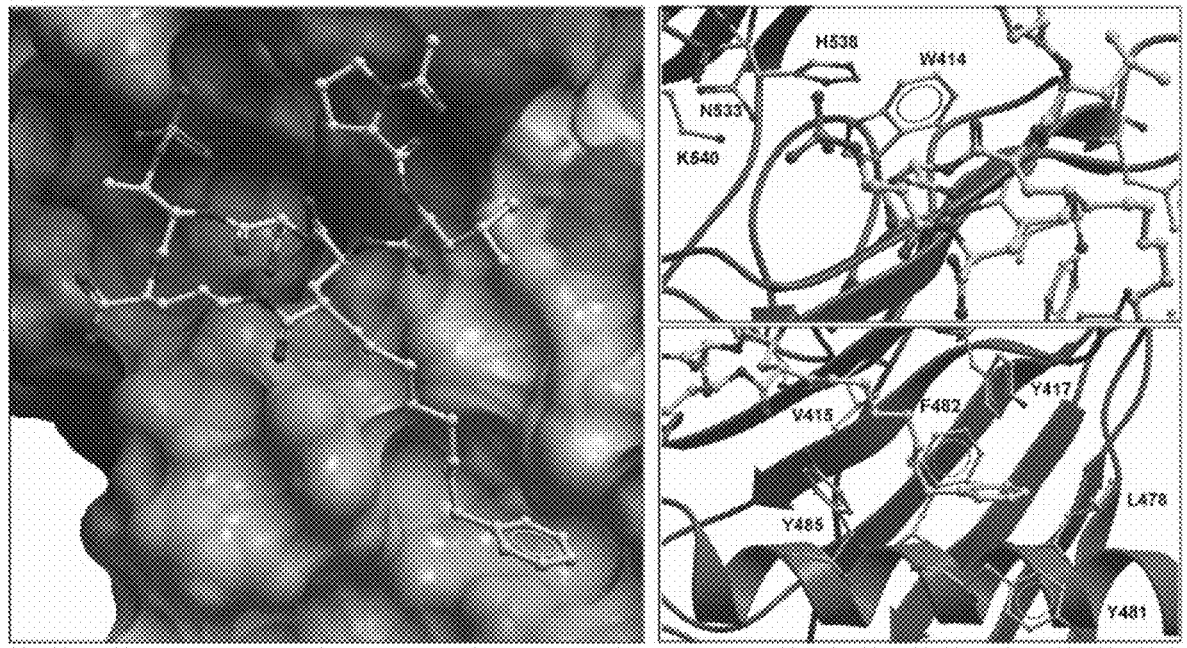
FIG. 7 Represents X-ray structure of the Plk1 PBD co-crystallized with cPLE*SpTO (15a). Key residues within the phosphate and cryptic binding pockets are labeled (right panels).

The biochemical assay results for all compounds are provided in FIG. 5A and FIG. 5B. In competitive ELISA assays, the bis-alkyl histidine macrocycle 7a (n=4 linker) is equipotent to the parent peptide 1 (4j). However, compounds 7b and 7c (n=5 and n=6, respectively) demonstrate several-fold enhancements in inhibitory potency. The smaller tripeptide 7d shows ~2.5-fold loss in affinity; however, the deceased molecular size may improve potency in cell-based applications.

While the cyclic bis-alkyl histidine peptides display significant improvements versus the parent compound 1, the synthesis of these compounds is somewhat inefficient in that it requires an on-resin alkylation followed by a solution-phase cyclization. Furthermore, removal of the benzyl protection group requires palladium on activated charcoal, and it was empirically found that the desired product can remain adsorbed to the activated charcoal, diminishing yields. Envisioning a more direct approach to macrocyclic PBD-binding ligands, second generation cyclic peptides were designed that could utilize on-resin cyclization between side chains following orthogonal deprotection. Allyl esters and carbamates have been extensively utilized in SPPS as orthogonal protecting groups prior to on-resin side chain cyclization. To take advantage of this chemistry, peptides that incorporated Alloc-protected amine residues at the C-terminus were designed and the central histidine residue was substituted with allyl-protected glutamic acid. Attention was focused on installing the crucial alkylphenyl moiety required to access the cryptic binding pocket and maintain high-affinity binding. There is literature precedent for the stereoselective alkylation of protected glutamic acids at the C4-position. Most notably, the Hanessian method utilizes lithium chelation-controlled enolate addition to electrophiles to generate C4-alkylated glutamic acids with high stereoselectivity.[18] Using this chemistry, the alkylphenyl-containing glutamic acid analog 11 (Scheme 2) was designed and synthesized. This analog can be accessed in 4 steps from commercial material with 40-50% overall yields.

Scheme 2.

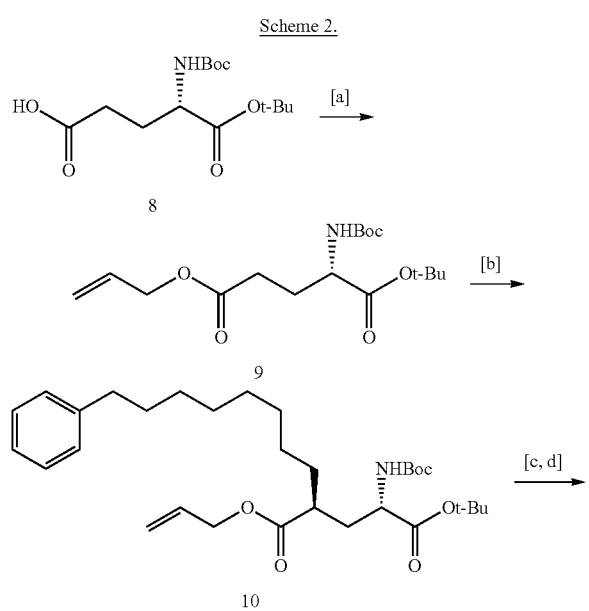

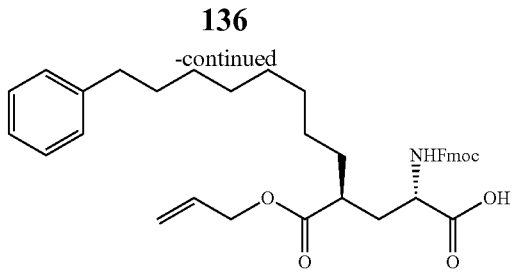

11

Reagents and conditions. [a] allyl alcohol (1.2 equiv.), triphenylphosphine (1.2 equiv.), diisopropylazodicarboxylate (DIAD, 1.2 equiv.), THF, 3 h, RT; [b] i) LiHMDS (2.2 equiv.), -78° C., THF, 2 h; ii) Ph(CH₂)₈I (1.5 equiv.), THF, -78° C., THF, 18 h; [c] 50% trifluoroacetic acid (v/v), triisopropylsilane (2.2 equiv.), DCM, 3 h, RT; [d] Fmoc—NHS (1.3 equiv.), DIEA (3 equiv.), THF, 18 h, RT.

With reagent 11 in hand, a set of cyclic peptides was designed to investigate the length and stereochemistry of the C-terminal amino acid. This set utilized both L- and D-stereochemistries of ornithine (n=3 methylenes) and lysine (n=4 methylenes) (Scheme 3). General SPPS protocols were used to incorporate the amino acid sequence on Rink amide resin up to the synthetic reagent 11 to give resins 12a-d. Following this coupling reaction, the allyl protection scheme was removed using Pd(PPh₃)₄ and on-resin cyclization was afforded by treatment with PyBOP to give resins 13a-d. Following cyclization, the Fmoc-protection was removed and the SPPS was continued to incorporate the final Leu and Pro residues to give resins 14a-d. Cleavage and global deprotection in a 95% trifluoroacetic acid cocktail provides the final compounds 15a-d without the need for further post-solid phase reactions.

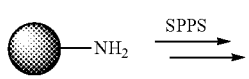

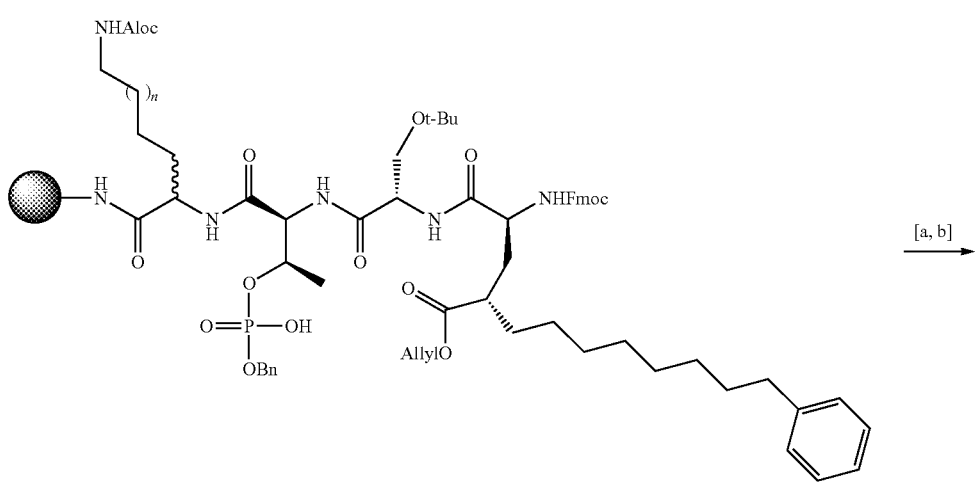

Resin 12a-d

-continued
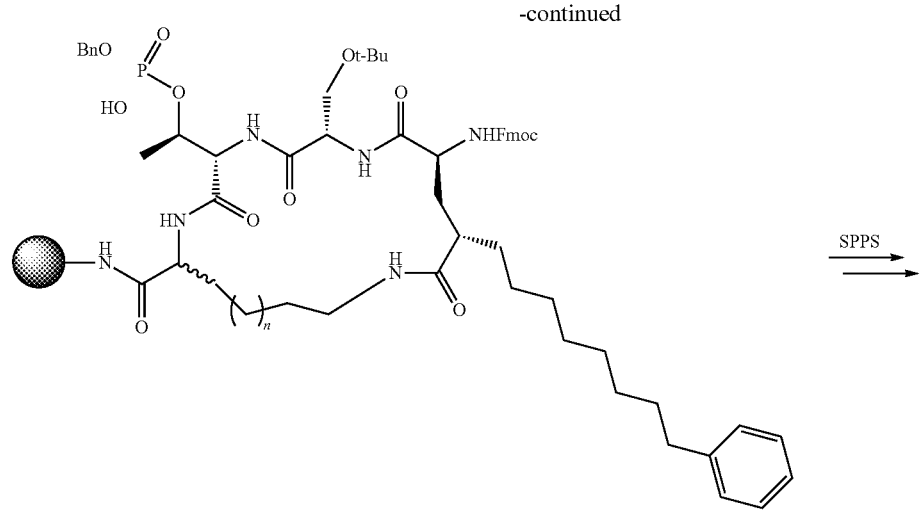
Resin 13a-d
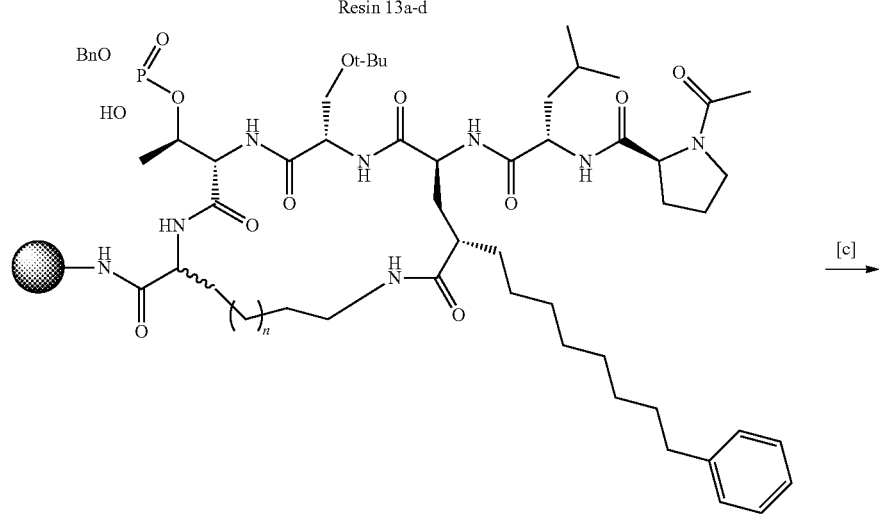
Resin 14a-d
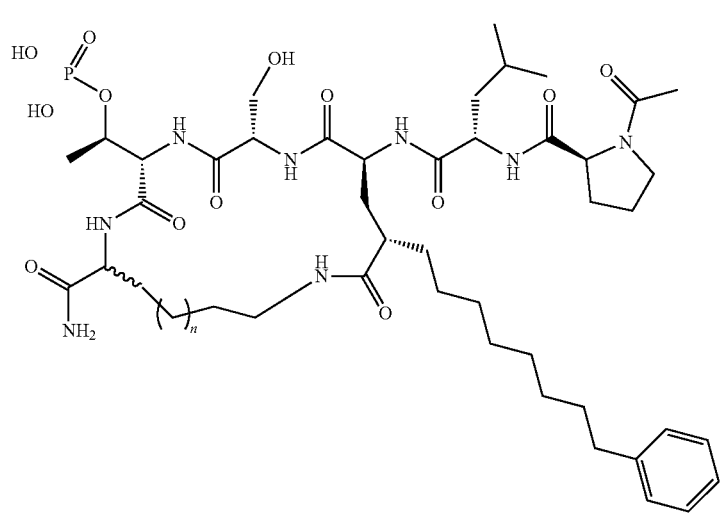
15a-d
Reagents and conditions. [a] Pd(PPh₃)₄ (0.3 equiv.), phenylsilane (10 equiv.), DCM, 3 x 30 minutes each, RT; [b] PyBOP (5 equiv.), DIEA (10 equiv.), DMF, 18 h, RT; [c] 95/2.5/2.5 trifluoroacetic acid/water/triisopropylsilane (v/v), 2 x 2 h each, RT.

In competitive ELISA assays, the L-Orn and L-Lys derivatives of the cyclic peptides (compounds 15a and 15c, respectively) demonstrated improved potencies versus the parent peptide 1. However, the corresponding D- analogs (compounds 15b and 15d) showed dramatic reductions in potency (FIG. 5B). Structures of some the examples that were tested in the cellular assays have been disclosed in Table 4.

Exemplary Synthesis of Macrocyle I:

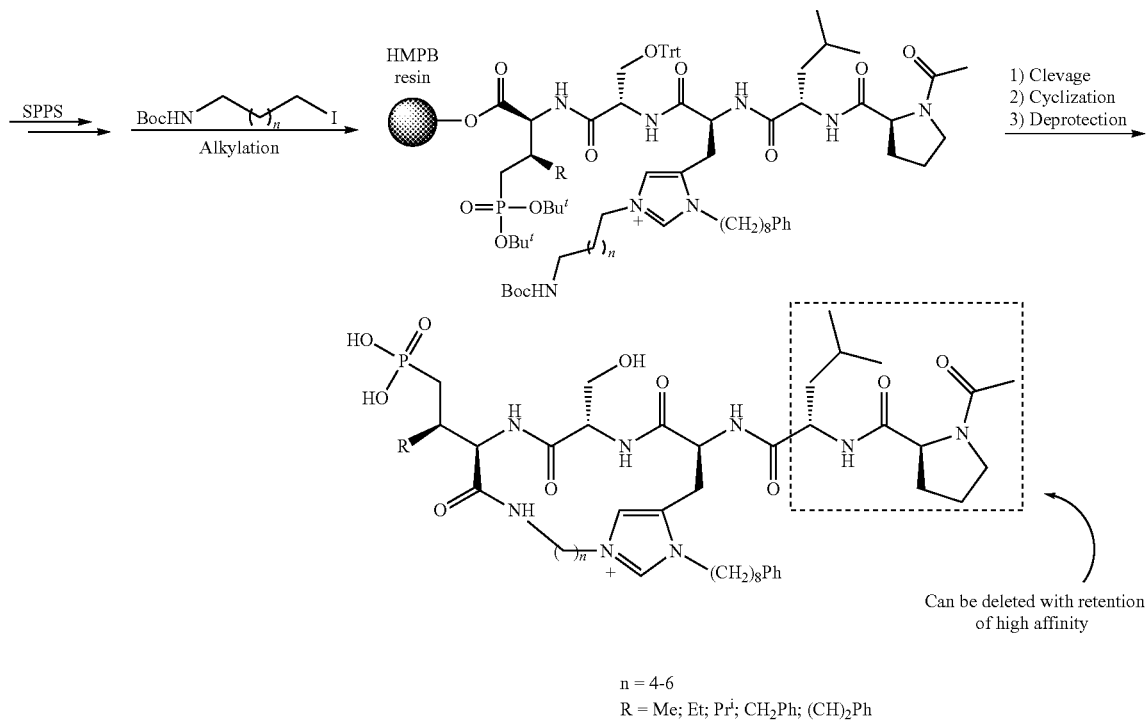

n = 4-6
R = Me; Et; Pr$^i$; CH$_2$Ph; (CH)$_2$Ph

Exemplary Synthesis of Macrocycle II:

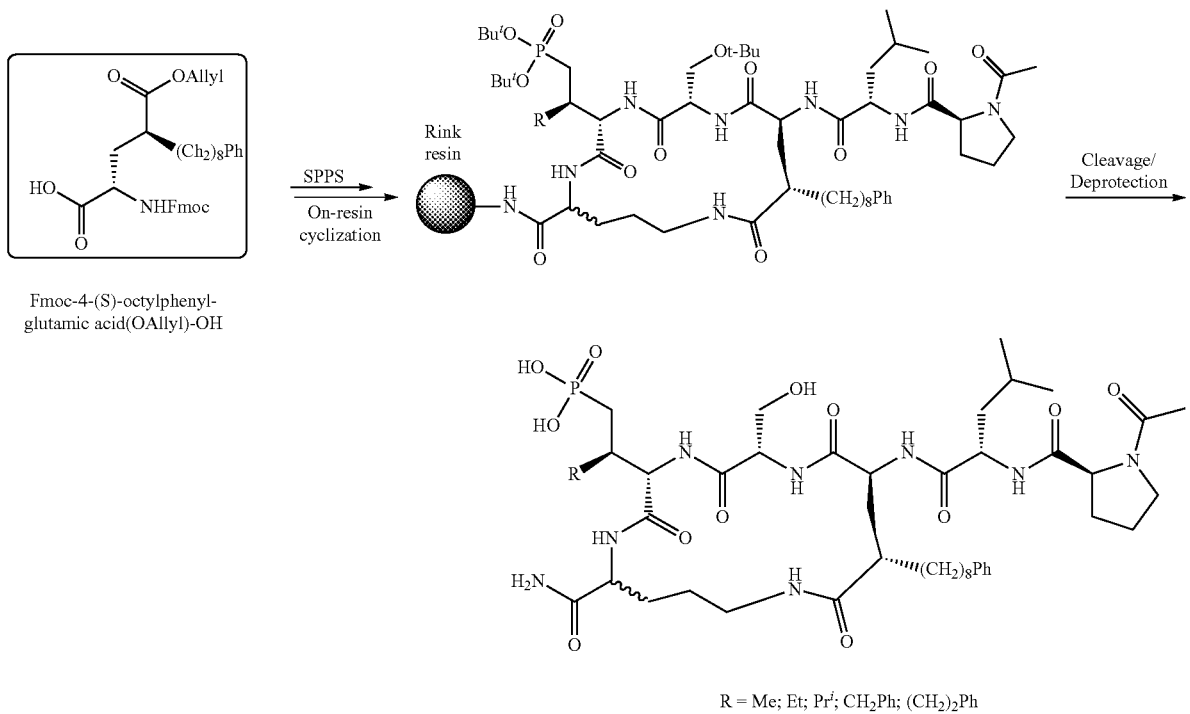

Fmoc-4-(S)-octylphenyl-glutamic acid(OAllyl)-OH

R = Me; Et; Pr$^i$; CH$_2$Ph; (CH$_2$)$_2$Ph

TABLE 4

Exemplary structures of compounds prepared and evaluated as part of this disclosure.

| Compound | Lot | Structure |
|---|---|---|
| cPLH*(n4)SpT 7a | DH_222J_35 | 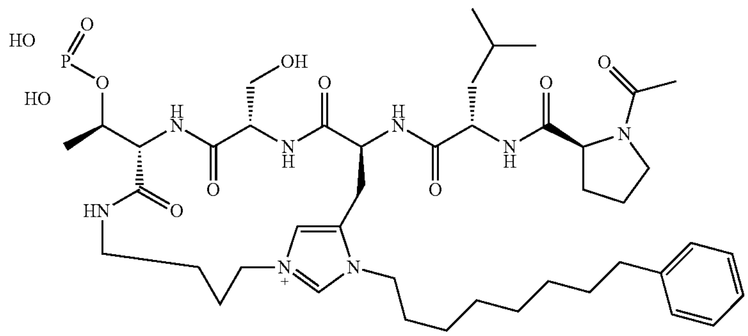 |
| cPLH*(n5)SpT 7b | DH_222J_34 | 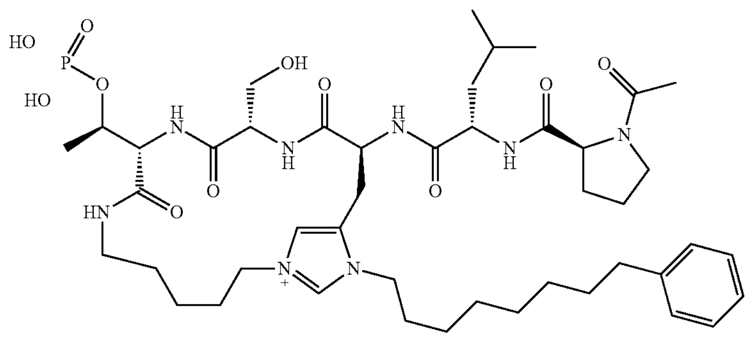 |
| cPLH*(n6)SpT 7c | DH_222J_33 | 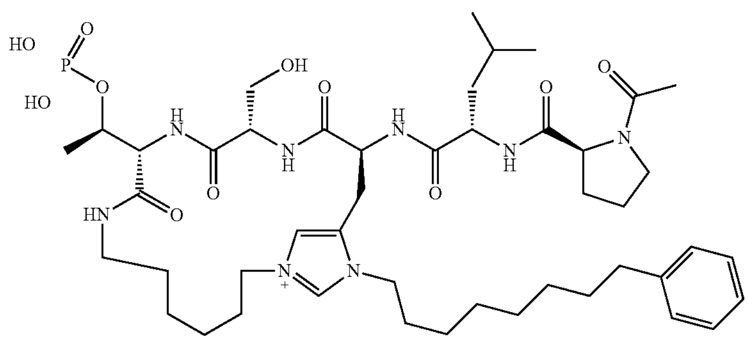 |
| cH*(n5)SpT 7d | DH_222J_82 | 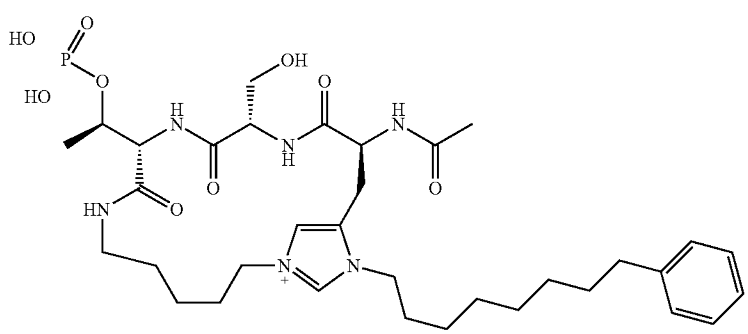 |

TABLE 4-continued
Exemplary structures of compounds prepared and evaluated as part of this disclosure.
| Compound | Lot | Structure |
| --- | --- | --- |
| cPLE*SpTO 15a | DH_222J_57 | 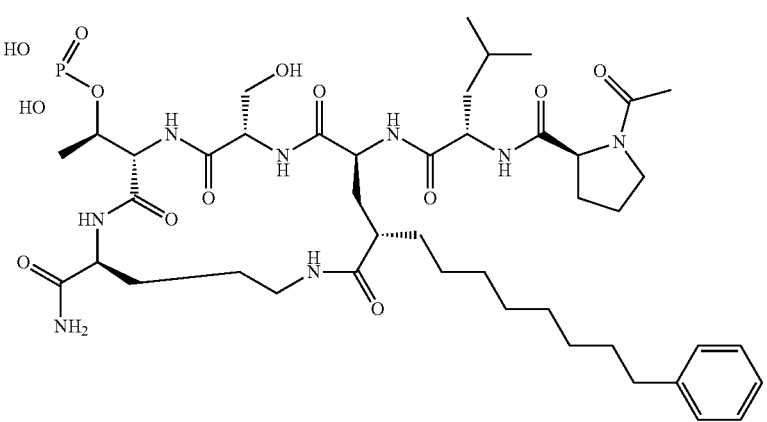 |
| cPLE*SpTo 15b | DH_222J_58 | 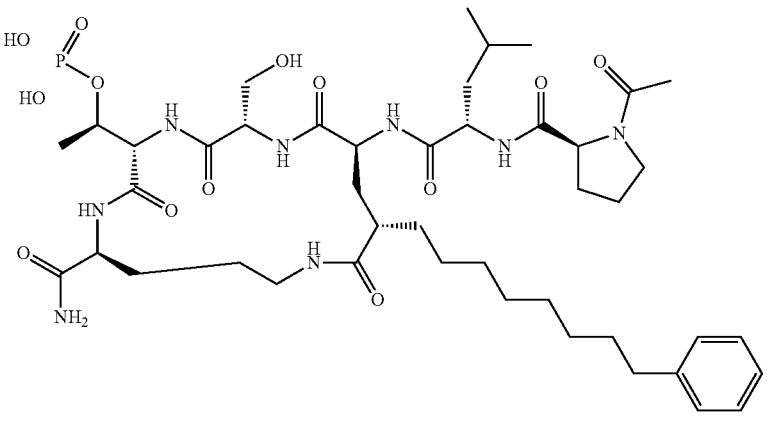 |
| cPLE*SpTK 15c | DH_222J_45 | 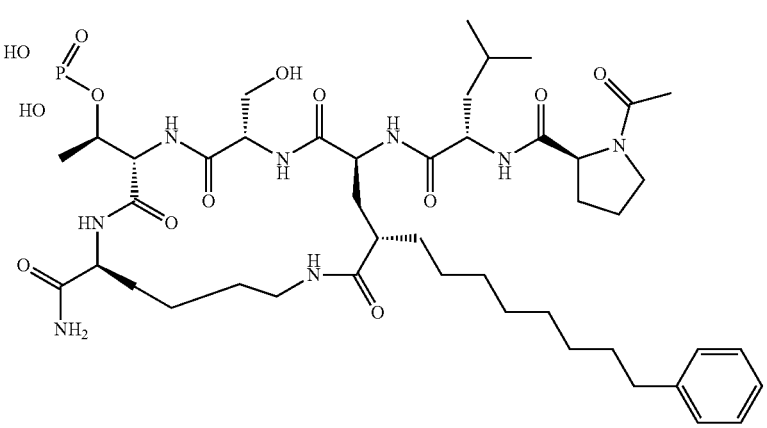 |

TABLE 4-continued

Exemplary structures of compounds prepared and evaluated as part of this disclosure.

| Compound | Lot | Structure |
|---|---|---|
| cPLE*SpTk 15d | DH_222J_59 | 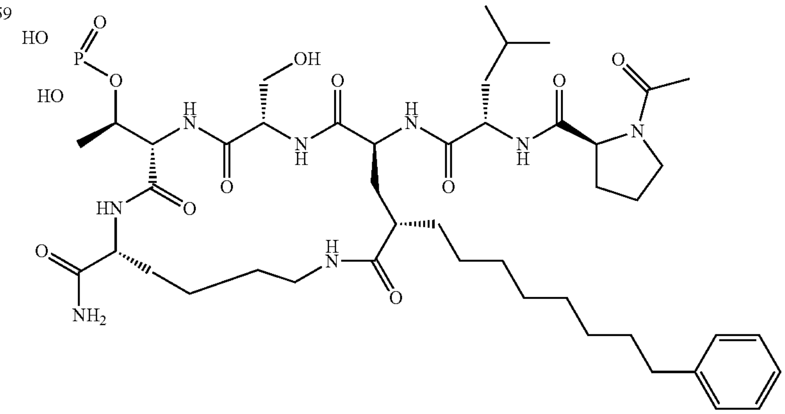 |

Example 5

Design of Initial Bi-valent Ligands

Figure 8:
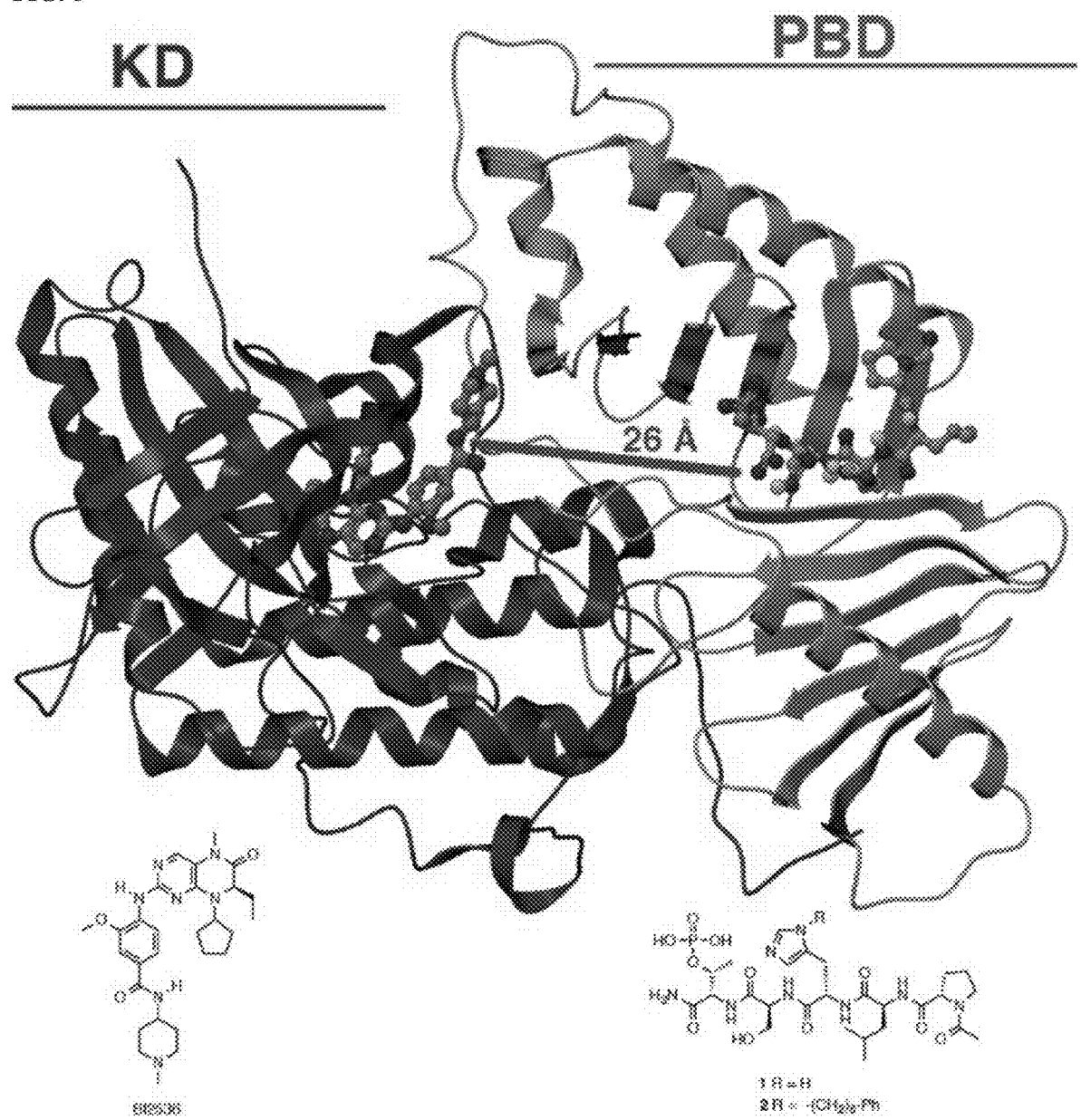
FIG. 8 discloses potential spacing and orientation of components for the construction of bivalent Plk1-binding ligands. The crystal structures of KD-bound BI2536 (PDB 2RKU) and PBD-bound 1 (PDB 3HIK) have been oriented by super positioning on the homologous components found in the zebrafish KD-PBD-*Drosophila* Map205$^{PBM}$ co-crystal structure (PDB: 4J7B).

Bi-valent ligands must be capable of simultaneously binding to both KD and PBD domains. While high affinity ligands for the individual domains are known, to date there have been no structures (either crystal or solution) of full-length Plk1, which would indicate the relative orientation of the two domains. However, the potential spatial organization of the domains has been informed by the recent crystal structure of a mixture of the isolated polo kinase KD and PBD (which have high homology to human Plk1) from zebrafish (*D. rerio*) and the PBD-binding motif of Map205 (Map205$^{PBM}$) from *Drosophila*, in which the KD appears to be held in a potentially relevant orientation relative to the PBD (PDB accession code 4J7B). Superposition of the human Plk1 KD complexed to BI2536 (a potent Plk1 kinase inhibitor, exhibiting an in vitro IC$_{50}$ value of 8 nM; PDB accession code 2RKU) onto the zebrafish KD and the human Plk1 PBD complexed to peptide 1 (PDB accession code 3HIK) onto the zebrafish PBD, respectively, provides a model from which to approximate inter-domain distances (FIG. 8).

Figure 9:
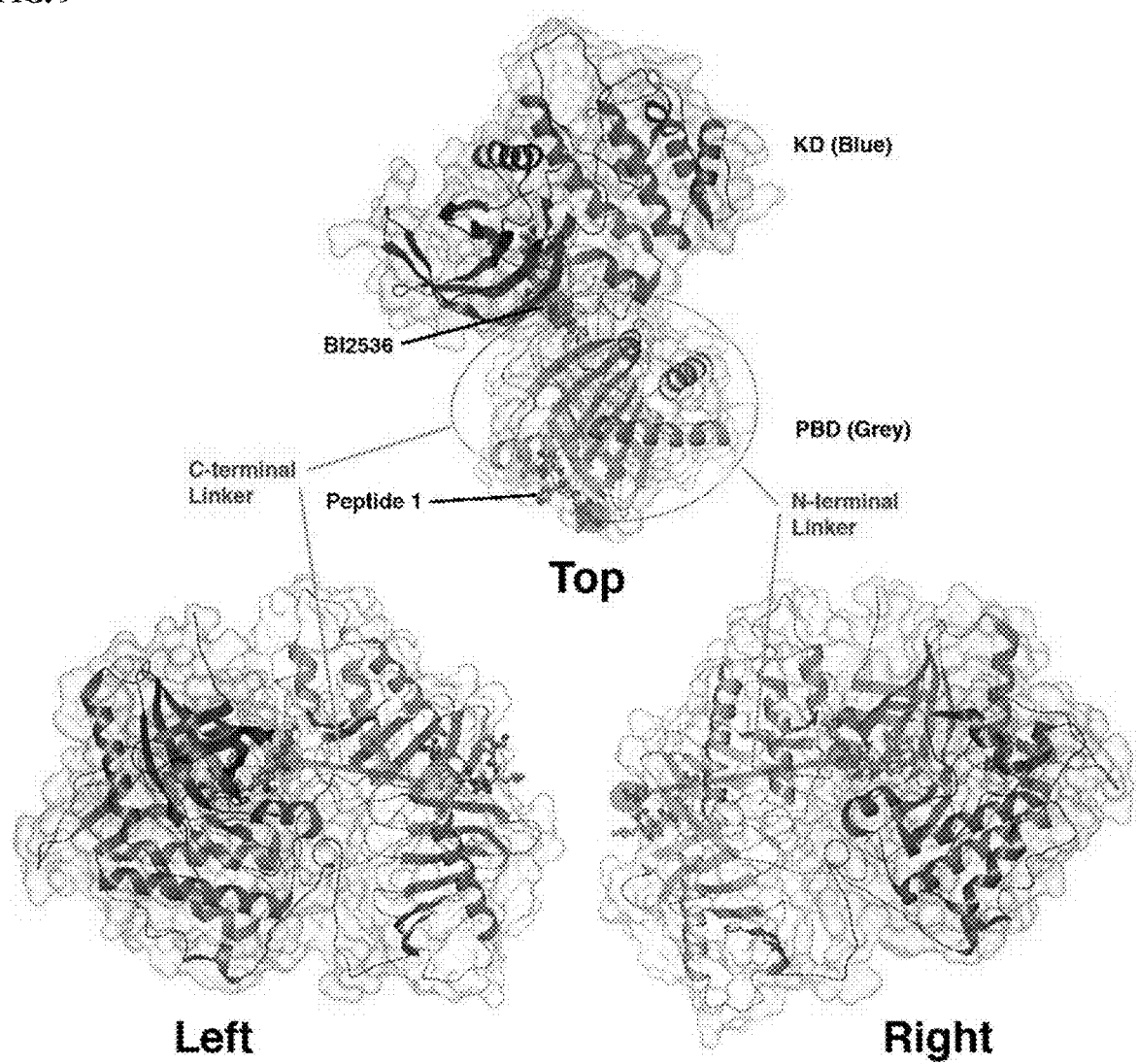
FIG. 9 discloses relative orientations of KD and PBD-bound ligands that suggest potential placement of linking segments. Attachment points are shown for BI2536 (red circle) and the peptide C-terminus (green dot) and N-terminus (blue dot). The structures have been obtained as described in FIG. 8.

The 2RKU crystal structure shows that the 1-methylpiperidin-4-amide moiety of BI2536 extends out from the KD catalytic cleft into solvent, indicating that this portion of the molecule could potentially be removed without undue deleterious effect. It is less clear whether optimum geometry could be achieved by tethering the BI2536 portion to the PBD-binding peptide from its C- or N-terminus. From FIG. 9, it is apparent that C-terminal linkage would be the most direct. However, the protein inter-domain linker (IDL) joining the KD to the PBD is thought to be highly flexible, and the relative orientations of the two domains could be quite variable (not restrained to what is shown in the 4J7B crystal structure). Therefore, examining N-terminal linkage in addition to C-terminal linkage is warranted. It has been previously shown that PBD-binding peptides are highly tolerant of N-terminal PEG chains bearing bulky flourophores.

Figure 10:
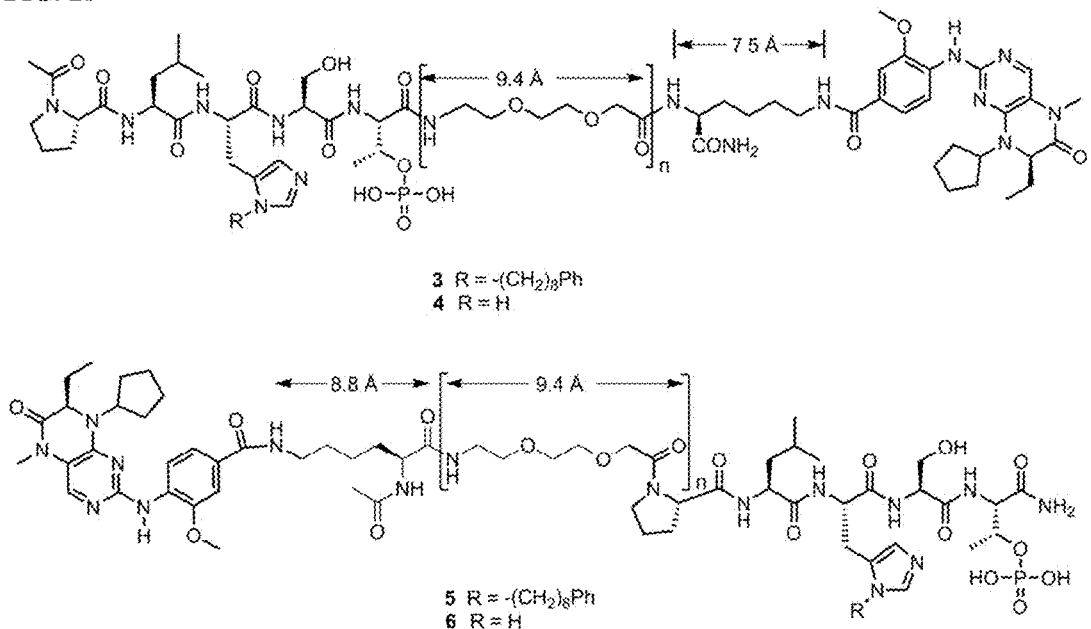
FIG. 10 represents structures of initial bi-valent constructs.

A set of bi-valent ligands were designed, in which peptides 1 and 2 were linked to the core structure of BI2536 by means of "mini-PEG" units, each of which spanned a maximum distance of approximately 9.4 Å. These consisted of both C-terminal (3 and 4) and N-terminal (5 and 6) linkages (FIG. 10). To facilitate solid-phase synthesis, a resin-bound Lys residue was employed as the starting point for each construct (Scheme 1). By varying the number of mini-PEG units, maximum spanning distances were achieved of approximately 17 Å (n=1), 26 Å (n=2), 36 Å (n=3) and 43 Å (n=4). A minimum required C-terminal spanning distance of 26 Å was anticipated based on the 4J7B crystal structure (FIG. 8).

Scheme 1. Protocol for the synthesis of bi-valent Plk1-binding ligands. Fmoc-Lys(ivDde)—OH and Fmoc—mini—PEG—OH are commercially available. The Fmoc—His*—OH (Qian, W. et al. Investigation of unanticipated alkylation at the N(pi) position of a histidyl residue under Mitsunobu conditions and synthesis of orthogonally protected histidine analogues. J. Org. Chem. 2011, 76, 8885-8890) and truncated BI2536 (Budin, G. et al. Bioorthogonal probes for polo-like knase 1 imaging and quantification. Angew. Chem. Int. Ed. Eng. 2011, 50, 9378-9381) were prepared according to literature procedures.

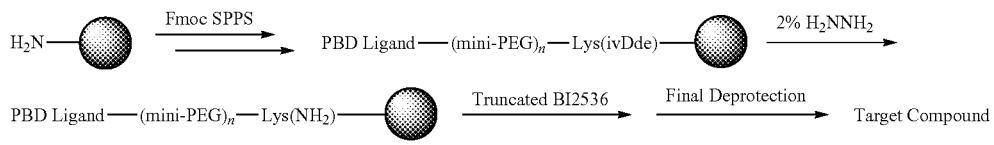

-continued

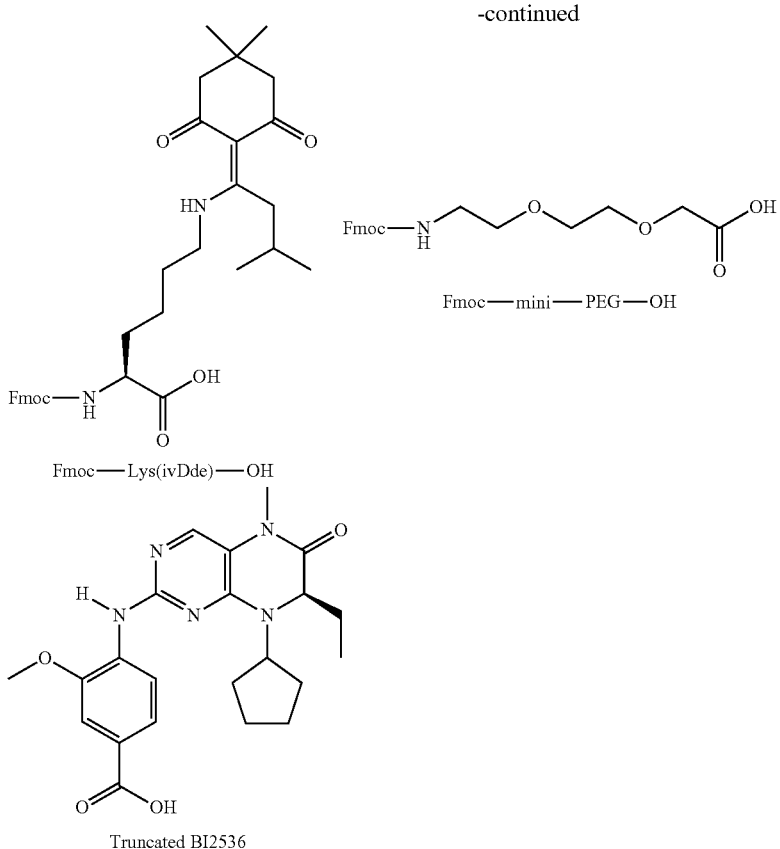

Truncated BI2536

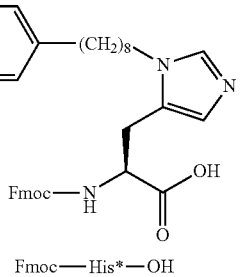

Fmoc—His*—OH

II. BIOLOGICAL EXAMPLES

Example 6

Enzyme-Linked Immunosorbent Assay (ELISA)-Based Inhibition Assay Against Full Length Plk1 and Plk1 PBD (43)

Transfection and Protein Lysate Production.

Plasmids encoding full length Plk1 (Plasmid #41160) (44) and Plk1 PBD (Plasmid #41162) (45) linked to a 3× myc tagged were purchased from Addgene (Deposited by Prof. Erich Nigg). HEK293T cells were plated on 10 cm culture dishes at 4M cells per plate. Following 24 h, the cells were transfected with 10 μg of plasmid DNA using 20 μL of TurboFect transfection reagent (Pierce Biotechnology) according to the manufacturer's instructions. Following 24 h, the cells were harvested using trypsin, washed with phosphate-buffered saline (PBS) 7.4 buffer, and lysed in lysis buffer (PBS 7.4+0.5% NP-40+protease/phosphatase inhibitor cocktail (Pierce Biotechnology)) using 3 freeze/thaw cycles. The lysed suspension was centrifuged at 10,000×G for 10 minutes to pellet membrane proteins and nuclei. The supernatant was removed to provide a crude cytosolic lysate containing expressed myc-tagged Plk1 or Plk1 PBD. The total protein concetration was determined using a Bicinchoninic Acid (BCA) assay kit (Pierce Biotechnology).

Example 7

Biochemical Evaluation of Cyclic PBD-Binding Ligands

The inhibitory potency was determined in an ELISA assay using full-length Plk1 as described below. Data points from three independent experiments were normalized and plotted versus concentration to provide an overall data plot (error bars showing standard error of the mean (SEM)). The averaged data was fit to a non-linear regression using GraphPad Prism 7 [model: "log(inhibitor) vs. response—Variable slope (four parameters)"]. $IC_{50}$ values for each individual curve were obtained by fitting to a non-linear regression and final $IC_{50}$ values were calculated as the average±SEM (n=3) (FIG. 5A and FIG. 5B).

In conclusion, high affinity binding a new class of macrocyclic PBD-binding peptidomimetic ligands were developed with potentially desirable pharmacokinetic properties. An efficient method to synthesize these potential clinical candidates has been developed. It is believed that the Technology embraced by the current disclosure will be fundamental to agents endowed with clinical potential.

Example 8

Figure 12:
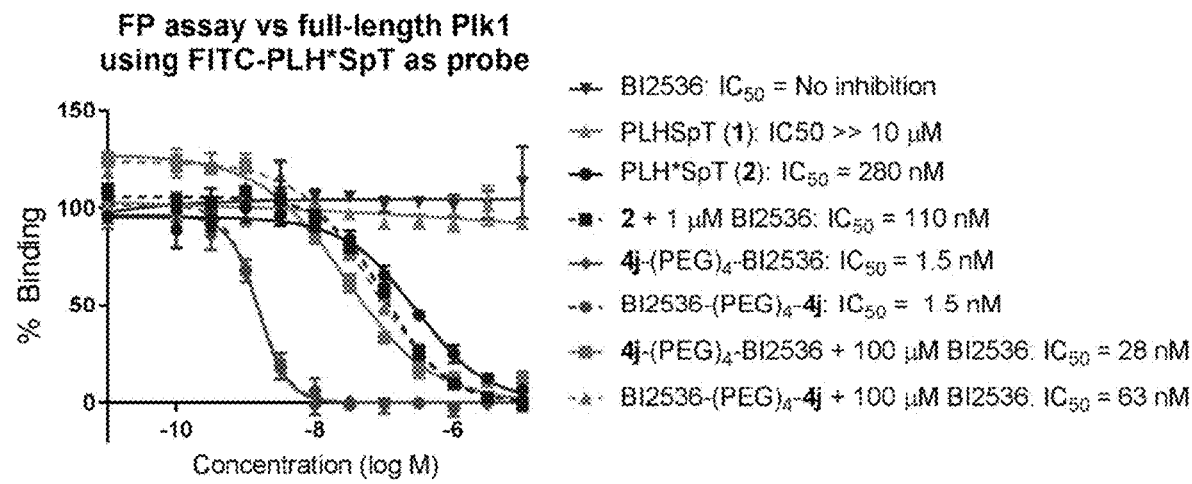
FIG. 12 Represents results from Flouresence Polarization (FP) assays, which measured the ability of synthetic constructs to compete with FITC-labeled PLH*SpT for binding to full-length Plk1.
Figure 13:
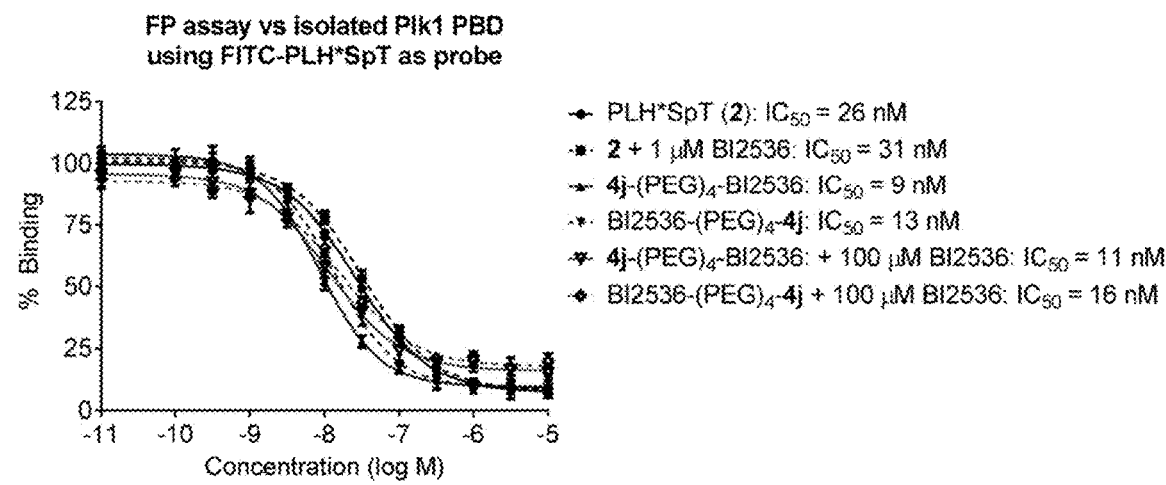
FIG. 13 Shows results from FP assays that measured the ability of synthetic constructs to compete with FITC-labeled PLH*SpT for binding to full-length Plk1.

Biological Evaluation of Initial Bi-Valent Ligands Having Tether Lengths of Four-Mini-PEG Units The binding affinities of the synthetic ligands were evaluated using fluorescence polarization (FP) assays, which measured the ability of ligands to inhibit the binding of FITC-labeled 2 to either full-length Plk1 (having both KD and PBD components) or to isolated PBD (lacking a KD component). It is worth noting that $IC_{50}$ values measured against the isolated PBD are lower than those measured against full-length Plk1. This is consistent with a literature report that PBD-dependent binding of full-length Plk1 to pS/pT epitopes is significantly reduced in comparison to the binding of isolated PBD. This difference is attributed to inhibitory interactions between the PBD and KD that affect equilibrium binding to phosphopeptides. The KD-binding "BI2536 motif" was tethered to peptide 2 (referred to as "4j) by four mini-PEG units from either the C-terminus or the N-terminus, designated as "4j-(PEG)$_4$-BI2536" and "BI2536-(PEG)$_4$-4j" respectively. Against full-length Plk1 the parent peptide 2 gave an $IC_{50}$ value of 280 nM, while 4j-(PEG)$_4$-BI2536 and BI2536-(PEG)$_4$-4j gave $IC_{50}$ values of 1.5 nM, respectively (FIG. 12). This data indicates that tethering BI2536 by four mini-PEG units to either the C-terminal and N-terminal positions of 2 results in significant enhancement of binding affinities. Moreover, in the presence of 100 μM BI2536, the bi-valent constructs decreased their affinities [4j-(PEG)$_4$-BI2536 $IC_{50}$=28 nM and BI2536-(PEG)$_4$-4j $IC_{50}$=63 nM] similar to the affinity of co-incubation of 2 with 1 μM BI2536. Repeating the above assays using the isolated PBD showed that BI2536 had no effect when tethered to 2 due to the absence of the KD (FIG. 13).

Figure 14:
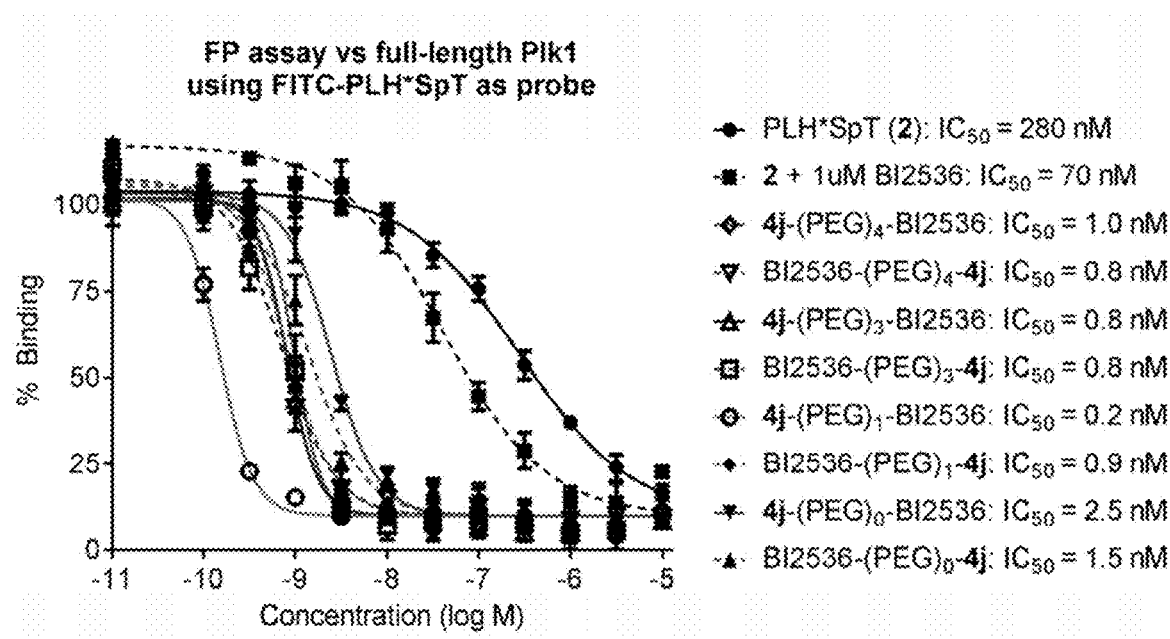
FIG. 14 discloses results from FP assays that measure the ability of synthetic constructs possessing different numbers of PEG linkers to compete with full-length Plk1 for FITC-labeled PLH*SpT.
Figure 15A:
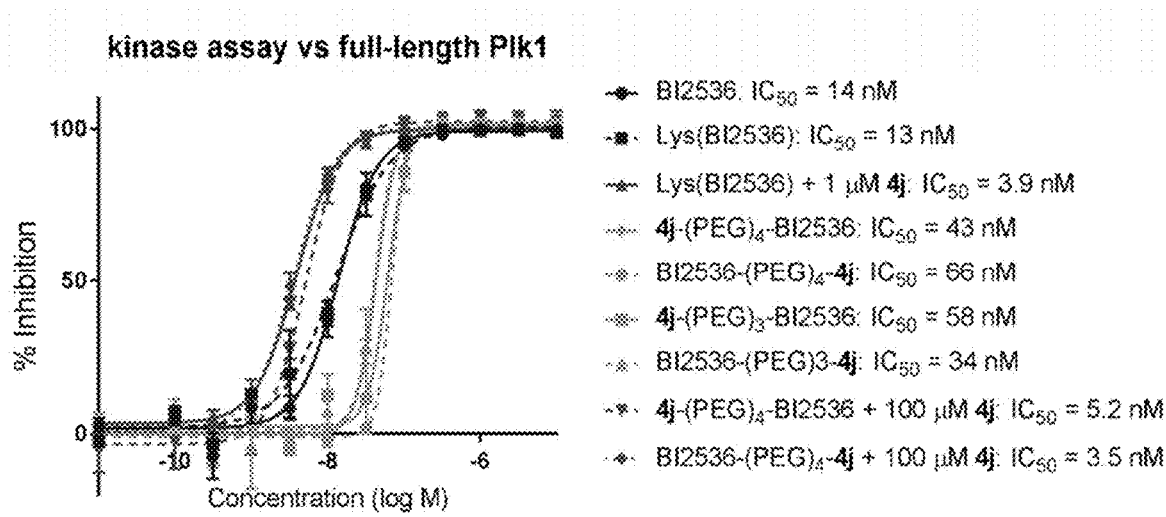
FIGS. 15A and 15B disclose results from kinase assays that measured the ability of synthetic constructs possessing different numbers of PEG linkers to inhibit the catalytic phosphorylation activity of full-length Plk1. (A) Three and four-PEG linkers; (B) One and zero-PEG linkers.
Figure 15B:
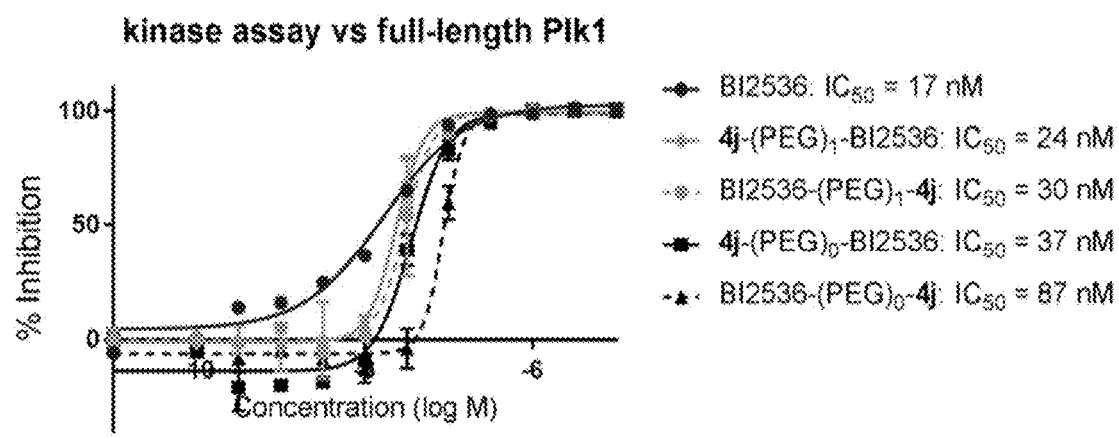

The results described above show that bi-valent ligands employing tethers four mini-PEG units in length show significantly enhanced binding affinities in KD-dependent fashion. However, distances between the PBD and KD ligand binding sites are not known, and the fact that these two domains are linked by a highly flexible region of Plk1 further emphasizes the uncertainty regarding optimum bi-valent linker composition and length. Therefore, the effects of shortening the linkers to zero, one and three mini-PEG units were explored (FIG. 14). The results showed that all compounds (ie, 0, 1, 3 and 4-PEGs) have greater affinities than parent 4j. The potencies of these compounds were also evaluated for inhibition of catalytic phosphorylation by the KD using a FRET-based kinase assay (FIGS. 10A and 10B). In this assay, Lys-conjugated BI2536 served as a control. The results showed that the bi-valent constructs stoichiometrically inhibited Plk1 kinase activity, as evidenced by the steep Hill slopes associated with the dose-response curves. Addition of excess 4j to dramatically decrease the potential for bivalent binding showed similar activity as was found with co-incubation of Lys(BI2536) and 1 μM 4j. This data was interpreted as supporting simultaneous binding of the bi-valent construct to both the Plk1 KD and PBD components.

Figure 11:
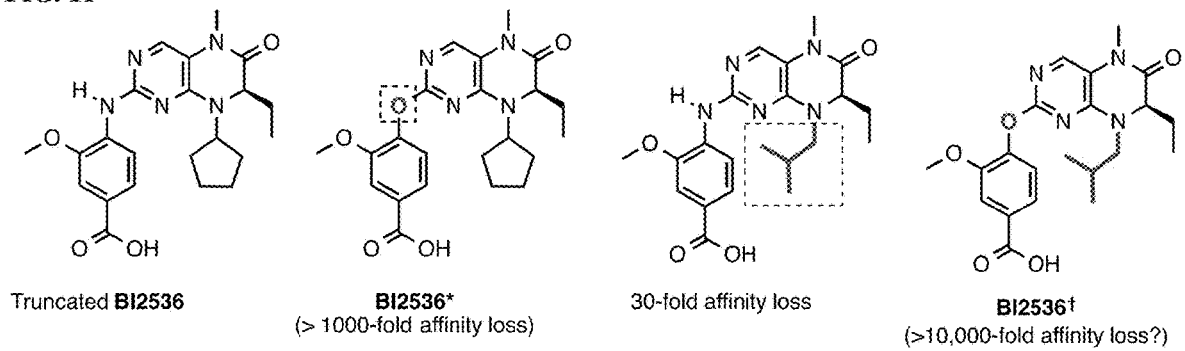
FIG. 11 Discloses structures of BI2536 and reduced-affinity variants BI2536* and BI2536$^{†}$.
Figure 16:
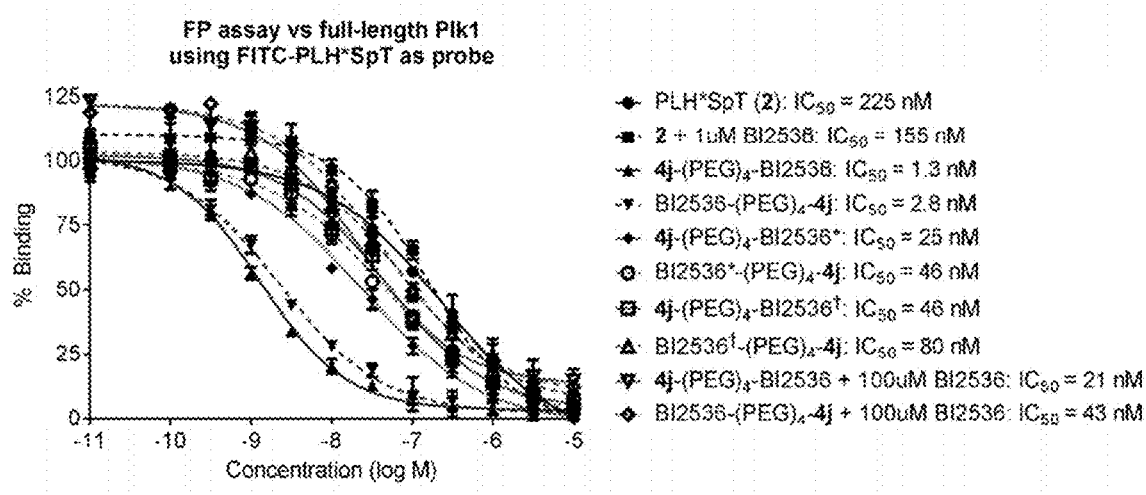
FIG. 16 Represents results from FP assays that measure the ability of synthetic constructs possessing different KD-binding components to compete with FITC-labeled PLH*SpT for binding to full-length Plk1.
Figure 17:
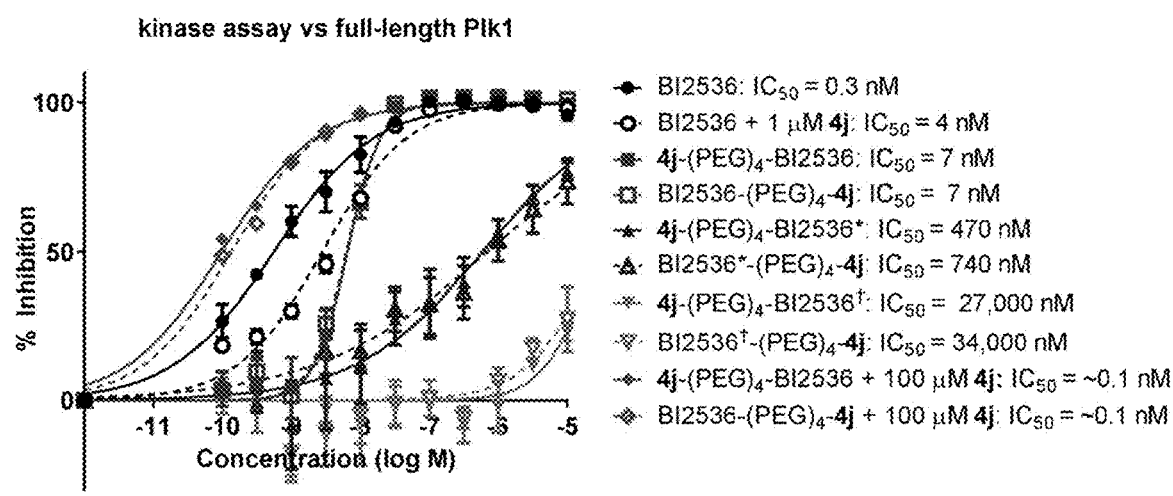
FIG. 17 discloses result from kinase assay that measured the ability of synthetic constructs possessing different KD-binder to inhibit the catalytic phosphorylation activity of full-length Plk1.

It was also confirmed that the KD- and PBD-binding components of the bi-valent constructs were binding as intended in their respective target domains. To confirm that the BI2536 motif is binding in the KD active site, the KD-binding affinity of the BI2536 component was attenuated by replacing a key nitrogen atom with oxygen (BI2536*, FIG. 11). For the parent BI2536, this simple change results in an approximate 1000-fold loss of affinity (Plk1 $K_i$=220 nM for BI2536* as compared to $K_i$=0.2 nM for BI2536). The affinity of BI2536* was attenuated even further by replacing its N-cyclopentyl group with an i-butyl group to yield BI2536$^†$ based on the fact that this change in BI2536 results in a 30-fold loss of potency (FIG. 11). As expected, the bivalent constructs incorporating BI2536* [4j-(PEG)$_4$-BI2536* and Bi2536*-(PEG)$_4$-4j] or BI2536$^†$ [4j-(PEG)$_4$-BI2536$^†$ and Bi2536$^†$-(PEG)$_4$-4j] showed significantly less affinities than the parent BI2536 containing compounds (FIG. 16). This tendency was also observed for the inhibition of phosphorylation by the KD (FIG. 17).

In conclusion, extremely high affinity PBD-binding compounds were developed by incorporating additional moieties that target Plk1 kinase domain. The results from FP assays measuring PBD-binding inhibition and kinase assays measuring inhibition of catalytic phosphorylation suggest the 4j-(PEG)$_n$-BI2536 and BI2536-(PEG)$_n$-4j, where n=1, 3 or 4 engage in bi-valent binding, simultaneously to both the KD and PBD components. This has allowed to achieve an approximate two orders-of-magnitude affinity enhancement relative to the best previously reported compounds. It is believed that the Technology embraced by the current disclosure will be fundamental to agents endowed with clinical potential.

III. ASSAYS

ELISA Inhibition Assay.

All assay steps were performed at room temperature with gentle shaking. A biotinylated phosphopeptide (sequence: Biotin-Ahx-PMQS(pT)PLN-NH$_2$) (46-48) was diluted with PBS 7.4 to 1 μM (from a 10 mM dimethylsulfoxide (DMSO) stock solution) and loaded onto the wells of a 96-well Neutravidin-coated plate (Pierce Biotechnology) at 100 μL per well for 1 hour. The wells were washed once with 150 μL PBST (PBS 7.4+0.05% Tween-20), and then 100 μL of 1% bovine serum albumin (BSA) in PBS 7.4 (blocking buffer) were added for 1 hour. The cytosolic lysate containing myc-tagged protein was diluted to 300 μg/mL in PBS 7.4 containing protease/phosphatase inhibitors (Pierce Biotechnology), mixed with competitive inhibitor (from a 10× stock in 5% DMSO/PBS), and allowed to pre-incubate for 1 h (100 μL per well in a 96-well plate, 30 μg total protein). The blocked ELISA plate was washed 2× with PBST (150 μL) and the pre-incubated lysates were added to the plate to incubate for 1 hour. The wells were washed 4× with PBST (150 μL), then probed with anti-myc primary antibody (1:1500 dilution for assays that include macrocyclic peptidomimetic ligand of the present disclosure and 1:3000 dilution for all other assays, mouse monoclonal, Pierce Biotechnology) for 1 hour. The wells were then washed 4× with PBST (150 μL), and incubated with rabbit anti-mouse horseradish peroxidase (HRP) conjugate (1:3,000 dilution for assays that include macrocyclic peptidomimetic ligands of the present disclosure and 1:10,000 dilution for all other assays, Pierce Biotechnology) for 1 hour. The wells were then washed 5× with PBST (150 μL) and incubated with Turbo TMB-ELISA solution (Pierce Biotechnology) until the desired absorbance is reached (5-10 minutes). The reaction was quenched by the addition of 2M aq. $H_2SO_4$ and the absorbance was measured at 450 nm using a BioTek Synergy 2 96-well plate reader.

Absorbance was plotted versus concentration (log M) and fit to a non-linear regression using GraphPad Prism 6 software (model: log(inhibitor) vs. response—Variable slope (four parameters)) to provide $IC_{50}$ values. $IC_{50}$ values from multiple independent experiments were normalized and averaged to provide values±standard deviation.

Those skilled in the art will recognize or be able to ascertain using no more than routine experimentation, many equivalents to the specific embodiments of the description described herein. Such equivalents are intended to be encompassed by the claims.

Example 9

Histine N(τ)-Cyclized Marcocycles as a New Genre of Polo-Like Kinase 1 Polo-Box Domain-Binding Inhibitors The field of protein-protein interaction (PPI) inhibitors has proven to be highly challenging, in part due to the extended protein interfaces that are often involved. However, significant progress can be made when key recognition features occur in localized, "hot spot" regions on the protein surface, which may be amenable to disruption by reduced-size constructs. Phosphodependent PPIs can be viewed as being hot-spot in nature, wherein phosphorylamino acid components serve as a critical binding determinant. There is wide interest in developing and applying new approaches to phospho-dependent PPI inhibitors, particularly given the importance of these interactions in cellular signal transduction. The serine/threonine-specific polo-like kinase 1 (Plk1) is a critical mediator in the initiation and progression of mitosis and it is recognized as a potential target for anticancer drug development. Plk1 localizes to mitotic structures through its C-terminal polo-box domain (PBD) by engaging in PPIs with phosphoserine (pSer) and phosphothreonine (pThr)-containing epitopes. The inventors have focused our attention on developing PBD-binding inhibitors based on peptidomimetic ligands starting from the pentapeptide PLHSpT (1). Through extensive studies, the inventors have examined various structural aspects of PBD recognition and binding of the key pThr residue. The inventors have also found by appending long-chain alkylphenyl moieties to different regions of the peptide, that we can achieve more than three orders-of-magnitude higher affinities by occupying a "cryptic" pocket on the PBD surface proximal to the pThr-binding site. This reflects a broader understanding that in addition to binding in the hot-spot region, a PPI inhibitor should interact with ancillary pockets on the protein surface and take advantage of protein adaptability. The inventors have accessed the cryptic pocket by tethering fragments from N-terminal regions of the peptide and from the N(π) position of the histidine residue located at the pThr-2 position. The peptidomimetic PLH*SpT (2) (where H* indicates the presence of a —(CH$_2$)$_8$Ph group at the N(π) position) is a representative example of the latter class of construct. Peptide 2 exhibits >1,000-fold enhanced PBD-binding affinity relative to the parent peptide 1.

When peptides serve as starting points for the development of PPI inhibitors, macrocyclization is often used to advance linear peptides toward peptide mimetics by restraining and preorganizing important components to orientations favorable for binding. However, application of head-to-tail cyclization strategies on 2 has been reported to result in three orders—of magnitude or greater loss of PBD-binding affinity. In contrast, the inventors have found that N(π),N(τ)-bis-alkylated His residues can serve as macrocycle bifurcated ring junctions, in which the cryptic pocket-accessing —(CH$_2$)$_8$Ph group projects from the imidazole N(π) position, while the N(τ) site serves as the site of attachment for ring closure with the N-terminus (see peptides of type 3 and 4, shown below). We have shown that cyclic pentapeptides of type 3 can be equipotent to the linear parent peptide 2, although cyclic tripeptides of type 4 have significantly reduced potencies in biochemical assays. The goal of our current work is to utilize bis-alkyl His residues as ring junctions that afford a new genre of macrocycles with improved affinities and decreased molecular size.

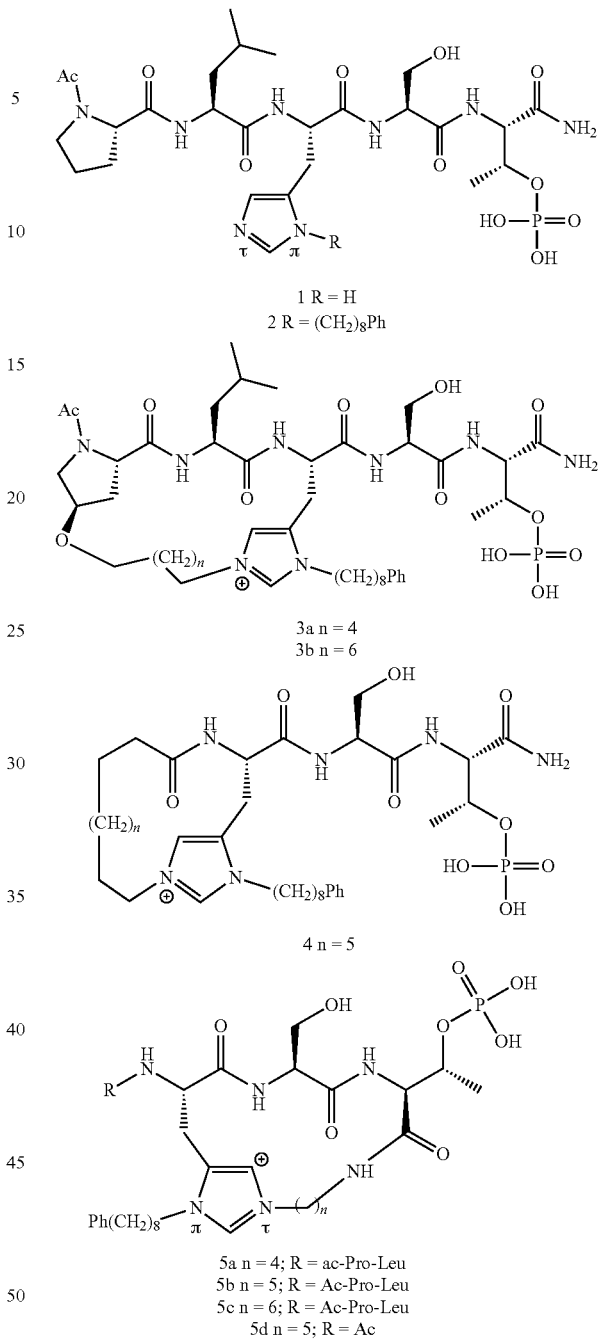

1 R = H
2 R = (CH$_2$)$_8$Ph 3a n = 4
3b n = 6

4 n = 5

5a n = 4; R = ac-Pro-Leu
5b n = 5; R = Ac-Pro-Leu
5c n = 6; R = Ac-Pro-Leu
5d n = 5; R = Ac

Macrocycle Design and Synthesis. The X-ray co-crystal structures of 2 bound to the PBD (PDB: 3RQ717) indicates that the His N(τ)-nitrogen is approximately 5.7 Å from the C-terminal carboxamide nitrogen (FIG. 18A). The inventors hypothesized that the most direct approach to a new family of cyclic ligands would be to use amide-forming macrocyclization reactions that employ methylene linkers of various sizes between the imidazole N(τ)-nitrogen and the C-terminus. A series of macrocycles were designed having ring-closing chains of four, five and six methylenes (5a, 5b and 5c, respectively, shown above). The required initial linear resin-bound pentapeptides (6a-6c) were synthesized on hyper-acid labile (4-hydroxymethyl-3-methoxy-phenoxy) butanoic acid (HMPB) resin using Fmoc-based solidphase peptide synthesis (SPPS) and previously reported reagent, N-Fmoc-His[N(π)-(CH$_2$)$_8$Ph]-OH (Qian, W.; Liu, F.; Burke, T. R., Jr. Investigation of unanticipated alkylation at the N(π) position of a histidyl residue under Mitsunobu conditions and synthesis of orthogonally protected histidine analogues. J. Org. Chem. 2011, 76, 8885-8890) (Scheme 1). It was discovered that that alkylation of the His N(τ)-nitrogen could be achieved using a microwave-assisted on-resin SN2 reaction with N-Bocprotected aminoalkyl iodides in similar yields as our previously reported Mitsunobu conditions (Qian, W.-J.; Park, J.-E.; Grant, R.; Lai, C. C.; Kelley, J. A.; Yaffe, M. B.; Lee, K. S.; Burke, T. R., Jr. Neighbor-directed histidine N(τ)-alkylation: A route to imidazolium-containing phosphopeptide macrocycles. Biopolymers Pept. Sci. 2015, 104, 663-673; Qian, W.-J.; Park, J.-E.; Lim, D.; Lai, C. C.; Kelley, J. A.; Park, S.-Y.; Lee, K. W.; Yaffe, M. B.; Lee, K. S.; Burke, T. R., Jr. Mono-anionic phosphopeptides produced by unexpected histidine alkylation exhibit high plk1 polo-box domain-binding affinities and enhanced antiproliferative effects in hela cells. Biopolymers Pept. Sci. 2014, 102, 444-455; and Qian, W.-J.; Burke, T. R., Jr. Mitsunobu mischief: Neighbor-directed histidine N(τ)-alkylation provides access to peptides containing selectively functionalized imidazolium heterocycles. Org. Biomol. Chem. 2015, 13, 4221-4225). Treatment of the resulting N(π),N(τ)-bis-alkylated resins (7a-7c) with dilute TFA (25% in DCM) provided the linear N(π),N(τ)-bis-alkylated Hiscontaining pentapeptides (8a-8c), while maintaining benzyl pThr phosphoryl protection. Macrocyclization was performed using PyBOP/HOBt and the phosphoryl benzyl protection was then removed to provide the desired type 5 ligands containing 4, 5, or 6 methylene linkers (5a-5c, respectively). Using a similar synthetic procedure, the cyclic tripeptide 5d, which contains the n=5 length linker of 5b but lacks the N-terminal "Pro-Leu" residues was synthesized.

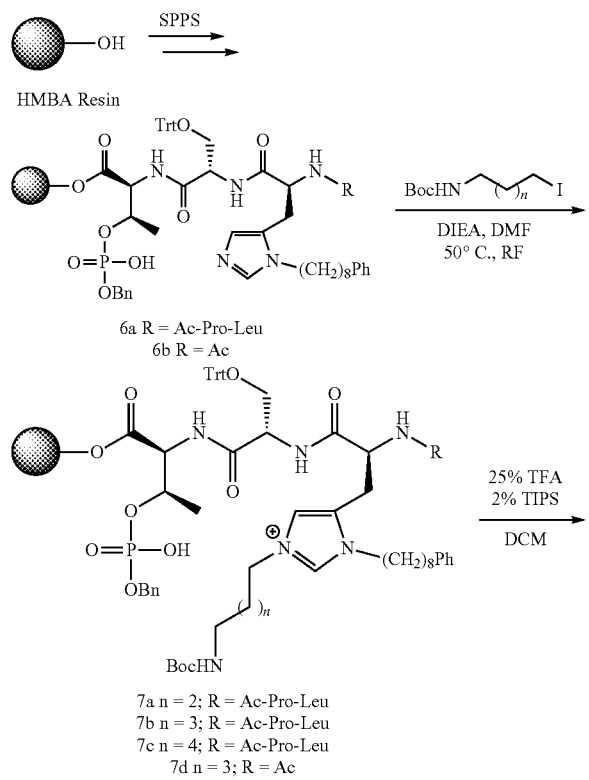

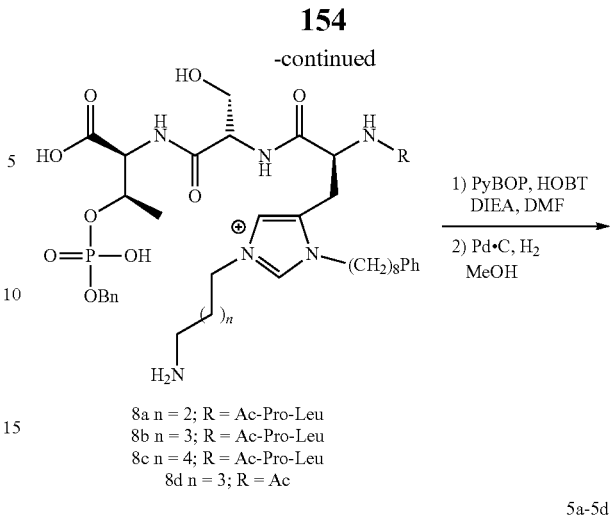

Biological Evaluation. The peptides were evaluated in ELISA assays that measured their ability to inhibit the interaction between full-length Plk1 and an immobilized pThr-containing peptide (Hymel, D.; Burke, T. R., Jr. Phosphatase-stable phosphoamino acid mimetics that enhance binding affinities with the polo-box domain of polo-like kinase 1. ChemMedChem 2017, 12, 202-206). Compared to the linear pentapeptide 2 (IC50=110 nM), the cyclic pentapeptide 5a (n=4) maintained similar potency (IC$_{50}$=160 nM), while 5b (n=5) and 5c (n=6) enhanced the potency by approximately 3-fold (IC$_{50}$=44 and 43 nM, respectively) (Table 1). In an effort to reduce overall size, cyclic tripeptide 5d, which lacks the "Pro-Leu" residues of 5b, was synthesized. Interaction of the N-terminal region of the peptide within a "pyrrolidine-binding pocket" on the surface of the PBD had been postulated to be important for overall binding affinity, and deletion of these residues from the open-chain parent 2 can typically result in a more than two orders-of-magnitude loss of inhibitory potency. In contrast, the tripeptide 5d retains potency (IC$_{50}$=320 nM) that is similar to the linear pentapeptide 2 (Table 4). An important aspect of developing peptidomimetic PBD binding inhibitors is to achieve selectivity for the Plk1 PBD versus the highly homologous PBDs of Plk2 and Plk3. Accordingly, the potency with which the most active cyclic ligands inhibit the binding of optimized pThr-containing fluorescence probes to the isolated PBDs of Plks 1-3 was measure (Hymel, D.; Burke, T. R., Jr. Phosphatase-stable phosphoamino acid mimetics that enhance binding affinities with the polo-box domain of polo-like kinase 1. ChemMedChem 2017, 12, 202-206). Consistent with previously reported results, the linear peptide 2 demonstrated more than 100-fold selectivity for Plk1 versus Plks 2 and 3. Compound 5a displayed similar selectivity as 2 with approximately 50- to 100-fold selectivity (Table 4). However, compounds 5b and 5c showed reduced selectivity of 16- to 25-fold for Plk1. Interestingly, the cyclic tripeptide 5d demonstrated an improved profile versus 2, with approximately 400- and 700-fold selectivity for Plk1 versus Plk2 and Plk3, respectively. It is important to note that ELISA assays are conducted using full-length Plk1 protein, whereas selectivity is evaluated using a fluorescence polarization (FP) assay with the isolated PBDs of Plks 1-3. Due to inhibitory inter-domain interactions between the KD and PBD, IC$_{50}$ values for full-length Plk1 can be increased by 10-fold or greater in comparison to isolated PBD.

TABLE 5

IC$_{50}$ Values for Biochemical Inhibition of Full-length Plk1 by ELISA or Isolated PBDs of Plks 1-3 by Fluorescence Polarization (FP).

| Cpd | ELISA IC$_{50}$, (nM)[a, b] Plk1 | FP IC$_{50}$, (nM)[a, b] Plk1 PBD | Plk2 PBD | Plk3 PBD |
|---|---|---|---|---|
| 2 | 110 ± 16 | 4 ± 0.4 | 570 ± 20 (142×)[c] | 1,200 ± 120 (300×) |
| 5a | 160 ± 35 | 10 ± 1.0 | 610 ± 20 (61×) | 970 ± 40 (97×) |
| 5b | 44 ± 11 | 6 ± 0.5 | 150 ± 10 (25×) | 130 ± 1 (22×) |
| 5c | 43 ± 5 | 5 ± 0.5 | 110 ± 10 (21×) | 80 ± 10 (16×) |
| 5d | 320 ± 23 | 8 ± 0.8 | 3,100 ± 17 (387×) | 5,500 ± 250 (687×) |

[a]Values determined as reported in the Supporting Information[14].
[b]IC50 values from multiple independent experimenta are normalized and averaged to provide values ± standard error of the mean (SEM).
[c]Fold-change relative to the Plk1 PBD.

X-ray Co-crystal Studies. To observe the effects of macrocyclization on binding geometries, the X-ray co-crystal structure of 5b bound to the isolated Plk1 PBD was solved at 1.45 Å resolution. It was observed that macrocyclic 5b overlays very well with PBD-bound linear peptide 2 (FIG. 18A). In 5b, the ring closing methylene chain is sufficiently long to allow the C-terminal pThr carboxamide to adopt a favorable trans amide conformation, as well as conserving hydrogen bonding interaction with the backbone amide of Leu491 (FIG. 18A). Importantly, the polymethylene ring-closing chain of 5b makes hydrophobic contacts with the sidechain of Leu490, which are not possible in the parent peptide 2. This interaction may also contribute to improved PBD-binding since contacts involving leucine residues are among the most frequent hydrophobic interactions observed in protein-ligand complexes.

The C-terminal macrocyclized peptidomimetics of type 5 extends the earlier studies examining N($\pi$),N($\tau$)-bis-alkylated His residues as ring junctions in N-terminal marocyclized constructs of type 3 and 4. It was discovered that ring closure in the manner exemplified by type 5 macrocycles, can significantly increase potencies in biochemical assays against full-length Plk1, while also maintaining adequate target selectivity for the Plk1 PBD versus the PBDs of Plk2 and Plk3. The X-ray co-crystal structures of macrocyclic ligands of types 3, 4, or 5 all show remarkably similar overlays with the parent linear peptide, particularly in the phosphoryl binding site. Given this observation, it is likely that the improved binding affinity for type 5 macrocycles is at least partially derived from better pre-organization of favorable binding interactions and decreased conformational rotation of the unbound ligand with a corresponding decrease in entropic loss upon binding. Based on the SAR, the 5- and 6-methylene linkers of 5b and 5c provide optimal length for pre-organization of the ligand. Importantly, C-terminal macrocyclization employing N($\pi$),N($\tau$)-bis-alkylated His residues as ring junctions with optimal linker length permits deletion of the "Pro-Leu" motif. This yields the tripeptide ligand 5d, which retains high affinity with improved target selectivity and significantly decreased molecular size. Future development of this tripeptide, particularly utilizing prodrug applications to mask the critical phosphate group, could lead to Plk1 PBD inhibitors with greatly improved membrane penetration and proteolytic stability for cell-based applications. This work should fundamentally impact the future development of peptide-based Plk1 PBD inhibitors.

Example 10

Efficient Synthesis of a Phosphatase-Stable Phospho-Threonine Analog for Use in Cell-Based Delivery of High-Affinity Ligands of the Polo-Like Kinase 1 Polo-Box Domain Polo-like kinase 1 (Plk1) is a serine/threonine kinase that plays critical roles in cell cycle regulation, particularly in the initial processes of mitosis. The enzyme has emerged as a clinically relevant target for the development of new anticancer agents. Aside from a canonical ATP-dependent kinase domain, Plk1 also contains a C-terminal polo-box domain (PBD), which is responsible for intracellular localization and allosteric regulation of the kinase domain through protein-protein interactions with phosphoserine (pSer) or phosphothreonine (pThr) containing peptide motifs. This domain represents an advantageous means to inhibit Plk1 kinase activity using small molecule or peptidomimetic ligands. Theoretically, such ligands could cause selective cytotoxicity in cancer cells overexpressing Plk1 by inhibiting normal Plk1 targeting, resulting in disordered mitotic function. Importantly, high affinity ligands to the PBD could avoid the selectivity issues associated with kinase inhibitors directed at ATP-binding sites. Previous work in our group has resulted in the discovery of nanomolar-affinity peptidomimetics built around "Ser-pThr" PBD recognition motifs. However, these agents have been limited by the hydrolytic lability of pThr to cellular phosphatases. This problem was overcome by replacing pThr with the phosphonate analog, 2(S)-amino-3(R)-methyl-4-phosphonobutanoic acid (Pmab), yet the synthesis of Pmab was long and impractical for obtaining quantities sufficient for medicinal chemistry efforts. The dianionic nature of the pThr/Pmab residues also impedes cell membrane penetration, significantly reducing cellular activity. To address these issues, a new route to Pmab was developed that allows its facile synthesis on gram-scales. Another approach the inventors are utilizing to address the poor cellular bioavailability of dianionic PBD-binding peptide mimics is by covalently attaching cell surface integrin-binding motifs, which are intended to induce cellular uptake. Efficient delivery of these peptide ligands to the cytosol could produce highly active synthetic probes to study the biochemistry of the PBD and its effects on Plk1 activity in vitro. More importantly, this work could lead to potent and selective anti-cancer agents targeted to tumors that overexpress a variety of cell-surface receptors.

Crystal Structures. Crystal structures of Polo-like kinase 1 (19A, PDB: 4J7B) and the polo-box domain bound to peptides containing a "Ser-pThr" binding motif (19B, PDB: 3HIK and 19C, PDB: 3RQ7). The alkyl-His containing peptide 3 accesses a cryptic hydrophobic channel in the PBD.

Compounds were evaluated for inhibition of Plk1 PBD binding to a pThrcontaining peptide by ELISA in cell lysates and by inhibition of cell proliferation in HeLa cells. Pmab=2(S)-amino-3(R)-methyl-4-phosphonobutanoic acid. The IC$_{50}$ of 2, 3, 4, and 5 are shown in Table 6.

TABLE 6

Efficacy of peptide and peptidomimetic ligands 2-5.

| Structure | Compound | | Cell Lysate ELISA IC$_{50}$ (μM) | HeLa Proliferation in vitro IC$_{50}$ (μM) |
|---|---|---|---|---|
| | Ac—PLHS(pT)—NH$_2$ | 2 | 36 [1] | N.D. |
| | Ac—PLH*S(pT)—NH$_2$ | 3 | 0.017 [1] | N.D. |
| 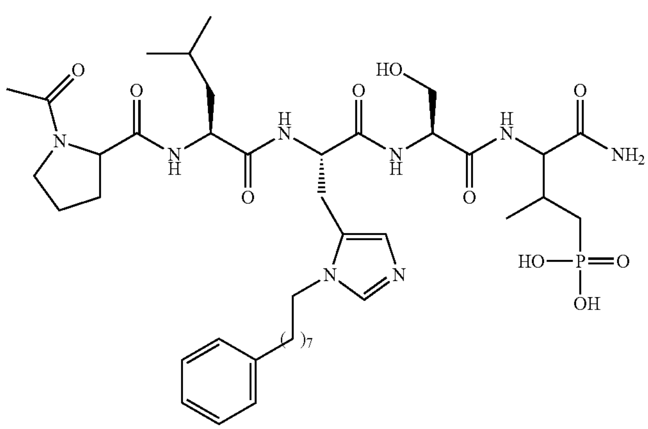 | Ac—PLH*S(Pmab)—NH$_2$ | 4 | 0.02 [2] | N.D. |
| 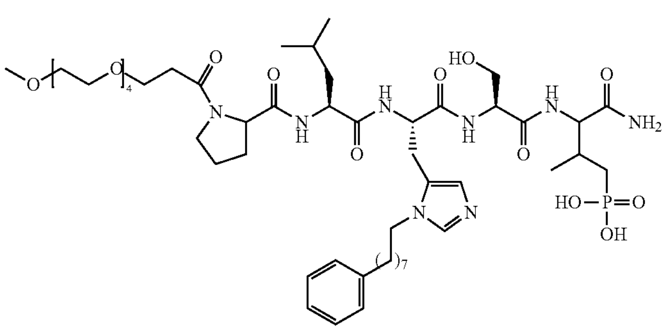 | PEG-PLH*S(Pmab)—NH$_2$ | 5 | 0.03 [1] | 380 [1] |

N.D. = Not determined due to lack of efficacy.

Scheme 1. The first and second-generation syntheses of the SPPS-compatible Pmab analog 9 converged at the key intermediate 8a. These syntheses were expensive, low yielding, and did not produce sufficient material to support medicinal chemistry efforts.

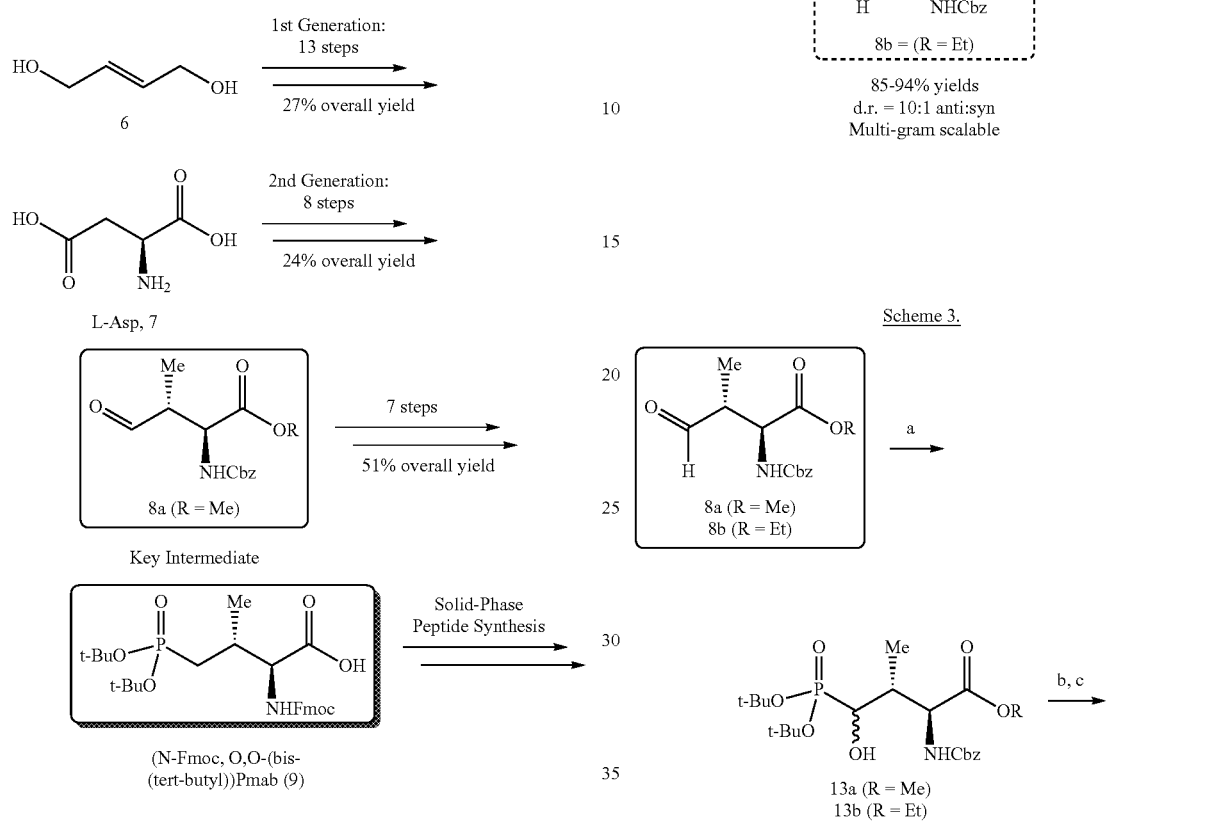

Scheme 2.
An anti-selective Mannich reaction using a previously reported N-Cbz glycinyl tosylate (10) provides access to the key intermediate 8b in excellent yield and stereoselectivity. This intermediate can be converted to the SPPScompatible Pmab analog 9 using the 7-step procedure utilized in the previous generation syntheses.

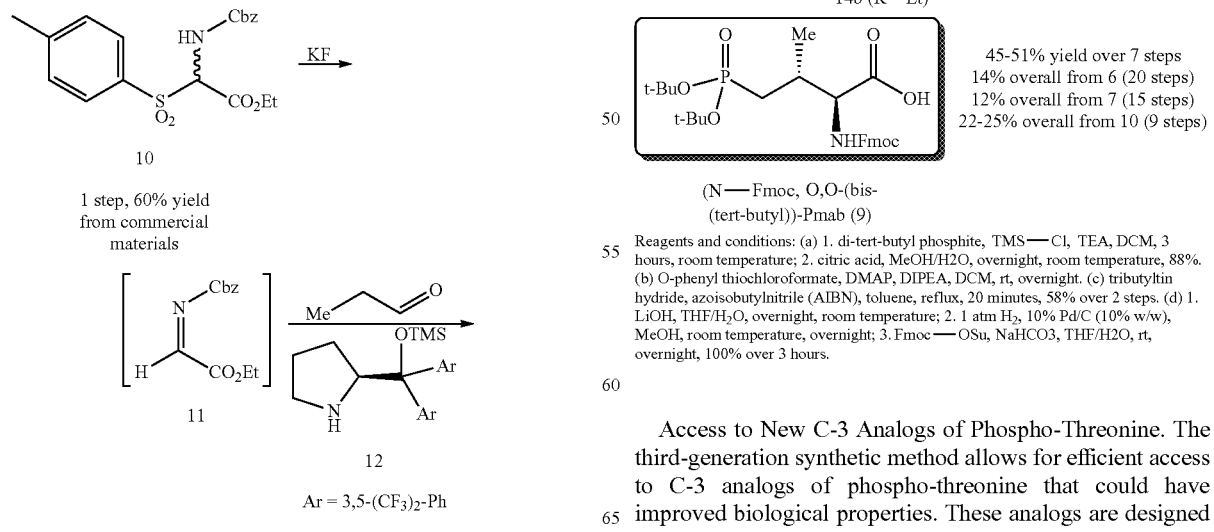

Reagents and conditions: (a) 1. di-tert-butyl phosphite, TMS—Cl, TEA, DCM, 3 hours, room temperature; 2. citric acid, MeOH/H2O, overnight, room temperature, 88%. (b) O-phenyl thiochloroformate, DMAP, DIPEA, DCM, rt, overnight. (c) tributyltin hydride, azoisobutylnitrile (AIBN), toluene, reflux, 20 minutes, 58% over 2 steps. (d) 1. LiOH, THF/H2O, overnight, room temperature; 2. 1 atm H2, 10% Pd/C (10% w/w), MeOH, room temperature, overnight; 3. Fmoc—OSu, NaHCO3, THF/H2O, rt, overnight, 100% over 3 hours.

Access to New C-3 Analogs of Phospho-Threonine. The third-generation synthetic method allows for efficient access to C-3 analogs of phospho-threonine that could have improved biological properties. These analogs are designed to interact with either Arg557 through pi-cation interactions, or with Leu491 through hydrophobic interactions.

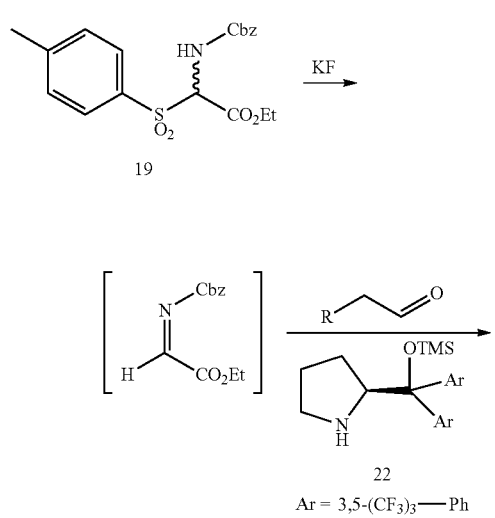

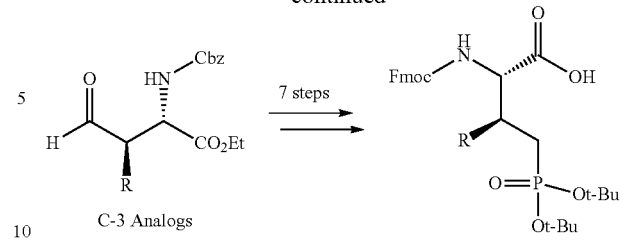

SPPS-compatible, phosphatase-stable pThr analogs

R = aliphatic or aromatic

Compounds were evaluated for inhibition of Plk1 PBD binding to a pThr-containing peptide by ELISA in cell lysates, the $IC_{50}$ of which are shown in Table 7. Compounds 2 and 3 were tested simultaneously for direct comparison of efficacy.

TABLE 7

Efficacy of peptidomimetic ligands 15 and 16 containing the C-3-benzyl-Pmab residue.

| Structure | Compound | | Cell Lysate ELISA $IC_{50}$ (μM) |
|---|---|---|---|
| 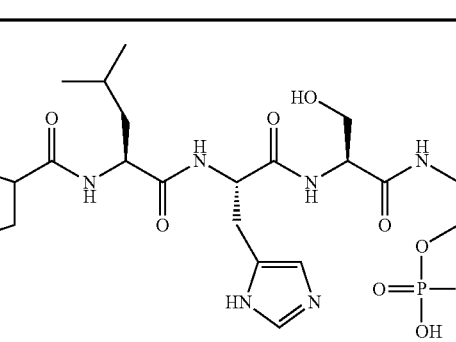 | Ac—PLHS(pT)—NH$_2$ | 2 | 18 |
| 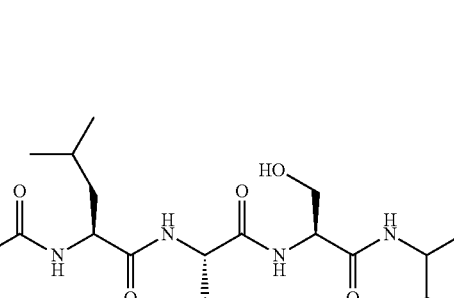 | Ac—PLHS[(3-Bn)—Pmab]—NH$_2$ | 15 | 50 |

TABLE 7-continued

Efficacy of peptidomimetic ligands 15 and 16 containing the C-3-benzyl-Pmab residue.

| Structure | Compound | | Cell Lysate ELISA IC$_{50}$ (μM) |
|---|---|---|---|
| 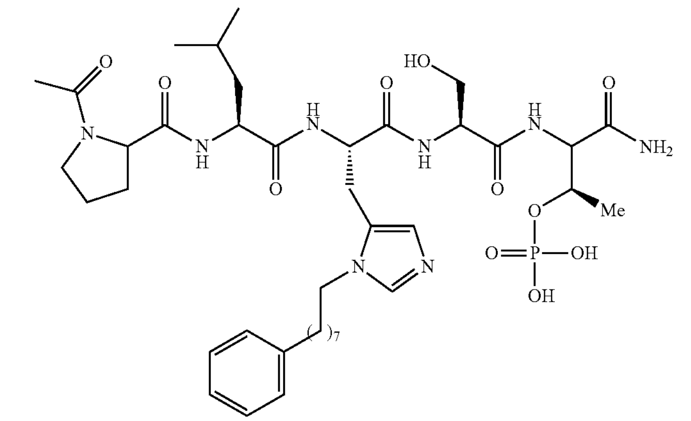 | Ac—PLH*S(pT)—NH$_2$ | 3 | 0.023 |
| 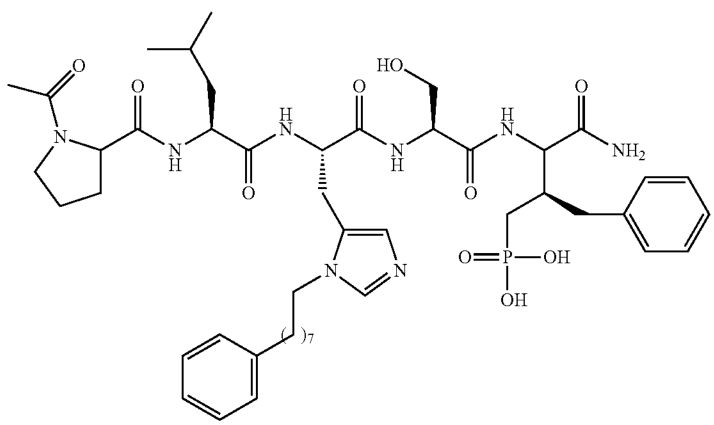 | Ac—PLH*S[(3-Bn)—Pmab]—NH$_2$ | 16 | 0.035 |

Improving Cellular Activity Through Cell-Surface Targeting.

Reported methods for the delivery of cell-impermeable peptides include cell-surface integrin binding motifs and poly-cationic cell-penetrating peptides.

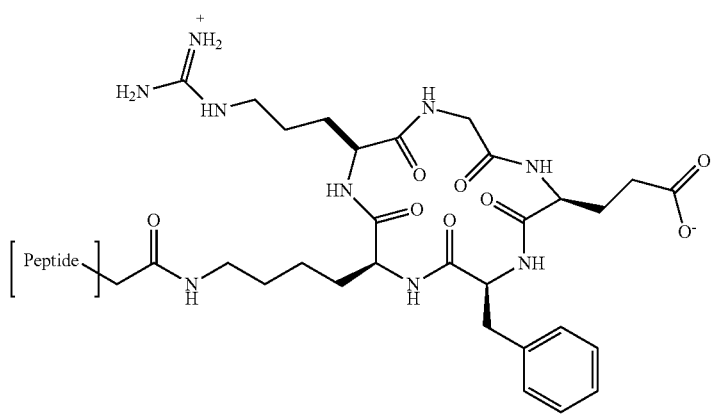

Cyclic RGD
Integrin-binding

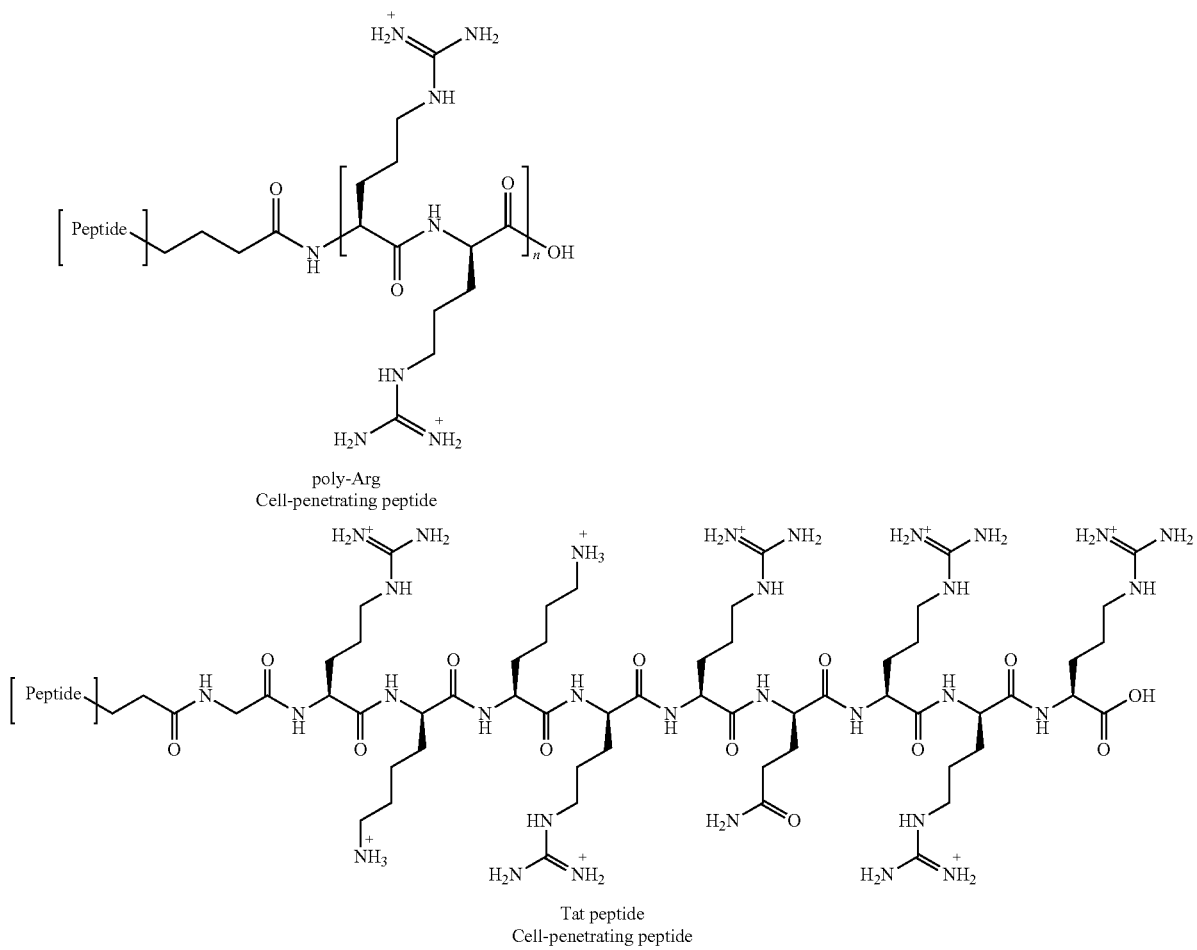

poly-Arg
Cell-penetrating peptide

Tat peptide
Cell-penetrating peptide

LLP2A is a high-affinity ligand for α4β1 integrin expressed on the surface of various cancer types. A fluorescent LLP2A analog (17) was synthesized and used to stain MOLT-4 cells that express abundant α4β1 integrin. Distinct staining is observed at the cell surface following a 1 hour treatment with 100 nM 17 at 37° C. This same probe analyzed by flow cytometry to determine the relative levels of expression in various leukemia and lymphoma cell lines. K562 cells are known to express little to no α4β1 integrin and served as the negative control.

The high-affinity PBD ligand PLH*S(Pmab) was conjugated to the high affinity integrin-binding LLP2A peptidomimetic (FIG. 21) to induce cellular uptake through targeted delivery to the cell surface. Utilizing the valine-citruline dipeptide cathepsin substrate or a disulfide will allow for cleavage of the linker and release of the PBD ligand.

Discussion. Nanomolar-affinity peptidomimetic ligands to the Plk1 PBD were developed. However, these ligands show hydrolysis of the pThr residue by cellular phosphatases and poor membrane penetration due to their dianionic nature. To address the hydrolytic lability, the inventors have shown that the pThr phosphonate analog, Pmab, maintains PBD binding affinity. A new synthetic route to a SPPS-compatible analog of Pmab was developed, which also allows for structural exploration at the C-3 position. To address the poor cell membrane penetration the peptidomimetics were conjugated, through cleavable linkers, to a known integrin-binding motif. These synthetic probes can provide valuable insights into the biology of Plk1 and the PBD, and assist in developing PBD-binding ligands into targeted anti-cancer agents.

Example 11

Phosphatase-Stable Phosphothreonine Alanogs that Improve the Affinity of Peptidomimetic Ligands of the Polo-Like Kinase 1 Polo-Box Domain Polo-like kinase 1 (Plk1) is a serine/threonine protein kinase that plays a critical role in cell cycle regulation, and aberrant expression of Plk1 has been observed in various cancers. As a result, this enzyme has emerged as a clinically relevant target for the development of new anti-cancer agents. Aside from a canonical ATP-dependent kinase domain, Plk1 also contains a C-terminal polo-box domain (PBD), which is responsible for allosteric regulation of the kinase domain through protein-protein interactions with phosphoserine (pSer) or phosphothreonine (pThr) containing peptide motifs. Previous work in our group has resulted in the discovery of peptides and peptide mimetics that contain "Ser-pThr" PBD recognition motifs and display low-nanomolar affinity for the PBD. These compounds are designed to cause selective cytotoxicity in cancer cells that overexpress Plk1 by inhibiting proper localization, resulting in disordered mitotic function. However, these compounds fail to inhibit Plk1 in cell-based assays due to the hydrolytic lability of pThr to cellular phosphatases, requiring substitution with the synthetic phosphonate analog (2S,3R) 2-amino-3-methyl-4-phosphonobutanoic acid (Pmab). Here, we present the development a gram-scale synthetic route to Fmoc-protected di-tert-butyl Pmab, an analog that is compatible with solid-phase peptide synthesis. This route significantly improves the quantities of Pmab that can be produced, which facilitates medicinal chemistry efforts. Moreover, we show this new route allows facile modification at the C3 position, which produces peptidomimetic ligands with improved PBD-binding affinity.

Phosphorylation is critical to many aspects of protein biochemistry and cell biology. Numerous kinases and phosphatases regulate the phosphorylation of key amino acids involved in enzymatic processes and cell signalling pathways (FIG. 22). Non-hydrolyzable analogs of these amino acids are important as biochemical probes and potentially therapeutic agents.

Pmab, a Phosphatase-Stable Analog of Phosphothreonine: Scheme 1. The first and second-generation syntheses of Pmab (Scheme 1), a phosphatase-stable analog of pThr, converged at the key intermediate 3. These syntheses were expensive, low yielding, and did not produce sufficient material to support medicinal chemistry efforts.

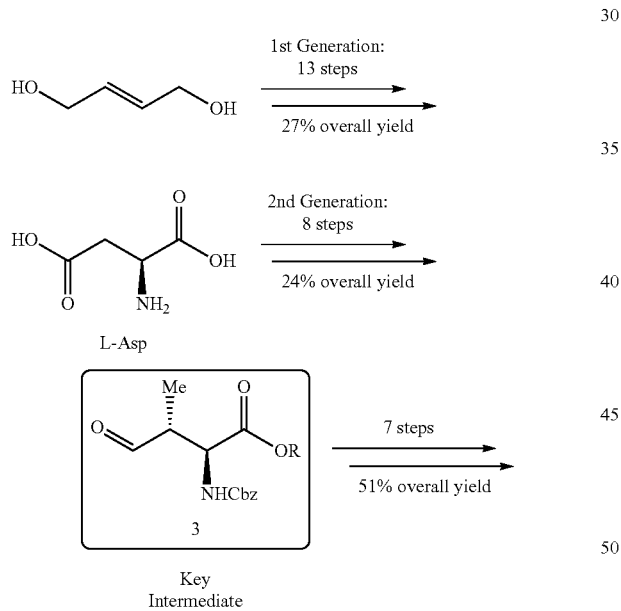

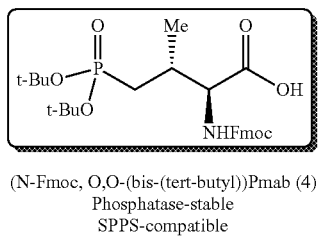

New Synthetic Route to Pmab and C3 Analogs.

Scheme 2. A reported anti-selective aminocatalytic Mannich reaction enables efficient synthesis of a key intermediate in the synthesis of 4.

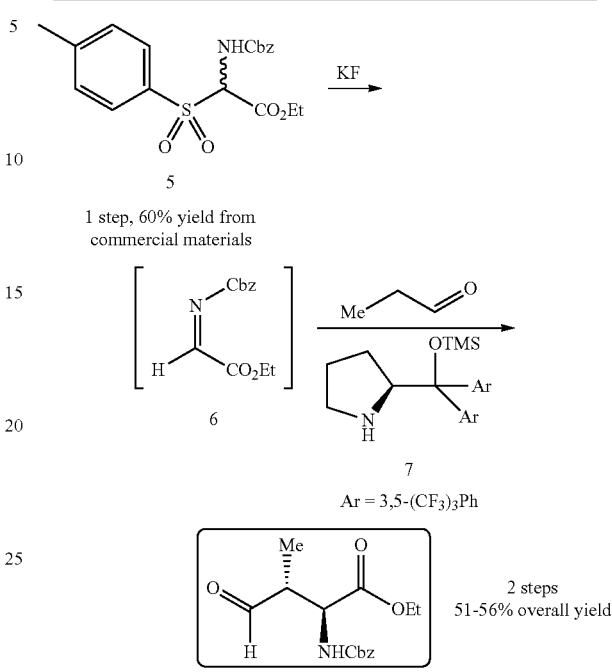

Scheme 3. Improved synthesis of 4 and novel analogs modified at the C3 position.

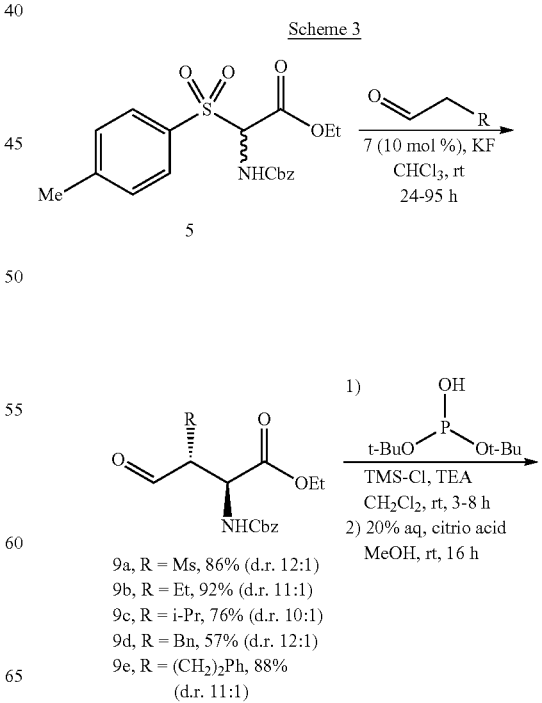

-continued

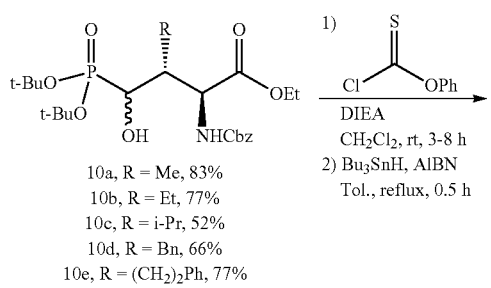

10a, R = Me, 83%
10b, R = Et, 77%
10c, R = i-Pr, 52%
10d, R = Bn, 66%
10e, R = (CH₂)₂Ph, 77%

1) 
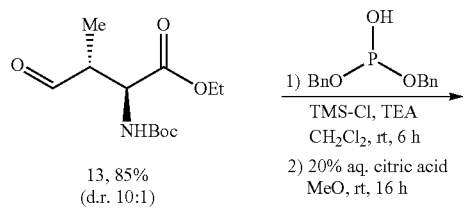
DIEA
CH₂Cl₂, rt, 3-8 h
2) Bu₃SnH, AIBN
Tol., reflux, 0.5 h

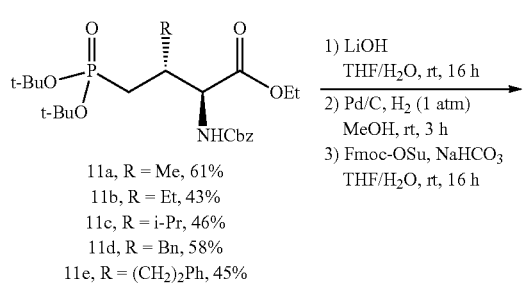

11a, R = Me, 61%
11b, R = Et, 43%
11c, R = i-Pr, 46%
11d, R = Bn, 58%
11e, R = (CH₂)₂Ph, 45%

1) LiOH
THF/H₂O, rt, 16 h
2) Pd/C, H₂ (1 atm)
MeOH, rt, 3 h
3) Fmoc-OSu, NaHCO₃
THF/H₂O, rt, 16 h

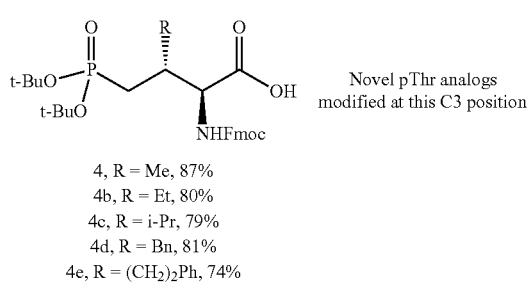

4, R = Me, 87%
4b, R = Et, 80%
4c, R = i-Pr, 79%
4d, R = Bn, 81%
4e, R = (CH₂)₂Ph, 74%

Novel pThr analogs modified at this C3 position

Compatability with Orthogonal Protection Schemes:
Scheme 4. Synthesis of di-benzyl protected Pmab for use in acid-labile solid-phase peptide chemistries.

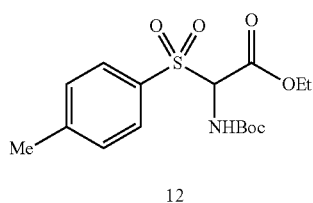

12

1. step, 65% from commercial materials

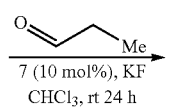

7 (10 mol%), KF
CHCl₃, rt 24 h

-continued

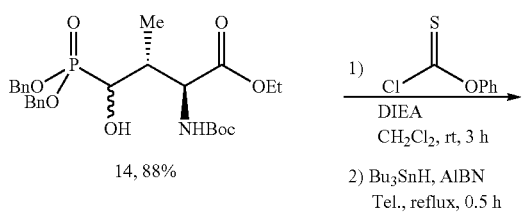

13, 85%
(d.r. 10:1)

1) BnO-P-OBn, OH
TMS-Cl, TEA
CH₂Cl₂, rt, 6 h
2) 20% aq. citric acid
MeO, rt, 16 h

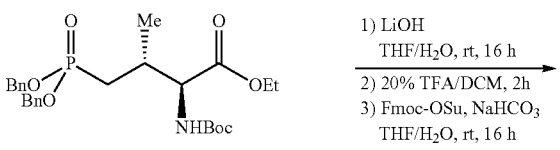

14, 88%

1) 
Cl-C(S)-OPh
DIEA
CH₂Cl₂, rt, 3 h
2) Bu₃SnH, AIBN
Tel., reflux, 0.5 h

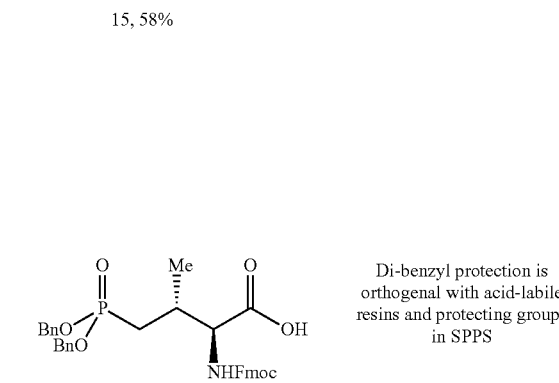

15, 58%

1) LiOH
THF/H₂O, rt, 16 h
2) 20% TFA/DCM, 2h
3) Fmoc-OSu, NaHCO₃
THF/H₂O, rt, 16 h 16, 80%

Di-benzyl protection is orthogenal with acid-labile resins and protecting groups in SPPS C3 Analogs of Pmab Improve PBD Binding Affinities.

FIG. 23A is an X-ray co-crystal structure of the PBD bound to 2 illustrating the proximity of the C3-methyl group with Arg557 and Leu491. FIG. 23B is a graph of competitive ELISA assays of PBD-binding ligands that utilize analogs of Pmab modified at the C3 position. Data points represent average±SEM from five independent experiments and fit using non-linear regression in GraphPad Prism 6. The IC$_{50}$ of the exemplary compounds are show in Table 8.

TABLE 8

Structures of IC$_{50}$ values for PBD-binding peptidomimetics that utilize C3 modified Pmab analogs.

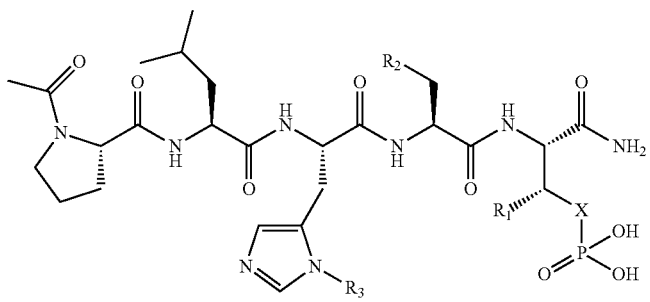

| Cmpd. | X | R$_1$ | R$_2$ | R$_3$ | IC$_{50}$ (μM)* |
|---|---|---|---|---|---|
| 1 (PLHSpT) | O | —Me | —OH | —H | ~475 |
| 2 (PLH*SpT) | O | —Me | —OH | —(CH$_2$)$_8$Ph | 0.17 ± 0.04 |
| 17 | CH$_2$ | —H | —OH | —(CH$_2$)$_8$Ph | 1.2 ± 0.3 |
| 18a | CH$_2$ | —Me | —OH | —(CH$_2$)$_8$Ph | 0.21 ± 0.06 |
| 18b | CH$_2$ | —Et | —OH | —(CH$_2$)$_8$Ph | 0.20 ± 0.06 |
| 18c | CH$_2$ | -iPr | —OH | —(CH$_2$)$_8$Ph | 0.06 ± 0.02 |
| 18d | CH$_2$ | —CH$_2$Ph | —OH | —(CH$_2$)$_8$Ph | 0.30 ± 0.08 |
| 18e | CH$_2$ | —(CH$_2$)$_2$Ph | —OH | —(CH$_2$)$_8$Ph | 0.07 ± 0.02 |
| 19a | CH$_2$ | -iPr | —H | —(CH$_2$)$_8$Ph | 11 ± 3 |
| 19b | CH$_2$ | —(CH$_2$)$_2$Ph | —H | —(CH$_2$)$_8$Ph | 70 ± 14 |

*Values represent average ± SEM from five independent experiments.

Phosphatase-Stability of Pmab-Containing Ligands. Competitive ELISA assay was performed for 2 and 15a following incubation in phosphatase-active crude cell lysates for the times indicated in FIG. 24. Data points represent average±SEM from three independent experiments and fit using non-linear regression in GraphPad Prism 6. The IC$_{50}$ for 2 and 18a are shown in Table 9.

TABLE 9

IC$_{50}$ for the inhibition of isolated PBD by 2 and 18a following incubation in phosphatase-active crude cell lysates

| Time (min) | 2 IC$_{50}$ (nM) | 18a IC$_{50}$ (nM) |
|---|---|---|
| 0 | 27 ± 10 | 14 ± 4 |
| 30 | 1,500 ± 500 | 11 ± 5 |
| 60 | >10,000 | 7 ± 2 |
| 120 | >10,000 | 14 ± 4 |

*Values represent average ± SEM from three independent experiments.

Example 12

Additional Examplary Bi-Valent Compounds of the Present Disclosure

Wortmannin is a known Plk1 covalent inhibitor that binds to the ATP-binding site. To use Wortmannin as a bivalent ligand component, it was converted to succinate ester 1 as shown in Scheme 1, as shown below. Then the bivalent ligands 2 and 3 were synthesized using standard Fmoc Solid Phase Peptide Synthesis (Scheme 2, FIG. 1).

Scheme 1. Synthesis of Wortmannin succinate 1.

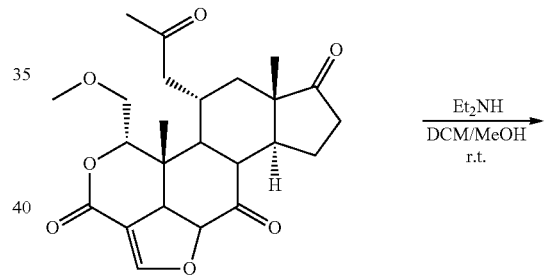

Wortmannin

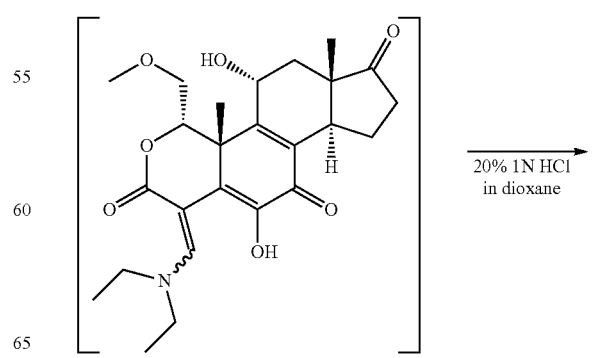

173
-continued
174
-continued
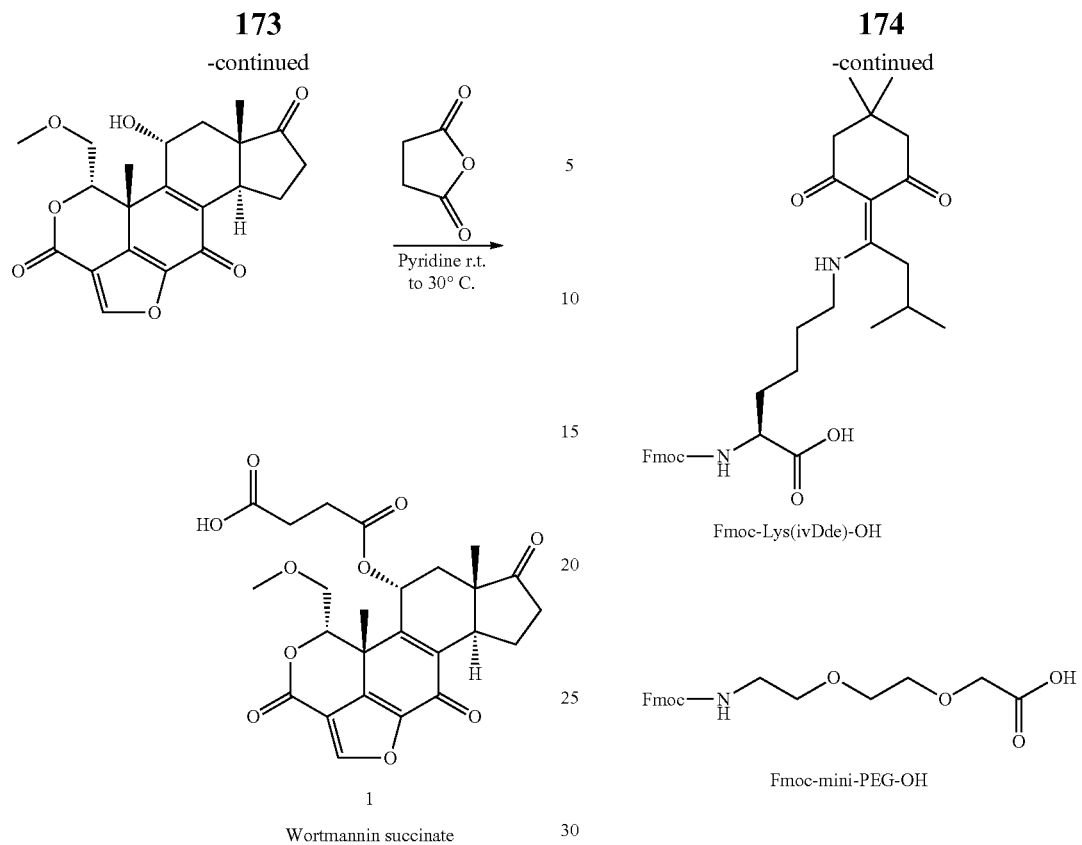
Scheme 2. Synthesis of bivalent compounds with Wortmannin
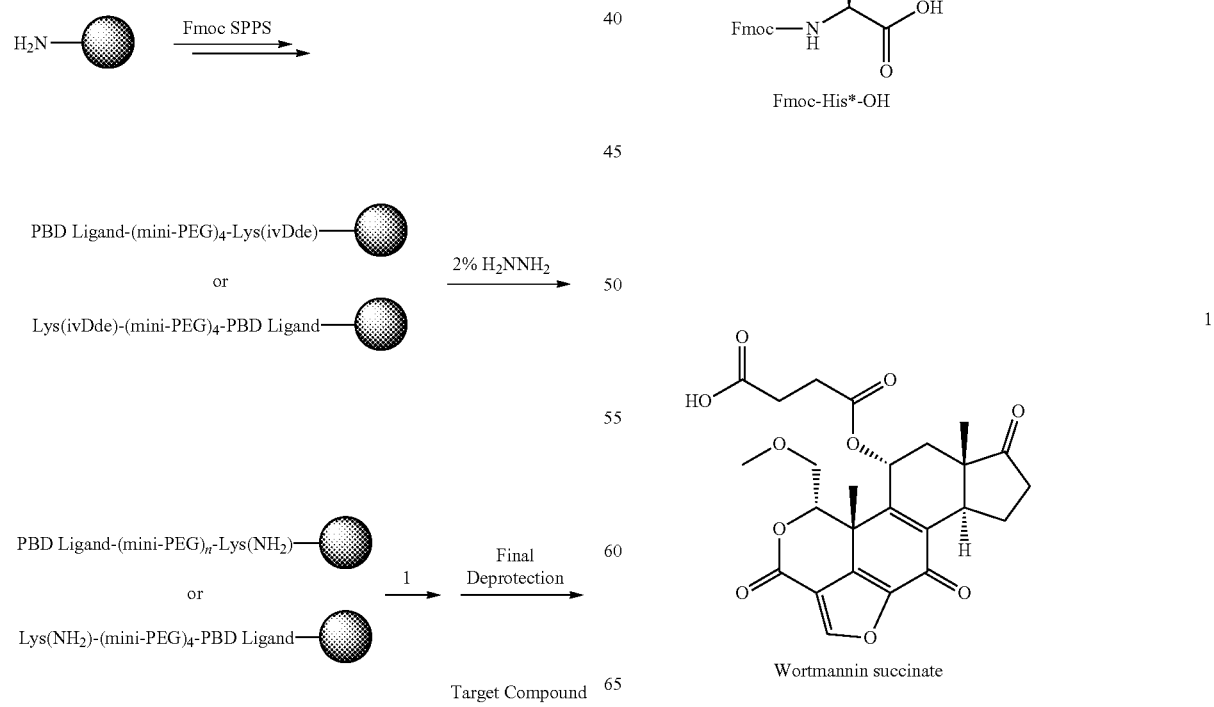

The resultant structures of compounds 2 and 3 are:

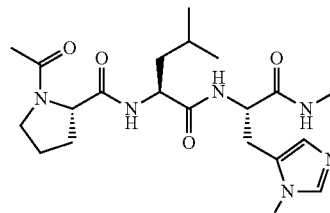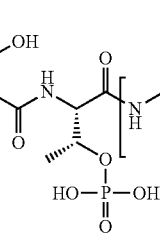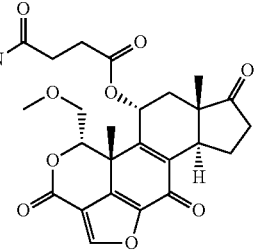

2: R = —(CH$_2$)$_8$Ph

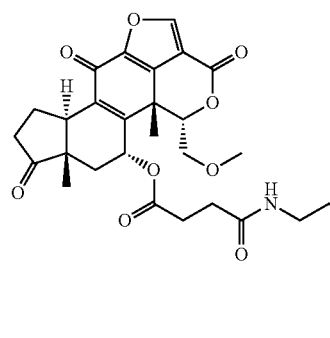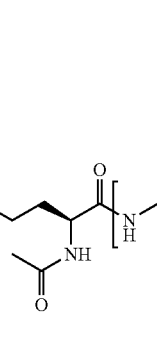

3: R = —(CH$_2$)$_8$Ph

Bivalent compounds 2 and 3 were evaluated by Fluorescence Polarization (FP) based Plk1 PBD-binding assays, the results of which are shown in FIG. 25. The bivalent ligands possessing Wortmannin were demonstrated to have greater affinity enhancement from parent pentapetide. This result is consistent with the bi-valent compounds of the present disclosure described above, thereby demonstrating that this conjugation method can be applied to other KD-binding compounds or inhibitors as a component of the bivalent ligand/compounds of the present disclosure.

Example 13

Non-Peptidic Direct Conjugation Method

A non-peptidic direct conjugation method was developed to avoid digestion of peptidic linker in the cells. Warious diamine-PEG linkers were utilized to conjugate KD-binding and PBD-binding components, as shown in Scheme 3 below. Additionally, a nonhydrolysable pThr mimetic, phosphonomethylaminobutyric acid ("Pmab" in which the phosphoryl ester has been replace with a methylene unit), was utilized to prepare stable ligands in cellular conditions. These compounds retained significant binding affinity relative to the phospho-parent, as shown in FIG. 26, and had the following chemical structures:

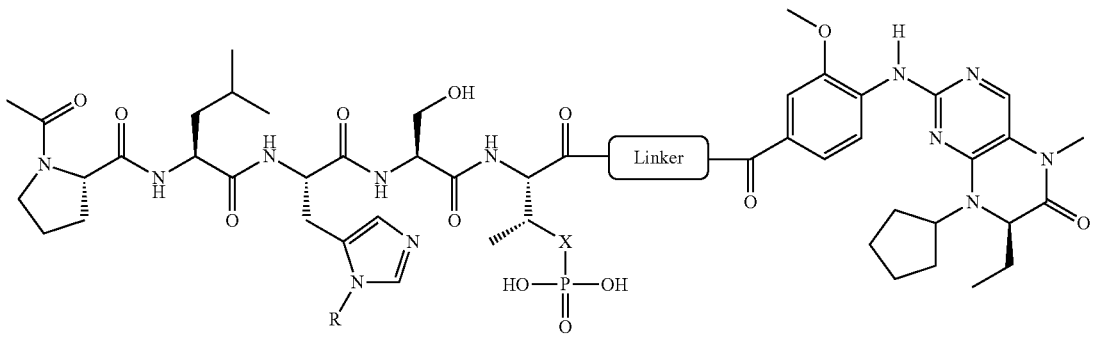

4: R = —(CH$_2$)$_8$Ph, X = O, Linker = 3PEG
5: R = —(CH$_2$)$_8$Ph, X = CH$_2$, Linker = 3PEG
6: R = —(CH$_2$)$_8$Ph, X = CH$_2$, Linker = 5PEG
7: R = —(CH$_2$)$_8$Ph, X = CH$_2$, Linker = 6PEG

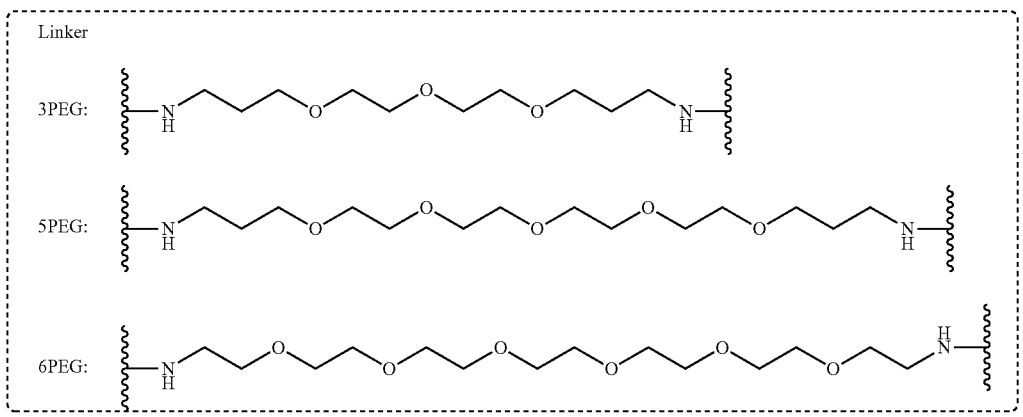

Scheme 3. Synthesis of bivalent ligands with diamine linker

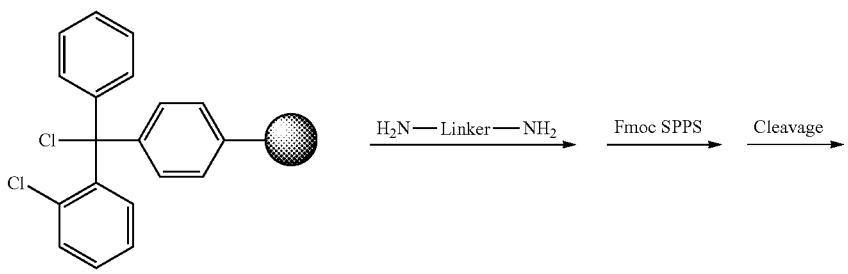

2-Chlorotrityl resin

-continued

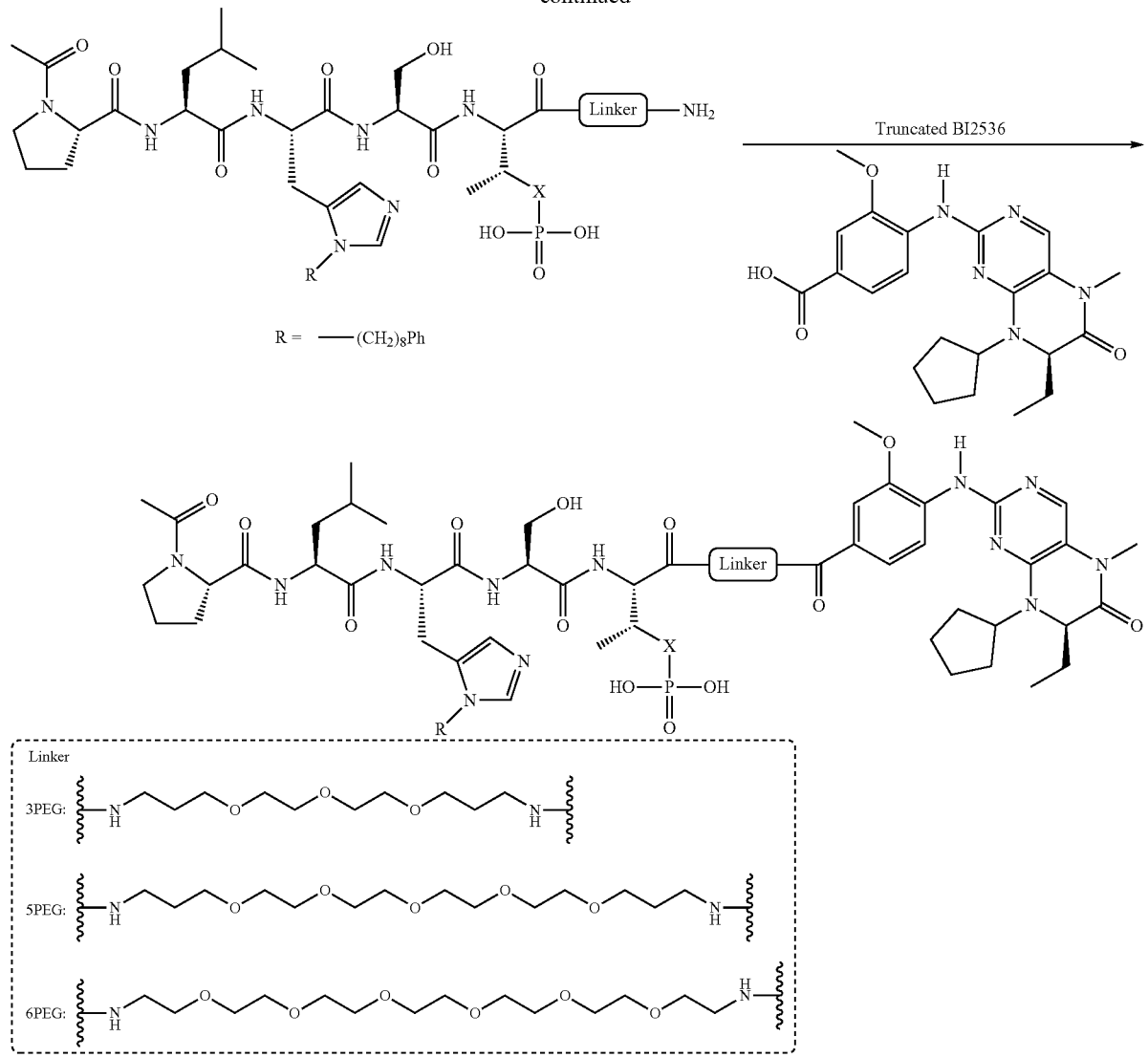

In particular, the bivalent ligands 4, 5, 6, and 7 were evaluated by FP assays. As shown in FIG. 26, the bivalent ligands with diamine linker have a greater affinity than the parent pentapeptide. This result demonstrate that this conjugation method and linker length can be utilized in bivalent ligands of the present disclosure.

Example 14

Exploration of Polo-Like Kinae 1 Inhibitors Targeting Intramolecular Protein-Protein Interaction The Plk1 is a serine/threonine kinase that plays crucial roles in mitosis. Plk1 is overexpressed in many cancers and its inhibition can result in antiproliferative effects on these cells. Therefore, Plk1 is an attractive target for cancer therapy. A number of high affinity inhibitors of Plk1 that target the ATP binding site in the catalytic KD have been reported. However, there are over five hundred genes encoding human kinases and kinases have highly conserved KDs. Therefore, it is a challenge to develop selective kinase inhibitors. In the case of Plk family members, there is an N-terminal KD and a C-terminal PBD, which is unique to Plk family. The PBD recognizes pS and pT-containing sequences and modulates the kinase activity of Plk1 through intramolecular protein-protein interactions with its KD. Moreover, the PBD also regulates distribution of Plk1 during mitosis. Highly potent peptide-based Plk1 PBD inhibitor (1) has low nano-molar affinity in vitro and induces incorrect distribution of Plk1 in mitosis when given to cells in culture. However, the efficacy of 1 is limited in whole cell assays due to poor cell membrane permeability. Phosphatase-stable analog 1* shows low cellular potency, presumably due to poor cell-membrane permeability. To improve cellular activity, bivalent ligands were developed that can bind KD and PBD regions of Plk1 simultaneously. Such agents provide extremely selective and potent ligands for Plk1. This should allow for the reduction in peptidic features of there PBD-binding ligands, thereby facilitate development of practical, cell-permeable Plk1 inhibitors.

Targeting the Polo-Box Domain. Bivalent constructs were designed to simultaneously bind to the Kd and PBD regions of Plk1. The structures of PBD-binding compounds 1 and 1* are shown in FIG. 27C. The Zebrafish Plk1 KD and PBD structure complexed with a D. melanogaster Map205-derived pepride (PDB: 4J7B) (FIG. 27A) and superimposed the human Plk1 Kd complexed with BI2536 (PDB: 2RKU) as well as the human Plk1 PBD complexed with 1 (PDB: 3RQ7) (FIG. 27D). That is, FIG. 27D shows the potential arrangement of human Plk1 KD complexed with Plk1 inhibitor BI2536 (2) and PBD complexed with 1 (PDB code: 3RQ7) obtained using a recent co-crystal structure of Zebrafish Plk1 domains (PDB: 4J7B). This demonstrates that the distance between the peperidine nitrogen of BI2536 and the C-terminal amide carbon of peptide 1 appeared to be approximately 27 Å. It was unclear what linker the required linker length and which end of the PBD-binding peptide the linker should be attached in order to suffessfully access both domains from peptide 1. As such, as shown in FIG. 27E, bivalent ligands where synthesized and evaluated wherein BI2536 (2) was tethered from the C-termini and N-termini of 1 using various length PEG chains.

FIG. 27B shows representative fluorescence microscopy images of immunostained cells treated with PBS (control) or compound 1*. In FIG. 27B, the asterisks indicate centrosomally localized Plk1 signals, the arrowed brackets indicate kinetochore-associated Plk1 signals, and arrowheads indicate misaligned chromosomes.

Synthesis of Bivalent Ligand. Synthesis for preparing exemplary bivalent ligands 4 and 5 are shown below. In particular, compound 3, which is a truncated version of BI2536 lacking the piperidine portion, was used for the KD-binding part of the bivalent constructs. Based on the co-crystal data, the piperidine moiety of BI2536 extends outside the binding pocket (FIG. 27D). Bivalent constructs 4 and 5 were synthesized using standard Fmoc chemistry.

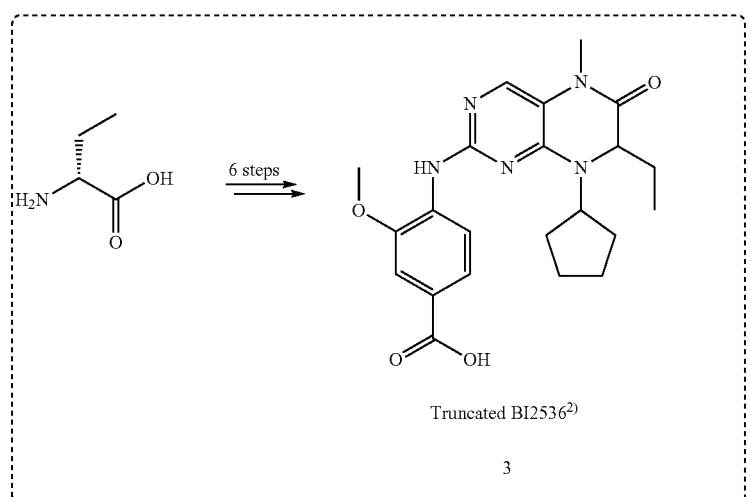

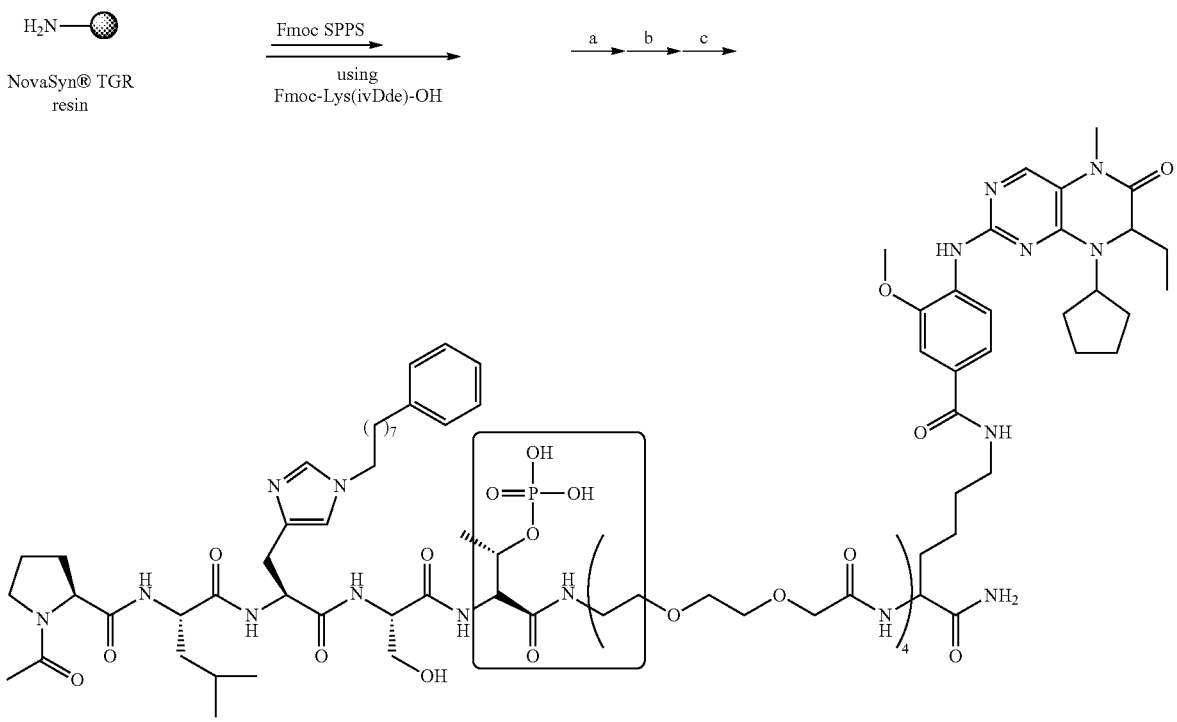

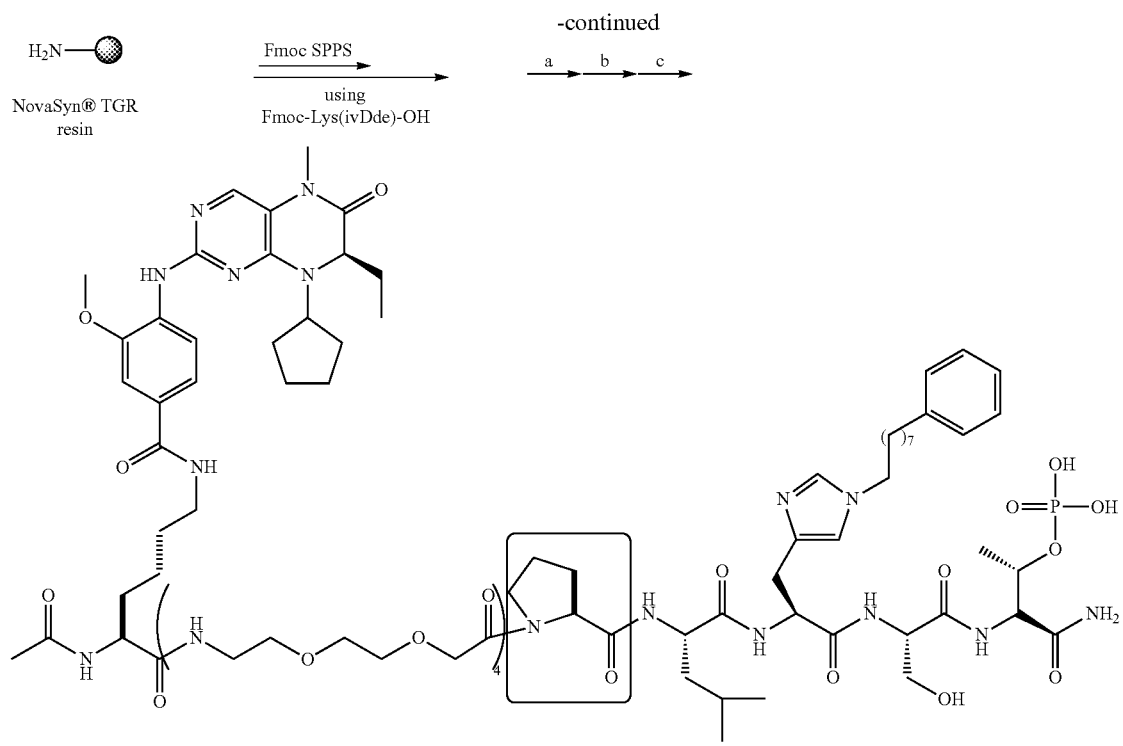

(a) 2% H2NNH2 in NMP; (b) 3, HATU, DIEA, NMP; (c) TFA/TIPS/H2O=95:2.5:2.5. The squares on 4 and 5 indicate attachment at the C-terminus and N-terminus, respectively.

Biological Evaluation of Bivalent Ligands. Peptides 4 and 5 were evaluated by FP assays using full-length Plk1 or isolated PBD with FITC-labeled 1 as a probe. FIG. 28A shows the FP assays for 4 and 5 against full-length Plk1. Compounds 4 and 5 demonstrated a 100-fold increase in binding affinity relative to 1. However, the affinities of 4 and 5 were similar to the monovalent 1 in an assay using PBD (i.e. lacking a KD component), as illustrated by FIG. 28B. Data points for FIGS. 28A and 28B represent average±SEM from three independent experiments and fit using nonlinear regression in GraphPad Prism 7.

Structure Activity Relationship (SAR)—Examination of Bivalent Ligands with Attenuated KD-binding Components. Bivalent constructs using forms of BI2536 that exhibit attenuated kinase inhibitory potencies. FIGS. 29A and 29B illustrate the design of attenuated KD-binding inhibitors and structures of associated bivalent inhibitors 8, 9, 10, and 11, respectively. As shown in FIG. 29A, the replacement of the exocyclic pyrimidine nitrogen of BI2536 with an isosteric oxygen has been reported to result in more than 100-fold attenuated of affinity, and the replacement of the cyclopentyl group with an isobutyl group also reduces potency by more than 30 fold. As such, BI2536* (6) and BI2536+ (7) as moderately and severely attenuated BI2536 derivatives, respectively (FIG. 29A). The corresponding C-terminal bivalent constructs (8 and 10, respectively) and N-terminal constructes (9 and 11, respectively) were prepared, as shown in FIG. 29B.

Effects of attenuated KD-binding components on biological activity of bivalent ligands. The above-recited constructs were evaluated in a full-length Plk1 FP binding assay, as well as Plk1 kinase assay (FIGS. 30A and 30B, respectively). Compounds 8-11, which have the attenuated forms of BI2536, had lower binding affinities than 4 and 5 (FIG. 30A). As shown in FIG. 30B, the inhibitory potencies of 8 and 10 were weaker than 4 and 5, while constructs 9 and 11 had reduced potencies. These results further demonstrate the co-operative interaction of the peptides with the KD and PBD portions of Plk1.

The Z-LYTE Ser/Thr 16 peptide kinase assay kit (Invitrogen) was used for the kinase assay. Data points represent average±SEM from three independent experiments and fit using non-linear regression in GraphPad Prism 7.

SAR study of linker length. The following study was undertaken to determine whether accessing the KD could be more optimally achieved from the C-terminus or N-terminus of 1 and the appropriate linker length for connecting the PBD-binding and KD-binding components. Because the initially homology modelling suggested that linker lengths of at least 27 Å were required (see above), the initial bivalent constructs 4 and 5 consisted of both C-terminal and N-terminal versions employing a linker with four mini-PEG units. However, the KD and PBD regions of Plk1 may be mobile, and interdomain distances might be highly variable. Thus, bivalent constructs that employ different linker lengths were prepared by varying the number of mini-PEG units (from n=0 to n=4), which were examined in full-length Plk1 FP bindig assays. The chemical structure of these compounds (4, 12, 14, 16, 5, 13, 15, and 17) are shown below. As shown in FIG. 31, it was surprising and unexpectedly observed that there does not appear to be a significant dependence in binding affinities on either linker length or attachment at the C-terminus or N-terminus of the peptides. Data points represent average±SEM from three independent experiments and fit using non-linear regression in GraphPad Prism 7.

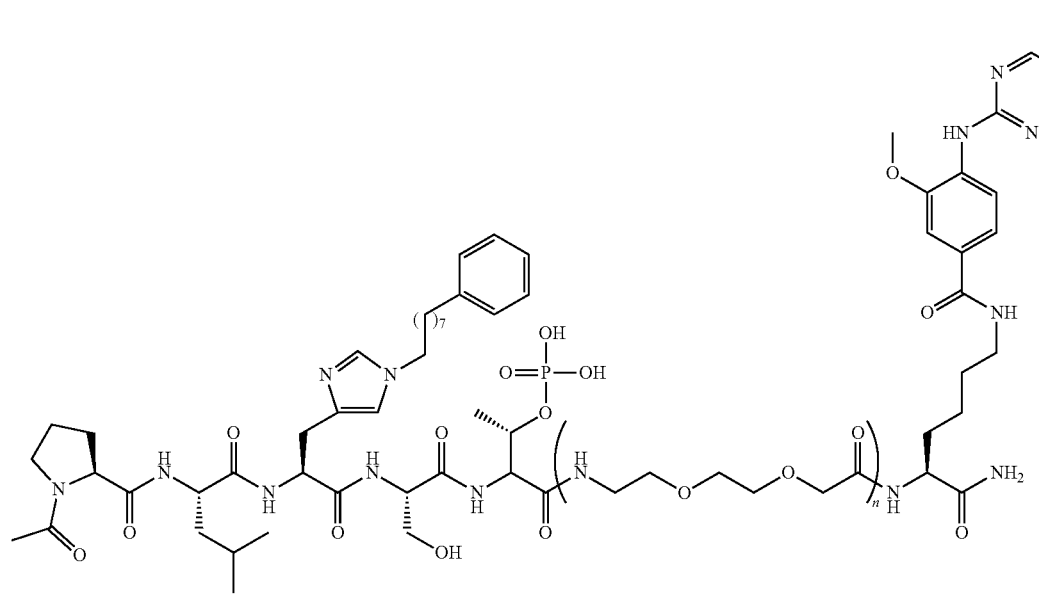
4: n = 4
12: n = 3
14: n = 1
16: n = 0
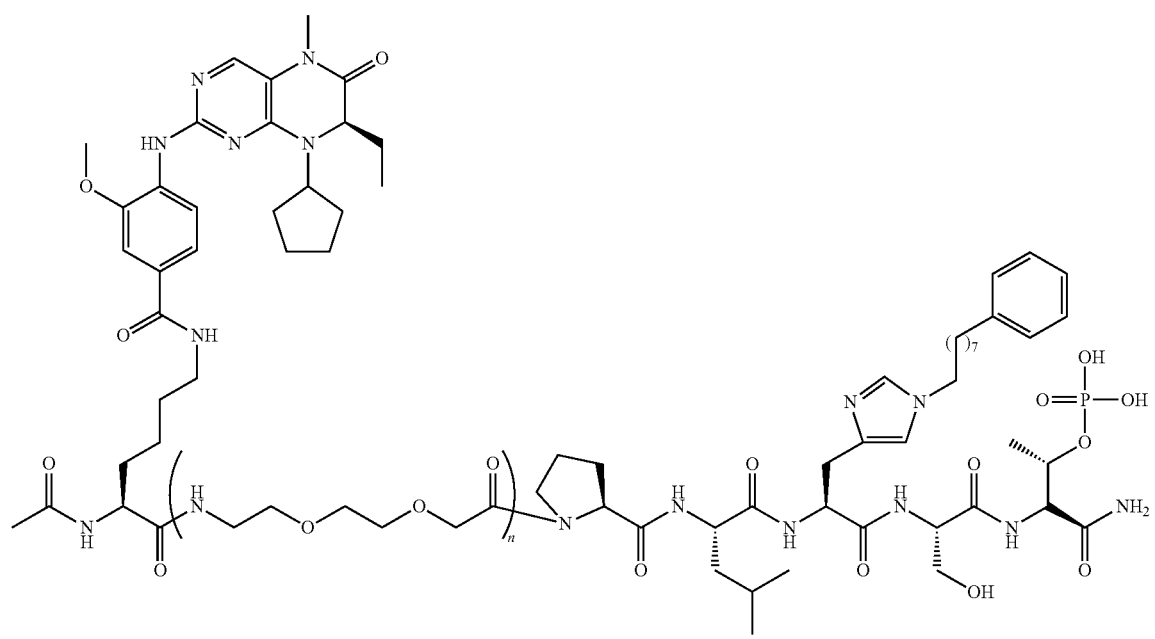
5: n = 4
13: n = 3
15: n = 1
17: n = 0

187

Discussion. Highly potent Plk1 inhibitors were designed to simultaneously bind the KD and PBD that have an approximate two orders-of-magnitude affinity enhancement relative to peptide 1, which was the best inhibitor described. Other studies not shown here demonstrate extremely fast on/off rates at the KD and much slower off rates at the PBD. Thus, it is hypothesized that the enhanced affinity observed by the bivalent ligands is a result of the PBD binding and the repetitive, rapid on/off binding at the KD.

Specific Embodiments

An aspect of the present disclosure provides a compound of Formula 2:

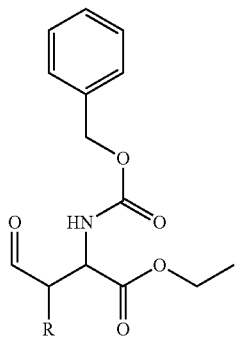

Formula 2 wherein:
R is optionally substituted cycloalkyl, optionally substituted phenylethyl, optionally substituted phenylpropyl, optionally substituted heteroarylalkyl, haloalkyl, optionally substituted morpholinomethyl,

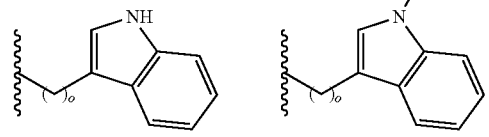

or optionally substituted indolylalkyl; and
Y is $CH_2$, NH, or O; or salt, solvate, or hydrate thereof.
1. The compound of claim 1, wherein:
R is

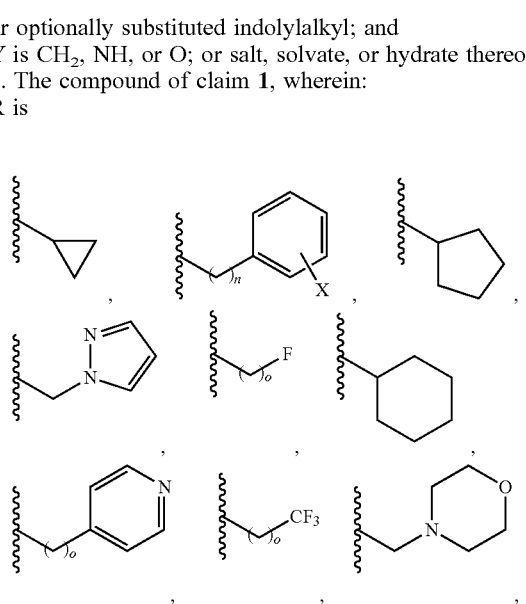

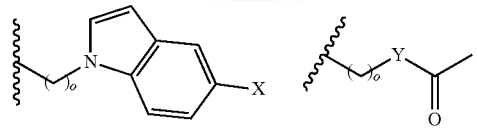

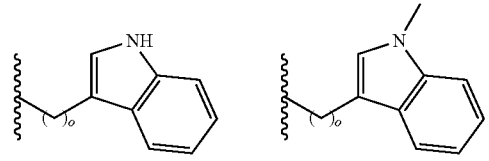

n is 2-3;
each o is independently 1-3;
each X is independently H, Me, Et, $CF_3$, F, Cl, Br, OMe, or $N(Me)_2$; and
Y is $CH_2$, NH, or O.

Another aspect of the present disclosure provides a compound of Formula 1:

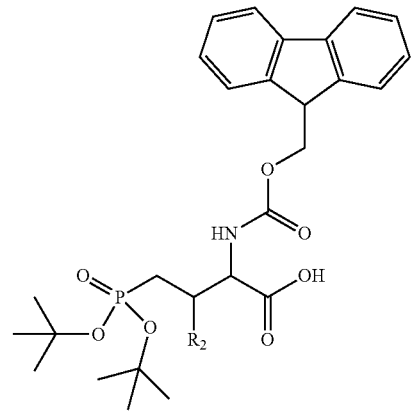

Formula 1 wherein:
$R_2$ is optionally substituted $C_2$-$C_4$ alkyl, optionally substituted cycloalkyl, optionally substituted aralkyl, optionally substituted heteroarylalkyl, haloalkyl, optionally substituted morpholinomethyl,

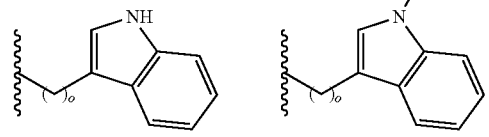

and
Y is $CH_2$, NH, or O; or optionally substituted indolylalkyl, or salt, solvate, or hydrate thereof.

2. The compound of claim 3, wherein:

R₂ is Et, Pr, i-Pr, Bu,

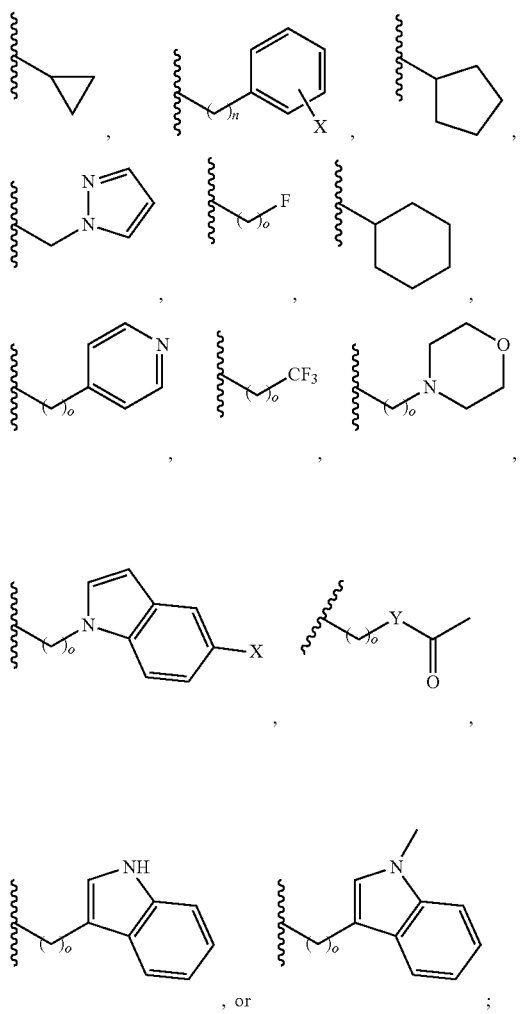

, or ;

each o is independently 1-3;

each X is independently H, Me, Et, CF₃, F, Cl, Br, OMe, or N(Me)₂; and

Y is CH₂, NH, or O.

A further aspect of the present disclosure provides a compound of Formula II or IIa:

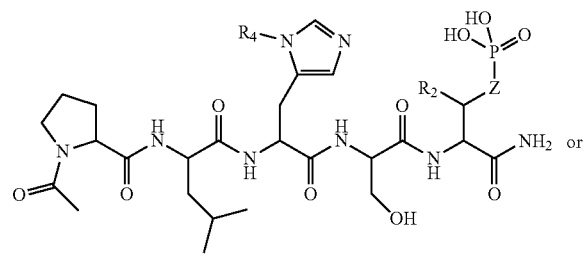

Formula II

-continued

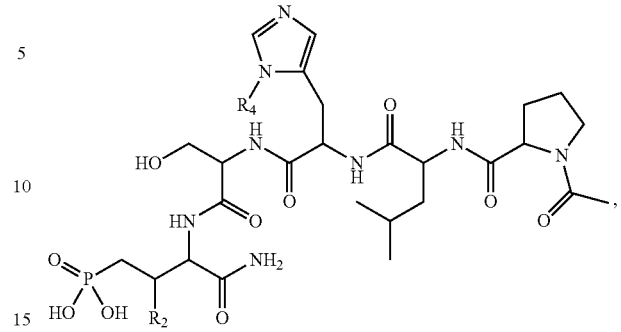

Formula IIa wherein:

R₂ is H, optionally substituted optionally substituted alkyl (e.g. C₂-C₄ alkyl), optionally substituted cycloalkyl, optionally substituted aralkyl, optionally substituted heteroarylalkyl, haloalkyl, optionally substituted morpholinomethyl,

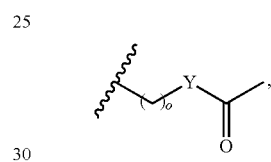

or optionally substituted indolylalkyl;

Y is CH₂, NH, or O;

Z is O or CH₂;

and

R₄ is optionally substituted aralkyl, or salt, solvate, or hydrate thereof.

In any aspect or embodiment described herein:

R₂ is Et, Pr, i-Pr, Bu,

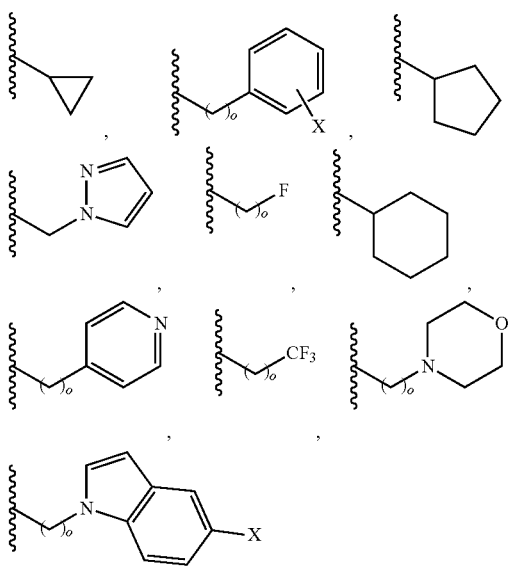

-continued

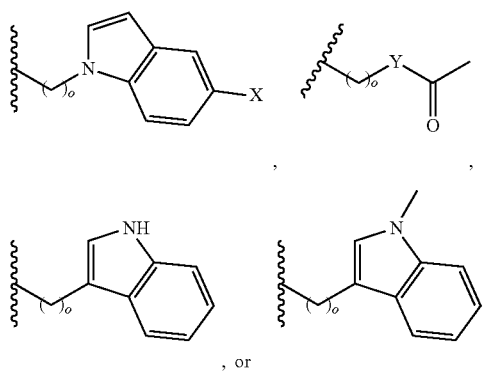

, or ;

each o is independently 1-3;
each X is independently H, Me, Et, CF$_3$, F, Cl, Br, OMe, or N(Me)$_2$;
Y is CH$_2$, NH, or O; and
R$_4$ is —(CH$_2$)$_8$-Ph.

An additional aspect of the present disclosure is a process to prepare of a compound of Formula 2, or salt, solvate, or hydrate thereof:

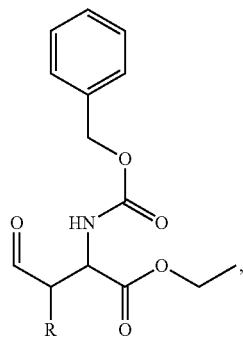

Formula 2 the process comprising:
a) reacting

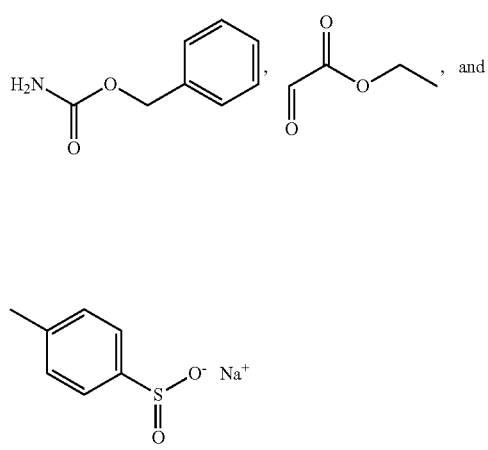

to afford compound 3,

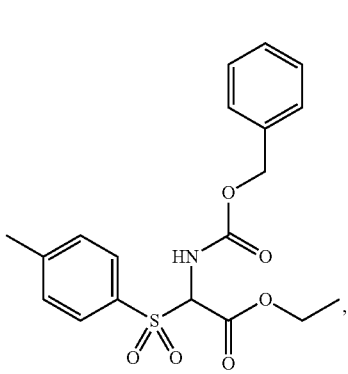 [SMILES: CCOC(=O)C(NC(=O)OCc1ccccc1)S(=O)(=O)c1ccc(C)cc1]

and
b) reacting compound 3,

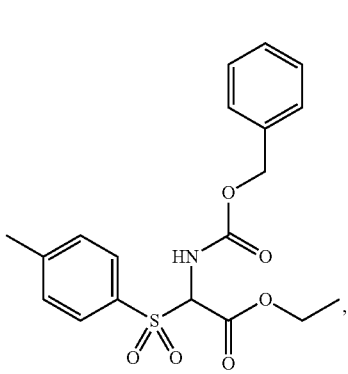 [SMILES: CCOC(=O)C(NC(=O)OCc1ccccc1)S(=O)(=O)c1ccc(C)cc1]

with a compound of Formula,

to afford a compound of Formula 2,

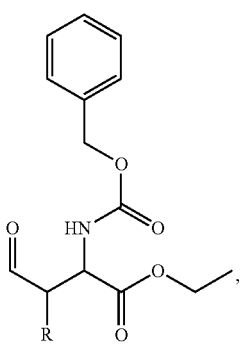

wherein R is optionally substituted cycloalkyl, optionally substituted phenylethyl, optionally substituted phenylpropyl, optionally substituted heteroarylalkyl, haloalkyl, optionally substituted morpholinomethyl,

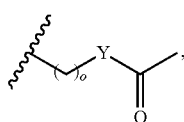

or optionally substituted indolylalkyl; and Y is CH$_2$, NH, or O, and o is 1-3.

In any aspect or embodiment described herein:
R is

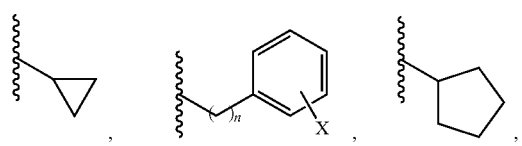

,

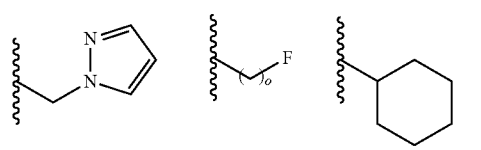

,

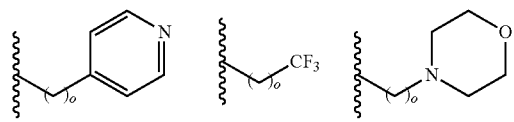

,

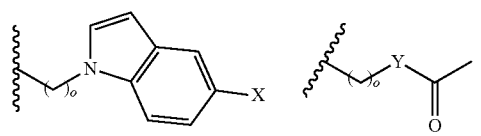

,

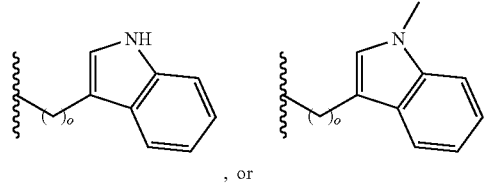

, or ;

n is 2-3;

each o is independently 1-3;

Y is CH$_2$, NH, or O; and each X is independently H, Me, Et, CF$_3$, F, Cl, Br, OMe, or N(Me)$_2$.

Another aspect of the present disclosure provides a process to prepare a compound of Formula 4, or salt, solvate, or hydrate thereof:

(Formula 4)

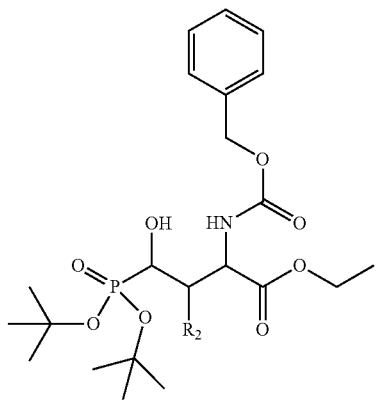

the process comprising:

a) phosphorylating a compound of Formula 3,

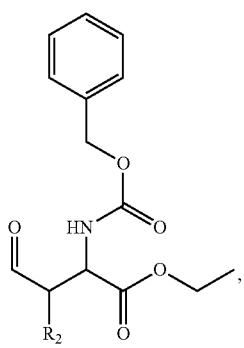

with di-tert-butylphosphite to afford a compound of Formula 4,

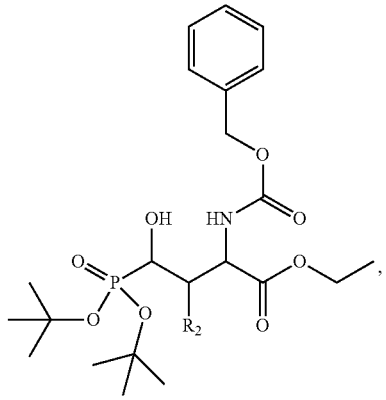

wherein:

R$_2$ is optionally substituted C$_2$-C$_4$ alkyl, optionally substituted cycloalkyl, optionally substituted aralkyl, optionally substituted heteroarylalkyl, haloalkyl, optionally substituted morpholinomethyl,

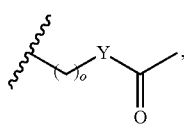

or optionally substituted indolylalkyl;

Y is CH$_2$, NH, or O; and o is 1-3.

In any aspect or embodiment described herein, the process further comprises the step of activating the alcohol within the compound of Formula 4,

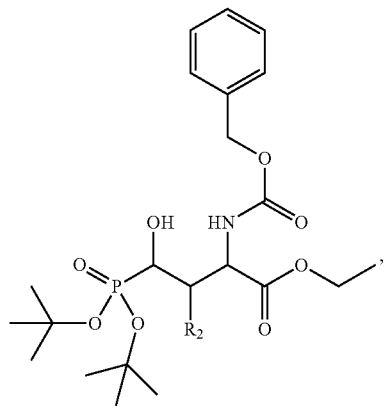

with O-phenyl thiochloroformate to afford a compound of Formula 5,

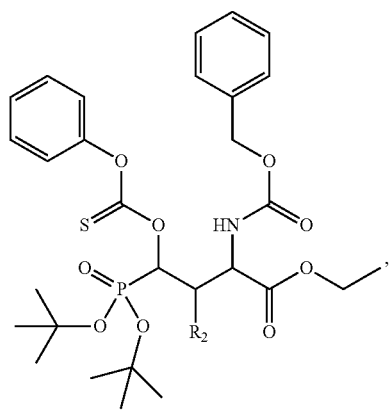

wherein R$_2$ is defined as above.

In any aspect or embodiment described herein, the process further comprises the step of reducing a compound of Formula 5,

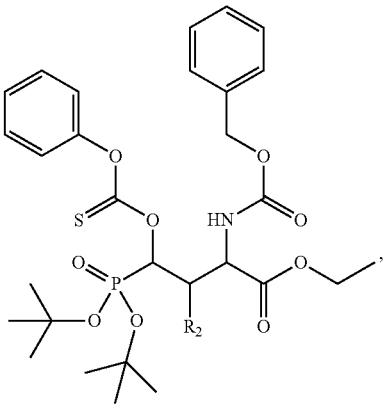

to afford a compound of Formula 6,

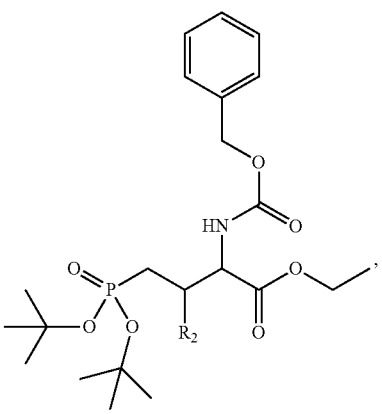

wherein R$_2$ is defined as above.

In any aspect or embodiment described herein, the process further comprises the step of hydrolyzing the ethyl ester of a compound of Formula 6,

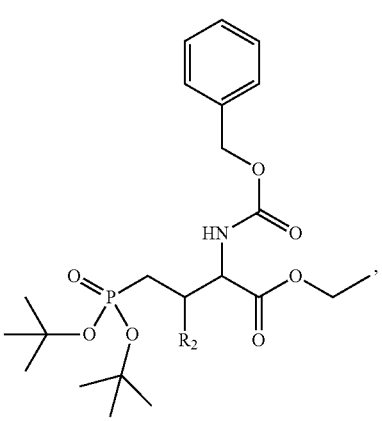

to afford a compound of Formula 7,

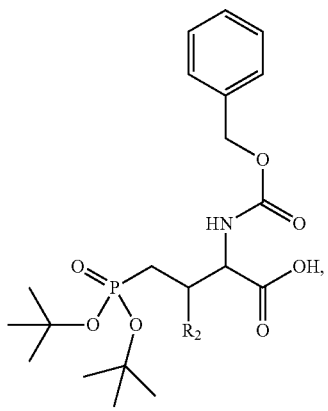

wherein R₂ is defined as above.

In any aspect or embodiment described herein, the process further comprises the step of deprotecting the benzyl carbamate of a compound of Formula 7,

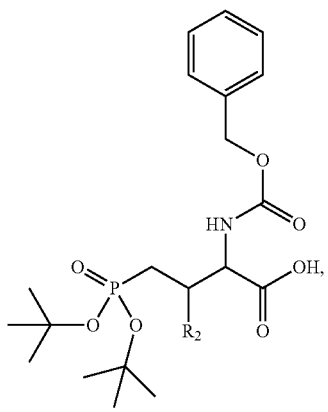

to afford a compound of Formula 8,

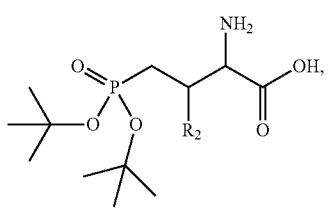

wherein R₂ is defined as above.

The process of claim 13, further comprising the step of protecting the amino functionality of a compound of Formula 8,

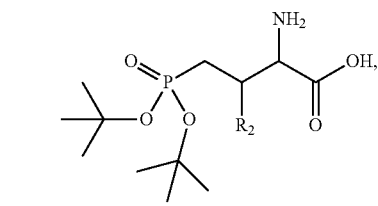

to afford a compound of Formula 1,

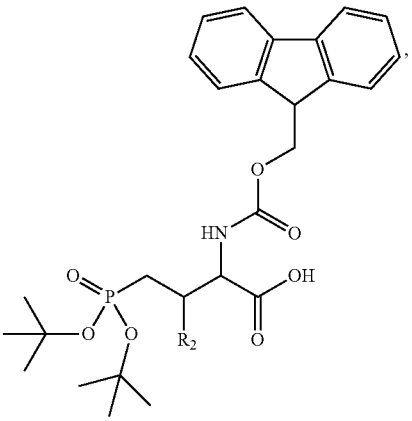

wherein R₂ is defined as above.

In any aspect or embodiment described herein:
R₂ is Me, Et, Pr, i-Pr, Bu,

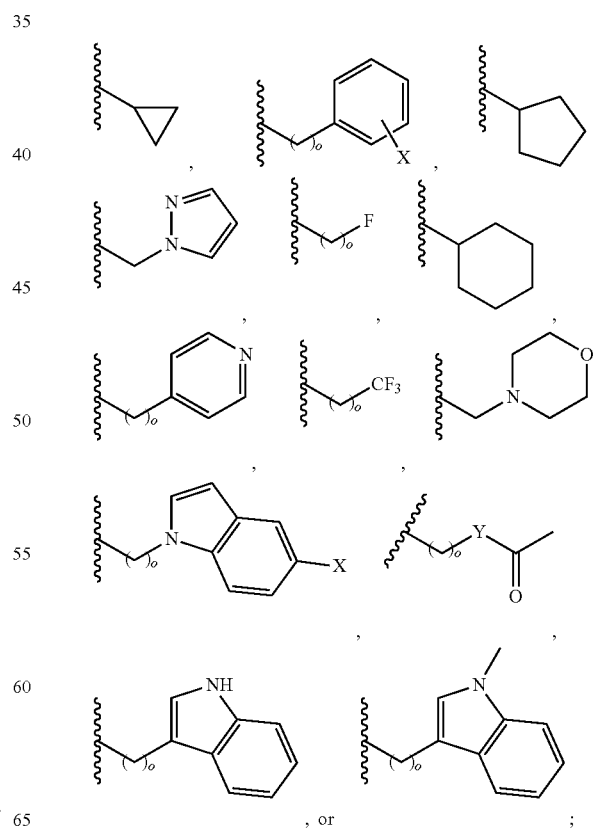

each o is independently 1-3;

Y is CH$_2$, NH, or O; and each X is independently H, Me, Et, CF$_3$, F, Cl, Br, OMe, or N(Me)$_2$.

An aspect of the present disclosure provides a process to prepare a compound of Formula IIa, or salt, solvate, or hydrate thereof:

Formula IIa

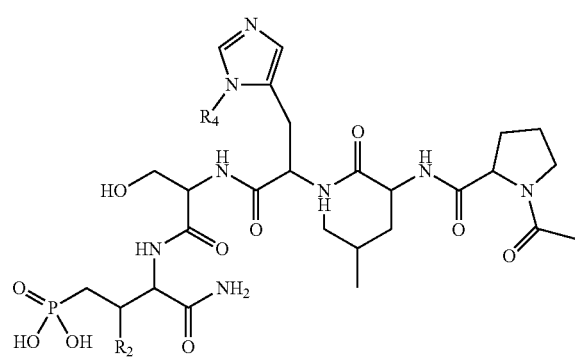

the process comprising:

a) phosphorylating a compound of Formula 9,

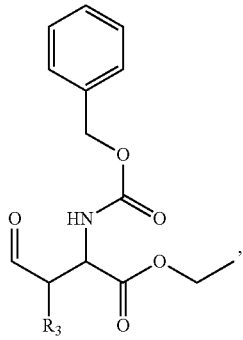

with di-tert-butylphosphite to afford a compound of Formula 10,

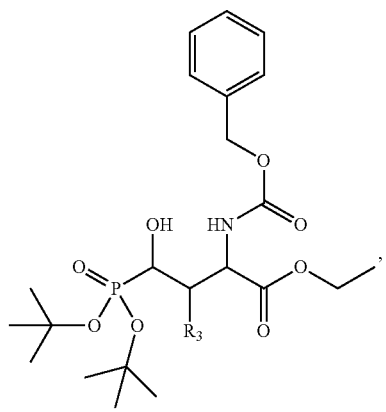

b) activating the alcohol within the compound of Formula 10, with O-phenyl thiochloroformate to afford a compound of Formula 11,

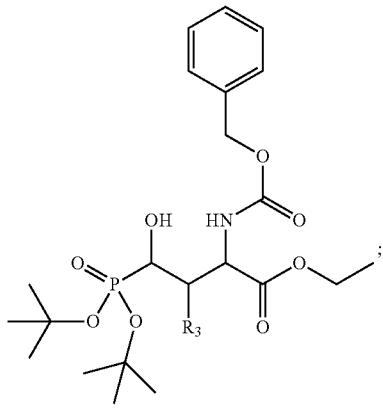

c) reducing a compound of Formula 11,

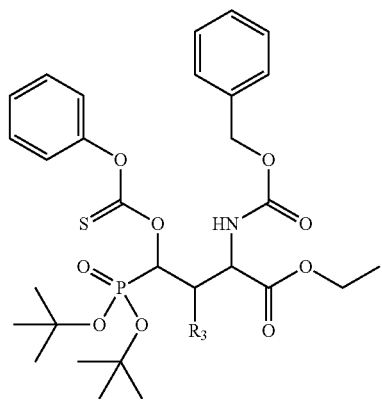

to afford a compound of Formula 12,

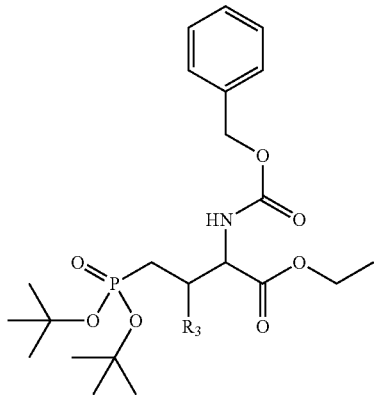

d) hydrolyzing the ethyl ester of a compound of Formula 12,

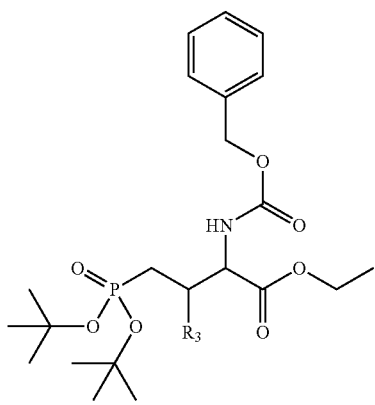

to afford a compound of Formula 13,

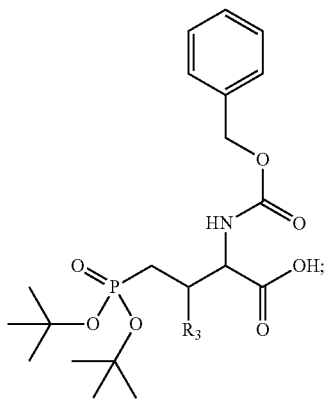

e) deprotecting the benzyl carbamate of a compound of Formula 13,

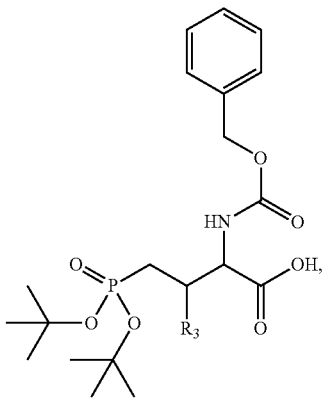

to afford a compound of Formula 14,

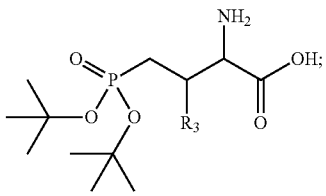

and f) protecting the amino functionality of a compound of Formula 14,

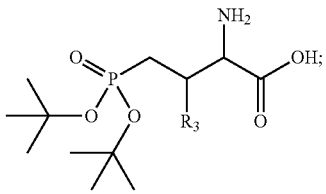

to afford a compound of Formula 15,

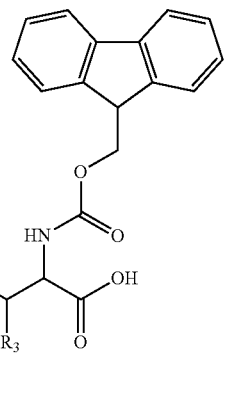

g) coupling an amino acid, analog or derivative thereof to the compound of Formula 15, wherein:

$R_3$ is optionally substituted $C_1$-$C_4$ alkyl, optionally substituted cycloalkyl, optionally substituted aralkyl, optionally substituted heteroarylalkyl, haloalkyl, optionally substituted morpholinomethyl,

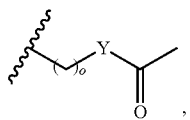

or optionally substituted indolylalkyl;

R$_2$ is Me, Et, Pr, i-Pr, Bu,

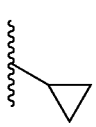,

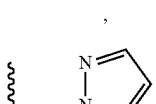,

,

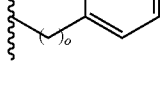,

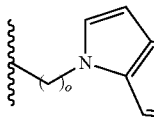,

,

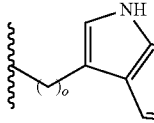,

;

each o is independently 1-3; each X is independently H, Me, Et, CF$_3$, F, Cl, Br, OMe, or N(Me)$_2$; and Y is CH$_2$, NH, or O;

Y is CH$_2$, NH, or O;

each R$_4$ is independently optionally substituted aralkyl; and o is 1-3.

In any aspect or embodiment described herein:

R$_3$ is Me, Et, Pr, i-Pr, Bu,

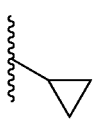, 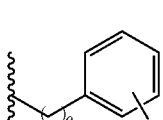, 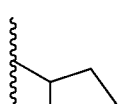,

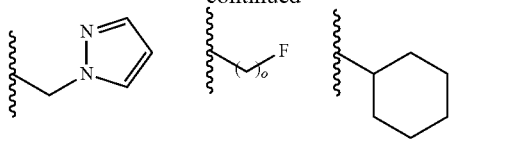

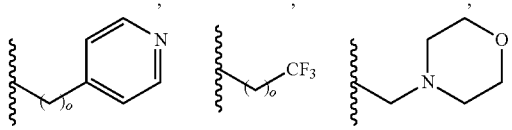

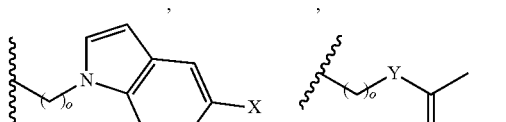

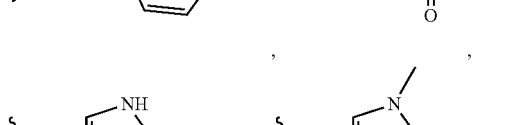

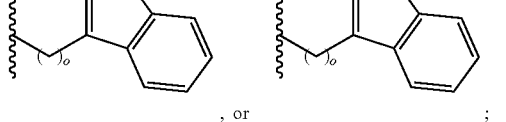, or ;

each o is independently 1-3;
Y is CH$_2$, NH, or O; and
each X is independently H, Me, Et, CF$_3$, F, Cl, Br, OMe, or N(Me)$_2$.

In any aspect or embodiment described herein:

R$_3$ is Me, Et, Pr, i-Pr, Bu,

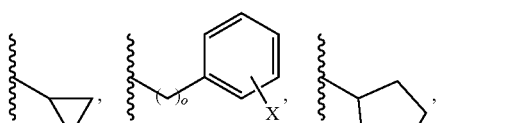

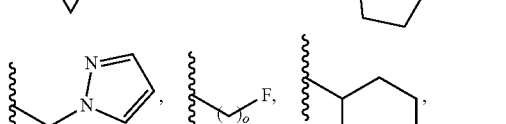

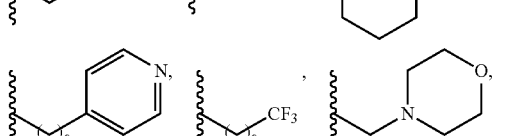

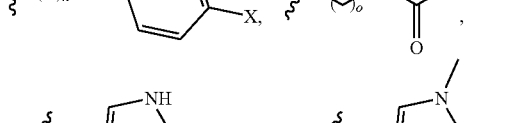

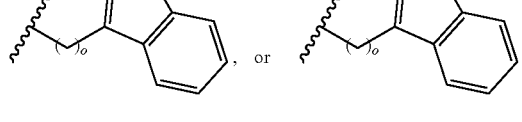

each o is independently 1-3;
each X is independently H, Me, Et, CF$_3$, F, Cl, Br, OMe, or N(Me)$_2$;
Y is CH$_2$, NH, or O; and
each R$_4$ is —(CH$_2$)$_8$-Ph.

An additional aspect of the present disclosure provides a peptido-mimetic compound comprising the compound of the present disclosure.

In any aspect or embodiment described herein, the peptido-mimetic is a polo box domain (PBD) ligand.

In any aspect or embodiment described herein, the ligand has the structure: $X_{0-6}$-Ser-[Z]-$X'_{0-8}$, wherein X is any amino acid, and Z refers to an amino acid analog of claim 1, and only one of X or X' can be zero.

In any aspect or embodiment described herein, Z is a C-3 substituted Pmab derived phosphatase stable analog of phospho-threonine or phospho-serine.

In any aspect or embodiment described herein, X is a naturally occurring amino acid.

In any aspect or embodiment described herein, the PBD ligand is a member selected from the group consisting of: FSQHKTS(Z)I, HS(Z), N-terminal modified HS(Z) peptidomimetic, GVLS(Z)LI, VLS(Z)L, N-terminal modified PLHS(Z)M and LHS(Z)M peptidomimetic, Cyclic GLH(oct-Ph)S(Y)C thioether peptidomimetic, FDPPLHS(Z)A, XDPPLHS(Z)A peptidomimetic (X=natural or non-natural amino acid), PLHS(Z)A, MQS(Z)PL, FMPPPMS(Z)M, LLCS(Z)PNGL, MQS(Z)PL, PMQS(Z)PLN, and MAGPMQS(Z)PLNGAYKK, wherein Z is a C-3 substituted Pmab derived phosphatase stable analog of phospho-threonine or phosphor-serine.

Yet a further aspect of the present disclosure provides a cyclic polo-box domain(PBD) ligand comprising the structure:

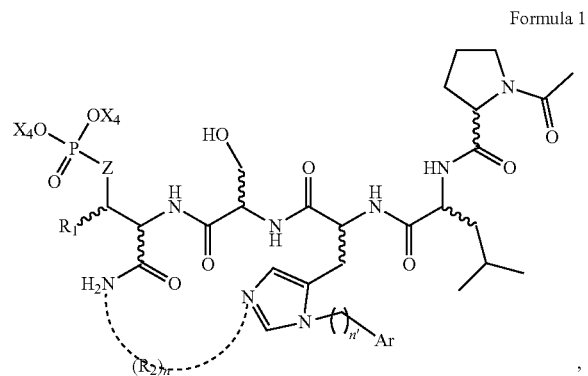

Formula 1 wherein:
n or n' is 1-20;
$R_2$ is an optionally substituted alkyl group or polyethylene glycol;
Z is O or $CH_2$;
$R_1$ is an optionally substituted alkyl, optionally substituted cycloalkyl, optionally substituted aralkyl, optionally substituted heteroarylalkyl, haloalkyl, optionally substituted morpholinomethyl,

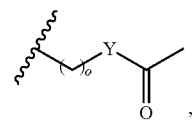

or optionally substituted indolylalkyl;
Y is $CH_2$, NH, or O; o is 0-10 and
Ar is an optionally substituted aryl, an optionally substituted heteroaryl, an optionally substituted aralkyl; an optionally substituted heteroarylalkyl;
$X_4$, for each occurrence independently, is H, alkyl, aryl-(C1-20)alkyl-, or alkenyl-(C1-20)alkyl; or
a pharmaceutically acceptable salt, solvate, hydrate, prodrug, or stereoisomer thereof.

In any aspect or embodiment described herein, n is 4-6; n' is 4-8 and R2 is a methylene group.

In any aspect or embodiment described herein, the ligand comprises structure:

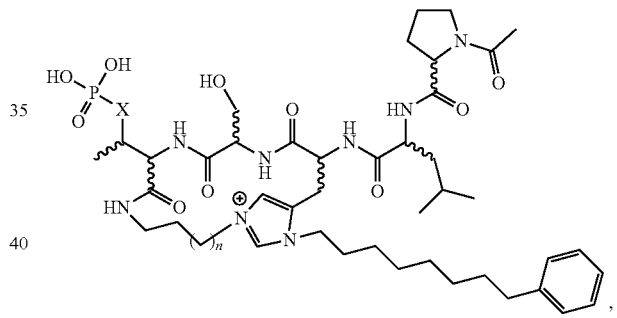

wherein:
X is CH2 or O;
n is 2-4; and
a pharmaceutically acceptable salt, solvate, hydrate, or stereoisomer thereof.

In any aspect or embodiment described herein, the ligand comprises structure:

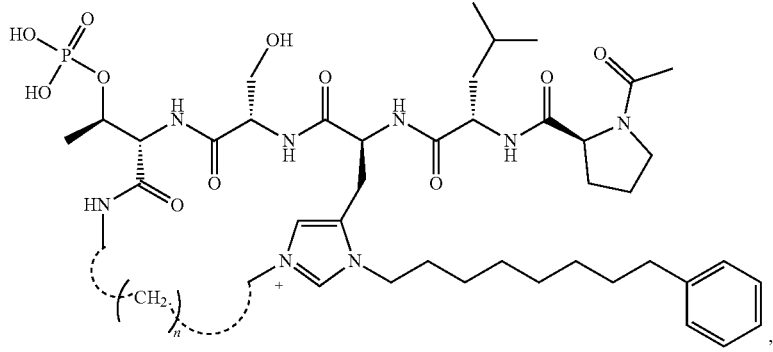

wherein:

n is 4-6, and a pharmaceutically acceptable salt, solvate, hydrate, or stereoisomer thereof.

An aspect of the present disclosure provides a cyclic polo-box domain(PBD) ligand comprising the structure:

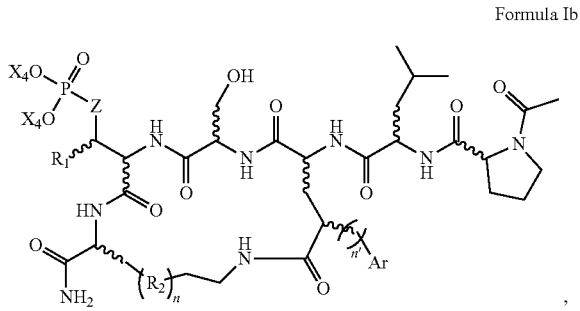

Formula Ib wherein:

Z is O or $CH_2$;

$R_1$ is an optionally substituted alkyl, optionally substituted cycloalkyl, optionally substituted aralkyl, optionally substituted heteroarylalkyl, haloalkyl, optionally substituted morpholinomethyl,

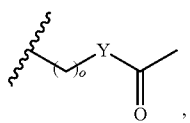

or optionally substituted indolylalkyl;

$R^2$ is an optionally substituted alkyl group or polyethylene glycol;

n or n' is 1-20;

Y is $CH_2$, NH, or O;

o is 0-10;

Ar is an optionally substituted aryl, an optionally substituted heteroaryl, an optionally substituted aralkyl; an optionally substituted heteroarylalkyl; and each $X_4$ is independently, is H, alkyl, aryl-(C1-20)alkyl-, or alkenyl-(C1-20)alkyl, or a pharmaceutically acceptable salt, solvate, hydrate, prodrug, or stereoisomer thereof.

In any aspect or embodiment described herein, n is 3-6; n' is 4-8 and R2 is a methylene group.

In any aspect or embodiment described herein, the macrocyclic ligand has the structure:

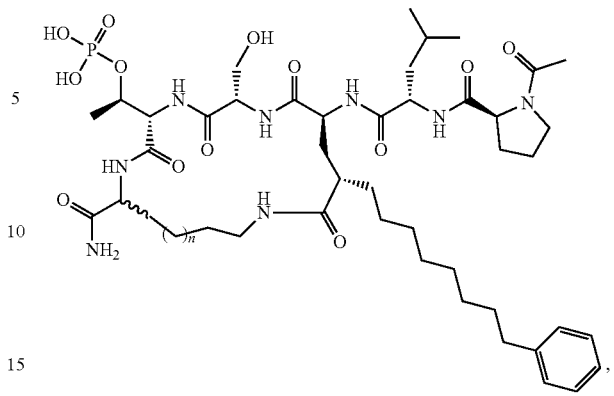

wherein n is 3-5, or salt, solvate, stereoisomer or hydrate thereof.

In any aspect or embodiment described herein the ligand has desirable pharmacokinetic properties with desirable efficacy.

Another aspect of the present disclosure provides an intermediate for synthesis of macrocyclic ligand of Formula Ib, wherein the intermediate is:

Structure III

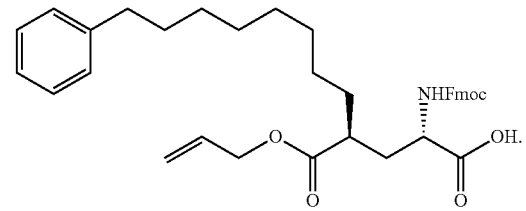

A further aspect of the present disclosure provides a process to prepare a compound of Formula Ib, or salt, solvate, stereoisomer or hydrate thereof:

Formula I

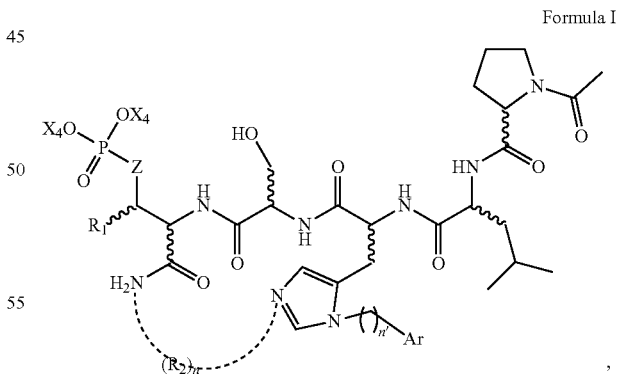

the process comprising:
performing solid state peptide synthesis(SSPS) on (4-hydroxymethyl-3-methoxyphenoxy) butanoic acid resin (HMPB resin) to get desired protected peptide backbone;
coupling an alkylene linker at N(τ) nitrogen using a microwave-assisted on-resin alkylation with alkyl iodides;

cleaving the peptide from resin and deprotection under mild acidic conditions;
cyclizing using PyBOP and phosphate deprotection using Pd/C to yield ligands of formula 1.

An additional aspect of the present disclosure provides a process to prepare a compound of Formula IIb, or salt, solvate, stereoisomer or hydrate thereof:

Formula Ib

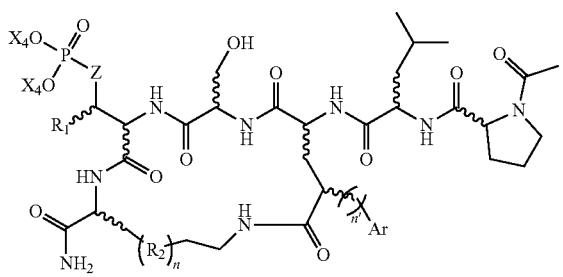

the process comprising:
- performing solid state peptide synthesis(SSPS) on alloc protected amino acids using Rink amide resin to get desired protected peptide backbone;
- deprotecting alloc group using Pd(PPh$_3$)$_4$;
- inducing on-resin cyclization using PyBOP;
- performing FMOC deprotection followed by continued SPPS; and
- cleaving and deprotecting in trifluoroacetic acid to yield ligands of Formula IIb.

An aspect of the present disclosure provides a process to prepare an intermediate required to synthesize a compound of Formula Ib:

Structure IIIb

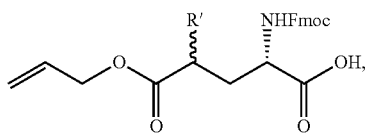

the process comprising:
- alloc protection of Boc protected Glutamic acid using allyl alochol;
- stereospecific alkylation at C-4 position using lithium chelation-controlled enolate addition;
- deprotection of Boc and t-butyl group;
- protection with Fmoc group to yield Structure IIIb.

An aspect of the present disclosure provides a cyclic polo-box domain ligand comprising the structure:

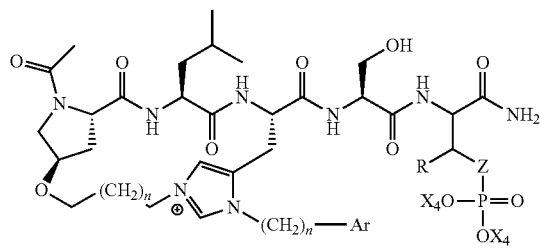

-continued

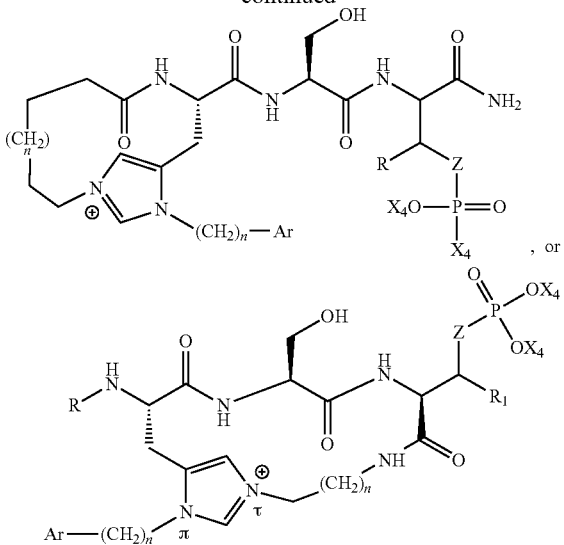

wherein:
n is 1-20;
Z is O or CH$_2$;
R$_1$ is an optionally substituted H, alkyl, optionally substituted cycloalkyl, optionally substituted aralkyl, optionally substituted heteroarylalkyl, haloalkyl, optionally substituted morpholinomethyl,

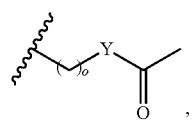

or optionally substituted indolylalkyl;
Y is CH$_2$, NH, or O;
Ar is an optionally substituted aryl, an optionally substituted heteroaryl, an optionally substituted aralkyl; an optionally substituted heteroarylalkyl;
X$_4$, for each occurrence independently, is H, alkyl, aryl-(C1-20)alkyl-, or alkenyl-(C1-20)alkyl;
or a pharmaceutically acceptable salt, solvate, hydrate, prodrug, or stereoisomer thereof.

In any aspect or embodiment described herein, the composition is labeled for the treatment of a hyperproliferative disorder.

In any aspect or embodiment described herein, the hyperproliferative disorder is cancer, wherein the cancer is selected from the group consisting of Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, and Thyroid Cancer.

Another aspect of the present disclosure provides a kit comprising at least one compound of the present disclosure (e.g., at least one PBD ligand or compound, at least one cyclic PBD ligand, at least one bivalent ligand, at least one bivalent compound, or a combination thereof), and instructions for use.

A further aspect of the present disclosure provides a method of treating cancer in a patient, wherein the method comprising administering to the patient at least one compound of the present disclosure (e.g., at least one PBD ligand or compound, at least one cyclic PBD ligand, at least one bivalent ligand, at least one bivalent compound, or a combination thereof) or the composition of the present disclosure, wherein the compound composition inhibits, prevents or treats cancer in the patient.

An aspect of the present disclosure provides a bivalent peptido-mimetic ligand according to the structure:

KD-IDL-PBD wherein:
KD is a kinase domain ligand;
IDL is a flexible interdomain linker comprising a bond or a chemical group; and
PBD is a polo-box domain ligand.

In any aspect or embodiment described herein, the PBD is a compound of the present disclosure (a bivalent ligand of the present disclosure, a cyclic polo-box domain ligand of the present disclosure, or a PBD ligand or compound of the present disclosure).

In any aspect or embodiment described herein, the PBD ligand is

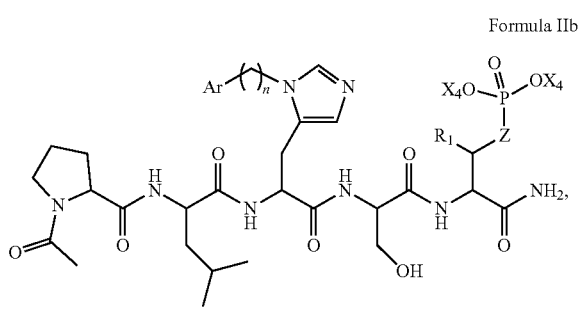

Formula IIb wherein:
n is 1-20; Z is O or CH$_2$;
R1 is H, an optionally substituted alkyl, optionally substituted cycloalkyl, optionally substituted aralkyl, optionally substituted heteroarylalkyl, haloalkyl, optionally substituted morpholinomethyl,

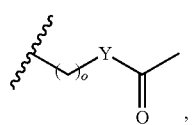

or optionally substituted indolylalkyl;
Y is CH$_2$, NH, or O; and
Ar is an optionally substituted aryl, an optionally substituted heteroaryl, an optionally substituted aralkyl; an optionally substituted heteroarylalkyl;
X$_4$, for each occurrence independently, is H, alkyl, aryl-(C1-20)alkyl-, or alkenyl-(C1-20)alkyl;

or a pharmaceutically acceptable salt, solvate, hydrate, prodrug, or stereoisomer thereof.

In any aspect or embodiment described herein, the PBD ligand is:

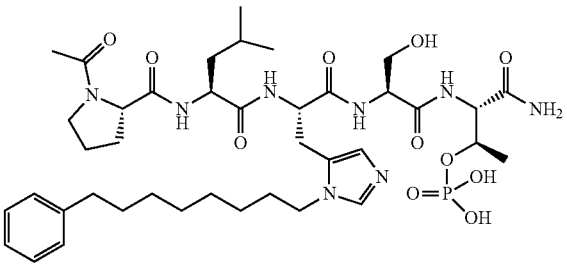

4j or a pharmaceutically acceptable salt, solvate, hydrate, or stereoisomer thereof.

In any aspect or embodiment described herein, the KD ligand comprises structure:

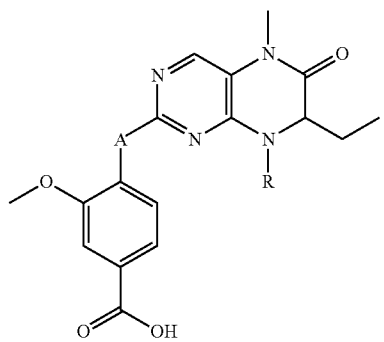

wherein:
A is O or NH; and
R is an alkyl, a cycloalkyl or an aromatic ring, or a pharmaceutically acceptable salt, solvate, hydrate, or stereoisomer thereof.

In any aspect or embodiment described herein, R is isobutyl or cyclopentyl.

In any aspect or embodiment described herein, the KD ligand is:

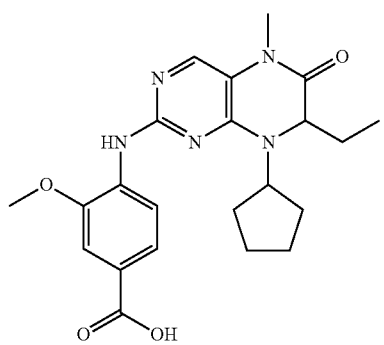

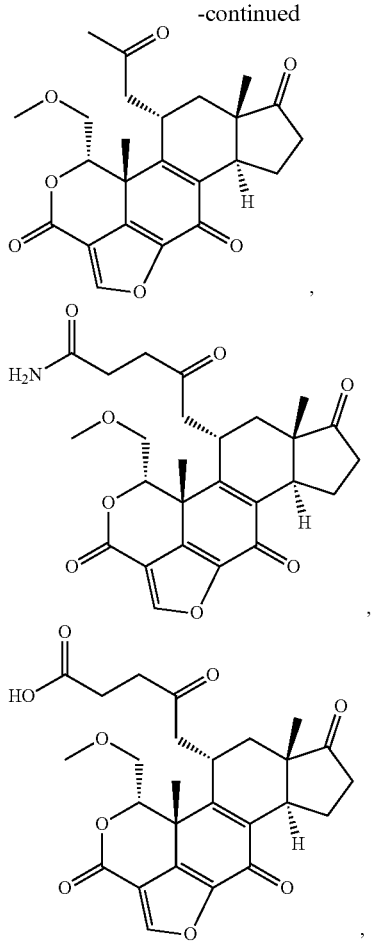

or a pharmaceutically acceptable salt, solvate, hydrate, or stereoisomer thereof.

In any aspect or embodiment described herein, the IDL comprises at least one of:

a polyethylene glycol (PEG) linker of structure: (PEG)n, wherein n=0-8;

a C1-C100 alkylene optionally with:

(i) one or more carbons of the chain substituted with N, O, or S;
(ii) at least one double bond;
(iii) at least one carbon substituted with an alkyl (e.g., C1-C6 alkyl), an alkoxyl (e.g., C1-C6 alkoxyl), an aryl (e.g., C4-C7 aryl), a heteroaryl (e.g., C4-C7 heteroaryl), a cycloalkyl (e.g., C3-C7 cycloalkyl), a heterocyclyl (e.g., C3-C7 heterocyclyl); or combinations thereof.

In any aspect or embodiment described herein, n is 0-4.

In any aspect or embodiment described herein, the KD is attached to the PBD through its C-terminal.

In any aspect or embodiment described herein, the KD is attached to the PBD through its N-terminal.

In any aspect or embodiment described herein, wherein the bivalent ligand comprising a structure:

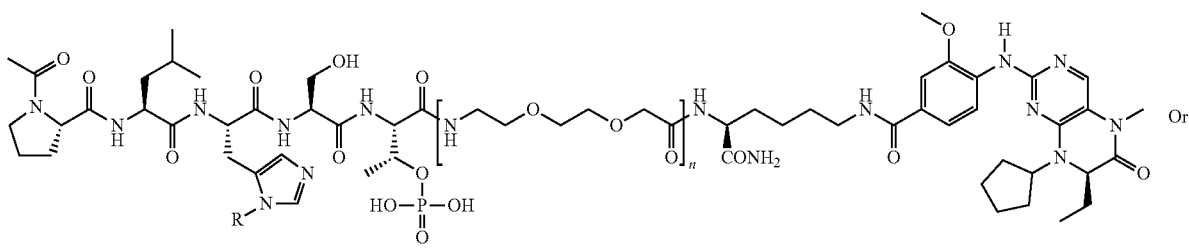

Or

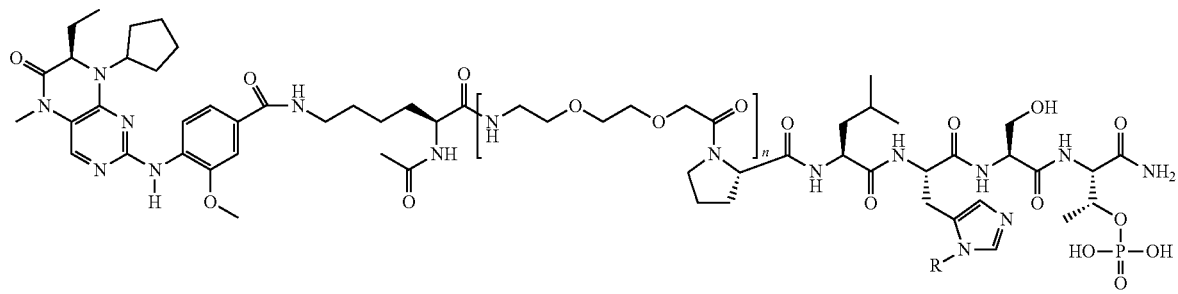

wherein, n = 0-4
R = (CH$_2$)$_8$Ph or H

-continued
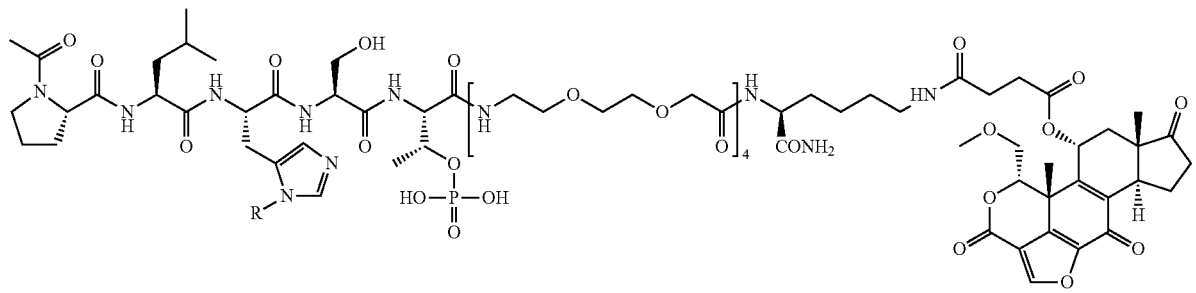
R = —(CH$_2$)$_8$Ph
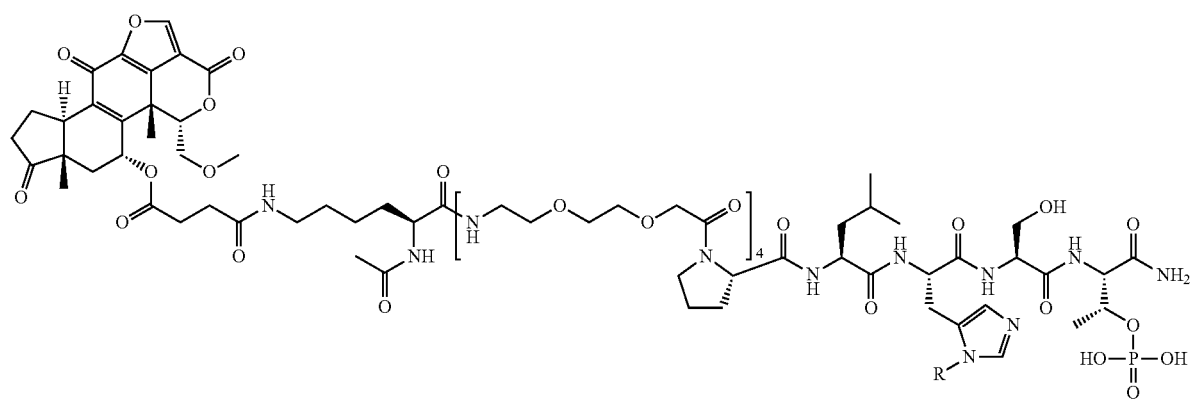
R = —(CH$_2$)$_8$Ph
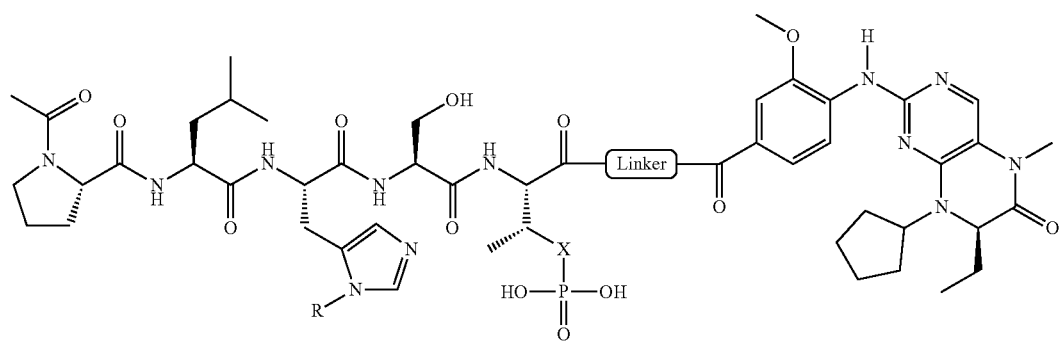
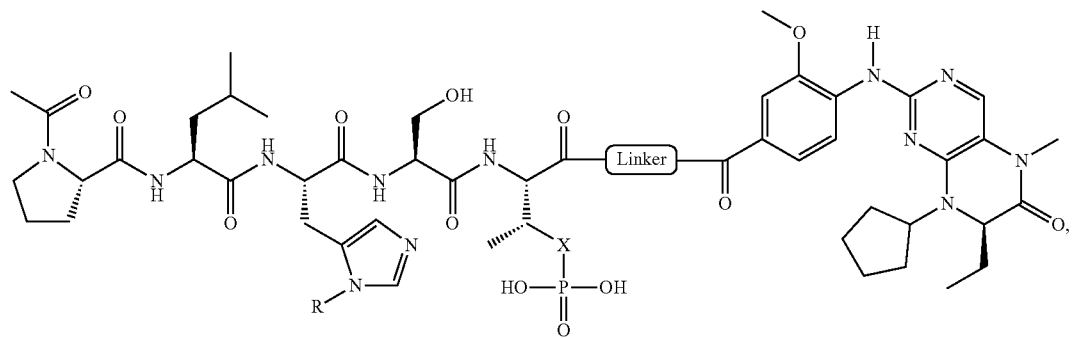

wherein:
R is —(CH2)8Ph;
X is O or CH2; and

is selected from:

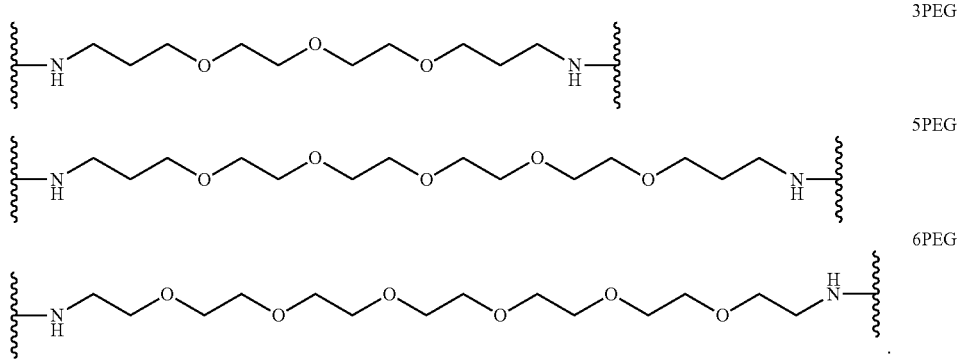

A further aspect of the present disclosure provides for a bivalent compound comprising a compound or PBD ligand of the present disclosure, a cyclic polo-box domain ligand of the present disclosure, or a bivalent ligand of the present disclosure covalently linked to a cell-surface ligand or binding moiety.

In any aspect or embodiment described herein, at least one of: the cell-surface ligand or binding moiety is a cell surface integrin binding moiety; the cell-surface ligand or binding moiety is LLP2A or a derivative or analog thereof; the cell-surface ligand or binding moiety binds a cell surface integrin; the cell-surface ligand or binding moiety binds $\alpha_4\beta_1$ integrin; the compound or the bivalent ligand is covalently linked to the cell-surface ligand or binding moiety via a cleavable linker; or combinations thereof.

In any aspect or embodiment described herein, the cleavable linker includes a disulfide bond or a valine-citruline dipeptide cathepsin substrate.

An aspect of the present disclosure provides a pharmaceutical composition comprising an effective amount of a compound of the present disclosure (e.g., at least one PBD ligand or compound, at least one cyclic PBD ligand, at least one bivalent ligand, at least one bivalent compound, or a combination thereof) in combination with a pharmaceutically acceptable carrier, additive or excipient.

Another aspect of the present disclosure provides a method of treating or preventing a hyperproliferative disorder in a subject comprising administering to a subject in need thereof, an effective amount of the composition of the present disclosure, wherein the composition is effective for the treatment or prevention of the hyperproliferative disorder.

In any aspect or embodiment described herein, the hyperproliferative disorder is cancer, wherein the cancer is selected from the group consisting of Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, and Thyroid Cancer.

An additional aspect of the present disclosure provides a kit comprising a container, at least one compound of the present disclosure (e.g., at least one PBD ligand or compound, at least one cyclic PBD ligand, at least one bivalent ligand, at least one bivalent compound, or a combination thereof), and optionally instructions for use.

A further aspect of the present disclosure provides a method of treating cancer in a patient, wherein the method comprising administering to the patient the composition of the present disclosure, wherein the composition inhibits, prevents or treats cancer in the patient.

INCORPORATION BY REFERENCE

The entire contents of all patents, published patent applications and other references cited herein are hereby expressly incorporated herein in their entireties by reference.

REFERENCES

1. Blume-Jensen, P.; Hunter, T. *Nature* 2001, 411, 355-365;
2. Rogers, L. D.; Foster, L. J. *Mol. BioSyst.* 2009, 5, 1122-1129;
3. Yaffe, M. B. *Nat. Rev. Mol. Cell Biol.* 2002, 3, 177-186.
4. Ladbury, J. E. *Protein Rev.* 2005, 3, 165-184.
5. Elia, A. E. H.; Yaffe, M. B. *In Modular Protein Domains*; Cesare, G., Ed.; Wiley-VCH Verlag GmbH & Co. KGaA: Weinheim, Germany, 2005, p 163-179.
6. Eisele, F.; Owen, D. J.; Waldmann, H. *Bioorg Med Chem* 1999, 7, 193-224.
7. Allentoff, A.; Mandiyan, S.; Liang, H.; Yuryev, A.; Vlattas, I.; Duelfer, T.; Sytwu, I.-I.; Wennogle, L. *Cell Biochem. Biophys.* 1999, 31, 129-140.
8. Richter, S.; Bergmann, R.; Pietzsch, J.; Ramenda, T.; Steinbach, J.; Wuest, F. *Biopolymers* 2009, 92, 479-488.
9. Schultz, C. *Bioorg. Med. Chem.* 2003, 11, 885-898.
10. Mathe, C.; Perigaud, C.; Gosselin, G.; Imbach, J.-L. *J. Org. Chem.* 1998, 63, 8547-8550.
11. Liu, W.-Q.; Vidal, M.; Mathe, C.; Perigaud, C.; Garbay, C. *Bioorg. Med. Chem. Lett.* 2000, 10, 669-672.

12. Liu, W.-Q.; Vidal, M.; Olszowy, C.; Million, E.; Lenoir, C.; Dhotel, H.; Garbay, C. *J. Med. Chem.* 2004, 47, 1223-1233.
13. Rothman, D. M.; Vazguez, M. E.; Vogel, E. M.; Imperiali, B. *J. Org. Chem.* 2003, 68, 6795-6798.
14. Goguen, B. N.; Aemissegger, A.; Imperiali, B. *J. Am. Chem. Soc.* 2011, 133, 11038-11041.
15. Hecker, S. J.; Erion, M. D. *J. Med. Chem.* 2008, 51, 2328-2345.16. Stankovic, C. J.; Surendran, N.; Lunney, E. A.; Plummer, M. S.; Para, K. S.; Shahripour, A.; Fergus, J. H.; Marks, J. S.; Herrera, R.; Hubbell, S. E.; Humblet, C.; Saltiel, A. R.; Stewart, B. H.; Sawyer, T. K. *Bioorg. Med. Chem. Lett.* 1997, 7, 1909-1914
17. Mandal, P. K.; Liao, W. S. L.; McMurray, J. S.; *Org Lett.* 2009, 11, 3394-3397.
18. Mandal, P. K.; Gao, F.; Lu, Z.; Ren, Z.; Ramesh, R.; Birtwistle, J. S.; Kaluarachchi, K. K.; Chen, X.; Bast, R. C.; Liao, W. S.; McMurray, J. S. *J. Med. Chem.* 2011, 54, 3549-3563.
19. Zhao, S.; Etzkorn, F. A. *Bioorg. Med. Chem. Lett.* 2007, 17, 6615-6618.
20. Ottinger, E. A.; Shekels, L. L.; Bernlohr, D. A.; Barany, G. *Biochemistry* 1993, 32, 4354-4361.
21. Hwang, Y.; Cole, P. A. *Org. Lett.* 2004, 6, 1555-1556.
22. McMurray, J. S.; Coleman, D. R. I. V.; Wang, W.; Campbell, M. L. *Biopolymers* 2001, 60, 3-31.
23. Attard, T. J.; O'Brien-Simpson, N.; Reynolds, E. C. *Int. J. Pept. Res. Ther.* 2007, 13, 447-468.
24. Toth, G. K.; Kele, Z.; Varadi, G.; *Curr. Org. Chem.* 2007, 11, 409-426.
25. Yun, S.-M.; Moulaei, T.; Lim, D.; Bang, J. K.; Park, J.-E.; Shenoy, S. R.; Liu, F.; Kang, Y. H.; Liao, C.; Soung, N.-K.; Lee, S.; Yoon, D.-Y.; Lim, Y.; Lee, D.-H.; Otaka, A.; Appella, E.; McMahon, J. B.; Nicklaus, M. C.; Burke, T. R., Jr.; Yaffe, M. B.; Wlodawer, A.; Lee, K. S. *Nat. Struct. Mol. Biol.* 2009, 16, 876-882.
26. Lu, C. H. S.; Liu, K.; Tan, L. P.; Yao, S. Q. *Chem. Eur. J.* 2012, 18, 28-39.
27. Burke, T. R., Jr.; Lee, K. *Acc. Chem. Res.* 2003, 36, 426-433.
28. (a) Shapiro, G.; Buechler, D.; Ojea, V.; Pombo-Villar, E.; Ruiz, M.; Weber, H. P. *Tetrahedron Lett.* 1993, 34, 6255-6258; (b) Perich, J. W. *Int. J. Pept. Protein Res.* 1994, 44, 288-294; (c) Nair, S. A.; Lee, B.; Hangauer, D. G. *Synthesis* 1995, 810-814; (d) Panigrahi, K.; Eggen, M.; Maeng, J.-H.; Shen, Q.; Berkowitz, D. B. *Chem. Biol.* 2009, 16, 928-936.
29. (a) Otaka, A.; Mitsuyama, E.; Kinoshita, T.; Tamamura, H.; Fujii, N. *J. Org. Chem.* 2000, 65, 4888-4899; (b) Liu, F.; Park, J.-E.; Lee, K. S.; Burke, T. R., Jr. *Tetrahedron* 2009, 65, 9673-9679.
30. Boutselis, I. G.; Yu, X.; Zhang, Z.-Y.; Borch, R. F. *J. Med. Chem.* 2007, 50, 856-864.
31. Arrendale, A.; Kim, K.; Choi, J.; Li, W.; Geahlen, R. L.; Borch, R. F. *Chem. BioL* 2012, 19, 764-771.
32. (a) Stankovic, C. J.; Surendran, N.; Lunney, E. A.; Plummer, M. S.; Para, K. S.; Shahripour, A.; Fergus, J. H.; Marks, J. S.; Herrera, R.; Hubbell, S. E.; Humblet, C.; Saltiel, A. R.; Stewart, B. H.; Sawyer, T. K. *Bioorg. Med. Chem. Lett.* 1997, 7, 1909-1914; (b) Mandal, P. K.; Liao, W. S. L.; McMurray, J. S. *Org. Lett.* 2009, 11, 3394-3397; (c) Mandal, P. K.; Gao, F.; Lu, Z.; Ren, Z.; Ramesh, R.; Birtwistle, J. S.; Kaluarachchi, K. K.; Chen, X.; Bast, R. C.; Liao, W. S.; McMurray, J. S. *J. Med. Chem.* 2011, 54, 3549 3563; (d) Zhao, S.; Etzkorn, F. A. *Bioorg. Med. Chem. Lett.* 2007, 17, 6615-6618.
33. (a) Yun, S.-M.; Moulaei, T.; Lim, D.; Bang, J. K.; Park, J.-E.; Shenoy, S. R.; Liu, F.; Kang, Y. H.; Liao, C.; Soung, N.-K.; Lee, S.; Yoon, D.-Y.; Lim, Y.; Lee, D.-H.; Otaka, A.; Appella, E.; McMahon, J. B.; Nicklaus, M. C.; Burke, T. R., Jr.; Yaffe, M. B.; Wlodawer, A.; Lee, K. S. *Nat. Struct. Mol. Biol.* 2009, 16, 876-882; (b) Liu, F.; Park, J.-E.; Qian, W. J.; Lim, D.; Gruber, M.; Berg, T.; Yaffe, M. B.; Lee, K. S.; Burke, T. R., Jr. *Nat. Chem. Biol.* 2011, 7, 595-601; (c) Liu, F.; Park, J.-E.; Qian, W.-J.; Lim, D.; Scharow, A.; Berg, T.; Yaffe, M. B.; Lee, K. S.; Burke, T. R., Jr. *ChemBioChem* 2012, 13, 1291-1296.
34. van de Weerdt, W. B. C. M.; Littler, D. R.; Klompmaker, R.; Huseinovic, A.; Fish, A.; Perrakis, A.; Medema, R. H. *Biochim. Biophys. Acta, Mol. Cell Res.* 2008, 1783, 1015-1022
35. (a) *Nat. Struct. Mol. Biol.* 2009, 16, 876-882; (b) *Nat. Chem. Biol.* 2011, 7, 595-601; (c) *ACS Chem. Biol.* 2012, 7, 805-810; (d) *ChemBioChem* 2012, 13, 1291-1296
36. U.S. Patent Publication No. 2012/0065146 A1.
37. International Patent Application Publication No. WO2010/132869 A2.
38. International Patent Application Publication No. WO2012/142245 A2.
39. Qian W, Liu F, Burke T R, Jr. Investigation of Unanticipated Alkylation at the N(pi) Position of a Histidyl Residue Under Mitsunobu Conditions and Synthesis of Orthogonally Protected Histidine Analogues. J Org Chem. 2011; 76(21):8885-90. doi: 10.1021/jo201599c. PubMed PMID: WOS:000296206400030.
40. Gianelli C, Sambri L, Carlone A, Bartoli G, Melchiorre P. Aminocatalytic Enantioselective anti-Mannich Reaction of Aldehydes with In Situ Generated N-Cbz and N-Boc Imines. Angewandte Chemie-International Edition. 2008; 47(45):8700-2. doi: 10.100$^2$/anie.200803819. PubMed PMID: WOS:000260727400034.
41. Galzerano P, Agostino D, Bencivenni G, Sambri L, Bartoli G, Melchiorre P. Controlling Stereoselectivity in the Aminocatalytic Enantioselective Mannich Reaction of Aldehydes with In Situ Generated N-Carbamoyl Imines. Chemistry-a European Journal. 2010; 16(20):6069-76. doi: 10.1002/chem.200903217. PubMed PMID: WOS: 000278596600029.
42. Nagano T, Kinoshita H. A new and convenient method for the synthesis of dehydroamino acids starting from ethyl N-Boc- and N-Z-alpha-tosylglycinates and various nitro compounds. Bull Chem Soc Jpn. 2000; 73(7):1605-13. doi: 10.1246/bcsj.73.1605. PubMed PMID: WOS: 000088837000020.
43. Liu F, Park J E, Qian W J, Lim D, Graber M, Berg T, Yaffe M B, Lee K S, Burke T R. Serendipitous alkylation of a Plk1 ligand uncovers a new binding channel. Nat Chem Biol. 2011; 7(9):595-601. doi: 10.1038/nhembio.614. PubMed PMID: WOS:000294381400009.
44. Golsteyn R M, Schultz S J, Bartek J, Ziemiecki A, Ried T, Nigg E A. CELL-CYCLE ANALYSIS AND CHROMOSOMAL LOCALIZATION OF HUMAN PLK1, A PUTATIVE HOMOLOG OF THE MITOTIC KINASES *DROSOPHILA POLO* AND *SACCHAROMYCES-CEREVISIAE* CDC5. J Cell Sci. 1994; 107:1509-17. PubMed PMID: WOS:A1994NW49500016.
45. Hanisch A, Wehner A, Nigg E A, Sillje H H W. Different Plk1 functions show distinct dependencies on polo-box domain-mediated targeting. Mol Biol Cell. 2006; 17(1): 448-59. doi: 10.1091/mbc.E05-08-0801. PubMed PMID: WOS:000234399300041.
46. Elia A E H, Rellos P, Haire L F, Chao J W, Ivins F J, Hoepker K, Mohammad D, Cantley L C, Smerdon S J, Yaffe M B. The molecular basis for phosphodependent substrate targeting and regulation of Plks by the Polo-box domain. Cell. 2003; 115(1):83-95. doi: 10.1016/s0092-8674(03)00725-6. PubMed PMID: WOS:000185815500011.
47. Reindl W, Strebhardt K, Berg T. A high-throughput assay based on fluorescence polarization for inhibitors of the polo-box domain of polo-like kinase 1. Anal Biochem. 2008; 383(2):205-9. doi: 10.1016/j.ab.2008.08.014. PubMed PMID: WOS:000260900900011.
48. Reindl W G, Yuan J P, Kramer A, Strebhardt K, Berg T. Inhibition of polo-like kinase 1 by blocking Polo-box domain-dependent protein-protein interactions. Chem Biol. 2008; 15(5):459-66. doi: 10.1016/j.chembiol.2008.03.013. PubMed PMID: WOS:000256183200010.
49. Lee, K. S.; Burke, T. R.; Park, J.-E.; Bang, J. K.; Lee, E. Recent advances and new Strategies in targeting Plk1 for anticancer therapy. Trends Pharmacol. Sci. 2015, 36, 858-877.
50. Yun, S.-M.; Moulaei, T.; Lim, D.; Bang, J. K.; Park, J.-E.; Shenoy, S. R.; Liu, F.; Kang, Y. H.; Liao, C.; Soung, N.-K.; Lee, S.; Yoon, D.-Y.; Lim, Y.; Lee, D.-H.; Otaka, A.; Appella, E.; McMahon, J. B.; Nicklaus, M. C.; Burke, T. R., Jr.; Yaffe, M. B.; Wlodawer, A.; Lee, K. S. Structural and functional analyses of minimal phosphopeptides targeting the polo-box domain of polo-like kinase 1. Nat. Struct. Mol. Biol. 2009, 16, 876-882.
51. Liu, F.; Park, J.-E.; Qian, W.-J.; Lim, D.; Scharow, A.; Berg, T.; Yaffe, M. B.; Lee, K. S.; Burke, T. R. Peptoid-peptide hybrid ligands targeting the polo box domain of polo-like kinase 1. ChemBioChem 2012, 13, 1291-1296.
52. Qian, W.-J.; Park, J.-E.; Lee, K. S.; Burke, T. R., Jr. Non-proteinogenic amino acids in the pThr-2 position of a pentamer peptide that confer high binding affinity for the polo box domain (PBD) of polo-like kinase 1 (Plk1) Bioor. Med. Chem. Lett. 2012, 22, 7306-7308.
53. Liu, F.; Park, J.-E.; Lee, K. S.; Burke, T. R. Preparation of orthogonally protected (2S,3R)-2-amino-3-methyl-4-phosphonobutyric acid (Pmab) as a phosphatase-stable phosphothreonine mimetic and its use in the synthesis of polo-box domain-binding peptides. Tetrahedron 2009, 65, 9673-9679.
54. Qian, W.-J.; Park, J.-E.; Liu, F.; Lee, K. S.; Burke, T. R., Jr. Effects on Polo-like kinase 1 Polo-box domain binding affinities of peptides incurred by structural variation at the phosphoamino acid position Bioorg. Med. Chem. 2013, 21, 3996-4003.
55. Qian, W.-J.; Lai, C. C.; Kelley, J. A.; Burke, T. R. Design and synthesis of Fmoc-Thr[PO(OH)(OPOM)] for the preparation of peptide prodrugs containing phosphothreonine in fully p[rotected form. Chem. Biodiversity 2014, 11, 784-791.
56. Qian, W.-J.; Burke, T. R., Jr. Mitsunobu mischief: Neighbor-directed histidine N(τ)-alkylation provides access to peptides containing selectively functionalized imidazolium heterocycles. Org. Biomol. Chem. 2015, 13, 4221-4225.
57. Qian, W.-J.; Park, J.-E.; Grant, R.; Lai, C. C.; Kelley, J. A.; Yaffe, M. B.; Lee, K. S.; Burke, T. R., Jr. Neighbor-directed histidine N(τ)-alkylation: A route to imidazolium-containing phosphopeptide macrocycles. Biopolymers Pept. Sci. 2015, 104, 663-673.
58. Qian, W.-J.; Park, J.-E.; Lim, D.; Lai, C. C.; Kelley, J. A.; Park, S.-Y.; Lee, K. W.; Yaffe, M. B.; Lee, K. S.; Burke, T. R. Mono-anionic phosphopeptides produced by unexpected histidine alkylation exhibit high plkl polo-box domain-binding affinities and enhanced antiproliferative effects in hela cells. Biopolymers Pept. Sci. 2014, 102, 444-455.
59. Ahn, M.; Han, Y.-H.; Park, J.-E.; Kim, S.; Lee, W. C.; Lee, S. J.; Gunasekaran, P.; Cheong, C.; Shin, S. Y., Sr.; Kim, H.-Y.; Ryu, E. K.; Murugan, R. N.; Kim, N.-H.; Bang, J. K. A new class of peptidomimetics targeting the polo-box domain of Polo-like kinase 1. J. Med. Chem. 2015, 58, 294-304.
60. Zhao, X. Z.; Hymel, D.; Burke, T. R., Jr. Application of oxime-diversification to optimize ligand interactions within a cryptic pocket of the polo-like kinase 1 polo-box domain. Bioorg. Med. Chem. Lett. 2016, 26, 5009-5012.
61. Krishnamurthy, V. M.; Estrofi, L. A.; Whitesides, G. M., Multivalency in ligand design. In Fragment-based Approaches in Drug Discovery, Erlanson, W. J. a. D. A., Ed. Wiley-VCH GmbH & Co.: Weinheim, Del., 2006; pp 11-53.
62. Smith, A. J. T.; Zhang, X.; Leach, A. G.; Houk, K. N. Beyond picomolar affinities: Quantitative aspects of non-covalent and covalent binding of drugs to proteins. J. Med. Chem. 2009, 52, 225-233.
63. Cox, K. J.; Shomin, C. D.; Ghosh, I. Tinkering outside the kinase ATP box: allosteric (type IV) and bivalent (type V) inhibitors of protein kinases. Future Med. Chem. 2011, 3, 29-43.
64. Lamba, V.; Ghosh, I. New directions in targeting protein kinases: focusing upon true allosteric and bivalent inhibitors. Curr. Pharm. Des. 2012, 18, 2936-2945.
65. Brandvold, K. R.; Santos, S. M.; Breen, M. E.; Lachacz, E. J.; Steffey, M. E.; Soellner, M. B. Exquisitely specific bisubstrate inhibitors of c-Src kinase. ACS CHem. Biol. 2015, 10, 1387-1391.
66. Gower, C. M.; Thomas, J. R.; Harrington, E.; Murphy, J.; Chang, M. E. K.; Cornella-Taracido, I.; Jain, R. K.; Schirle, M.; Maly, D. J. Conversion of a Single Polypharmacological Agent into Selective Bivalent Inhibitors of Intracellular Kinase Activity. ACS Chem. Biol. 2016, 11, 121-131.
67. Johnson, T. K.; Soellner, M. B. Bivalent Inhibitors of c-Src Tyrosine Kinase That Bind a Regulatory Domain. Bioconjugate Chem. 2016, Ahead of Print.
68. Weiss, L.; Efferth, T. Polo-like kinase 1 as target for cancer therapy. Exp. Hematol. Oncol. 2012, 1, 38 (doi: 10.1186/2162-3619-1-38).
69. Jencks, W. P. On the attribution and additivity of binding energies. Proc. Natl. Acad. Sci. USA 1981, 78, 4046-4050.
70. Xu, J.; Shen, C.; Wang, T.; Quan, J. Structural basis for the inhibition of Polo-like kinase 1. Nat. Struct. Mol. Biol. 2013, 20, 1047-1053.
71. Kothe, M.; Kohls, D.; Low, S.; Coli, R.; Rennie, G. R.; Feru, F.; Kuhn, C.; Ding, Y.-H. Selectivity-determining residues in Plk1. Chemical Biology & Drug Design 2007, 70, 540-546.
72. Budin, G.; Yang, K. S.; Reiner, T.; Weissleder, R. Bioorthogonal probes for polo-like knase 1 imaging and quantification. Angew. Chem. Int. Ed. Eng. 2011, 50, 9378-9381.
73. Chen, L.; Yap, J. L.; Yoshioka, M.; Lanning, M. E.; Fountain, R. N.; Raje, M.; Scheenstra, J. A.; Strovel, J. W.; Fletcher, S. BRD4 structure-activity relationships of dual PLK1 kinase/BRD4 bromodomain inhibitor BI-2536. ACS Med. Chem. Lett. 2015, 6, 764-769.
74. International Patent Application Publication No. WO 2014/153101 A2.

75. Niida, A.; Tanigaki, H.; Inokuchi, E.; Sasaki, Y.; Oishi, S.; Ohno, H.; Tamamura, H.; Wang, Z. X.; Peiper, S. C.; Kitaura, K.; Otaka, A.; Fujii, N., Stereoselective synthesis of 3,6-disubstituted-3,6-dihydropyridin-2-ones as potential diketopiperazine mimetics using organocopper-mediated anti-S(N)2' reactions and their use in the preparation of low-molecule CXCR4 antagonists. J. Org. Chem. 2006, 71 (10), 3942-3951.

76. Maharvi, G. M.; Bharucha, A. E.; Fauq, A. H., Synthesis of a DOTA (Gd3+)-conjugate of proton-pump inhibitor pantoprazole for gastric wall imaging studies. Bioorg. Med. Chem. Lett. 2013, 23 (9), 2808-2811.

77. Culcasi, M.; Casano, G.; Lucchesi, C.; Mercier, A.; Clement, J. L.; Pique, V.; Michelet, L.; Krieger-Liszkay, A.; Robin, M.; Pietri, S., Synthesis and Biological Characterization of New Aminophosphonates for Mitochondrial pH Determination by P-31 NMR Spectroscopy. J. Med. Chem. 2013, 56 (6), 2487-2499.

78. Hanessian, S.; Margarita, R., 1,3-asymmetric induction in dianionic allylation reactions of amino acid derivatives-synthesis of functionally useful enantiopure glutamates, pipecolates and pyroglutamates. Tetrahedron Lett. 1998, 39 (33), 5887-5890.

79. Hymel, D.; Burke, T. R., Phosphatase-Stable Phosphoamino Acid Mimetics That Enhance Binding Affinities with the Polo-Box Domain of Polo-like Kinase 1. ChemMedChem 2017, 12 (3), 202-206.

What is claimed is:

1. A bivalent peptido-mimetic ligand according to the structure:

KD-IDL-PBD wherein:
    KD is a kinase domain ligand;
    IDL is a flexible interdomain linker comprising a bond or a chemical group; and
    PBD is a polo-box domain ligand;
    wherein the PBD ligand is Fomula IIb

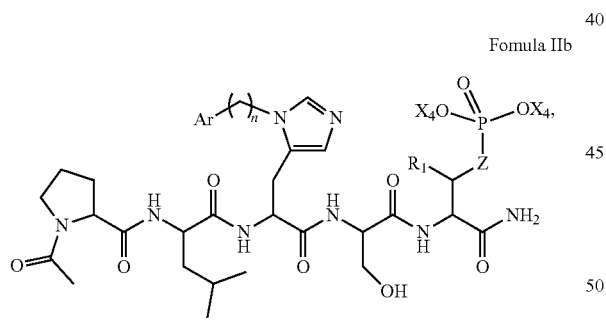

wherein:
    n is 1-20; Z is O or CH$_2$;
    R1 is H, an optionally substituted alkyl, optionally substituted cycloalkyl, optionally substituted aralkyl, optionally substituted heteroarylalkyl, haloalkyl, optionally substituted morpholinomethyl,

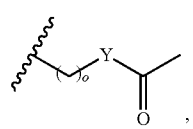

or optionally substituted indolylalkyl;

Y is CH$_2$, NH, or O; and
Ar is an optionally substituted aryl, an optionally substituted heteroaryl, an optionally substituted aralkyl; an optionally substituted heteroarylalkyl;
X$_4$, for each occurrence independently, is H, alkyl, aryl-(C1-20)alkyl-, or alkenyl-(C1-20)alkyl;
the KD ligand is:

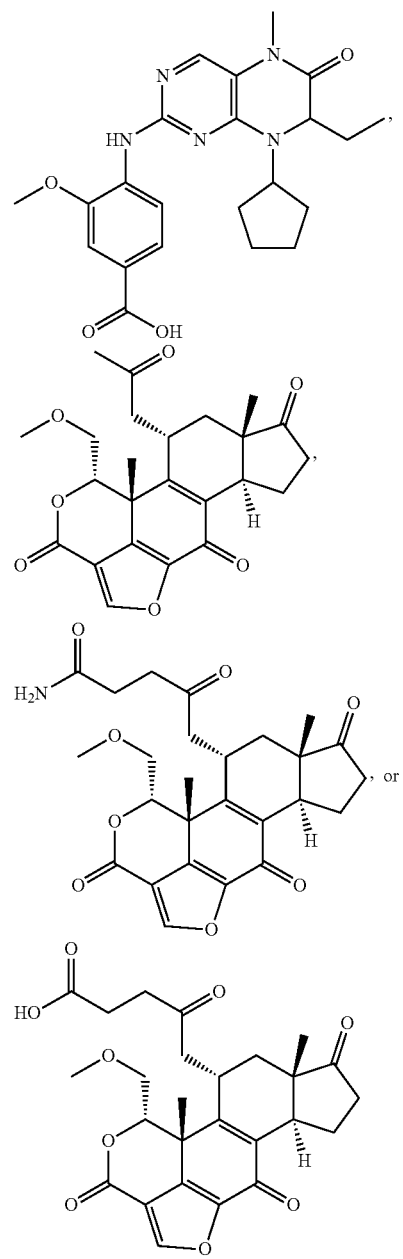

wherein A is O or NH; and
R is an alkyl, a cycloalkyl or an aromatic ring;
and the IDL comprises at least one of:
    a polyethylene glycol (PEG) linker of structure: (PEG)n, wherein n=0-8;
    a C1-C100 alkylene optionally with:
        (i) one or more carbons of the chain substituted with N, O, or S;

(ii) at least one double bond;
(iii) at least one carbon substituted with an alkyl, an alkoxyl, an aryl, a heteroaryl, a cycloalkyl, a heterocyclyl; or combinations thereof;

or a pharmaceutically acceptable salt, solvate, hydrate, prodrug, or stereoisomer thereof.

2. The bivalent ligand of claim 1, wherein the PBD ligand is:

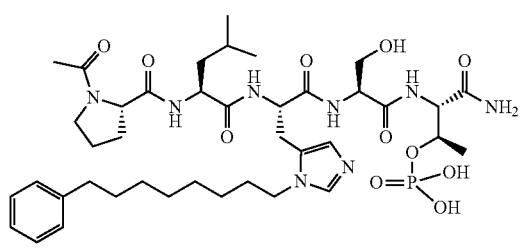

4j or a pharmaceutically acceptable salt, solvate, hydrate, or stereoisomer thereof.

3. The bivalent ligand of claim 1, wherein the KD ligand is:

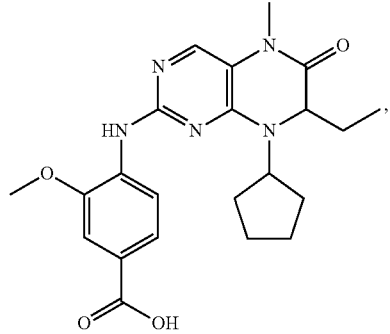

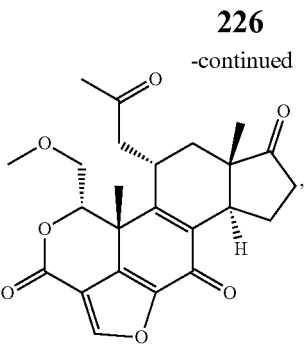

-continued

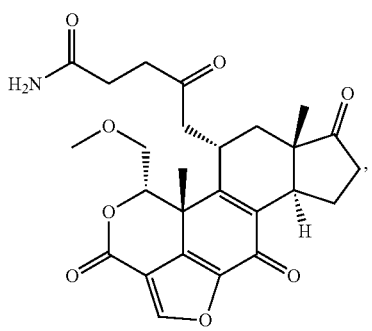

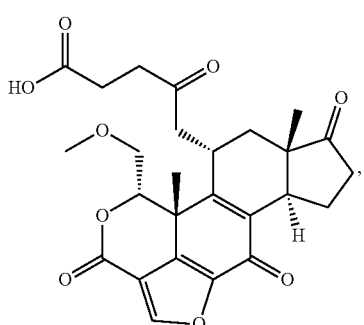

or a pharmaceutically acceptable salt, solvate, hydrate, or stereoisomer thereof.

4. A bivalent peptido-mimetic ligand comprising a structure selected from:

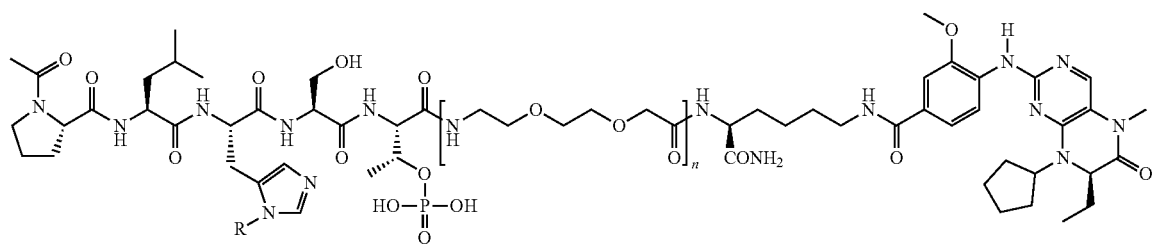

wherein, n = 0-4, and
R = (CH$_2$)$_8$Ph or H;

-continued
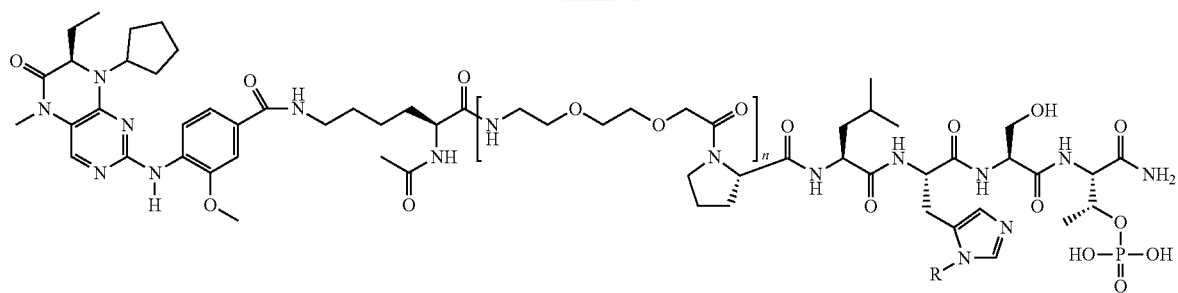
wherein, n = 0-4, and
R = (CH₂)₈Ph or H;
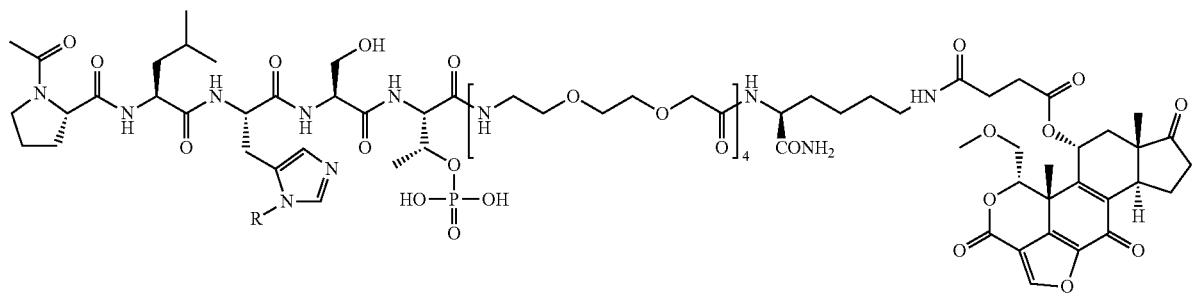
wherein, R = —(CH₂)₈Ph;
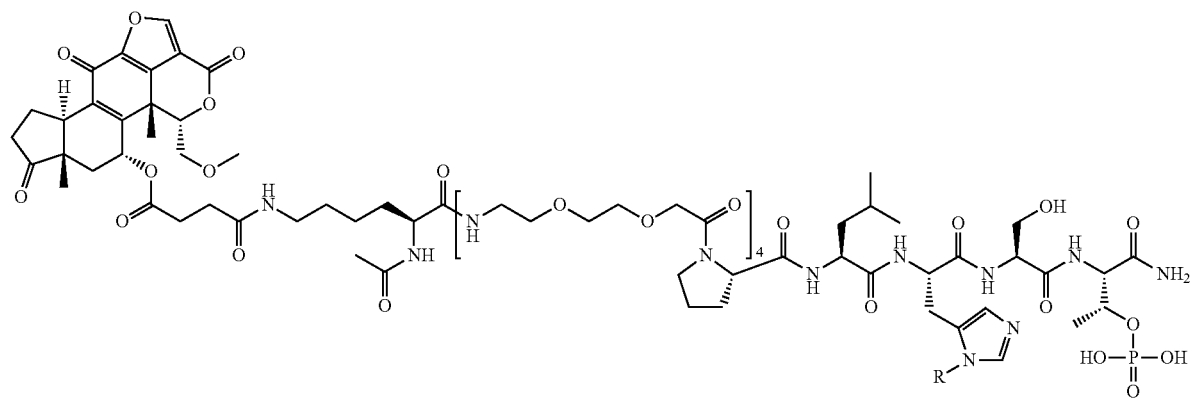
wherein, R = —(CH₂)₈Ph;
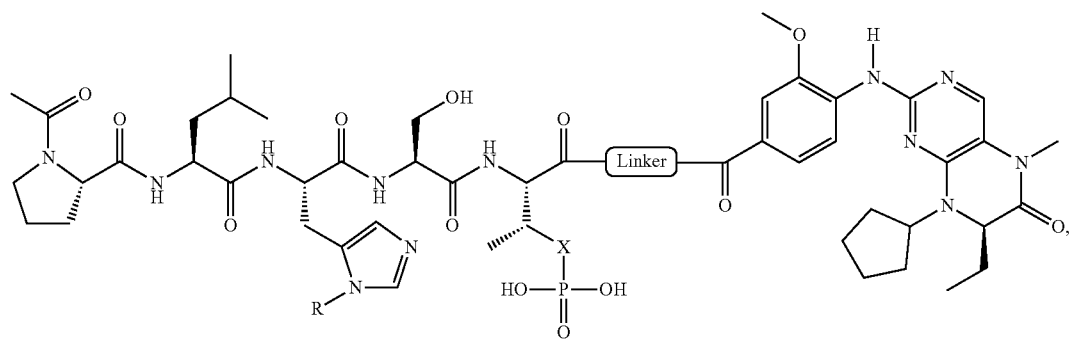

wherein:
R is (CH2)8Ph;
X is O or CH2; and

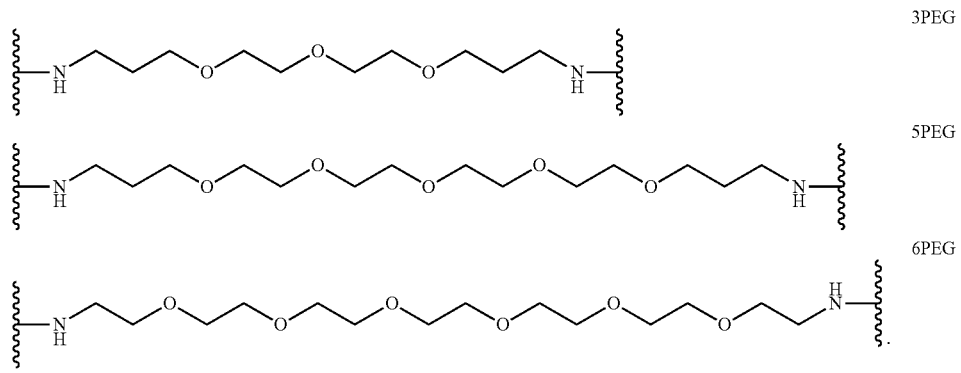

is selected from:

5. A pharmaceutical composition comprising an effective amount of a compound according to claim 1 in combination with a pharmaceutically acceptable carrier, additive or excipient.

6. A pharmaceutical composition comprising an effective amount of a compound according to claim 4 in combination with a pharmaceutically acceptable carrier, additive or excipient.

* * * * *